(12) United States Patent
Kelly et al.

(10) Patent No.: US 7,504,401 B2
(45) Date of Patent: Mar. 17, 2009

(54) ANTI-CANCER AGENTS AND USES THEREOF

(75) Inventors: Martha Kelly, Collegeville, PA (US); Bruce D. Dorsey, Ambler, PA (US); Gary A. Flynn, Tucson, AZ (US)

(73) Assignee: Locus Pharmaceuticals, Inc., Blue Bell, PA (US)

( * ) Notice: Subject to any disclaimer, the term of this patent is extended or adjusted under 35 U.S.C. 154(b) by 279 days.

(21) Appl. No.: 10/928,401

(22) Filed: Aug. 30, 2004

(65) Prior Publication Data

US 2006/0270686 A1  Nov. 30, 2006

Related U.S. Application Data

(60) Provisional application No. 60/498,705, filed on Aug. 29, 2003, provisional application No. 60/528,695, filed on Dec. 12, 2003.

(51) Int. Cl.
*A61K 31/497* (2006.01)
*A61K 31/4439* (2006.01)
*A61K 31/421* (2006.01)
*A61K 31/404* (2006.01)
*C07D 401/10* (2006.01)
*C07D 403/10* (2006.01)
*C07D 413/10* (2006.01)

(52) U.S. Cl. .............. 514/255.05; 514/339; 514/374; 514/414; 514/415; 544/405; 546/315; 548/236; 548/465; 548/469

(58) Field of Classification Search ............ 514/255.05, 514/339, 374, 414, 415; 544/405; 546/315; 548/236, 465, 469
See application file for complete search history.

(56) References Cited

U.S. PATENT DOCUMENTS

| | | | |
|---|---|---|---|
| 4,727,064 A | 2/1988 | Pitha | |
| 4,764,604 A | 8/1988 | Muller | |
| 5,011,832 A | 4/1991 | Dininno et al. | |
| 5,024,998 A | 6/1991 | Boder | |
| 5,208,329 A | 5/1993 | Dininno et al. | |
| 5,250,549 A | 10/1993 | Yoshino et al. | |
| 5,523,408 A | 6/1996 | Batt et al. | |
| 5,567,711 A | 10/1996 | Sheppard et al. | |
| 5,578,609 A | 11/1996 | Batt et al. | |
| 5,643,922 A | 7/1997 | Sheppard et al. | |
| 5,654,305 A | 8/1997 | Sheppard et al. | |
| 5,760,276 A | 6/1998 | Beard et al. | |
| 5,763,635 A | 6/1998 | Vuligonda et al. | |
| 5,879,438 A | 3/1999 | Fujita et al. | |
| 6,117,875 A | 9/2000 | Shimazaki et al. | |
| 6,251,936 B1 | 6/2001 | Wrobel et al. | |
| 6,355,669 B1 | 3/2002 | Yamauchi et al. | |
| 6,420,396 B1 | 7/2002 | Albers et al. | |
| 6,426,345 B1 | 7/2002 | Shimazaki et al. | |
| 7,053,071 B2 | 5/2006 | Dawson et al. | |
| 7,094,801 B2 | 8/2006 | Sikorski et al. | |
| 2002/0016461 A1 | 2/2002 | Albers et al. | |
| 2002/0107251 A1 | 8/2002 | Shimazaki et al. | |
| 2002/0187978 A1* | 12/2002 | Tang et al. | ............ 514/227.8 |
| 2003/0055263 A1 | 3/2003 | Priepke et al. | |
| 2003/0229058 A1 | 12/2003 | Moran et al. | |
| 2004/0067996 A1 | 4/2004 | Sheppeck | |
| 2005/0075384 A1 | 4/2005 | Sheppeck et al. | |

FOREIGN PATENT DOCUMENTS

| | | |
|---|---|---|
| CA | 2092211 A1 | 9/1993 |
| CA | 2099445 | 1/1994 |

(Continued)

OTHER PUBLICATIONS

Magnus et al. "Photo-Fries rearrangment for the synthesis of the diazonamide macrocycle" Tetrahedron Letters, 2001, vol. 42, Iss 41, pp. 7193-7196.*

(Continued)

*Primary Examiner*—Rei-tsang Shiao
*Assistant Examiner*—Joseph R Kosack
(74) *Attorney, Agent, or Firm*—Pepper Hamilton LLP

(57) ABSTRACT

The present invention is in the area of novel compounds and salts thereof, their syntheses, and their use as anti-cancer agents. The compounds include compounds of Formula I:

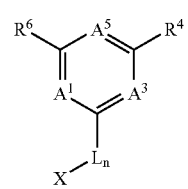

and solvates, hydrates and pharmaceutically-acceptable salts thereof, wherein $A^1$ is N or $CR^1$; $A^3$ is N or $CR^3$; $A^5$ is N or $CR^5$; $R^1$, $R^3$-$R^6$ and L are defined in the specification; n is 0 or 1; and X is an optionally-substituted aryl group having 6-10 carbons in the ring portion, an optionally-substituted 6-membered heteroaryl group having 1-3 nitrogen atoms in the ring portion, an optionally-substituted 5-membered heteroaryl group having 0-4 nitrogen atoms in the ring portion and optionally having 1 sulfur atom or 1 oxygen atom in the ring portion, or an optionally-substituted heteroaryl group in which a 6-membered ring is fused either to a 5-membered ring or to a 6-membered ring, wherein in each case 1, 2, 3 or 4 ring atoms are heteroatoms independently selected from nitrogen, oxygen and sulfur. They are effective against a broad range of cancers, especially leukemia, non-small cell lung and colon.

60 Claims, No Drawings

FOREIGN PATENT DOCUMENTS

| | | |
|---|---|---|
| EP | 470514 | 2/1992 |
| EP | 1300133 | 4/2003 |
| EP | 1457485 | 9/2004 |
| JP | 03291668 | 12/1991 |
| JP | 10189246 | 7/1998 |
| WO | WO 93/06100 | 4/1993 |
| WO | WO 93/12084 | 6/1993 |
| WO | WO 96/01825 | 1/1996 |
| WO | WO 96/04241 | 2/1996 |
| WO | WO 96/10012 | 4/1996 |
| WO | WO 96/16054 | 5/1996 |
| WO | WO 96/41800 | 12/1996 |
| WO | WO 97/17070 A1 | 5/1997 |
| WO | WO 97/24355 A1 | 7/1997 |
| WO | WO 98/07702 | 2/1998 |
| WO | WO 98/47861 | 10/1998 |
| WO | WO 98/49136 | 11/1998 |
| WO | WO 99/11634 | 3/1999 |
| WO | WO 99/23072 A1 | 5/1999 |
| WO | WO 99/42446 | 8/1999 |
| WO | WO 99/51562 | 10/1999 |
| WO | WO 99/61435 | 12/1999 |
| WO | WO 00/12504 | 3/2000 |
| WO | WO 00/35864 A1 | 6/2000 |
| WO | WO 00/035909 | 6/2000 |
| WO | WO 02/100398 | 12/2000 |
| WO | WO 02/18335 | 3/2002 |
| WO | WO 02/24642 | 3/2002 |
| WO | WO 02/24645 | 3/2002 |
| WO | WO 02/055517 | 7/2002 |
| WO | WO 02/083134 | 10/2002 |
| WO | WO 02/096426 | 12/2002 |
| WO | WO 02/096867 A2 | 12/2002 |
| WO | WO 02/098407 | 12/2002 |
| WO | WO 02/098408 | 12/2002 |
| WO | WO 02/098409 | 12/2002 |
| WO | WO 02/098410 | 12/2002 |
| WO | WO 02/098414 | 12/2002 |
| WO | WO 02/098510 | 12/2002 |
| WO | WO 02/100396 | 12/2002 |
| WO | WO 02/100397 | 12/2002 |
| WO | WO 03/006443 A2 | 1/2003 |
| WO | WO 03/030841 | 4/2003 |
| WO | WO 03/042164 | 5/2003 |
| WO | WO 03/053368 | 7/2003 |
| WO | WO 03/053941 | 7/2003 |
| WO | WO 2004/058200 | 7/2004 |
| WO | WO 2004/099192 | 11/2004 |
| WO | WO 2005/016862 | 2/2005 |
| WO | WO 2005/100298 | 10/2005 |
| WO | WO 2006/006172 | 1/2006 |
| WO | WO 2006/008038 | 1/2006 |
| WO | WO 2006/053109 | 5/2006 |
| WO | WO 2006/053227 | 5/2006 |
| WO | WO 2006/055625 | 5/2006 |
| WO | WO 2006/094236 | 9/2006 |
| WO | WO 2006/137465 | 12/2006 |
| WO | WO 2007/017289 | 2/2007 |
| WO | WO 2007/041494 | 4/2007 |

OTHER PUBLICATIONS

Poste, G., et al., "Lipid Vesicles as Carriers for Introducing Biologically Active Materials into Cells", Prescott, Ed., Chap. 4, *Meth. Cell. Biol.*, 14: 33-71, 1976.
Effenberger, F., et al., "Nucleophile Substitution von Nitrit in Nitrobenzolen, Nitrobiphynylen and Nitronaphthalinen" *Chem. Ber.*, 124: 163-73, 1991 (with Engl. Abstract).
Dickinson, R.P., et al., "Thromboxane Modulating Agents. 3. 1-H-Imidizole-1-ylalkyl- and 3-Pyridinylalkyl-Substituted 3-[2-[(Arylsulfonyl)amino]ethyl]benzenepropanoic Acid Derivatives as Dual Thromboxane Synthase Inhibitor/Thromboxane Receptor Antagonists", *J.Med. Chem.*, 40: 3442-52, 1997.
Earley, J.V. and Gilman, N.W., "Synthesis of Substituted (2-Aminophenyl)-3-(And-4-)Pyridinylmethanones", *Synth. Comm.*, 15(14): 1271-76, 1985.
Dumont, F., et al., "Synthesis of 7-Bromo-5-Iodo-4-Oxo-1, 4-Dihydroquinoline-2-Carboxylic Acid", *Bull. Soc. Chim. Belg.* 104:-507, 1995.
Boulton and Coller, "Kinetics, Stoichiometry and Mechanism in the Bromination of Aromatic Heterocycles, III Aqueous Bromination of Indazole", *Aust. J. Chem.*, 27: 2343-2347, 1974.
Ranu, B.C., et al., "A Simple and Improved Procedure for Selective Ring Bromination of Alkyl-Substituted Aromatic Hydrocarbons on the Surface of Alumina", *Synth. Comm.*, 22(8): 1095-1099, 1992.
Charpentier, B., et al., "Synthesis, structure-affinity relationships, and biological activities of ligands binding to retinoic acid receptor subtypes", *J. Med. Chem.*, 38: 4993-5006,, 1995.
Estep, K.G., "An Efficient Synthesis of 4-Hydroxy-1H-Indole-2-Carbonitrile and its Conversion to DPI 201-106" *Synth. Comm.*, 25(4): 507-514, 1995.
Wang, Y.C., et al., "First Enantioselective Total Synthesis of (-)-Tejedine", *Org. Lett.*, 4(16): 2675-2678, 2002.
Clark, R.L., et al., "2-(Substituted phenyl)oxazolo[4,5-b]pyridines and 2-(substituted phenyl)oxazolo[5,4-b]pyridines as nonacidic antiinflammatory agents", *J. Med. Chem.*, 21: 1158-1162, 1978.
Water for Injection, United States Pharmacopeia/National Formulary for 1995, p. 1635-6-, Pub. U.S. Pharmacopeial Convention, Inc., Rockville, MD, 1994.
Mukherjee, S., et al., "Studies in Sulfur Heterocycles. Part 8. 3,4-Dihydro-thieno[2,3-i][1]benzoxepin-5(2H)-one, a New Heterocyclic System and a key intermediate in the synthesis of novel polycondensed sulpher hetercycles", *J. Chem. Res. Synop.*, 5, 192-193, 1993.
Kosuge, T., et al., "Synthesis and Some Reaction sof 6-Bromoxiindole", *Chem. Pharm. Bull.*, 33(4): 1414-1418, 1985.
Bringmann, G. et al., "3D QSAR Investigations on Antimalarial Naphthylisoquinoline Alkaloids by Comparative Molecular Similarity indices Analysis (CoMSIA), Based on Different Alignment Approaches", *J. Chem. Inf. Comput. Sci*, 43: 304-316, 2003.
Jordan, M.A., et al., "Microtubules as a target for anticancer drugs", *Nature Rev. Cancer*, 4:253-265, 2004.
Feldman, K.S., et al., "Diazonamide Synthesis Studies: Use of Negishi Coupling to Fashion D Diazonamide-Related Biaryls with Defined Azial Chirality", *Organic Letters*, 4(20): 3525-3528.
Batt, D.G., et al., "Heteroatom- and carbon-linked biphenyl analogs of Brequinar as immunosuppressive agents", *Bioorganic & Medicinal Chem. Letters*, 8:1745-1750, 1998.
Chambon, P., "A decade of molecular biology of retinoic acid receptors", *The FASEB Journal*, 10(9):940-954,, 1996.
Nagpal, S., et al., "Recent Developments in receptor=Selective Retinoids", *Current Pharmaceutical Design*, 6:919-931, 2000.
Wei, Li-Na, "Retinoid Receptors and Their Coregulators", *Annu. Rev. Pharmacol. Toxicol.*, 43:47-72, 2003.
Cincinelli, R., et al., "A novel atypical retinoid endowed with proapoptotic and antitumor activity", *J. Med. Chem.*, 46(6):909-912, 2003.
Altucci, L. et al., "The promise of retinoids to fight against cancer", *Nature Rev. Cancer*, 1(3):181-193, 2001.
Morjani, H., et al., "Surface-Enhanced Raman Scattering and Fluorescence Spectroscopy Reveal Molecular Interactions of All-trans Retinoic Acid and RARγ Ligand-Binding Domain", *Biospectroscopy*, 4:297-302, 1998.
Klaholz, B.P. et al., "Conformational adaptation of agonists to the human nuclear receptor RARγ", *Nature Structural Biology*, 5(3), 199-201, 1998.
Klaholz, B.P., et al., "Structural Basis for Isotype Selectivity of the Human Retinoic Acid Nuclear Receptor", *J. Mol. Biol.*, 302:155-170, 2002.
Blondel, A., et al., "Retinoic Acid Receptor: A Simulation Analysis of Retinoic Acid Binding and the Resulting Conformational Changes", *J. Mol. Biol.*, 291:101-115,. 1999.
Renaud, J.P., et al., "Crystal structure of the RAR-γ ligand-binding domain bound to all-trans retinoic acid", *Nature*, 378:681-689, 1995.

Thacher, S.M., et al., "Therapeutic Applications for Ligands of Retinoid Receptors", *Current Pharmaceutical Design*, 6:25-58, 2000.

Nagl, S.B., et al, "Evolutionary Constraint Networks in Ligand-Binding Domains: An Information-Theoretic Approach", *Pacific Symposium on Biocomputing*, 90-101, 1999.

Rochel, N., et al, "Purification of the Human RARγ Ligand-Binding Domain and Crystallization of Its Complex with All-trans Retinoic Acid", *Biochemical and Biophysical Research Communications*, 230(2):293-296, 1997.

Schapira, M., et al., "Rational discovery of novel nuclear hormone receptor antagonists", *PNAS*, 97(3):1008-1013, 2000.

LG Life Sciences (South Korea), AACR-NCI-EORTC, Internat. Conf. on Mol. Targ. Cancer Thera. (2001), Abstract 589.

* cited by examiner

ANTI-CANCER AGENTS AND USES THEREOF

This application claims the benefit under 35 U.S.C. § 119 (e) of U.S. Provisional Appl. No. 60/498,705, filed Aug. 29, 2003, and of U.S. Provisional Appl. No. 60/528,695, filed Dec. 12, 2003, both of which are hereby incorporated by reference in their entirety.

BACKGROUND OF THE INVENTION

1. Field of the Invention

The present invention is in the area of novel compounds and salts thereof, their syntheses, and their use as anti-cancer agents.

2. Related Art

The cell cycle is a normal, highly regulated ordered set of events that culminates in cell growth and division. The cell cycle progresses through a protein synthetic phase (G1), a DNA synthetic phase (S) and a mitotic stage (G2/M). Deregulation of the cell cycle by altering key enzymatic and genetic steps can lead to unchecked cell growth and proliferation leading to cancer development.

Blocking the cell cycle with pharmacological inhibitors of key molecular targets that drive the cell cycle through mitosis is a strategy for inhibiting unchecked tumor proliferation. Such inhibitors would be effective anti-cancer agents by slowing or halting tumor growth and proliferation.

There are a number of anti-cancer agents in various stages of clinical development that block cell cycle progression at the G1, S and the G2/M phase. Compounds that block at G2/M include the anti-mitotic natural product 13-hydroxy-15-oxozoapatlin, the phosphatase inhibitors okadeic acid and sodium orthovanadate and the DNA intercalating agents imidazoacridinones. Other G2/M blocking agents have unidentified molecular targets. Such agents include polyphenol resveratrol, thymoquinone and quinoxaline 1,4-dioxides. A need continues to exist for potent, small molecules that block cell cycle progression.

SUMMARY OF THE INVENTION

A first aspect of the present invention is directed to novel compounds of Formula I.

A second aspect of the present invention is directed to pharmaceutical compositions comprising at least one compound of Formula I, or a salt thereof, and one or more pharmaceutically-acceptable excipients.

A further aspect of the present invention is directed to a method of treating a condition that results from abnormal cell growth, cellular differentiation, tumor growth or invasion with one or more compounds of Formula I.

A further aspect of the invention is directed to a method of treating cancer, particularly wherein the cancer is leukemia, soft-tissue sarcomas, or non-small cell lung, myeloma, colon, CNS, melanoma, ovarian, renal, prostate, breast, cervical or pancreatic cancer, particularly leukemia, non-small cell lung or colon cancer, with one or more compounds of Formula I.

A further aspect of the invention is directed to hindering or blocking cell cycle progression by contacting one or more cells with one or more compounds of Formula I.

A further aspect of the present invention is directed to a method of synthesizing compounds of Formula I.

DETAILED DESCRIPTION OF THE INVENTION

A novel class of small molecules that blocks cell cycle progression has now been discovered.

Compounds of the present invention include compounds of Formula I:

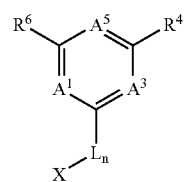

and pharmaceutically-acceptable salts and solvates thereof, wherein:

$A^1$ is N or $CR^1$, wherein $R^1$ is hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, aminocarbonylamino, monoalkylaminocarbonylamino, dialkylaminocarbonylamino, N-alkyl-N-alkoxycarbonyl-amino, N-alkyl-N-aminocarbonyl-amino, N-alkyl-N-monoalkylaminocarbonyl-amino or N-alkyl-N-dialkylaminocarbonyl-amino;

$A^3$ is N or $CR^3$, wherein $R^3$ is hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, aminocarbonylamino, monoalkylaminocarbonylamino, dialkylaminocarbonylamino, N-alkyl-N-alkoxycarbonyl-amino, N-alkyl-N-aminocarbonyl-amino, N-alkyl-N-monoalkylaminocarbonyl-amino or N-alkyl-N-dialkylaminocarbonyl-amino;

$A^5$ is N or $CR^5$;

$R^4$ is 1-indolyl or 1-indazolyl, each of which is optionally substituted by one or two substituents independently selected from the group consisting of halo, hydroxy, nitro, cyano, alkyl, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl and dialkylaminocarbonylalkyl, or $R^4$ is adamantyl, or $R^4$ is selected from the group consisting of

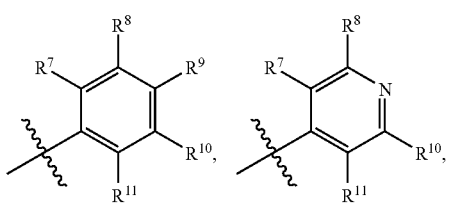

-continued

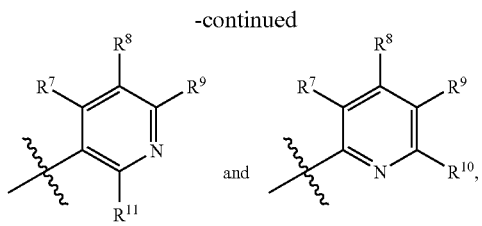

wherein R[7], R[8], R[9], R[10] and R[11] are independently selected from the group consisting of hydrogen, halogen, hydroxy, alkyl, haloalkyl, hydroxyalkyl, alkoxy, cyano amino, monoalkylamino, dialkylamino, formylamino, alkylcarbonylamino, sulfonylamino, alkylsulfonylamino and phenyl, or any two adjacent R groups, together with the carbon atoms to which they are attached, form a 5- or 6-membered aromatic, heteroaromatic or fully or partially unsaturated non-aromatic ring, which ring has 0-2 oxygen atoms, 0-2 sulfur atoms, 0-3 nitrogen atoms and 2-6 carbon atoms, and which ring, together with the phenyl or pyridyl ring to which it is fused, forms a bicyclic moiety, wherein said bicyclic moiety is optionally substituted with one or two substituents independently selected from the group consisting of halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, carboxy, alkoxycarbonyl, aminocarbonyl, monoalkylaminocarbonyl, dialkylaminocarbonyl, alkanoyl, haloalkanoyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl and dialkylaminosulfonyl;

R[5] and R[6] are independently selected from the group consisting of hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, benzyloxycarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, ureido, N-alkylureido, N'-alkylureido, N,N'-dialkylureido, N,N',N'-trialkylureido, N',N'-dialkylureido, N'-alkoxy-N'-alkylureido, tetrazolyl, 2-oxopyrrolidin-1-yl, 2-oxo-piperidin-1-yl, benzyl and benzyloxy, wherein said benzyl and benzyloxy are optionally substituted with one or two substituents independently selected from the group consisting of halo, hydroxy, alkyl, alkoxy, amino, monoalkylamino, dialkylamino, nitro and cyano;

n is 0 or 1, and L is a linker selected from the group consisting of —R[a]—N(R[x])—R[b]—, —N(C(O)—CH$_3$)—, —R[a]—S—R[b]—, —R[a]—O—R[b]— —S(O)—, —S(O)$_2$—, C$_{1-4}$ alkylene, —C(O)—, —C(=N—OH)—, —CH(OH)—, —C(R[x])(OH)—, —CH(OR[x])—, —C(R[x])(OR[y])—, —NH—C(O)—, —N(R[x])—C(O)—, —C(O)—NH—, —C(O)—N(R[x])—, —S(O)$_2$—NH—, —S(O)$_2$—N(R[x])—, —NH—S(O)$_2$—, —N(R[x])—S(O)$_2$— and —NH—S(O)$_2$—CH$_2$—, wherein R[x] and R[y] are independently alkyl, and R[a] and R[b] are independently C$_{0-4}$ alkylene; and X is Ar, HetAr or BiHetAr, wherein Ar is an aryl group having 6-10 carbons in the ring portion, HetAr is a 6-membered heteroaryl group having 1-3 nitrogen atoms in the ring portion, or HetAr is a 5-membered heteroaryl group having 0-4 nitrogen atoms in the ring portion and optionally having 1 sulfur atom or 1 oxygen atom in the ring portion, and BiHetAr is a heteroaryl group in which a 6-membered ring is fused either to a 5-membered ring or to a 6-membered ring, wherein in each case 1, 2, 3 or 4 ring atoms are heteroatoms independently selected from nitrogen, oxygen and sulfur;

wherein Ar, HetAr and BiHetAr are each optionally substituted with one or two substituents independently selected from the group consisting of halo, hydroxy, alkyl, alkenyl, alkynyl, cycloalkyl, haloalkyl, hydroxyalkyl, alkoxy, alkoxyalkyl, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, morpholinyl and formyloxyalkoxyalkyl;

provided that:
(1) A[1], A[3] and A[5] are not all nitrogen;
(2) when A[1] is CR[1], A[3] is CR[3], A[5] is CR[5] and X is optionally-substituted phenyl:
  at least one of R[1], R[5] or R[6] is other than hydrogen, halo, alkyl, alkenyl, alkynyl, cycloalkyl, haloalkyl, hydroxyalkyl, alkoxy, nitro, aminoalkyl, monoalkylaminoalkyl, dialkylaminoalkyl or amino; and
R[4] is selected from the group consisting of

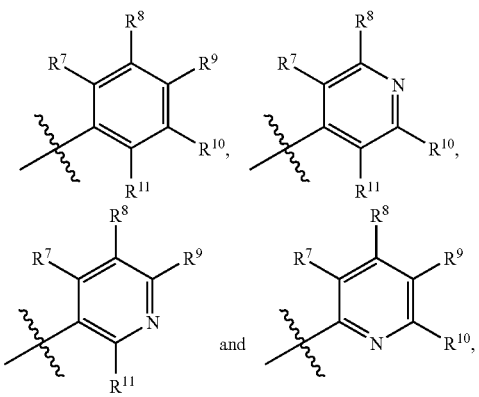

wherein any two adjacent groups selected from R[7], R[8], R[9], R[10] and R[11], together with the carbon atoms to which they are attached, form a 5- or 6-membered aromatic, heteroaromatic or fully or partially unsaturated non-aromatic ring, which ring has 0-2 oxygen atoms, 0-2 sulfur atoms, 0-3 nitrogen atoms and 2-6 carbon atoms, and which ring, together with the phenyl or pyridyl ring to which it is fused, forms a bicyclic moiety, particularly a bicyclic moiety selected from indanyl, benzo[1,3]dioxolyl, 1,3-dihydro-indol-2-onyl, quinolinyl, benzofuranyl, indazolyl, benzothienyl and indolyl, more particularly a bicyclic moiety selected from benzo[1,3]dioxolyl, 1,3-dihydro-indol-2-onyl, indazolyl and indolyl, wherein said bicyclic moiety is optionally substituted with one or two substituents independently selected from the group consisting of halo, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, carboxy, alkoxycarbonyl, aminocarbonyl, monoalkylaminocarbonyl, dialkylaminocarbonyl, alkanoyl, haloalkanoyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl and dialkylaminosulfonyl;

(3) when each of $R^1$, $R^5$ and $R^6$ is independently hydrogen, halo, alkyl, alkenyl, alkynyl, cycloalkyl, haloalkyl, hydroxyalkyl, alkoxy, nitro, aminoalkyl, monoalkylaminoalkyl, dialkylaminoalkyl or amino:

X is HetAr or BiHetAr; and $R^4$ is selected from the group consisting of

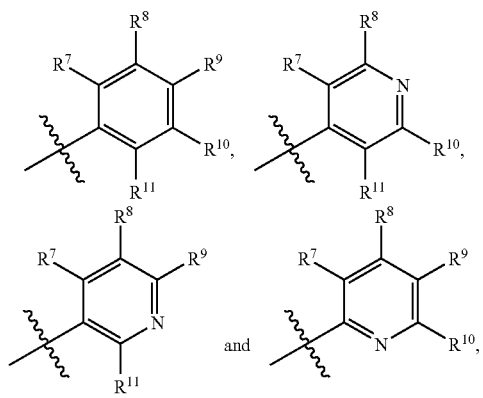

wherein any two adjacent groups selected from $R^7$, $R^8$, $R^9$, $R^{10}$ and $R^{11}$, together with the carbon atoms to which they are attached, form a 5- or 6-membered aromatic, heteroaromatic or fully or partially unsaturated non-aromatic ring, which ring has 0-2 oxygen atoms, 0-2 sulfur atoms, 0-3 nitrogen atoms and 2-6 carbon atoms, and which ring, together with the phenyl or pyridyl ring to which it is fused, forms a bicyclic moiety, particularly a bicyclic moiety selected from indanyl, benzo[1,3]dioxolyl, 1,3-dihydro-indol-2-onyl, quinolinyl, benzofuranyl, indazolyl, benzothienyl and indolyl, more particularly a bicyclic moiety selected from benzo[1,3]dioxolyl, 1,3-dihydro-indol-2-onyl, indazolyl and indolyl, wherein said bicyclic moiety is optionally substituted with one or two substituents independently selected from the group consisting of halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, carboxy, alkoxycarbonyl, aminocarbonyl, monoalkylaminocarbonyl, dialkylaminocarbonyl, alkanoyl, haloalkanoyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl and dialkylaminosulfonyl; and (4) when one of $A^1$, $A^3$ or $A^5$ is nitrogen, and the other two are not nitrogen:
at least one of $R^5$ or $R^6$ is other than hydrogen, halo, alkyl, alkenyl, alkynyl, cycloalkyl, haloalkyl, hydroxyalkyl, alkoxy, nitro, aminoalkyl, monoalkylaminoalkyl, dialkylaminoalkyl or amino.

When n has the value 0, the group X is directly bonded to the ring containing groups $A^1$, $A^3$ and $A^5$ ("the A ring"). When n has the value 1, the linker L is a divalent radical bonded to both the A ring and the X group, and written such that the left end of the radical is bonded to the A ring, while the right end is bonded to the X group. For example, when L is —S(O)$_2$—NH—, the compound represented contains the following functionality: A ring-S(O)$_2$—NH—X.

$R^a$ and $R^b$ are independently $C_{0-4}$ alkylene, meaning that independently each represents a diradical of a straight- or branched-chain alkane having 1-4 carbon atoms, or represents a covalent bond (the meaning of $C_0$ alkylene). Thus, examples of —$R^a$—N($R^x$)—$R^b$—, —$R^a$—S—$R^b$— and —$R^a$—O—$R^b$— include —NH—, —N(CH$_3$)—, —O—, —S—, —S—CH$_2$—, —NH—CH$_2$—, —N(CH$_3$)—CH$_2$—, —O—CH$_2$—, —CH$_2$S— and —CH$_2$—O—CH$_2$CH$_2$—.

Suitable 5- and 6-membered aromatic, heteroaromatic or fully or partially unsaturated non-aromatic rings formed by adjacent R groups, together with the carbon atoms to which they are attached, include cyclopentene, cyclopentadiene, furan, dihydrofuran, pyrrole, pyrroline, pyrazole, pyrazoline, imidazole, triazole, thiophene, dihydrothiophene, dithiole, dioxole, oxathiole, thiazole, isothiazole, oxazole, isoxazole, oxadiazole, oxathiazole, pyran, dihydropyran, dioxin, pyridine, pyridazine, pyrimidine, pyrazine, triazine, oxazine, isoxazine, oxadiazine, oxathiazine and the like. Each of these rings, together with the phenyl or pyridyl ring to which it is fused, forms a bicyclic moiety that is optionally substituted as described above.

Suitable values of Ar include phenyl, naphthyl, tetrahydronaphthyl, indanyl, indenyl and the like. Each of these rings is optionally substituted as described above.

Suitable values of HetAr include pyrrolyl, furanyl, thienyl, pyrazolyl, imidazolyl, triazolyl, tetrazolyl, thiazolyl, thiadiazolyl, isothiazolyl, oxazolyl, isoxazolyl, oxadiazolyl, oxathiazolyl, pyridinyl, pyridazinyl, pyrimidinyl, pyrazinyl, triazinyl and the like. Each of these rings is optionally substituted as described above. Additionally, the corresponding N-oxides of these rings are intended to be included.

Suitable values of BiHetAr groups include indolyl, benzofuranyl, benzo[b]thienyl, isoindolyl, isobenzofuranyl, benzo[c]thienyl, benzimidazolyl, benzoxazolyl, benzothiazolyl, benzo[1,3]dioxolyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[3,4-b]pyridinyl, pyrrolo[3,4-c]pyridinyl, furo[2,3-b]pyridinyl, furo[2,3-c]pyridinyl, furo[3,2-c]pyridinyl, furo[3,2-b]pyridinyl, thieno[2,3-b]pyridinyl, thieno[2,3-c]pyridinyl, thieno[3,2-c]pyridinyl, thieno[3,2-b]pyridinyl, imidazo[4,5-b]pyridinyl, imidazo[4,5-c]pyridinyl, oxazolo[4,5-b]pyridinyl, oxazolo[4,5-c]pyridinyl, oxazolo[5,4-c]pyridinyl, oxazolo[5,4-b]pyridinyl, thiazolo[4,5-b]pyridinyl, thiazolo[4,5-c]pyridinyl, thiazolo[5,4-c]pyridinyl, thiazolo[5,4-b]pyridinyl, imidazo[4,5-b]pyrazinyl, oxazolo[4,5-b]pyrazinyl, thiazolo[4,5-b]pyrazinyl, purinyl, oxazolo[5,4-d]-pyrimidinyl, oxazolo[4,5-d]pyrimidinyl, thiazolo[5,4-d]pyrimidinyl, thiazolo[4,5-d]pyrimidinyl, imidazo[4,5-c]pyridazinyl, imidazo[4,5-d]-pyridazinyl, oxazolo[5,4-c]pyridazinyl, oxazolo[4,5-d]pyridazinyl, oxazolo[4,5-c]pyridazinyl, thiazolo[5,4-c]pyridazinyl, thiazolo[4,5-d]pyridazinyl, thiazolo[4,5-c]pyridazinyl, quinolinyl, isoquinolinyl, cinnolinyl, quinazolinyl, quinoxalinyl, phthalazinyl, benzo[d][1,2,3]triazinyl, benzo[1,2,4]triazinyl, [1,5]naphthyridinyl, [1,6]naphthyridinyl, [1,7]naphthyridinyl, [1,8]naphthyridinyl, [2,6]naphthyridinyl, [2,7]naphthyridinyl, pyrido[2,3-c]pyridazinyl, pyrido[3,4-c]pyridazinyl, pyrido[4,3-c]pyridazinyl, pyrido[3,2-c]pyridazinyl, pyrido[2,3-d]pyridazinyl, pyrido[3,4-d]pyridazinyl, pyrido[2,3-d]pyrimidinyl, pyrido[3,4-d]pyrimidinyl, pyrido[3,4-d]pyrimidinyl, pyrido[3,2-d]pyrimidinyl, pyrido[2,3-b]

pyrazinyl, pyrido[3,4-b]pyrazinyl and the like. Each of these groups is optionally substituted as described above. Additionally, the corresponding N-oxides of these rings are intended to be included.

In all aspects of the invention, the above provisos (1), (2), (3) and (4) apply, even if not expressly stated. A particular proviso does not apply if a group of compounds excludes compounds excluded by the proviso. For example, proviso (4) does not apply to a group of compounds in which the A ring is benzene.

One group of useful compounds of Formula I includes those wherein at least one of $R^5$ or $R^6$ is other than hydrogen. Another group of useful compounds of Formula I includes those wherein $A^1$ is $CR^1$; $A^3$ is $CR^3$, and $R^3$ is hydrogen; $A^5$ is $CR^5$; and at least one of $R^1$, $R^5$ or $R^6$ is other than hydrogen. Another group of useful compounds of Formula I includes those wherein $A^1$ is $CR^1$, and $R^1$ is hydrogen; $A^3$ is $CR^3$, and $R^3$ is hydrogen; $A^5$ is $CR^5$, and $R^5$ is hydrogen; and $R^6$ is other than hydrogen.

Useful compounds of Formula I include those having an $IC_{50}$ of less than about 30 µM as measured by either of the assays described in Example 125; and those considered to be active compounds, as determined by any of the assays described in Examples 126 or 127.

In one embodiment, the compounds are of Formula II:

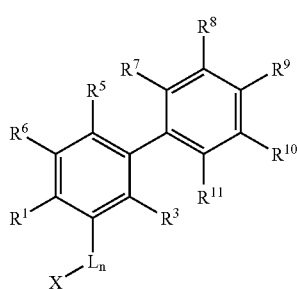

II or pharmaceutically-acceptable salts or solvates thereof, wherein three of $R^7$, $R^8$, $R^9$, $R^{10}$ and $R^{11}$ are hydrogen, and the other two are independently selected from the group consisting of hydrogen, halogen, hydroxy, alkyl, haloalkyl, hydroxyalkyl, alkoxy, cyano, amino, monoalkylamino, dialkylamino, formylamino, alkylcarbonylamino, alkoxycarbonylamino, sulfonylamino, alkylsulfonylamino and phenyl; X is HetAr; n is 1; and $R^1$, $R^3$, $R^5$, $R^6$ and L are defined as above.

One group of useful compounds in this embodiment includes those wherein:

$R^1$ is hydrogen or hydroxy;

$R^3$ is hydrogen;

$R^5$ is selected from the group consisting of hydrogen, benzyl and ($C_{1-4}$ alkoxy)benzyl;

$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxopyrrolidin-1-yl;

L is selected from the group consisting of —NH—, —N($R^x$)—, —N(C(O)—CH$_3$)—, —C(O)—, —C(=N—OH)—, —$R^a$—S—$R^b$—, —S(O)$_2$—, —$R^a$—O—$R^b$—, and —C(CH$_3$)(OH)—, wherein $R^x$ is $C_{1-4}$ alkyl, and $R^a$ and $R^b$ are independently $C_{0-4}$ alkylene; and X is selected from the group consisting of pyridinyl, 1-oxypyridinyl and pyrazinyl, each of which is optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

In this embodiment, useful compounds include those wherein $R^1$, $R^3$ and $R^5$ are each hydrogen; and $R^6$ is other than hydrogen.

In this embodiment, useful compounds include those wherein three of $R^7$, $R^8$, $R^9$, $R^{10}$ and $R^{11}$ are hydrogen, and the other two are independently selected from the group consisting of hydrogen, halo, phenyl, $C_{1-4}$ alkyl, halo($C_{1-4}$)alkyl, amino, mono($C_{1-4}$)alkylamino, di($C_{1-4}$)alkylamino and $C_{1-4}$ alkylsulfonylamino. More useful compounds include those wherein four of $R^7$, $R^8$, $R^9$, $R^{10}$ and $R^{11}$ are hydrogen, and the other is selected from the group consisting of hydrogen, chloro, trifluoromethyl, dimethylamino, methylsulfonylamino and phenyl. More useful compounds include those wherein $R^7$, $R^8$, $R^9$, $R^{10}$ and $R^{11}$, together with the phenyl ring to which they are attached, form a moiety selected from the group consisting of phenyl, 2-chlorophenyl, 3-phenylphenyl, 2-trifluoromethylphenyl, 3-dimethylaminophenyl and 3-methanesulfonylaminophenyl.

In this embodiment, useful $R^1$ include hydrogen.

In this embodiment, useful $R^3$ include hydrogen.

In this embodiment, useful $R^5$ include hydrogen.

In this embodiment, useful $R^6$ include hydroxyl, ($C_{1-4}$ alkyl)carbonylamino, ($C_{1-4}$ alkoxy)carbonylamino and ($C_{1-4}$ alkyl)sulfonylamino. More useful $R^6$ include hydroxyl and ($C_{1-4}$ alkyl)carbonylamino, particularly hydroxyl.

In this embodiment, useful L include —NH—, —N($R^x$)— and —C(O)—, wherein $R^x$ is $C_{1-6}$ alkyl. More useful L include —NH— and —C(O)—, particularly —NH—.

In this embodiment, useful X include pyridyl optionally substituted once with a substituent selected from the group consisting of cyano, halo, $C_{1-4}$ alkoxy, $C_{1-4}$ alkyl and carbamoyl. More useful X include pyridyl, particularly 3-pyridyl.

In this embodiment, one useful group of compounds includes those wherein $R^1$, $R^3$ and $R^5$ are each hydrogen; $R^6$ is hydroxyl, ($C_{1-4}$ alkyl)carbonylamino, ($C_{1-4}$ alkoxy)carbonylamino or ($C_{1-4}$ alkyl)sulfonylamino; L is —NH—, —N($R^x$)— or —C(O)—, wherein $R^x$ is $C_{1-6}$ alkyl; and X is pyridyl optionally substituted once with a substituent selected from the group consisting of cyano, halo, $C_{1-4}$ alkoxy, $C_{1-4}$ alkyl and carbamoyl.

In this group, useful compounds include those wherein $R^6$ is hydroxyl.

In this group, useful compounds include those wherein L is —NH—.

In this group, useful compounds include those wherein X is pyridyl, particularly 3-pyridyl.

In one embodiment, the compounds are of Formula II:

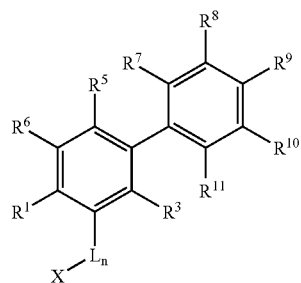

or pharmaceutically-acceptable salts or solvates thereof, wherein any two adjacent groups selected from $R^7$, $R^8$, $R^9$, $R^{10}$ and $R^{11}$, together with the carbon atoms to which they are attached, form a 5- or 6-membered aromatic, heteroaromatic or fully or partially unsaturated non-aromatic ring, which ring has 0-2 oxygen atoms, 0-2 sulfur atoms, 0-3 nitrogen atoms and 2-6 carbon atoms, and which ring, together with the phenyl ring to which it is fused, forms a bicyclic moiety, wherein said bicyclic moiety is optionally substituted with one or two substituents independently selected from the group consisting of halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, carboxy, alkoxycarbonyl, aminocarbonyl, monoalkylaminocarbonyl, dialkylaminocarbonyl, alkanoyl, haloalkanoyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl and dialkylaminosulfonyl; n is 1; and $R^1$, $R^3$, $R^5$, $R^6$, L and X are defined as above.

In this embodiment, one useful group of compounds are those wherein the bicyclic moiety is unsubstituted.

In this embodiment, one useful group of compounds are those wherein X is HetAr.

In this embodiment, one useful group of compounds includes those wherein $R^1$ is hydrogen or hydroxy;

$R^3$ is hydrogen;

$R^5$ is selected from the group consisting of hydrogen, benzyl and ($C_{1-4}$ alkoxy)benzyl;

$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl) ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxopyrrolidin-1-yl;

L is selected from the group consisting of —NH—, —N($R^x$)—, —N(C(O)—CH$_3$)—, —C(O)—, —C(=N—OH)—, —$R^a$—S—$R^b$—, —S(O)$_2$—, —$R^a$—O—$R^b$—, and —C(CH$_3$)(OH)—, wherein $R^x$ is $C_{1-4}$ alkyl, and $R^a$ and $R^b$ are independently $C_{0-4}$ alkylene; and X is selected from the group consisting of pyridinyl, 1-oxypyridinyl and pyrazinyl, each of which is optionally substituted with one or two substitutents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy ($C_{1-4}$)alkyl.

In this embodiment, one useful group of compounds includes those wherein $R^1$, $R^3$ and $R^5$ are each hydrogen; and $R^6$ is other than hydrogen.

In this embodiment, useful bicyclic moieties include indanyl, benzo[1,3]dioxolyl, 1,3-dihydro-indol-2-onyl, quinolinyl, benzofuranyl, indazolyl, benzothienyl and indolyl, each of which is optionally substituted with one or two substitutents selected from the group consisting of halo, $C_{1-4}$ alkyl, cyano, $C_{2-5}$ alkanoyl and halo($C_{2-5}$)alkanoyl. Benzimidazolyl may also be useful. More useful bicyclic moieties include indan-5-yl, indan-4-yl, benzo[1,3]dioxol-5-yl, benzo[1,3]dioxol-4-yl, 1,3-dihydro-indol-2-on-4-yl, quinolin-8-yl, benzofuran-4-yl, indazol-4-yl, indazol-7-yl, benzo[b]thiophen-4-yl, indol-7-yl, indol-5-yl, indol-6-yl and indol-4-yl, each of which is optionally substituted with one substitutent selected from the group consisting of fluoro, chloro, methyl, cyano and trifluoroacetyl. More useful bicyclic moieties include indan-5-yl, indan-4-yl, benzo[1,3]dioxol-5-yl, benzo[1,3]dioxol-4-yl, 1,3-dihydro-indol-2-on-4-yl, quinolin-8-yl, benzofuran-4-yl, indazol-4-yl, indazol-7-yl, benzo[b]thiophen-4-yl, 1-methyl-indol-7-yl, indol-5-yl, indol-6-yl, indol-4-yl, 7-fluoro-indol-4-yl, 2-cyano-indol-4-yl, 2-methyl-indol-4-yl, 3-trifluoroacetyl-indol-4-yl, 1-methyl-indol-4-yl and 3-chloro-indol-4-yl.

More useful bicyclic moieties include indol-4-yl optionally substituted with one substitutent selected from the group consisting of halo, $C_{1-4}$ alkyl, $C_{2-5}$ alkanoyl and halo($C_{2-5}$) alkanoyl, and indol-4-yl optionally subsituted with cyano. More useful bicyclic moieties include indol-4-yl optionally substituted once with chloro, fluoro, methyl or trifluoroacetyl. More useful bicyclic moieties include indol-4-yl.

In this embodiment, useful $R^1$ include hydrogen and hydroxy. More useful $R^1$ include hydrogen.

In this embodiment, useful $R^3$ include hydrogen.

In this embodiment, useful $R^5$ include hydrogen, benzyl and ($C_{1-4}$ alkoxy)benzyl. More useful $R^5$ include hydrogen.

In this embodiment, useful $R^6$ include hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl) ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxopyrrolidin-1-yl. More useful $R^6$ include hydrogen, halo, hydroxyl, $C_{1-4}$ alkyl, $C_{1-4}$ alkoxy, benzyloxy, ($C_{1-4}$ alkoxy)benzyloxy, amino, ($C_{1-4}$ alkyl)carbonylamino, ($C_{1-4}$ alkoxy)carbonylamino, benzyloxycarbonylamino, ($C_{1-4}$ alkyl)sulfonylamino, N',N'-di($C_{1-4}$ alkyl)ureido, carbamoyl, ($C_{1-4}$ alkoxy)carbonyl, cyano, nitro and 2-oxo-pyrrolidin-1-yl. More useful $R^6$ include hydrogen, chloro, hydroxyl, methyl, methoxy, 4-methoxybenzyloxy, amino, acetylamino, propanoylamino, methoxycarbonylamino, benzyloxycarbonylamino, methylsulfonylamino, N',N'-dimethylureido, carbamoyl, methoxycarbonyl, cyano, nitro and 2-oxopyrrolidin-1-yl.

In this embodiment, useful $R^6$ also include hydroxyl. In this embodiment, useful $R^6$ also include $(C_{1-4}$ alkyl)carbonylamino, $(C_{1-4}$ alkoxy)carbonylamino and $(C_{1-4}$ alkyl)sulfonylamino.

In this embodiment, useful L include —NH—, —N($R^x$)—, —N(C(O)—CH$_3$)—, —C(O)—, —C(=N—OH)—, —$R^a$—S—$R^b$—, —S(O)$_2$—, —$R^a$—O—$R^b$— and —C(CH$_3$)(OH)—, wherein $R^x$ is $C_{1-4}$ alkyl, and $R^a$ and $R^b$ are independently $C_{0-4}$ alkylene. More useful L include —NH—, —N(CH$_3$)—, —C(O)—, —C(=N—OH)—, —S—CH$_2$—, —S(O)$_2$—, —O— and —C(CH$_3$)(OH)—. More useful L include —NH—, —N($R^x$)— and —C(O)—. More useful L include —NH—. More useful L also include —C(O)—.

In this embodiment, useful X when X is HetAr include pyridinyl, 1-oxy-pyridinyl and pyrazinyl, each of which is optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$) alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$) alkoxy($C_{1-4}$)alkyl. More useful X when X is HetAr include pyridin-2-yl, pyridin-3-yl, 1-oxy-pyridin-3-yl, pyridin-4-yl and pyrazinyl, each of which is optionally substituted with one or two substituents selected from the group consisting of chloro, methyl, ethyl, hydroxy, hydroxymethyl, methoxy, amino, dimethylamino, cyano, carbamoyl, morpholin-1-yl and (2-formyloxyethoxy)methyl. More useful X when X is HetAr include pyridin-2-yl, pyridin-3-yl, 6-cyano-pyridin-3-yl, 6-chloro-pyridin-3-yl, 2-chloro-pyridin-3-yl, 6-hydroxy-pyridin-3-yl, 6-methyl-pyridin-3-yl, 5-methyl-pyridin-3-yl, 2-ethyl-pyridin-3-yl, 6-hydroxymethyl-pyridin-3-yl, 6-amino-pyridin-3-yl, 2-dimethylamino-pyridin-3-yl, 6-carbamoyl-pyridin-3-yl, 6-methoxy-pyridin-3-yl, 2-((2-formyloxyethoxy)methyl)-pyridin-3-yl, 1-oxy-pyridin-3-yl, pyridin-4-yl, 2-chloro-pyridin-4-yl, 2-chloro-6-methyl-pyridin-4-yl, 2,6-dimethyl-pyridin-4-yl, 2-cyano-6-methyl-pyridin-4-yl, 2-methoxy-pyridin-4-yl, 3-methoxy-pyridin-4-yl, 2-(morpholin-1-yl)-pyridin-4-yl, pyrazinyl and 5-cyano-pyrazin-2-yl. More useful X when X is HetAr include pyridyl optionally substituted by one substituent selected from the group consisting of methyl, cyano, chloro, hydroxy, hydroxymethyl, amino, methoxy and carbamoyl. More useful X when X is HetAr include pyridyl, particularly pyrid-3-yl.

One useful group of values for X include pyridinyl, 1-oxy-pyridinyl and pyrazinyl, each of which is optionally substituted with one substituent selected from the group consisting of halo, $C_{1-4}$ alkyl, hydroxy, hydroxy($C_{1-4}$)alkyl and amino, or one substituent selected from the group consisting of halo, $C_{1-4}$ alkyl, hydroxy, hydroxy($C_{1-4}$)alkyl, amino, $C_{1-4}$ alkoxy, cyano and carbamoyl. Another useful group of values for X include pyridyl optionally substituted with one substituent selected from the group consisting of methyl, chloro, hydroxy, hydroxymethyl and amino.

In this embodiment, one useful group of compounds includes those wherein $R^5$ is hydrogen; $R^6$ is hydroxyl, $(C_{1-4}$ alkyl)carbonylamino, $(C_{1-4}$ alkoxy)carbonylamino or $(C_{1-4}$ alkyl)sulfonylamino, particularly hydroxyl or $(C_{1-4}$ alkyl)carbonylamino; L is —NH—, —N($R^x$)— or —C(O)—, particularly —NH— or —C(O)—, more particularly —NH—; and X is pyridyl, particuarly 3-pyridyl.

In this embodiment, one useful group of compounds are those wherein:

$R^1$, $R^3$ and $R^5$ are each hydrogen;

the bicylic moiety is indol-4-yl optionally substituted with one substituent selected from the group consisting of halo, $C_{1-4}$ alkyl, cyano, $C_{2-5}$ alkanoyl and halo($C_{2-5}$)alkanoyl;

$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, $(C_{1-4}$ alkoxy)benzyloxy, amino, mono($C_{1-4}$)alkylamino, di($C_{1-4}$)alkylamino, $(C_{1-4}$ alkyl)carbonylamino, $(C_{1-4}$ alkoxy)carbonylamino, benzyloxycarbonylamino, $(C_{1-4}$ alkyl)sulfonylamino, ureido, N—$(C_{1-4}$ alkyl)ureido, N'—$(C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, $(C_{1-4}$ alkoxy)carbonyl, cyano, nitro and 2-oxo-pyrrolidin-1-yl;

L is selected from the group consisting of —NH—, —N(CH$_3$)—, —C(O)—, —C(=N—OH)—, —S—CH$_2$—, —S(O)$_2$—, —O— and —C(CH$_3$)(OH)—; and X is selected from the group consisting of pyridinyl, 1-oxy-pyridinyl and pyrazinyl, each of which is optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

In this group, useful bicylic moieties include indol-4-yl.

In this group, useful $R^6$ include hydroxyl, $(C_{1-4}$ alkyl)carbonylamino, $(C_{1-4}$ alkoxy)carbonylamino and $(C_{1-4}$ alkyl)sulfonylamino. More useful $R^6$ include hydroxyl, acetylamino, methoxycarbonylamino and methylsulfonylamino.

In this group, useful L include —NH— and —C(O)—.

In this group, useful X include pyridyl optionally substituted once with a substituent selected from the group consisting of cyano, halo, $C_{1-4}$ alkoxy, $C_{1-4}$ alkyl, carbamoyl and morpholin-1-yl. More useful X include pyridyl optionally substituted once with a substituent selected from the group consisting of cyano, chloro, methoxy, methyl, ethyl, carbamoyl and morpholin-1-yl. More useful X include pyridyl, particularly pyrid-3-yl. More useful X also include pyrid-4-yl.

In this embodiment, one useful group of compounds includes those wherein:

$R^1$ and $R^3$ are each hydrogen; and $R^5$ and $R^6$ are each other than hydrogen.

In this group, one useful group of compounds includes those wherein:

the bicyclic moiety is indol-4-yl or benzo[b]thiophen-4-yl;

$R^5$ and $R^6$ are independently selected from the group consisting of $(C_{1-4}$ alkyl)sulfonylamino, $(C_{1-4}$ alkoxy)carbonylamino, $(C_{1-4}$ alkyl)carbonylamino, hydroxyl, benzyl and $(C_{1-4}$ alkoxy)benzyl;

L is —NH— or —C(O)—; and

X is pyridyl optionally substituted once with a substituent selected from the group consisting of cyano, halo, $C_{1-4}$ alkoxy, $C_{1-4}$ alkyl and carbamoyl.

In this group, useful bicyclic moieties include indol-4-yl.

In this group, useful $R^5$ and $R^6$ include hydroxyl, benzyl and $(C_{1-4}$ alkoxy)benzyl. More useful $R^5$ include benzyl and methoxybenzyl. More useful $R^6$ include hydroxyl.

In this group, useful L include —NH—.

In this group, useful X include pyridyl, particularly pyrid-3-yl.

In this embodiment, one useful group of compounds includes those wherein:

$R^3$, $R^5$ and $R^6$ are each hydrogen; and $R^1$ is other than hydrogen.

In this group, one useful group of compounds includes those wherein:
the bicyclic moiety is indol-4-yl;
$R^1$ is selected from the group consisting of ($C_{1-4}$ alkyl)sulfonylamino, ($C_{1-4}$ alkoxy)carbonylamino, ($C_{1-4}$ alkyl)carbonylamino, hydroxyl and amino;
L is —NH— or —C(O)—; and
X is pyridyl optionally substituted once with a substituent selected from the group consisting of cyano, halo, $C_{1-4}$ alkoxy, $C_{1-4}$ alkyl and carbamoyl.

In this group, useful $R^1$ include hydroxyl and amino.
In this group, useful L include —C(O)—.
In this group, useful X include pyridyl, particularly pyrid-3-yl.

In this embodiment, one useful group of compounds are those wherein X is Ar.

In this embodiment, one useful group of compounds are those wherein:
$R^1$, $R^3$ and $R^5$ are each hydrogen; and
$R^6$ is other than hydrogen.

In this embodiment, one useful group of compounds are those wherein:
$R^1$ is hydrogen or hydroxy;
$R^3$ is hydrogen;
$R^5$ is selected from the group consisting of hydrogen, benzyl and ($C_{1-4}$ alkoxy)benzyl;
the bicylic moiety is indol-4-yl optionally substituted with one substitutent selected from the group consisting of halo, $C_{1-4}$ alkyl, cyano, $C_{2-5}$alkanoyl and halo($C_{2-5}$)alkanoyl;
$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxo-pyrrolidin-1-yl;
L is selected from the group consisting of —NH—, —N($R^x$)—, —N(C(O)—CH$_3$)—, —C(O)—, —C(=N—OH)—, —$R^a$—S—$R^b$—, —S(O)$_2$—, —$R^a$—O—$R^b$— and —C(CH$_3$)(OH)—, wherein $R^x$ is $C_{1-4}$ alkyl, and $R^a$ and $R^b$ are independently $C_{0-4}$ alkylene; and
X is phenyl optionally substituted with one or two substitutents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl) aminocarbonyl, di($C_{1-4}$ alkyl)aminocarbonyl, morpholin-1-yl and formyloxy($C_{1-4}$)alkoxy($C_{1-4}$)alkyl.

In this group, useful bicylic moieties include indol-4-yl.
In this group, useful $R^6$ include ($C_{1-4}$ alkyl)sulfonylamino, ($C_{1-4}$ alkoxy)carbonylamino, ($C_{1-4}$ alkyl)carbonylamino and hydroxyl.
In this group, useful L include —NH— and —C(O)—.
In this group, useful X include phenyl optionally substituted once with a substituent selected from the group consisting of cyano, halo, $C_{1-4}$ alkoxy, $C_{1-4}$ alkyl and carbamoyl.

In this group, one useful group of compounds are those wherein:
$R^1$, $R^3$ and $R^5$ are each hydrogen;
the bicyclic moiety is indol-4-yl;
$R^6$ is ($C_{1-4}$ alkyl)sulfonylamino, ($C_{1-4}$ alkoxy)carbonylamino, ($C_{1-4}$ alkyl)carbonylamino or hydroxyl;
L is —NH— or —C(O)—; and
X is phenyl optionally substituted once with a substituent selected from the group consisting of cyano, halo, $C_{1-4}$ alkoxy, $C_{1-4}$ alkyl and carbamoyl.

In this group, useful $R^6$ include hydroxyl.
In this group, useful L include —NH—.
In this group, useful X include phenyl and cyanophenyl.

In one embodiment, the compounds are of Formula III:

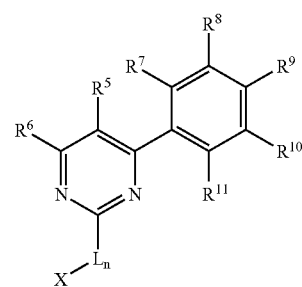

or pharmaceutically-acceptable salts or solvates thereof, wherein X is HetAr; n is 1; and $R^5$-$R^{11}$ and L are defined as above.

In this embodiment, useful $R^5$ include hydrogen.

In this embodiment, one useful group of compounds are those wherein:
$R^5$ is selected from the group consisting of hydrogen, benzyl and ($C_{1-4}$ alkoxy)benzyl;
the bicylic moiety is indol-4-yl optionally substituted with one substitutent selected from the group consisting of halo, $C_{1-4}$ alkyl, cyano, $C_{2-5}$ alkanoyl and halo($C_{2-5}$)alkanoyl;
$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxo-pyrrolidin-1-yl;
L is selected from the group consisting of —NH—, —N($R^x$)—, —N(C(O)—CH$_3$)—, —C(O)—, —C(=N—OH)—, —$R^a$—S—$R^b$—, —S(O)$_2$—, —$R^a$—O—$R^b$— and —C(CH$_3$)(OH)—, wherein $R^x$ is $C_{1-4}$ alkyl, and $R^a$ and $R^b$ are independently $C_{0-4}$ alkylene; and
X is selected from the group consisting of pyridinyl, 1-oxy-pyridinyl and pyrazinyl, each of which is optionally substituted with one or two substitutents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl) aminocarbonyl, morpholin-1-yl and formyloxy($C_{1-4}$)alkoxy($C_{1-4}$)alkyl.

In this embodiment, useful bicyclic moieties include indol-4-yl.

In this embodiment, useful $R^6$ include ($C_{1-4}$ alkyl)sulfonylamino, ($C_{1-4}$ alkoxy)carbonylamino, ($C_{1-4}$ alkyl)carbonylamino, $C_{1-4}$ alkoxy and hydroxyl.

In this embodiment, useful L include —NH— and —C(O)—.

In this embodiment, useful X include pyridyl optionally substituted once with a substituent selected from the group consisting of cyano, halo, $C_{1-4}$ alkoxy, $C_{1-4}$ alkyl and carbamoyl.

In this embodiment, one useful group of compounds are those wherein:
$R^5$ is hydrogen;
the bicyclic moiety is indol-4-yl;
$R^6$ is ($C_{1-4}$ alkyl)sulfonylamino, ($C_{1-4}$ alkoxy)carbonylamino, ($C_{1-4}$ alkyl)carbonylamino, $C_{1-4}$ alkoxy or hydroxyl;
L is —NH— or —C(O)—; and
X is pyridyl optionally substituted once with a substituent selected from the group consisting of cyano, halo, $C_{1-4}$ alkoxy, $C_{1-4}$ alkyl and carbamoyl.

In this group, useful $R^6$ include hydroxyl and $C_{1-4}$ alkoxy. More useful $R^6$ include hydroxyl and methoxy.

In this group, useful L include —NH—.

In this group, useful X include pyridyl, particularly pyrid-3-yl.

In one embodiment, the compounds are of Formula IV:

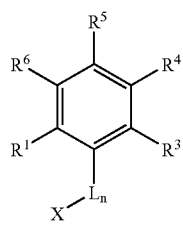

IV or pharmaceutically-acceptable salts or solvates thereof, wherein $R^4$ is adamantyl; n is 1; X is HetAr; and $R^1$, $R^3$-$R^6$ and L are defined as above.

In this embodiment, useful $R^1$ include hydrogen.
In this embodiment, useful $R^3$ include hydrogen.
In this embodiment, useful $R^5$ include hydroxyl.
In this embodiment, useful $R^6$ include hydrogen.
In this embodiment, useful L include —C(H)(OH)— and —C(O)—.
In this embodiment, useful X include pyridyl, particularly pyrid-3-yl.

In one embodiment, the compounds are of Formula IV:

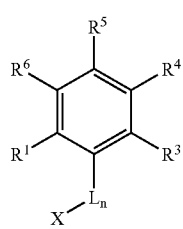

IV or pharmaceutically-acceptable salts or solvates thereof, wherein $R^4$ is 2-, 3- or 4-quinolinyl or 1-indolyl, each of which is optionally substituted by one or two substituents independently selected from the group consisting of halo, nitro and cyano; n is 1; X is HetAr; and $R^1$, $R^3$-$R^6$ and L are defined as above.

In this embodiment, useful $R^1$ include hydrogen.
In this embodiment, useful $R^3$ include hydrogen.

In this embodiment, useful $R^5$ include hydrogen.
In this embodiment, useful $R^6$ include hydroxyl.
In this embodiment, useful L include —NH— and —C(O)—.
In this embodiment, useful X include pyridyl and quinolin-3-yl. More useful X include pyridyl, particularly pyrid-3-yl.

In one embodiment, the compounds are of Formula V:

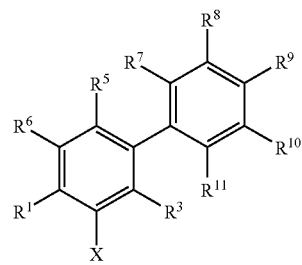

V wherein any two adjacent groups selected from $R^7$, $R^8$, $R^9$, $R^{10}$ and $R^{11}$, together with the carbon atoms to which they are attached, form a 5- or 6-membered aromatic, heteroaromatic or fully or partially unsaturated non-aromatic ring, which ring has 0-2 oxygen atoms, 0-2 sulfur atoms, 0-3 nitrogen atoms and 2-6 carbon atoms, and which ring, together with the phenyl ring to which it is fused, forms a bicyclic moiety, wherein said bicyclic moiety is optionally substituted with one or two substituents independently selected from the group consisting of halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, carboxy, alkoxycarbonyl, aminocarbonyl, monoalkylaminocarbonyl, dialkylaminocarbonyl, alkanoyl, haloalkanoyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl and dialkylaminosulfonyl; X is HetAr or BiHetAr; and $R^1$, $R^3$, $R^5$ and $R^6$ are defined as above.

In this embodiment, one group of useful compounds includes those wherein $R^1$, $R^3$ and $R^5$ are each hydrogen; and $R^6$ is other than hydrogen.

In this embodiment, useful bicyclic moieties include indol-4-yl.

In this embodiment, useful $R^6$ include ($C_{1-4}$ alkyl)carbonylamino, ($C_{1-4}$ alkoxy)carbonylamino, ($C_{1-4}$ alkyl)sulfonylamino and hydroxyl. More useful $R^6$ include acetylamino, methoxycarbonylamino, methylsulfonylamino and hydroxyl.

In this embodiment, useful compounds X include pyridinyl, pyrazinyl, benzoxazol-2-yl and oxazolo[4,5-b]pyridin-2-yl, each of which is optionally substituted once with a substituent selected from the group consisting of cyano, halo, $C_{1-4}$ alkoxy, $C_{1-4}$ alkyl and carbamoyl. More useful X include pyridin-3-yl, pyridin-4-yl, benzoxazol-2-yl and oxazolo[4,5-b]pyridin-2-yl, each of which is optionally substituted once with $C_{1-4}$ alkoxy. More useful X include pyridin-3-yl, 6-methoxy-pyridin-3-yl, pyridin-4-yl, benzoxazol-2-yl and oxazolo[4,5-b]pyridin-2-yl.

In this embodiment, one useful group of compounds includes those wherein:
$R^1$, $R^3$ and $R^5$ are each hydrogen;
the bicyclic moiety is indol-4-yl;

$R^6$ is ($C_{1-4}$ alkyl)carbonylamino, ($C_{1-4}$ alkoxy)carbonylamino, ($C_{1-4}$ alkyl)sulfonylamino or hydroxyl; and X is selected from the group consisting of pyridinyl, pyrazinyl, benzoxazol-2-yl and oxazolo[4,5-b]pyridin-2-yl, each of which is optionally substituted once with a substituent selected from the group consisting of cyano, halo, $C_{1-4}$ alkoxy, $C_{1-4}$ alkyl and carbamoyl.

In this group, useful $R^6$ include acetylamino, methoxycarbonylamino, methylsulfonylamino or hydroxyl.

In this group, useful X include pyridin-3-yl, pyridin-4-yl, benzoxazol-2-yl and oxazolo[4,5-b]pyridin-2-yl, each of which is optionally substituted once with $C_{1-4}$ alkoxy. More useful X include pyridin-3-yl, pyridin-4-yl and benzoxazol-2-yl.

Also useful are compounds of Formula VI:

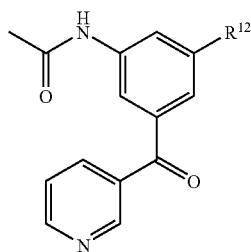

VI wherein $R^{12}$ is halo, particularly chloro or bromo, more particularly bromo. These compounds are useful to the same extent that compounds of Formula I are useful, and all aspects of the invention described for compounds of Formula I are intended to include these compounds as well.

A second aspect of the present invention is directed to pharmaceutical compositions comprising at least one compound of Formula I, wherein $A^1$, $A^3$, $A^5$, $R^4$, $R^6$, L, n and X are as defined above, or a pharmaceutically acceptable salt or solvate thereof, and one or more pharmaceutically-acceptable excipients.

A further aspect of the present invention is directed to a method of treating a condition that results from abnormal cell growth, cellular differentiation, tumor growth or invasion by administering a pharmaceutically-effective amount of one or more compounds of Formula I, wherein $A^1$, $A^3$, $A^5$, $R^4$, $R^6$, L, n and X are as defined above, to an animal.

A further aspect of the invention is directed to a method of treating cancer, particularly wherein the cancer is leukemia, soft-tissue sarcomas, or non-small cell lung, myeloma, colon, CNS, melanoma, ovarian, renal, prostate, breast, cervical or pancreatic cancer, particularly leukemia, non-small cell lung or colon cancer, by administering a pharmaceutically-effective amount one or more compounds of Formula I, wherein $A^1$, $A^3$, $A^5$, $R^4$, $R^6$, L, n and X are as defined above, to an animal.

A further aspect of the invention is directed to hindering or blocking cell cycle progression by contacting one or more cells, particularly cancerous cells, with one or more compounds of Formula I, wherein $A^1$, $A^3$, $A^5$, $R^4$, $R^6$, L, n and X are as defined above. Cancerous cells useful in this aspect of the invention include leukemia cells, soft-tissue sarcoma cells, and non-small cell lung, myeloma, colon, CNS, melanoma, ovarian, renal, prostate, breast, cervical and pancreatic cancer cells, particularly leukemia, non-small cell lung and colon cancer cells.

A further aspect of the present invention is directed to a method of making compounds of Formula I, wherein $A^1$, $A^3$, $A^5$, $R^4$, $R^6$, L, n and X are as defined above.

Compounds within the scope of the invention are described in the Examples. Examples of compounds include, but are not limited to, the following:

5-(pyridin-3-ylamino)-biphenyl-3-ol;
2'-chloro-5-(pyridin-3-ylamino)-biphenyl-3-ol;
5-(pyridin-3-ylamino)-2'-trifluoromethyl-biphenyl-3-ol;
3'-dimethylamino-5-(pyridin-3-ylamino)-biphenyl-3-ol;
3-(1H-indazol-7-yl)-5-(pyridin-3-ylamino)-phenol;
3-(1H-indol-4-yl)-5-(pyridin-3-ylamino)-phenol;
2-benzyl-3-(1H-indol-4-yl)-5-(pyridin-3-ylamino)-phenol;
3-benzo[b]thiophen-4-yl-2-(4-methoxybenzyl)-5-(pyridin-3-ylamino)-phenol;
3-benzo[b]thiophen-4-yl-5-(pyridin-3-ylamino)-phenol;
3-(1H-indazol-4-yl)-5-(pyridin-3-ylamino)-phenol;
3-(2-methyl-1H-indol-4-yl)-5-(pyridin-3-ylamino)-phenol;
[3-benzo[b]thiophen-4-yl-5-(4-methoxybenzyloxy)-phenyl]-pyridin-3-yl-amine;
5-(pyridin-3-ylamino)-[1,1';3',1'']terphenyl-3-ol;
3-(1H-indol-4-yl)-5-(pyridin-2-ylamino)-phenol;
3-(indan-5-yl)-5-(pyridin-3-ylamino)-phenol;
3-(indan-4-yl)-5-(pyridin-3-ylamino)-phenol;
3-(pyridin-3-ylamino)-5-quinolin-8-yl-phenol;
[4-(1H-indol-4-yl)-6-methoxypyrimidin-2-yl]-pyridin-3-yl-amine;
[3-hydroxy-5-(1H-indol-4-yl)-phenyl]-pyridin-3-yl-methanone;
N-[3-(1H-indol-4-yl)-phenyl]-N-pyridin-3-yl-acetamide;
[3-(1H-indol-4-yl)-phenyl]-pyridin-3-yl-amine, hydrochloride salt;
2,2,2-trifluoro-1-{4-[3-hydroxy-5-(pyridine-3-carbonyl)-phenyl]-1H-indol-3-yl-ethanone;
3-(1H-indol-4-yl)-5-(1-oxypyridin-3-ylamino)-phenol;
[3-hydroxy-5-(1H-indol-4-yl)-phenyl]-pyridin-3-yl-methanone oxime;
3-(6-nitro-indol-1-yl)-5-(pyridin-3-ylamino)-phenol;
1-[3-hydroxy-5-(pyridin-3-ylamino)-phenyl]-1H-indole-5-carbonitrile;
(6-chloropyridin-3-yl)-[3-hydroxy-5-(1H-indol-4-yl)-phenyl]-methanone;
[3-hydroxy-5-(1H-indol-4-yl)-phenyl]-(6-hydroxypyridin-3-yl)-methanone;
6-(1H-indol-4-yl)-2-(pyridin-3-ylamino)-pyrimidin-4-ol;
5-[3-hydroxy-5-(1H-indol-4-yl)-phenylamino]-pyridin-2-ol;
3-(1H-indol-4-yl)-5-(pyridin-3-yloxy)-phenol;
[3-hydroxy-5-(1H-indol-4-yl)-phenyl]-pyrazin-2-yl-methanone;
2-adamantan-2-yl-4-(hydroxy-pyridin-3-yl-methyl)-phenol;
3-(1-methyl-1H-indol-7-yl)-5-(pyridin-3-ylamino)-phenol;
3-benzo[1,3]dioxol-5-yl-5-(pyridin-3-ylamino)-phenol;
3-(1-methyl-1H-indol-4-yl)-5-(pyridin-3-ylamino)-phenol;
[3-(1H-indol-4-yl)-5-methoxyphenyl]-pyridin-3-yl-amine;
[3-hydroxy-5-(1H-indol-4-yl)-phenyl]-(6-hydroxymethyl-pyridin-3-yl)-methanone;
4-[3-hydroxy-5-(pyridin-3-ylamino)-phenyl]-1,3-dihydro-indol-2-one;
3-(1-hydroxy-1-pyridin-3-yl-ethyl)-5-(1H-indol-4-yl)-phenol;
[3-hydroxy-5-(1H-indol-4-yl)-phenyl]-(6-methyl-pyridin-3-yl)-methanone;
N-[5'-hydroxy-3'-(pyridin-3-ylamino)-biphenyl-3-yl]-methanesulfonamide;
(3-adamantan-2-yl-4-hydroxyphenyl)-pyridin-3-yl-methanone;

[3-(1H-indol-4-yl)-5-nitrophenyl]-pyridin-3-yl-amine;
3-(1H-indol-5-yl)-5-(pyridin-3-ylamino)-phenol;
3-(1H-indol-4-yl)-5-(pyridin-4-ylamino)-phenol;
3-(1H-indol-7-yl)-5-(pyridin-3-ylamino)-phenol;
3-(1H-indol-4-yl)-5-(pyrazin-2-ylamino)-phenol;
3-(1H-indol-6-yl)-5-(pyridin-3-ylamino)-phenol;
3-(pyridin-3-ylamino)-5-quinolin-3-yl-phenol;
3-(1H-indol-4-yl)-5-(methyl-pyridin-3-yl-amino)-phenol;
3-(3-chloro-1H-indol-4-yl)-5-(pyridin-3-ylamino)-phenol;
(6-amino-pyridin-3-yl)-[3-hydroxy-5-(1H-indol-4-yl)-phenyl]-methanone;
[3-(1H-indol-4-yl)-5-methyl-phenyl]-pyridin-3-yl-amine;
[3-hydroxy-5-(1H-indol-4-yl)-phenyl]-(5-methyl-pyridin-3-yl)-methanone;
(2-chloro-pyridin-3-yl)-[3-hydroxy-5-(1H-indol-4-yl)-phenyl]-methanone;
5-[3-hydroxy-5-(1H-indol-4-yl)-phenylamino]-pyrazine-2-carbonitrile;
[2-hydroxy-5-(1H-indol-4-yl)-phenyl]-pyridin-3-yl-methanone;
[3-chloro-5-(1H-indol-4-yl)-phenyl]-pyridin-3-yl-amine;
[3-(5-fluoro-indol-1-yl)-5-hydroxy-phenyl]-pyridin-3-yl-methanone;
[3-hydroxy-5-(1H-indol-4-yl)-phenyl]-(6-methoxy-pyridin-3-yl)-methanone;
[3-(1H-indol-4-yl)-5-(pyridin-3-carbonyl)-phenyl]-carbamic acid benzyl ester;
[3-amino-5-(1H-indol-4-yl)-phenyl]-pyridin-3-yl-methanone;
3-benzo[1,3]dioxol-4-yl-5-(pyridin-3-ylamino)-phenol;
[3-(1H-indol-4-yl)-5-(pyridin-3-ylamino)-phenyl]-benzoic acid methyl ester;
3-(1H-indol-4-yl)-5-(pyridin-3-ylamino)-benzonitrile;
5-[3-hydroxy-5-(1H-indol-4-yl)-phenylamino]-pyridin-2-carboxylic acid amide;
N-[3-(1H-indol-4-yl)-5-(pyridin-3-carbonyl)-phenyl]-acetamide;
3-(1H-indol-4-yl)-5-phenylamino-phenol;
N-[3-(1H-indol-4-yl)-5-(pyridin-3-carbonyl)-phenyl]-methanesulfonamide;
[3-(1H-indol-4-yl)-5-(pyridin-3-carbonyl)-phenyl]-carbamic acid methyl ester;
N-[3-(1H-indol-4-yl)-5-(pyridin-3-carbonyl)-phenyl]-propionamide;
5-[3-Hydroxy-5-(1H-indol-4-yl)-phenylamino]-pyridine-2-carbonitrile;
3-[3-(1H-Indol-4-yl)-5-(pyridin-3-ylamino)-phenyl]-1,1-dimethyl-urea;
3-(1H-Indol-4-yl)-5-(pyrazin-2-ylamino)-benzamide;
N-[3-(1H-Indol-4-yl)-5-(pyridine-3-sulfonyl)-phenyl]-acetamide;
N-[3-(1H-Indol-4-yl)-5-(pyridine-4-carbonyl)-phenyl]-acetamide;
3-(1H-Indol-4-yl)-5-(pyridin-3-ylamino)-benzamide;
N-[3-(1H-Indol-4-yl)-5-(pyridin-3-ylmethylsulfanyl)-phenyl]-acetamide;
formic acid 2-{3-[3-hydroxy-5-(1H-indol-4-yl)-phenylamino]-pyridin-2-ylmethoxy}-ethyl ester;
[3-(1H-indol-4-yl)-5-(pyridin-3-ylamino)-phenyl]-carbamic acid methyl ester;
N-[3-(1H-indol-4-yl)-5-(pyridin-3-ylamino)-phenyl]-methanesulfonamide;
N-[3-(1H-indol-4-yl)-5-(2-methoxy-pyridine-4-carbonyl)-phenyl]-acetamide;
[3-amino-5-(1H-indol-4-yl)-phenyl]-(2-methoxy-pyridin-4-yl)-methanone;
N-[3-(2-chloro-pyridine-4-carbonyl)-5-(1H-indol-4-yl)-phenyl]-acetamide;
1-[3-(1H-indol-4-yl)-5-(pyridine-3-carbonyl)-phenyl]-pyrrolidin-2-one;
N-[3-(1H-indol-4-yl)-5-oxazolo[4,5-b]pyridin-2-yl-phenyl]-acetamide;
3-(1H-indol-4-yl)-5-pyridin-3-yl-phenol;
4-[3-hydroxy-5-(pyridin-3-ylamino)-phenyl]-1H-indole-2-carbonitrile;
N-[3-(2-cyano-1H-indol-4-yl)-5-(pyridine-3-carbonyl);
N-[3-(1H-indol-4-yl)-5-(pyridine-4-carbonyl)-phenyl]-methanesulfonamide;
N-[3-(2-chloro-pyridine-4-carbonyl)-5-(1H-indol-4-yl);
N-[3-(2-chloro-6-methyl-pyridine-4-carbonyl)-5-(1H-indol-4-yl)-phenyl]-methanesulfonamide;
methyl 3-(6-cyanopyridin-3-ylamino)-5-(1H-indol-4-yl)phenylcarbamate;
(2-amino-5-(1H-indol-4-yl)phenyl)-(pyridin-3-yl)methanone
3-(2-ethylpyridin-3-ylamino)-5-(1H'-indol-4-yl)phenol;
4-(3-hydroxy-5-(1H-indol-4-yl)phenylamino)benzonitrile;
3-(2-(dimethylamino)pyridin-3-ylamino)-5-(1H-indol-4-yl)phenol;
N-[3-(2-methoxy-pyridine-4-carbonyl)-5-(1H-indol-4-yl)-phenyl]-methanesulfonamide;
[3-(1H-indol-4-yl)-5-oxazolo[4,5-b]pyridin-2-yl-phenyl] carbamic acid methyl ester
[3-(1H-indol-4-yl)-5-(2-methoxy-pyridin-4-ylamino)-phenyl]-carbamic acid methyl ester
[3-(2-chloro-6-methyl-pyridin-4-ylamino)-5-(1H-indol-4-yl)-phenyl]-carbamic acid methyl ester
3-(2-cyano-6-methyl-pyridin-4-ylamino)-5-(1H-indol-4-yl)-phenyl]-carbamic acid methyl ester
N-[3-benzooxazol-2-yl-5-(1H-indol-4-yl)-phenyl]-acetamide;
[3-benzooxazol-2-yl-5-(1H-indol-4-yl)-phenyl]-carbamic acid methyl ester;
N-[3-benzooxazol-2-yl-5-(1H-indol-4-yl)-phenyl]-methanesulfonamide;
[3-benzofuran-4-yl-5-(2-methoxy-pyridin-4-ylamino)-phenyl]-carbamic acid methyl ester
[3-(2,6-dimethyl-pyridin-4-ylamino)-5-(1H-indol-4-yl)-phenyl]-carbamic acid methyl ester
3-(2-chloro-pyridin-4-ylamino)-5-(1H-indol-4-yl)-phenyl]-carbamic acid methyl ester
[3-(1H-indol-4-yl)-5-(2-morpholin-4-yl-pyridin-4-ylamino)-phenyl]-carbamic acid methyl ester or
[3-(1H-indol-4-yl)-5-pyridin-3-yl-phenyl]-carbamic acid methyl ester;
N-[3-(1H-indol-4-yl)-5-pyridin-3-yl-phenyl]-acetamide;
[3-(1H-indol-4-yl)-5-pyridin-4-yl-phenyl]-carbamic acid methyl ester;
N-[3-(1H-indol-4-yl)-5-pyridin-4-yl-phenyl]-methanesulfonamide;
N-[3-(1H-indol-4-yl)-5-pyridin-4-yl-phenyl]-acetamide;
N-[3-(1H-indol-4-yl)-5-(6-methoxy-pyridin-3-yl)-phenyl]-acetamide;
[3-(7-fluoro-1H-indol-4-yl)-5-(pyridin-3-ylamino)-phenyl]-carbamic acid methyl ester;
N-[3-bromo-5-(pyridine-3-carbonyl)-phenyl-acetamide;
and pharmaceutically-acceptable salts or solvates thereof.

The invention disclosed herein is also meant to encompass the in vivo metabolic products of the disclosed compounds. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to man, allowing sufficient time for metabolism to occur and isolating its conversion products from the urine, blood or other biological samples.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached, or a sulfur atom to which three different groups are attached, where the sulfur atom and its attached groups form a sulfoxide, sulfinic ester, sulfonium salt or sulfite.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present in a greater concentration than its mirror image molecule.

The compounds of Formula I may also be solvated, especially hydrated. Hydration may occur during manufacturing of the compounds or compositions comprising the compounds, or the hydration may occur over time due to the hygroscopic nature of the compounds.

When any variable occurs more than one time in any constituent or in Formula I, its definition on each occurrence is independent of its definition at every other occurrence. Also, combinations of substituents and/or variables are permissible only if such combinations result in stable compounds.

Definitions

The term "alkyl" as employed herein by itself or as part of another group refers to both straight and branched chain radicals of up to 10 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2-10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, most preferably from 2 to 4 carbon atoms in length.

The term "alkynyl" is used herein to mean a straight or branched chain radical of 2-10 carbon atoms, unless the chain length is otherwise limited, wherein there is at least one triple bond between two of the carbon atoms in the chain, including, but not limited to, ethynyl, 1-propynyl, 2-propynyl, and the like. Preferably, the alkynyl chain is 2 to 8 carbon atoms in length, most preferably from 2 to 4 carbon atoms in length.

In all instances herein where there is an alkenyl or alkynyl moiety as a substituent group, the unsaturated linkage, i.e., the vinyl or ethenyl linkage, is preferably not directly attached to a nitrogen, oxygen or sulfur moiety.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "aryl" as employed herein by itself or as part of another group refers to monocyclic or bicyclic aromatic groups containing from 6 to 12 carbons in the ring portion, preferably 6-10 carbons in the ring portion. Typical examples include phenyl, biphenyl, naphthyl or tetrahydronaphthyl.

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "heteroaryl" as employed herein refers to groups having 5 to 14 ring atoms; 6, 10 or 14 pi electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The phrase "saturated or partially unsaturated heterocycle" as employed herein, by itself or as part of another group, refers to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be optionally fused to a benzene ring.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)" as employed herein, by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl" as employed herein, by itself or as part of another group, refers to cycloalkenyl groups containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "halogen" or "halo" as employed herein by itself or as part of another group refers to chlorine, bromine, fluorine or iodine.

The term "monoalkylamine" or "monoalkylamino" as employed herein by itself or as part of another group refers to the group $NH_2$ wherein one hydrogen has been replaced by an alkyl group, as defined above.

The term "dialkylamine" or "dialkylamino" as employed herein by itself or as part of another group refers to the group $NH_2$ wherein both hydrogens have been replaced by alkyl groups, as defined above.

The term "hydroxyalkyl" as employed herein refers to any of the above alkyl groups wherein one or more hydrogens thereof are substituted by one or more hydroxyl moieties.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "carboxyalkyl" as employed herein refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound form a saturated or unsaturated 5-, 6-, or 7-membered ring.

The terms "hydroxy" and "hydroxyl" are used interchangeably to refer to the radical —OH. The terms "pyridyl" and "pyridinyl" are used interchangeably to refer to a monovalent radical of pyridine. The terms "carbamoyl" and "aminocarbonyl" are used interchangeably to refer to the radical $NH_2$—C(O)—. The terms "ureido" and "aminocarbonylamino" are used interchangeably to refer to the radical $NH_2$—C(O)—NH—.

The phrase "optionally substituted" when not explicitly defined refers to a group or groups being optionally substituted with one or more substituents independently selected from the group consisting of hydroxy, nitro, trifluoromethyl, halogen, $C_{1-6}$ alkyl, $C_{1-6}$ haloalkyl, $C_{1-6}$ alkoxy, $C_{1-6}$ alkylenedioxy, $C_{1-6}$ aminoalkyl, $C_{1-6}$ hydroxyalkyl, $C_{2-4}$ alkenyl, $C_{2-4}$ alkynyl, $C_{6-10}$ aryl, phenoxy, benzyloxy, 5-10 membered heteroaryl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, $C_{2-6}$ alkoxycarbonylalkyl, carboxy, $C_{2-6}$ hydroxyalkoxy, ($C_{1-6}$)alkoxy($C_{2-6}$) alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis ($C_{2-10}$ carboxyalkyl)amino, $C_{2-6}$ carboxyalkoxy, $C_{2-6}$ carboxyalkyl, carboxyalkylamino, guanidinoalkyl, hydroxyguanidinoalkyl, cyano, trifluoromethoxy, perfluoroethoxy, aminocarbonylamino, mono($C_{1-4}$)alkylaminocarbonylamino, di($C_{1-4}$)alkylaminocarbonylamino, N—($C_{1-4}$)alkyl-N-aminocarbonyl-amino, N—($C_{1-4}$)alkyl-N-mono($C_{1-4}$) alkylaminocarbonyl-amino or N—($C_{1-4}$)alkyl-N-di($C_{1-4}$) alkylaminocarbonyl-amino.

Preferred optional substituents include one or more substituents independently selected from the group consisting of nitro, hydroxy, carboxy, $C_{1-4}$ alkoxy, $C_{1-4}$ alkyl, halo, $C_{1-4}$ haloalkyl, $C_{1-4}$ alkylthio, thio, amino, mono($C_{1-4}$)alkylamino and di($C_{1-4}$)alkylamino.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate and undecanoate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; and aralkyl halides like benzyl and phenethyl bromides and others. Preferred acids for forming acid addition salts include HCl, acetic acid, trifluoroacetic acid and fumaric acid.

Compositions and Methods of Use

Compositions of the present invention include pharmaceutical compositions comprising a compound of Formula I, wherein $A^1, A^3, A^5, R^4, R^6$, L, n and X are defined above, and one or more pharmaceutically acceptable excipients. Preferred compositions of the present invention are pharmaceutical compositions comprising a compound selected from a preferred group of compounds of Formula I as defined above, and one or more pharmaceutically acceptable excipients.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which can contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragée coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid nonionic surface-active agent or may be a solid anionic surface-active agent. It is preferred to use the solid anionic surface-active agent in the form of a sodium salt.

A further form of topical administration is to the eye. The compounds and compositions of the present invention are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 (1976)).

Compounds of the present invention are useful for treating, inhibiting or preventing abnormal cell growth, cellular differentiation, tumor growth and invasion. They are effective against a broad range of cancers such as leukemia, non-small cell lung, myeloma, colon, CNS, melanoma, ovarian, renal, prostate, breast, cervical, soft-tissue sarcomas, pancreatic, especially leukemia, non-small cell lung and colon cancer. These cancers and conditions are merely meant to be illustrative and are by no means meant to be a limiting or exhaustive list.

The compounds of the present invention may be administered in an effective amount within the dosage range of about 0.1 mg/kg to about 200 mg/kg, preferably from about 1.0 mg/kg to about 100 mg/kg body weight. The compounds are preferably administered in compositions in which the compound is present in a concentration of about 0.01 µM to about 100 µM, or in a concentration of about 0.03 µg/mL to about 30 µg/mL. Compounds of the present invention may be administered in a single daily dose, or the total daily dosage may be administered in divided doses of two, three or four times daily.

Preparation of Compounds

The present invention is also concerned with the syntheses of compounds of Formula I. The synthesis starts with the preparation of Intermediate A(3) prepared as shown in Scheme 1, according to Effenberger, F. et al., *Chem. Ber.* 124:163-73 (1991).

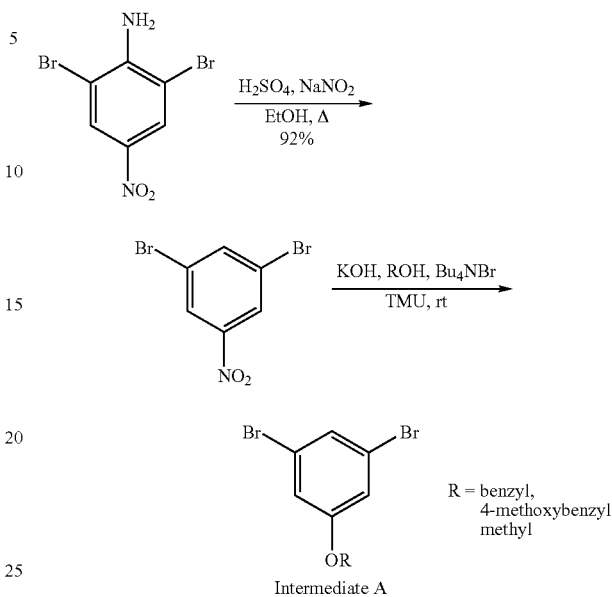

As shown in Schemes 2-4, Buchwald coupling of Intermediate A gives Intermediate B. Suzuki reaction of Intermediate B with an aryl boronic acid or aryl pinacol boronate gives Compound D. Alternatively, Intermediate B can be converted to the corresponding pinacol boronate C, which undergoes a Suzuki reaction with an aryl boronate to give Compound D. The alkyl or benzylic groups can be removed under standard conditions to give the hydroxyl compound E.

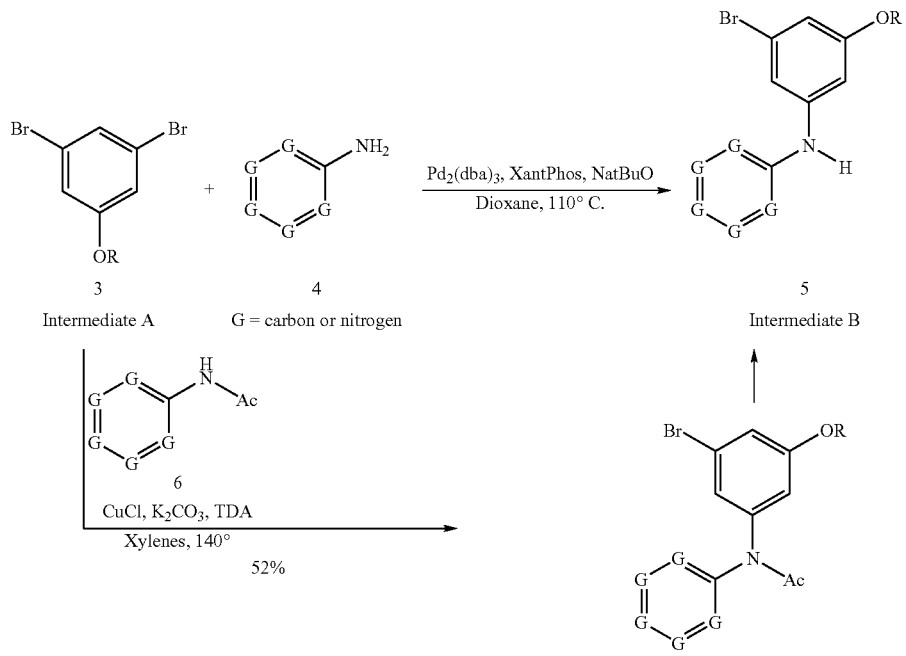

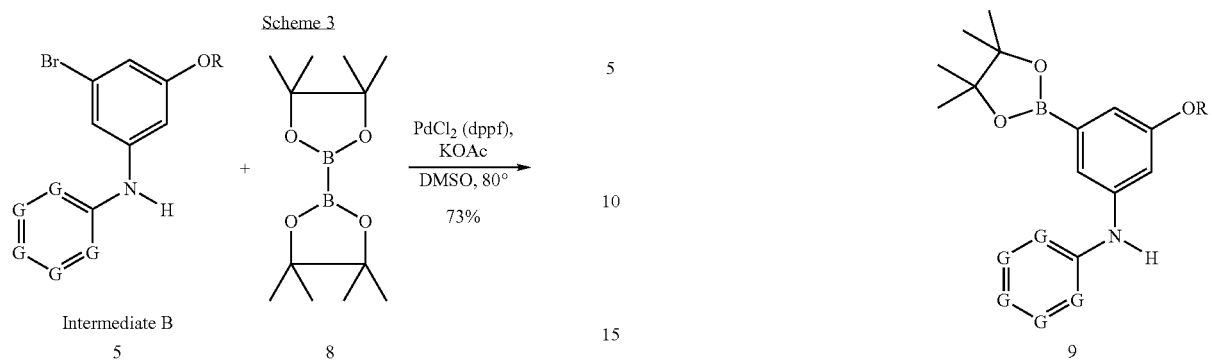
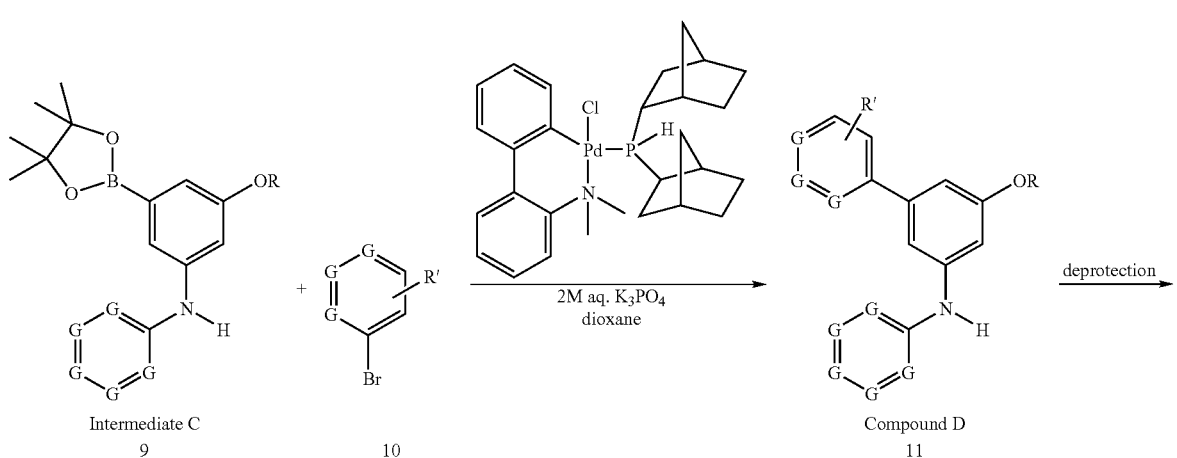

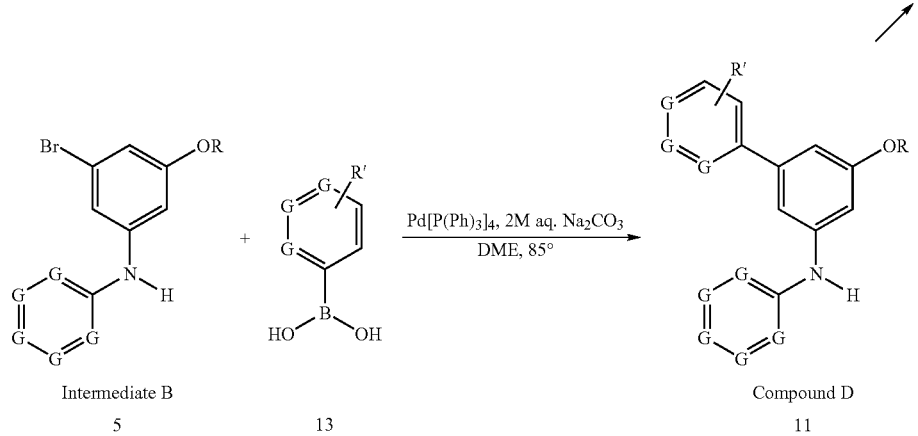
The above synthesis can be carried out on a solid support, as shown in Scheme 5.
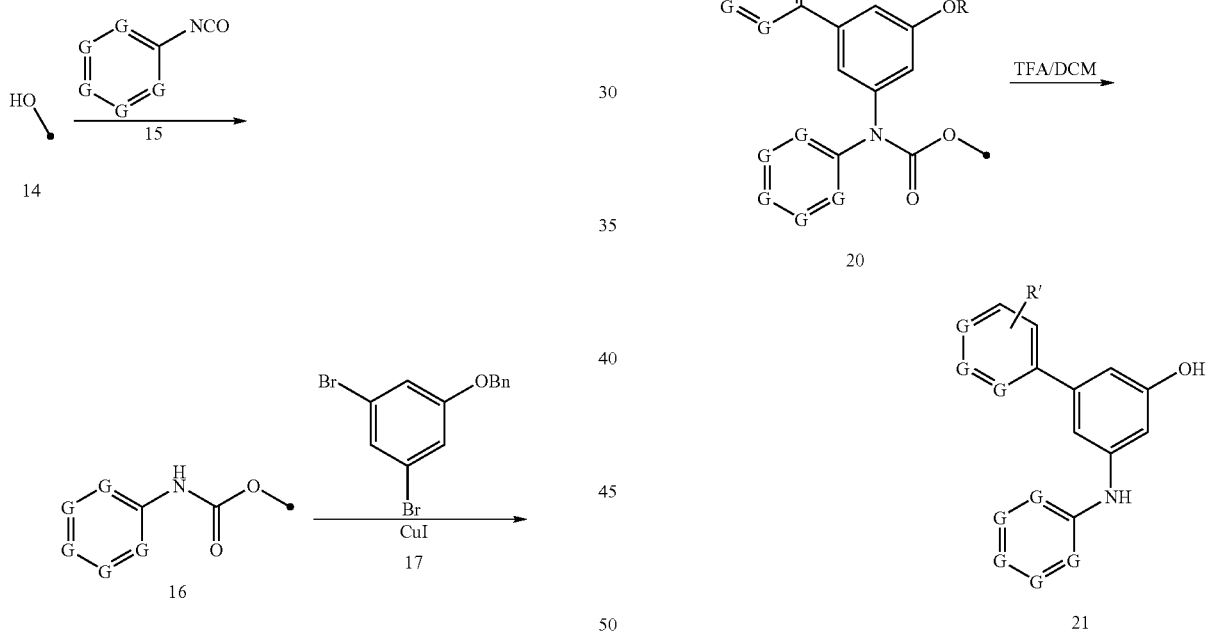
Alternatively, intermediates used in solution phase can be linked to a resin through the phenol oxygen as shown in Scheme 6.
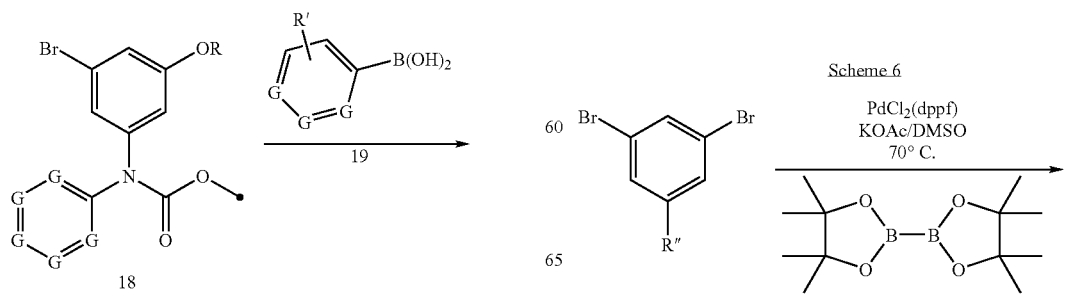

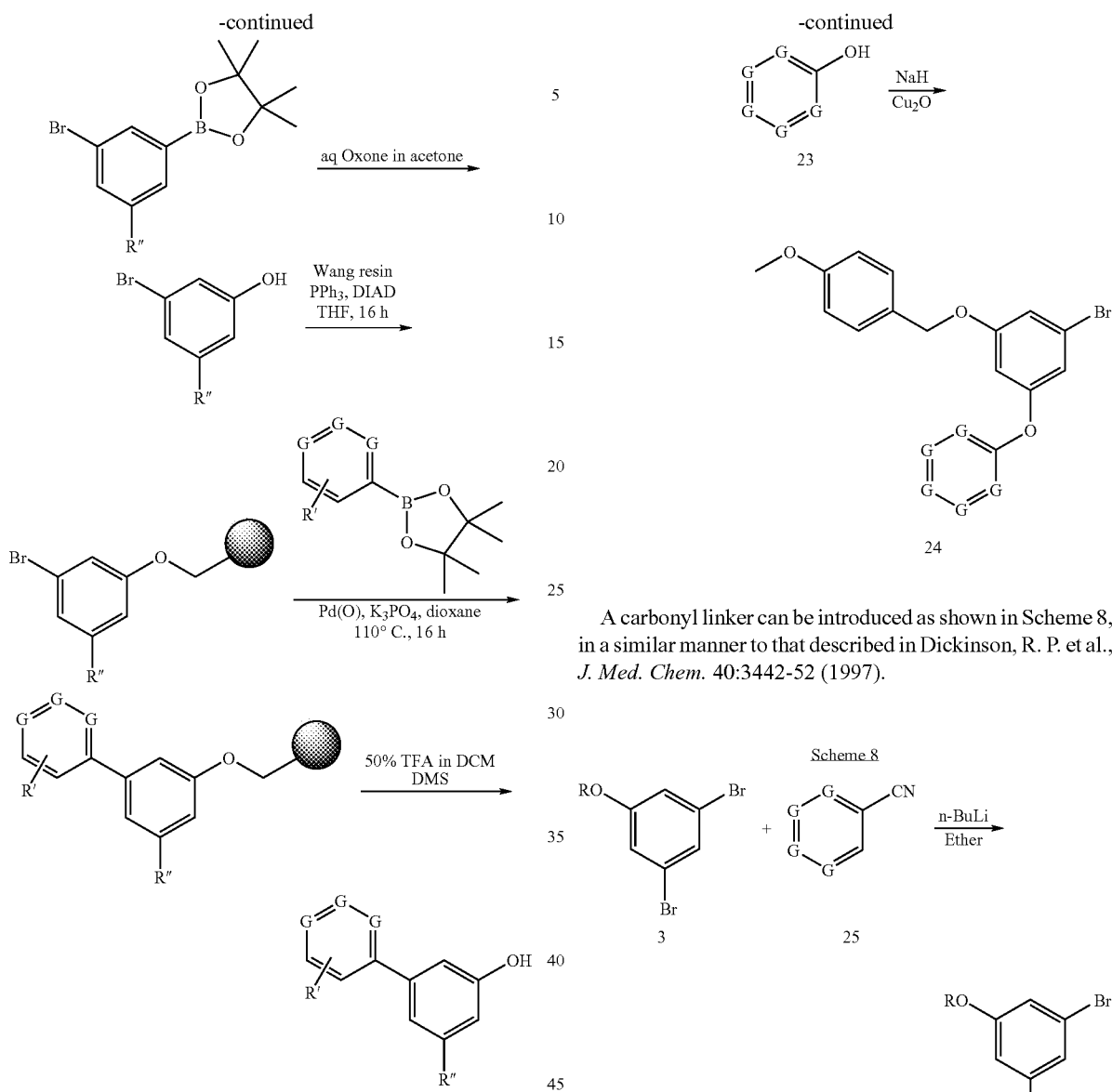

Compounds with an oxygen linker can be prepared by the reaction of Intermediate A with an alcohol in the presence of a copper catalyst to give an intermediate that is analogous to Intermediate B, as shown in Scheme 7. This intermediate can be carried on to compounds of Formula I in the manner shown above.

A carbonyl linker can be introduced as shown in Scheme 8, in a similar manner to that described in Dickinson, R. P. et al., *J. Med. Chem.* 40:3442-52 (1997).

Compounds with a central pyrimidine can be prepared as shown in Scheme 9.

Scheme 7

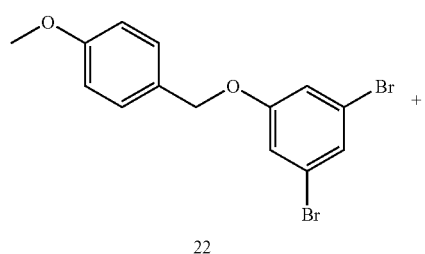

Scheme 9

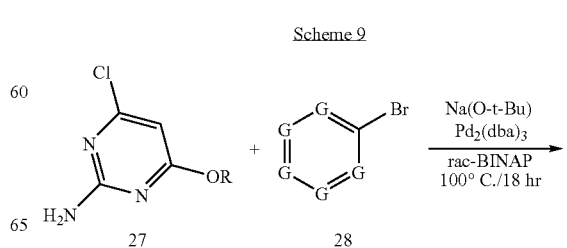

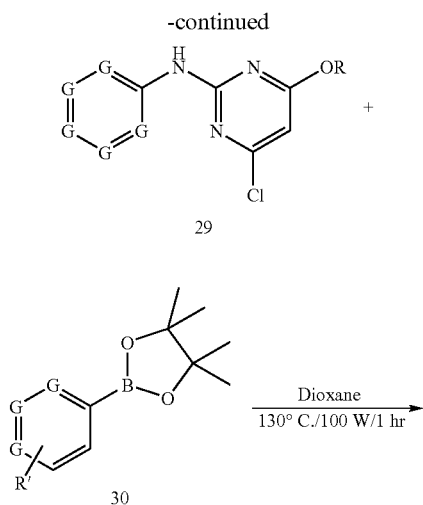

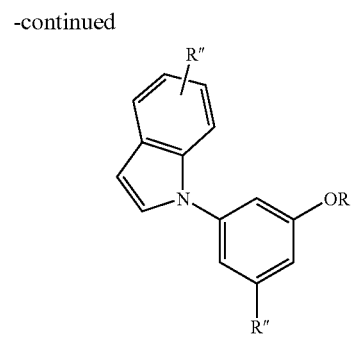

A nitrogen substituent can be introduced using the palladium catalyzed reaction of carbamic acid benzyl ester to an aryl bromide as shown in Scheme 11. The benzyl ester can be removed, and the aniline derivatized with a variety of electrophiles. Alternatively, a group such as acetamide, methyl carbamate or methanesulfonamide can be added directly to the aryl bromide as shown in Scheme 12.

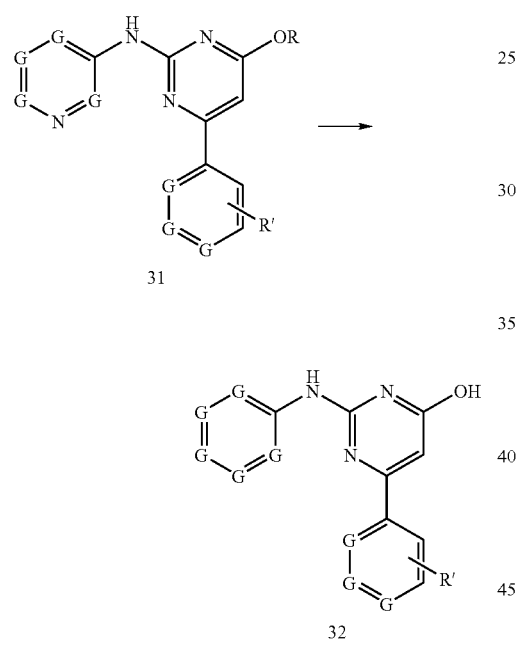

Indoles and other groups can be attached to the core ring through the nitrogen using copper chemistry as shown in Scheme 10.

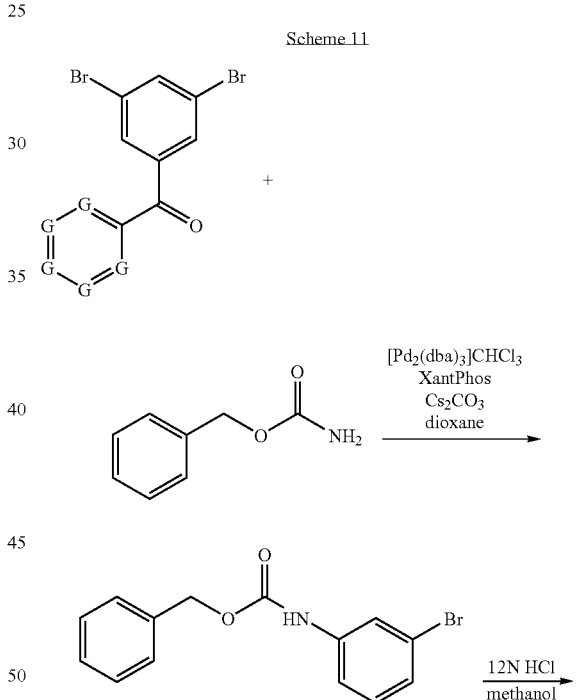

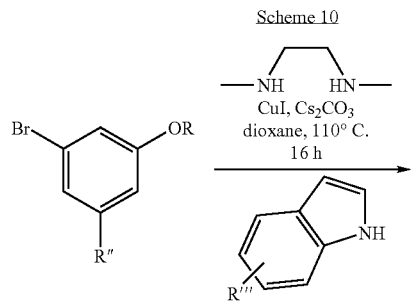

-continued

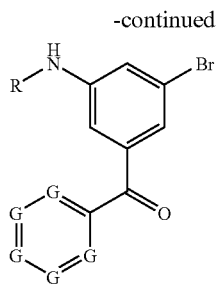 

Suzuki reaction →

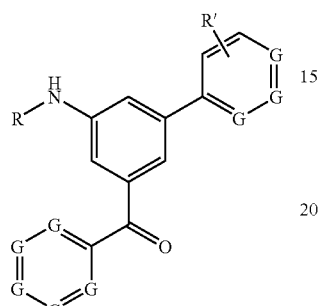

Scheme 12

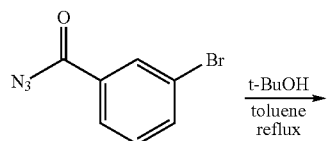

Compounds in which n is 0 can be prepared from 3-bromo-5-iodo-phenylamine as shown in Scheme 13. The amine can be derivatized. The X group is introduced by a Suzuki reaction. The aryl bromide intermediate then undergoes a second Suzuki reaction.

Scheme 13

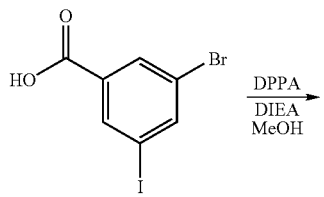

-continued

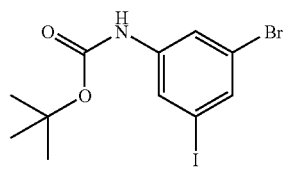

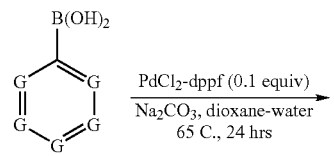

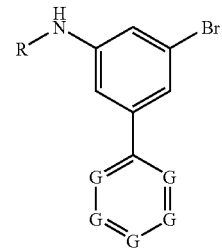

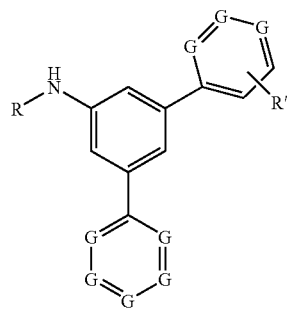

Alternatively, the 3,5-dibromo-1-heterocycle-substituted benzene can be prepared as shown in Scheme 14. This heterocycle can be derivatized as shown in previous schemes.

Scheme 14

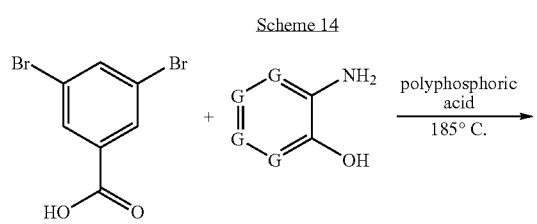

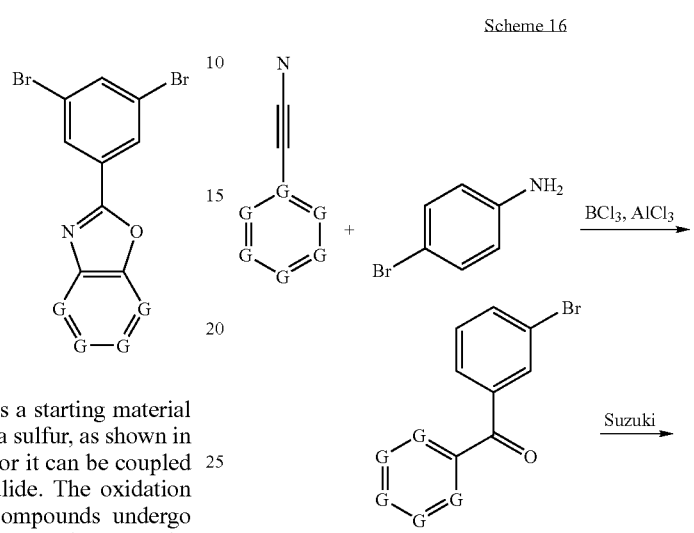

3,5-Dichlorobenzenethiol can serve as a starting material for compounds with a linker containing a sulfur, as shown in Scheme 15. The thiol can be alkylated, or it can be coupled with an aromatic or heteroaromatic halide. The oxidation state can be adjusted. The dichloro compounds undergo Buchwald and Suzuki reactions in a manner analogous to the dibromointermediates.

Friedel Crafts reaction of 4-bromophenylamine with an aromatic or heteroaromatic nitrile under conditions described by Earley, J. V. and Gilman, N. W., *Synth. Comm.* 15:1271-76 (1985) provides the intermediates shown in Scheme 16. These compounds can further undergo a Suzuki reaction.

Scheme 15

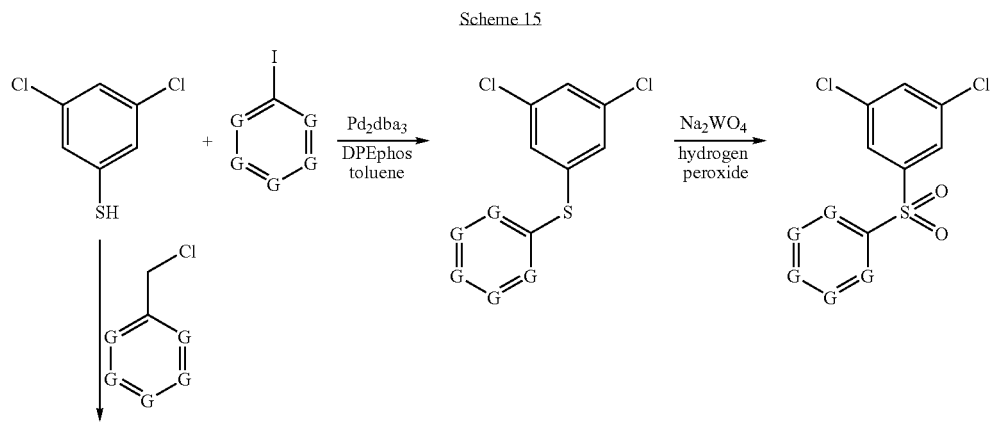

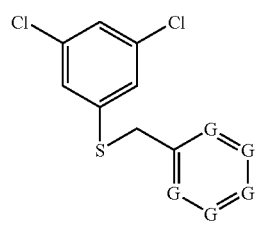

-continued

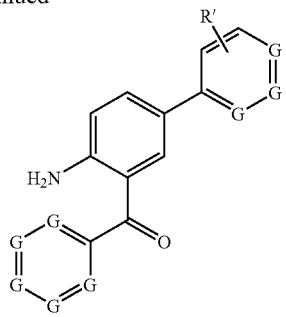

The following examples illustrate, but do not limit, the compounds, methods and compositions of the present invention. Other suitable modifications and adaptations of the variety of conditions and parameters normally encountered in clinical therapy and which are obvious to those skilled in the art are within the spirit and scope of the invention.

EXAMPLES

The compounds in the examples below were synthesized by the following general procedures.

Example 1

1,3-Dibromo-5-nitrobezene (The named compound was synthesized according to Dumont, *Bull. Soc. Chim. Bel.,* 505 (1995). This compound is also commercially available from Karl Industries, Aurora, Ohio.) To a suspension of 2,6-dibromo-4-nitroaniline (75.0 g, 254 mmol) in ethanol (1 L) was added $H_2SO_4$ (100 mL). The mixture was heated to reflux and sodium nitrite (50.5 g, 730 mmol) was added portion-wise over a period of 15 min. The mixture was heated at reflux for 3 h and was then cooled to room temperature. The formed thick suspension was poured on ice water (1000 mL) upon which more solid precipitated. The solid was filtered and the filter cake washed with water (2×250 mL) and dried in an oven at 20 mbar/30° C. to give 66.2 g (93%) of 1,3-dibromo-5-nitrobenzene as a brown solid.

Example 2

3,5-Dibromo-1-benzyloxybenzene (According to Effenberger, *Chem. Ber.* 163 (1991).) 1,3-dibromo-5-nitrobenzene (2.81 g, 10.0 mmol), freshly powdered potassium hydroxide (1.00 g, 17.8 mmol) and tetrabutylammonium bromide (0.32 g, 1.00 mmol) were dissolved in tetramethyl urea (TMU, 8 mL). Oxygen was bubbled through the reaction mixture for 5 min and a solution of benzyl alcohol (1.30 g) in TMU (2 mL) was added drop-wise at room temperature over a period of 1 h. The mixture was stirred for 6 h at room temperature during which oxygen was bubbled through. The reaction mixture was poured on ice (30 g) and was extracted with tert-butylmethyl ether (2×50 mL). The combined organics were dried ($MgSO_4$) and concentrated to give the crude product which was purified by FC (120 g $SiO_2$, AcOEt/heptane 1:4) to provide 3.15 g (92%) of 3,5-dibromo-1-benzyloxybenzene.

Example 3

3,5-Dibromo-1-p-methoxy-benzyloxybenzene 1,3-dibromo-5-nitrobenzene (30.0 g, 107 mmol), freshly powdered potassium hydroxide (10.8 g, 192 mmol) and tetrabutylammonium bromide (3.42 g, 10.7 mmol) were dissolved in tetramethyl urea (TMU, 90 mL). A solution of p-methoxybenzyl alcohol (17.8 g, 128 mmol) in TMU (30 mL) was added drop-wise at room temperature over a period of 1 h. The mixture was stirred for 48 h at room temperature. The reaction mixture was poured on ice (160 g) and was extracted with tert-butylmethyl ether (4×200 mL). The combined organics were dried ($MgSO_4$) and concentrated to give the crude product which was purified by FC (2.5 kg $SiO_2$, AcOEt/heptane 1:9) to provide 29.6 g of 3,5-dibromo-1-p-methoxy-benzyloxybenzene which was not completely pure but which crystallized upon standing. The solid was taken up in methanol (27 mL) and the formed slurry was stirred at 60° C. for 10 min. The suspension was cooled to 0-5° C. and then filtered. The filter cake was washed with cold methanol (2×15 mL) and dried to provide 28.1 g (71%) of 3,5-dibromo-1-p-methoxy-benzyloxybenzene as an off-white solid.

Example 4

(3-Benzyloxy-5-bromo-phenyl)-pyridin-3-yl-amine

An oven-dried flask was charged with (±)-BINAP (1.05 g, 1.68 mmol), $Pd_2(dba)_3$ $CHCl_3$-complex (580 mg, 0.56 mmol) and then flushed with argon. Degassed toluene (28 mL) was added and the solution was stirred for 10 min. The catalyst solution was added to a mixture of 3,5-dibromo-1-benzyloxybenzene (38.3 g, 112 mmol), 3-aminopyridine (5.27 g, 56.0 mmol) and sodium tert-butoxide (7.54 g, 78.4 mmol) in degassed toluene (250 mL) and the mixture was heated to 80-90° C. for 24 h (conversion not complete). The reaction mixture was cooled to room temperature and brine (500 mL) was added. The mixture was extracted with ethyl acetate (500 mL) and the layers were separated. The organic layer was washed with brine (2×300 mL), dried ($Na_2SO_4$) and concentrated to give the crude product. FC ($SiO_2$, AcOEt/heptane 2:1) gave 8.06 g (41%) of (3-benzyloxy-5-bromo-phenyl)-pyridin-3-yl-amine as yellow solid. 3,5-Dibromo-1-benzyloxybenzene was recovered, repurified and reused.

Example 5

(3-P-methoxybenzyloxy-5-bromo-phenyl)-pyridin-3-yl-amine

An oven-dried flask was charged with (±)-BINAP (504 mg, 0.81 mmol), $Pd_2(dba)_3$ $CHCl_3$-complex (278 mg, 0.27 mmol) and then flushed with argon. Degassed toluene (50 mL) was added and the solution was stirred for 10 min. A second oven-dried flask was charged with 3,5-dibromo-1-p-methoxy-benzyloxybenzene (20.0 g, 53.8 mmol), 3-aminopyridine (2.72 g, 26.9 mmol) and sodium tert-butanolate (3.61 g, 37.6 mmol) in degassed toluene (100 mL) and the mixture was heated to 90° C. The catalyst solution was then added to the mixture and the reaction mixture was stirred at 90° C. for 40 h. The reaction mixture was cooled to room temperature and brine (120 mL) and AcOEt (120 mL) were added and the mixture was filtered over Hyflo. The filtrate was transferred to a separatory funnel and the layers were separated. The aqueous layer was extracted with AcOEt (2×100 mL) and the layers were separated. The organic layer was washed with brine (2×80 mL), dried ($Na_2SO_4$) and concentrated to give the crude product. FC ($SiO_2$, AcOEt/heptane 1:2→2:1) gave 7.96 (75%) of (3-p-methoxybenzyloxy-5-bromo-phenyl)-pyridin-3-yl-amine as yellow oil. 3,5-Dibromo-1-p-methoxy-benzyloxybenzene was recovered, repurified and can be reused.

Example 6

[3-Benzyloxy-5-(4,4,5,5-tetramethyl-[1,3,2]dioxaborolan-2-yl)-phenyl]pyridin-3-yl-amine A round bottom flask was charged with (3-benzyloxy-5-bromo-phenyl)-pyridin-3-ylamine, (2.24 g, 6.30 mmol), bis(pinacolato)diboron (1.76 g, 6.93 mmol), potassium acetate (1.78 g, 18.9 mmol) and Pd(dppf)$Cl_2$ $CH_2Cl_2$ complex (255 mg, 0.32 mmol). DMSO (44 mL) was added under argon and the mixture was heated to 80° C. for 20 h. After completion of the reaction, the mixture was cooled to rt, filtered over Hyflo and the filter cake washed with isobutyl acetate (2×5 mL). The filtrate was diluted with water (100 mL) and the mixture was extracted with isobutyl acetate (3×150 mL). The combined organics were dried ($Na_2SO_4$) and concentrated under reduced pressure to give the crude material (3.94 g). FC on silica gel (120 g, AcOEt/heptane 7:1) provided pure [3-benzyloxy-5-(4,4,5,5-tetramethyl-[1,3,2]dioxaborolan-2-yl)-phenyl]-pyridin-3-yl-amine (1.85 g, 73%) as a white solid.

Example 7

[3-P-methoxybenzyloxy-5-(4,4,5,5-tetramethyl-[1,3,2]dioxaborolan-2-yl)-phenyl]-pyridin-3-yl-amine A round bottom flask was charged with (3-p-methoxybenzyloxy-5-bromo-phenyl)-pyridin-3-yl-amine (623 mg, 1.62 mmol), bis(pinacolato)diboron (453 mg, 1.78 mmol), potassium acetate (477 mg, 4.86 mmol) and Pd(dppf)$Cl_2$ $CH_2Cl_2$ complex (65 mg, 0.08 mmol). DMSO (10 mL) was added under argon and the mixture was heated to 80° C. for 2 h. After completion of the reaction, the mixture was cooled to room temperature, filtered over Hyflo and the filter cake washed with ethyl acetate (2×5 mL). The filtrate was diluted with brine (100 mL) and the mixture was extracted with ethyl acetate (3×15 mL). The combined organics were dried ($Na_2SO_4$) and concentrated under reduced pressure to give the crude material. Flash chromatography on silica gel (40 g, AcOEt/heptane 2:1→3:1) provided pure 3-p-methoxybenzyloxy-5-(4,4,5,5-tetramethyl-[1,3,2]dioxaborolan-2-yl)-phenyl]-pyridin-3-yl-amine (640 mg, 91%) as an off-white solid.

Example 8

3-(1H-Indol-4-yl)-5-(pyridin-3-ylamino)-phenol (a) [3-Benzyloxy-5-(1H-indol-4-yl)-phenyl]-pyridin-3-yl-amine. A round bottom flask was charged with 4-bromoindole (32 mg, 0.16 mmol) and tetrakistriphenylphosphine palladium (9.2 mg, 0.008 mmol). 1,2-Dimethoxyethane (1 mL) was added under argon and the mixture was stirred for 10 min at room temperature. A solution of [3-benzyloxy-5-(4,4,5,5-tetramethyl-[1,3,2]dioxaborolan-2-yl)-phenyl]-pyridin-3-yl-amine (79 mg, 0.20 mmol) in DME (3 mL) and 2M aqueous $Na_2CO_3$ (0.16 mL, 1.12 mmol) were added and the mixture was heated at reflux overnight. The mixture was cooled to room temperature, filtered over Hyflo and the filter cake washed with ethyl acetate (2×5 mL). The filtrate was concentrated under reduced pressure and the oily residue was taken up in brine/AcOEt 1:1 (20 mL). The layers were separated and the aqueous layer was extracted with AcOEt (10 mL). The combined organics were dried ($Na_2SO_4$) and concentrated under reduced pressure to give the crude material (89 mg). Flash chromatography on silica gel (8 g, AcOEt/heptane 3:1) provided pure [3-benzyloxy-5-(1H-indol-4-yl)-phenyl]-pyridin-3-yl-amine (22 mg, 35%) as a yellow oil.

(b) 3-(1H-Indol-4-yl)-5-(pyridin-3-ylamino)-phenol. [3-Benzyloxy-5-(1H-indol-4-yl)-phenyl]-pyridin-3-yl-amine (65 mg, 0.16 mmol) was dissolved in methanol (2 mL). 5% Pd/C (65 mg) was added under argon followed by formic acid (2 mL) and ammonium formate (40 mg). The mixture was stirred at room temperature for 12 h after which the reaction was not complete. More ammonium formate (20 mg) was added and the mixture was stirred for 7 h. The catalyst was filtered over Hyflo and the filter cake was washed with formic acid (2 mL) followed by methanol (2 mL). The filtrate was concentrated and the residue was taken up in ethyl acetate. The solution was neutralized with sat. $NaHCO_3$ solution (2 mL) to pH=5-6. The layers were separated and the aqueous layer was extracted with ethyl acetate (10 mL). The combined organics were dried ($Na_2SO_4$) and concentrated under reduced pressure to furnish the crude product. Flash chromatography (2 g $SiO_2$, AcOEt/heptane 6:1), provided 3-(1H-indol-4-yl)-5-(pyridin-3-ylamino)-phenol (17 mg, ca. 35%) as oil. This material was further purified on a preparative SFC. $^1$H NMR (400 MHz, DMSO-$d_6$): δ 11.18 (s, 1H), 9.36 (s, 1H), 8.36 (d, J=2.7 Hz, 1H), 8.32 (s, 1H), 8.00 (dd, J=4.6, 1.3 Hz, 1H), 7.48 (ddd, J=8.4, 2.7,1.4 Hz, 1H), 7.38-7.33 (m, 2H), 7.22 (dd, J=8.3, 4.6 Hz, 1H), 7.11 (t, J=7.7 Hz, 1H), 7.00 (d, J=6.8 Hz, 1H), 6.78 (d, J=1.6 Hz, 1H), 6.58 (t, J=1.6 Hz, 1H), 6.55-6.51 (m, 2H).

Example 9

3-(1H-Indazol-7-yl)-5-(pyridin-3-ylamino)-phenol (a) Boronic acid of 7-bromoindazole.
(i) 7-Aminoindazole. 7-Nitroindazole (1.00 g, 6.13 mmol) was dissolved in ethanol (100 mL). 10% Pd/C (0.25 g) was added and the mixture was hydrogenated for 10 min at room temperature and ambient pressure. The catalyst was filtered over Hyflo and the filter cake was washed with ethanol. The filtrate was concentrated in vacuo to provide the crude amine. Flash chromatography on silica gel (AcOEt/hexanes 2:1) gave 7-aminoindazole (697 mg, 85%).

(ii) 7-Bromoindazole. (Coller, *Aust. J. Chem.* 27:2343 (1974)) A solution of 7-aminoindazole (3.45 g, 25.9 mmol) in concentrated HBr (25 mL) was diluted with water (8.5 mL) and cooled to −10° C. A cooled solution of sodium nitrite (755 mg, 10.9 mmol) in water (11.5 mL) was added slowly. More sodium nitrite (1.14 g, 16.5 mmol) was added portion-wise as a solid. The reaction solution was stirred at −5° C. for 15 min and then a cooled solution of CuBr (3.94 g, 27.5 mmol) in concentrated HBr (11.5 mL) was added drop-wise over a period of 15 min. The reaction mixture was stirred for 2 h at room temperature and was then neutralized with sat. $NaHCO_3$ solution. The quenched mixture was diluted with water (50 mL). The mixture was filtered and the filter cake was washed with AcOEt (300 mL). The layers of the filtrate were separated and the aqueous layer was extracted with AcOEt (3×200 mL). The combined organics were dried ($Na_2SO_4$) and concentrated under reduced pressure to give 7-bromoindazole (1.88 g, 37%).

(iii) Indazole 7-pinacol boronate. A round bottom flask was charged with 7-bromoindazole (200 mg, 1.01 mmol), bis(pinacolato)diboron (335 mg, 1.32 mmol), potassium acetate (285 mg, 3.03 mmol) and Pd(dppf)Cl$_2$ CH$_2$Cl$_2$ complex (41 mg, 0.05 mmol). Dry DMSO (4 mL) was added under argon and the mixture was heated to 100° C. for 48 h. The reaction mixture was then cooled to rt, filtered over Hyflo and the filter cake washed with TBME (50 mL). Brine (20 mL) was added to the filtrate and the layers were separated. The aqueous layer was extracted with TBME (2×25 mL) and the combined organics were washed with water (2×20 mL), dried (Na$_2$SO$_4$) and concentrated to provide the crude product (323 mg). Flash chromatography over SiO$_2$ (16 g, AcOEt/heptane 1:4) provided the pure indazole 7-pinacol boronate (181 mg, 74%).

(iv) Boronic acid of 7-bromoindazole. Indazole 7-pinacol boronate (247 mg, 1.01 mmol) was dissolved in 2 M aqueous HCl (5 mL) and the mixture was heated to 80° C. for 20 h. The reaction mixture was cooled to room temperature, neutralized with 1M NaOH solution (12 mL) to pH 6 and extracted with ethyl acetate (3×20 mL). The combined organics were washed with water (5 mL), dried (Na$_2$SO$_4$), filtered and concentrated under reduced pressure to provide the crude boronic acid (148 mg). The crude material was purified by flash chromatography (CH$_2$Cl$_2$/MeOH 95:5) to give 120 mg (74%) of the boronic acid of 7-bromoindazole.

(b) [3-benzyloxy-5-(1H-indazol-4-yl)-phenyl]-pyridin-3-yl-amine. Suzuki coupling: A round bottom flask was charged with the boronic acid of 7-bromoindazole (144 mg, 0.89 mmol) and tetrakistriphenylphosphine palladium (35 mg, 0.03 mmol). 1,2-Dimethoxyethane (4 mL) was added under argon and the mixture was stirred for 10 min at room temperature. A solution of 3-benzyloxy-5-bromo-phenyl)-pyridin-3-yl-amine (213 mg, 0.60 mmol) in DME (4.5 mL) and 2M aq Na$_2$CO$_3$ (0.60 mL, 1.24 mmol) were added and the mixture was heated at reflux for 24 h. More tetrakistriphenylphosphine palladium (70 mg, 0.06 mmol) was added and the mixture was refluxed for another 24 h. After completion of the reaction, the mixture was cooled to room temperature, filtered over Hyflo and the filter cake was washed with ethyl acetate (2×20 mL). The filtrate was concentrated under reduced pressure and the oily residue was taken up in brine/AcOEt 1:1 (80 mL). The layers were separated and the aqueous layer was extracted with AcOEt (40 mL). The combined organics were dried (Na$_2$SO$_4$) and concentrated under reduced pressure to give the crude material (450 mg). Flash chromatography on silica gel (15 g, AcOEt/heptane 3:1) provided pure [3-benzyloxy-5-(1H-indazol-4-yl)-phenyl]-pyridin-3-yl-amine (230 mg, 98%) as a yellow oil.

(c) 3-(1H-Indazol-7-yl)-5-(pyridin-3-ylamino)-phenol. Deprotection: [3-Benzyloxy-5-(1H-indazol-4-yl)-phenyl]-pyridin-3-yl-amine (189 mg, 0.48 mmol) was dissolved in trifluoroacetic acid (4 mL). Thioanisole (0.85 mL, 7.20 mmol) was added and the reaction solution was stirred for 15 h at room temperature. After completion the reaction was neutralized with sat. NaHCO$_3$ solution (45 mL) to pH 7 and extracted with ethyl acetate (2×30 mL). The combined organics were washed with brine (30 mL), dried (Na$_2$SO$_4$) and concentrated under reduced pressure to provide the crude product. Flash chromatography (10 g SiO$_2$, AcOEt/heptane 10:1→AcOEt) provided 3-(1H-Indazol-7-yl)-5-(pyridin-3-ylamino)-phenol (115 mg, 80%) as an off-white to beige solid. $^1$H NMR (400 MHz, CDCl$_3$): δ 13.04 (s, 1H), 9.47 (s, 1H), 8.39 (d, J=2.5 Hz, 1H), 8.34 (s, 1H), 8.11 (s, 1H), 8.01 (d, J=4.4 Hz, 1H), 7.71 (d, J=8.0 Hz, 1H), 7.62-7.51 (m, 2H), 7.29 (d, J=6.8 Hz, 1H), 7.22 (dd, J=8.2, 4.7 Hz, 1H), 7.15 (t, J=7.6 Hz, 1H), 6.78 (s, 1H), 6.58 (s, 1H), 6.54 (s, 1H).

Example 10

3'-Dimethylamino-5-(pyridin-3-ylamino)-biphenyl-3-ol (a) 3-Dimethylaminophenylboronic acid. 3-Bromo-N,N-dimethylaniline (500 mg, 2.50 mmol) was dissolved in THF (8 mL) and the solution was cooled to −78° C. n-Butyllithium (1.6M in hexanes, 1.56 mL, 3.75 mmol) was added drop-wise at −78° C. and the reaction mixture was stirred at this temperature for another 5 min. Trimethylborate (1.11 mL, 10.0 mmol) was added and the mixture was stirred for 1 h at −78° C. and was then left to warm to −20° C. over a period of 20 min. 2M HCl (3 mL) was added and the mixture was stirred for 5 min and was then neutralized by the addition of sat. NaHCO$_3$ solution. The mixture was extracted with AcOEt (3×10 mL) and the combined organics were concentrated under reduced pressure to provide the crude boronic acid. Flash chromatography on silica gel eluting with acetone/CH$_2$Cl$_2$ 1:1 provided 3-dimethylaminophenylboronic acid (251 mg, 61%).

(b) 3-Benzyloxy-3'-dimethylamino-5-(pyridin-3-ylamino)-biphenyl. A round bottom flask was charged with (3-benzyloxy-5-bromo-phenyl)-pyridin-3-yl-amine (200 mg, 0.56 mmol) and tetrakistriphenylphosphine palladium (20 mg, 0.017 mmol). 1,2-Dimethoxyethane (5 mL) was added under argon and the mixture was stirred for 10 min at room temperature. A solution of 3-dimethylamino-phenylboronic acid (110 mg, 0.67 mmol) in ethanol/DME 1:2 (2.5 mL) and 2M aqueous Na$_2$CO$_3$ (0.56 mL, 1.12 mmol) were added and the mixture was heated at reflux overnight. After completion of the reaction, the mixture was cooled to room temperature, filtered over Hyflo and the filter cake washed with ethyl acetate (2×5 mL). The filtrate was concentrated under reduced pressure and the oily residue was taken up in brine/AcOEt 1:1 (20 mL). The layers were separated and the aqueous layer was extracted with AcOEt (10 mL). The combined organics were dried (Na$_2$SO$_4$) and concentrated under reduced pressure to give the crude material (260 mg). Flash chromatography on silica gel (12 g, AcOEt/heptane 2:1) provided pure 3-benzyloxy-3'-dimethylamino-5-(pyridin-3-ylamino)-biphenyl (169 mg, 76%) as a yellow oil.

(c) 3'-Dimethylamino-5-(pyridin-3-ylamino)-biphenyl-3-ol. 3-Benzyloxy-3'-dimethylamino-5-(pyridin-3-ylamino)-biphenyl (80 mg, 0.20 mmol) was taken up in 2M aq. HCl (1.5 mL). The mixture was heated to reflux for 27 h and was then cooled to room temperature, neutralized with 1M NaOH solution (3.6 mL) to pH=7 and extracted with ethyl acetate (3×10 mL). The combined organics were washed with water (10 mL), dried (Na$_2$SO$_4$) and concentrated under reduced pressure to provide the crude product. FC (5 g SiO$_2$, AcOEt/heptane 6:1) provided 3'-dimethylamino-5-(pyridin-3-ylamino)-biphenyl-3-ol (40 mg, 66%) as yellow solid. $^1$H NMR (400 MHz, acetone-d$_6$): δ 8.44 (d, J=2.5 Hz, 1H), 8.07 (d, J=4.5 Hz, 1H), 7.60-7.52 (m, 2H), 7.26-7.18 (m, 3H), 6.95-6.84 (m, 3H), 6.74 (dd, J=8.2, 2.7 Hz, 1H), 6.69 (s, 1H), 6.66 (s, 1H), 2.99 (s, 6H).

Examples 11-13

5-(Pyridin-3-ylamino)-2'-trifluoromethyl-biphenyl-3-ol

2'-Chloro-5-(pyridin-3-ylamino)-biphenyl-3-ol

5-(Pyridin-3-ylamino)-biphenyl-3-ol

These compounds were prepared from the commercially-available boronic acids and Intermediates B in the same manner as described for Example 9, and deprotected in the same manner as for Example 8.

5-(Pyridin-3-ylamino)-2'-trifluoromethyl-biphenyl-3-ol $^1$H NMR (400 MHz, acetone-$d_6$): δ 8.46 (s, 1H), 8.43 (d, J=2.5 Hz, 1H), 8.07 (d, J=4.7 Hz, 1H), 7.79 (d, J=7.8 Hz, 1H), 7.68 (t, J=7.3 Hz, 1H), 7.63-7.53 (m, 3H), 7.43 (d, J=7.6 Hz, 1H), 7.21 (dd, J=8.2, 4.7 Hz, 1H), 6.70 (s, 1H), 6.59 (s, 1H), 6.40 (s, 1H)

2'-Chloro-5-(pyridin-3-ylamino)-biphenyl-3-ol $^1$H NMR (400 MHz, acetone-$d_6$): δ 8.46 (s, 1H), 8.44 (d, J=2.8 Hz, 1H), 8.08 (d, J=4.5 Hz, 1H), 7.65-7.55 (m, 2H), 7.50 (d, J=6.8 Hz, 1H), 7.45-7.33 (m, 3H), 7.22 (dd, J=8.4, 4.7 Hz, 1H), 6.69 (s, 2H), 6.49 (s, 1H).

5-(Pyridin-3-ylamino)-biphenyl-3-ol $^1$H NMR (400 MHz, acetone-$d_6$): δ 8.45 (d, J=2.5 Hz, 1H), 8.41 (s, 1H), 8.09 (d, J=4.5 Hz, 1H), 7.59 (d, J=7.4 Hz, 4H), 7.43 (t, J=7.6 Hz, 2H), 7.34 (t, J=7.3 Hz, 1H), 7.24 (dd, J=8.2, 4.7 Hz, 1H), 6.89 (s, 1H), 6.70 (s, 1H), 6.67 (s, 1H).

Examples 14-15

3-Indan-5-yl-5-(pyridin-3-ylamino)-phenol

3-Indan-4-yl-5-(pyridin-3-ylamino)-phenol

Preparation of the mixture of boronic acids. (According to Ranu, *Synth. Comm.* 1095 (1992) Bromine (6.40 g, 40.0 mmol) adsorbed on alumina (30 g, neutral, Brockmann grade 1) was added to indane (4.70 g, 40.0 mmol) also adsorbed on alumina (30 g, neutral, Brockmann grade 1). The mixture was stirred until the color of the bromine disappeared (tlc showed completion). The reaction mixture was filtered through silica gel (100 g eluting with $CH_2Cl_2$) and the filtrate was concentrated in vacuo to provide the crude bromoindane (7.40 g) as a brown oil. The crude material was purified by flash chromatography (200 g $SiO_2$, hexanes) to give a mixture of 2 mono-brominated indanes and a dibrominated indane (5.95 g, 68%) as yellow oil.

An oven-dried flask was charged with the mixture of bromoindanes (340 mg, 1.73 mmol) and dry THF (2 mL) under argon. The solution was cooled to −78° C. and butyllithium (1.6 M in hexanes, 1.30 mL) was added drop-wise. The reaction mixture was stirred for 15 min at −78° C. and trimethyl borate (385 μL, 3.46 mmol) was added drop-wise. The reaction solution was left to warm to −20° C. over a period of 2.5 h and was then quenched with 1M aqueous HCl (2 mL). The mixture was left to warm to room temperature, was diluted with MTBE (20 mL) and the layers were separated. The organic layer was washed with $H_2O$ (5 mL) and brine 5 mL), dried ($Na_2SO_4$) and concentrated to give the crude boronic acid (232 mg). Flash chromatography (20 g $SiO_2$, AcOEt/heptane 1:4→1:2) provided a mixture of 4- and 5-indane boronic acid (123 mg, 44%).

The boronic acids were converted to 3-indan-5-yl-5-(pyridin-3-ylamino)-phenol and 3-indan-4-yl-5-(pyridin-3-ylamino)-phenol in a ratio of 85:15 by the method described in Example 9. This mixture was separated by preparative LC to give the individual compounds. 3-Indan-5-yl-5-(pyridin-3-ylamino)-phenol $^1$H NMR (400 MHz, $CD_2Cl_2$): δ 8.51 (s, 1H), 8.10 (s, 1H), 7.39-7.45 (m, 2H), 7.32 (d, J=7.8 Hz, 1H), 7.19-7.27 (m, 2H), 6.77 (s, 1H), 6.73 (s, 1H), 6.66 (s, 1H), 6.05 (s, 1H), 2.93 (q, J=6.8 Hz, 4H), 2.10 (m, 2H).

3-Indan-4-yl-5-(pyridin-3-ylamino)-phenol $^1$H NMR (400 MHz, $CD_2Cl_2$): δ 8.46 (s, 1H), 8.14 (d, J=4.3 Hz, 1H), 7.45 (d, J=7.8 Hz, 1H), 7.12-7.24 (m, 4H), 6.67 (s, 1H), 6.59 (s, 1H), 6.53 (s, 1H), 5.88 (s, 1H), 2.92-3.00 (m, 4H), 1.99-2.09 (m, 2H).

Example 16

[3-Benzo[B]thiophen-4-yl-5-(4-methoxy-benzyloxy)-phenyl]-pyridin-3-yl-amine (a) Trifluoro-methanesulfonic acid benzo[b]thiophen-4-yl ester. (J. Chem. Res. Synop. 192 (1993))

(i) 6-Bromo-6,7-dihydro-4-benzothio[b]phenone. 6,7-Dihydro-4-benzothio[b]phenone (3.04 g, 20.0 mmol) was dissolved in dry ether (125 mL). The solution was cooled to −10° C. A solution of bromine (3.20 g, 20.0 mmol) in $CCl_4$ (10 mL) and a few drops of ether was added drop-wise to the reaction solution in a manner that the red color of the solution disappeared before the next drop was added. After completion of the addition the solution was maintained for 10 min at −10° C. and was then stirred at room temperature for 12 h (reaction was not complete). The reaction mixture was cooled to 0-5° C. and water (100 mL) was added drop-wise. Ether (50 mL) was added and the layers were separated. The aqueous layer was extracted with ether (50 mL) and the combined organics were dried ($Na_2SO_4$), filtered and concentrated to provide the crude product. Flash chromatography ($SiO_2$, AcOEt/heptane 1:4) gave pure 6-bromo-6,7-dihydro-4-benzothio[b]phenone (2.94 g, 63%).

(ii) 4-Hydroxybenzthiophene. A round bottom flask was charged with 6-bromo-6,7-dihydro-4-benzothio[b)phenone (2.80 g, 12.1 mmol), lithium bromide (2.37 g, 27.3 mmol), lithium carbonate (1.79 g, 24.2 mmol) and dry DMF. The mixture was heated at reflux under argon for 3 h. The solvent was removed under high vacuum and the residue was taken up in ice-water (30 mL) and acidified with 1M HCl (40 mL) to pH 1. The mixture was extracted with TBME (3×50 mL) and the combined organics were extracted with 10% NaOH solution (3×20 mL). The combined aqueous layers were acidified to pH 3-4 with 1M HCl (60 mL) and extracted with TBME (3×50 mL). The combined organics were dried ($MgSO_4$), filtered and concentrated in vacuo to provide the crude product as a dark solid. Flash chromatography ($SiO_2$, AcOEt/heptane 1:4) provided pure 4-hydroxybenzthiophene (1.70 g, 91%) as a yellow solid.

(iii) Trifluoromethanesulfonic acid benzo[b]thiophen-4-yl ester. 4-Hydroxybenzthiophene (1.00 g, 6.66 mmol) was dissolved in dry $CH_2Cl_2$ (10 mL) under argon. Triethylamine (1.40 mL, 9.99 mmol) was added and the reaction solution was cooled to 0-5° C. A solution of trifluoromethanesulfonic acid anhydride (2.07 g, 7.32 mmol) in $CH_2Cl_2$ (2 mL) was added drop-wise and the mixture was stirred at 0° C. for 10 min. 10% $Na_2CO_3$ solution (5 mL) was added and the mixture was diluted with $CH_2Cl_2$ (10 mL) and water (10 mL). The layers were separated and the aqueous layer was extracted with $CH_2Cl_2$ (2×10 mL). The combined organics were washed with brine (10 mL), dried ($Na_2SO_4$), filtered and concentrated. Flash chromatography ($SiO_2$, AcOEt/heptane 1:6) gave pure trifluoromethanesulfonic acid benzo[b] thiophen-4-yl ester (1.72 g, 87%) as a yellow oil.

(b) [3-benzo[b]thiophen-4-yl-5-(4-methoxy-benzyloxy)-phenyl]-pyridin-3-yl-amine. Suzuki coupling: A 10 mL Schlenk flask was charged with (3-p-methoxybenzyloxy-5-bromo-phenyl)-pyridin-3-yl-amine (200 mg, 0.46 mmol), trifluoro-methanesulfonic acid benzo[b]thiophen-4-yl ester (155 mg, 0.55 mmol), $K_3PO_4$ (195 mg, 0.92 mmol) and dry THF (4 mL). The mixture was degassed for 10 min with argon and $PdCl_2$(dppf) $CH_2Cl_2$ complex (19 mg, 0.023 mmol) was added. The dark red mixture was heated at reflux for 6 h, cooled to room temperature and diluted with AcOEt (20 mL) and sat. $NaHCO_3$ (20 mL) The layers were separated and the aqueous layer was extracted with AcOEt (2×20 mL). The combined organics were washed with brine (20 mL), dried ($Na_2SO_4$) and concentrated to provide the crude product. Flash chromatography ($SiO_2$, AcOEt/heptane 2:1) gave [3-benzo[b]thiophen-4-yl-5-(4-methoxy-benzyloxy)-phenyl]-pyridin-3-yl-amine (198 mg, 95%). $^1$H NMR (400 MHz, acetone-$d_6$): δ 8.45 (d, J=2.7 Hz, 1H), 8.10 (d, J=4.7 Hz, 1H), 7.96 (d, J=7.6 Hz, 1H), 7.74 (s, 1H), 7.66 (d, J=5.5 Hz, 1H), 7.58 (t, J=4.1 Hz, 1H), 7.47 (d, J=5.7 Hz, 1H), 7.45-7.38 (m, 4H), 7.23 (dd, J=8.3, 4.6 Hz, 1H), 6.97 (d, J=8.6 Hz, 2H), 6.91 (s, 1H), 6.84 (s, 1H), 6.77 (s, 1H), 5.13 (s, 2H), 3.81 (s, 3H).

Examples 17-18

3-Benzo[B]thiophen-4-yl-5-(pyridin-3-ylamino)-phenol

3-Benzo[B]thiophen-4-yl-2-(4-methoxy-benzyl)-5-(pyridin-3-ylamino)-phenol

[3-benzo[b]thiophen-4-yl-5-(4-methoxy-benzyloxy)-phenyl]-pyridin-3-yl-amine (35 mg, 0.08 mmol) was dissolved in $CH_2Cl_2$ (1 mL) and thioanisole (188 μL, 1.60 mmol) was added. The solution was cooled to 0° C. and trifluoroacetic acid (0.1 mL) was added. The reaction mixture was stirred at room temperature for 5 h and was then quenched with water (3 mL). Sat. $NaHCO_3$ solution was added until pH 7 and the mixture was extracted with $CH_2Cl_2$ (4×10 mL). The combined organics were washed with brine (5 mL), dried ($Na_2SO_4$) and concentrated. Flash chromatography ($SiO_2$, $CH_2Cl_2$/MeOH 95:5) provided 3-benzo[b]thiophen-4-yl-5-(pyridin-3-ylamino)-phenol (17 mg, 58%). 3-Benzo[b]thiophen-4-yl-2-(4-methoxy-benzyl)-5-(pyridin-3-ylamino)-phenol was also isolated from this reaction. 3-Benzo[b]thiophen-4-yl-5-(pyridin-3-ylamino)-phenol $^1$H NMR (300 MHz, methanol-$d_4$): δ 8.2 (d, 1H), 7.8 (d, 1H), 7.7 (d, 1H), 7.45 (d, 1H), 7.4 (two d, 2H), 7.2 (m, 2H), 7.1 (dd, 1H), 6.4 (s, 1H), 6.35 (s, 1H), 6.3 (s, 1H).

3-Benzo[b]thiophen-4-yl-2-(4-methoxy-benzyl)-5-(pyridin-3-ylamino)-phenol $^1$H NMR (400 MHz, methanol-$d_4$): δ 8.27 (d, J=2.1 Hz, 1H), 7.90 (d, J=4.3 Hz, 1H), 7.83 (d, J=8.2 Hz, 1H), 7.53 (ddd, J=8.4, 2.7, 1.2 Hz, 1H), 7.38 (d, J=5.5 Hz, 1H), 7.25 (t, J=7.6 Hz, 1H), 7.20 (dd, J=8.3, 4.8 Hz, 1H), 7.09 (dd, J=7.2, 0.8 Hz, 1H), 6.87 (d, J=5.5 Hz, 1H), 6.76 (d, J=2.3 Hz, 1H), 6.61 (d, J=8.6 Hz, 2H), 6.51 (d, J=8.8 Hz, 2H), 6.47 (d, J=2.3 Hz, 1H), 3.64 (s, 3H).

Example 19

2-Benzyl-3-(1H-indol-4-yl)-5-(pyridin-3-ylamino)-phenol

This was obtained as a by-product in a similar manner to 3-benzo[b]thiophen-4-yl-2-(4-methoxy-benzyl)-5-(pyridin-3-ylamino)-phenol. $^1$H NMR (400 MHz, acetone-$d_6$): δ 10.30 (s, 1H), 8.43 (d, J=2.7 Hz, 1H), 8.30 (s, 1H), 8.02 (dd, J=4.7, 1.4 Hz, 1H), 7.53 (ddd, J=8.2, 2.7, 1.4 Hz, 1H), 7.49 (s, 1H), 7.40 (d, J=8.2 Hz, 1H), 7.33 (d, J=3.1 Hz, 1H), 7.17 (dd, J=8.4, 4.7 Hz, 1H), 7.03-7.09 (m, 3H), 6.96-7.01 (m, 1H), 6.94 (d, J=7.7 Hz, 2H), 6.80-6.84 (m, 2H), 6.67 (d, J=2.3 Hz, 1H), 6.27 (dd, J=3.1, 0.8 Hz, 1H), 4.04 (s, 1H), 3.76 (s, 3H).

Example 20

3-(1H-Indazol-4-yl)-5-(pyridin-3-ylamino)-phenol (a) 4-Bromoindazole. A 350 mL 5-necked flask was charged with benzene (127 mL) and potassium acetate (4.24 g, 43.2 mmol). 3-Bromo-2-methyl-aniline (6.00 g, 42.4 mmol) was added over a period of 5 min to the white suspension followed by acetic anhydride (12.0 mL, 127 mmol). A thick white suspension was formed at this point. The mixture was heated to 80° C. and isopentyl nitrite (8.46 g, 43.2 mmol) was added and the orange suspension was heated at 80° C. overnight. The reaction mixture was cooled, filtered and the filter cake was washed with benzene (3×30 mL). The filtrate was concentrated under reduced pressure to remove the solvent and the residue was heated to 60° C. Conc. HCl (2.0 mL) was added and the mixture was stirred at 70° C. for 1 h. More conc. HCl was added (2.0 mL) and the mixture was stirred at 70° C. for 3 h. The mixture was cooled, diluted with water and toluene until the solid was completely dissolved. The layers were separated and the aqueous layer was extracted with toluene (3×50 mL). The combined organics were concentrated until product began to crystallize. The suspension was cooled to 0° C. and the precipitated solid was filtered to provide 4-bromoindazole as a beige solid (4.45 g, 53%).

(b) 4-Bromo-1-(2-trimethylsilanyl-ethoxymethyl)-1H-indazole. A solution of 4-bromoindazole (585 mg, 2.97 mmol) in dry DMF (5 mL) was cooled to 0° C. under argon. Sodium hydride (60% dispersion, 142 mg, 3.56 mmol) was added and the suspension was stirred for 2 h at 0-5° C. SEM-chloride (265:L, 3.86 mmol) was added at 0-5° C. and the reaction mixture was left to warm to room temperature and stirred for 1 h. The mixture was cooled to 0° C. and quenched with water (15 mL) and was then extracted with isobutyl acetate (3×20 mL). The combined organics were dried ($Na_2SO_4$) and concentrated to provide the crude product as a mixture of isomers. Flash chromatography ($SiO_2$, AcOEt/heptane 6:1) provided pure 4-bromo-1-(2-trimethylsilanyl-ethoxymethyl)-1H-indazole (770 mg, 75%) as a yellow oil.

(c) 3-(1H-Indazol-4-yl)-5-(pyridin-3-ylamino)-phenol. A 50 mL Schlenk flask was charged with 3-p-methoxybenzyloxy-5-(4,4,5,5-tetramethyl-[1,3,2]dioxaborolan-2-yl)-phenyl]-pyridin-3-yl-amine (540 mg, 1.25 mmol), 4-bromo-1-(2-trimethylsilanyl-ethoxymethyl)-1H-indazole (491 mg, 1.50 mmol) and dioxane (6 mL) under argon. Aqueous 2M $K_3PO_4$ (1.30 mL, 2.50 mmol) solution was added and the mixture was heated to 100° C. and a solution of chloro(di-2-norbornylphosphino)(2'dimethylamino-1,1'-biphenyl-2-yl) palladium (II) (35 mg, 0.06 mmol) in degassed dioxane (4 mL) was added. The reaction mixture was stirred at 100° C. for 5 h and was then cooled to room temperature. The reaction mixture was diluted with AcOEt (30 mL) and brine (20 mL) and filtered over Hyflo. The filtrate was transferred to a separatory funnel and the layers were separated. The aqueous layer was extracted with AcOEt (2×20 mL) and the combined organics were dried ($Na_2SO_4$) and concentrated under reduced pressure to give the crude product. Flash chromatography ($SiO_2$, AcOEt/heptane 1:1) gave pure Suzuki product (557 mg, 74%).

The Suzuki product (550 mg, 1.00 mmol) was dissolved in THF (3 mL). Ethylene diamine (0.67 mL, 10.0 mmol) and 1M solution of TBAF in THF (3.0 mL, 3.0 mmol) was added. The reaction solution was heated at reflux for 7 d during which more TBAF solution (3×1.0 mL) was added. The reaction mixture was cooled, diluted with AcOEt (30 mL) and washed with 0.1M HCl (20 mL). The layers were separated and the aqueous layer was washed with AcOEt (2×29 mL). The combined organics were washed with sat. NaHCO$_3$ (20 mL) and water (20 mL) and dried (Na$_2$SO$_4$). Concentration and filtration of the residue through a short plug of silica gel (AcOEt) provided the intermediate product (265 mg). This intermediate was dissolved in dimethylsulfide (3.5 mL) and the solution was cooled to 0° C. BF$_3$.OEt$_2$ (0.294 mL, 2.34 mmol) was added and the mixture was stirred for 2 h at 0° C. and 2 h at room temperature. The reaction mixture was quenched with sat. NaHCO$_3$ solution (10 mL) and extracted with AcOEt (2×10 mL). The combined organics were dried (Na$_2$SO$_4$) and evaporated under reduced pressure. Silica gel chromatography of the crude material (SiO$_2$, 97:2:1) gave 3-(1H-indazol-4-yl)-5-(pyridin-3-ylamino)-phenol (136 mg) which was contaminated with BHT from the THF. The beige solid was taken up in TBME/heptane 1:1 (4 mL) and the suspension stirred at room temperature for 15 min. Filtration of the solid provided 3-(1H-Indazol-4-yl)-5-(pyridin-3-ylamino)-phenol (87 mg, 29%). $^1$H NMR (400 MHz, acetone-d$_6$): δ 12.33 (s, 1H), 8.48 (d, J=2.3 Hz, 1H), 8.46 (s, 1H), 8.19 (s, 1H), 8.10 (d, J=4.7 Hz, 1H), 7.68 (s, 1H), 7.62 (d, J=8.4 Hz, 1H), 7.57 (d, J=8.4 Hz, 1H), 7.42 (t, J=7.7 Hz, 1H), 7.28-7.22 (m, 2H), 7.00 (s, 1H), 6.82 (s, 1H), 6.75 (s, 1H).

Example 21

3-(2-Methyl-1H-indol-4-yl)-5-(pyridin-3-ylamino)-phenol (a) Trifluoro-methanesulfonic acid 1-(tert-butyl-dimethyl-silanyl)-2-methyl-1H-indol-4-yl ester. 4-Hydroxy-2-methylindole (1.00 g, 6.79 mmol) was taken up in dry CH$_2$Cl$_2$ (10 mL). Triethylamine (1.40 mL, 12.2 mmol) was added and the solution was cooled to 0° C. in an ice bath. A solution of trifluoromethanesulfonic acid anhydride (1.23 mL, 7.47 mmol) in CH$_2$Cl$_2$ (2 mL) was added drop-wise. The reaction mixture was stirred for 10 min at 0° C. and was diluted with CHCl$_3$ and extracted with sat. K$_2$CO$_3$. The organic layer was dried over K$_2$CO$_3$, filtered and concentrated under reduced pressure. The residue was taken up in dry THF (3 mL) and sodium hydride (60% dispersion, 360 mg, 9.00 mmol) was added portion wise. After the hydrogen evolution had ceased, a solution of tert-butyldimethylsilyl chloride (1.13 g, 7.50 mmol) in dry THF (2 mL) was added and the mixture was stirred overnight at room temperature. The reaction mixture was diluted with CH$_2$Cl$_2$ (20 mL), washed with sat. NH$_4$Cl solution (10 mL), dried (Na$_2$SO$_4$), filtered and concentrated to provide the crude product. Flash chromatography (SiO$_2$, AcOEt/heptane 1:50) gave pure trifluoro-methanesulfonic acid 1-(tert-butyl-dimethyl-silanyl)-2-methyl-1H-indol-4-yl ester (1.70 g, 64%).

(b) [3-[1-(tert-butyl-dimethyl-silanyl)-2-methyl-1H-indol-4-yl]-5-(4-methoxy-benzyloxy)-phenyl]-pyridin-3-yl-amine. A 50 mL Schlenk flask was charged with 3-p-methoxybenzyloxy-5-(4,4,5,5-tetramethyl-[1,3,2]dioxaborolan-2-yl)-phenyl)-pyridin-3-yl-amine (500 mg, 1.16 mmol), trifluoromethanesulfonic acid 1-(tert-butyl-dimethyl-silanyl)-2-methyl-1H-indol-4-yl ester (546 mg, 1.39 mmol), K$_3$PO$_4$ (504 mg, 1.74 mmol) and dry THF (10 mL). The mixture was degassed for 15 min with argon and PdCl$_2$(dppf) CH$_2$Cl$_2$ complex (64 mg, 0.06 mmol) was added. The dark red mixture was heated at reflux for 18 h, cooled to room temperature and diluted with AcOEt (30 mL) and sat. NaHCO$_3$ (20 mL). The layers were separated and the aqueous layer was extracted with AcOEt (20 mL). The combined organics were washed with brine (20 mL), dried (Na$_2$SO$_4$) and concentrated to provide the crude product. Flash chromatography (SiO$_2$, AcOEt/heptane 1:2) gave [3-[1-(tert-butyl-dimethyl-silanyl)-2-methyl-1H-indol-4-yl]-5-(4-methoxy-benzyloxy)-phenyl]-pyridin-3-yl-amine (264 mg, 41%).

(c) 3-(2-Methyl-1H-indol-4-yl)-5-(pyridin-3-ylamino)-phenol. 1-[3-[1-(tert-Butyl-dimethyl-silanyl)-2-methyl-1H-indol-4-yl]-5-(4-methoxy-benzyloxy)-phenyl]-pyridin-3-yl-amine (133 mg, 0.24 mmol) was dissolved in dimethylsulfide (5 mL). The solution was cooled to 0-5° C. and BF$_3$.OEt$_2$ (30 μL, 0.24 mmol) was added drop-wise. The mixture was stirred for 2 h at 0-5° C. until completion of the reaction. A second equivalent of BF$_3$.OEt$_2$ (2×15 μL) was added during this time. The reaction mixture was quenched with sat. NaHCO$_3$ (5 mL) and was diluted with AcOEt (10 mL). The layers were separated and the aqueous layer was extracted with AcOEt (2×10 mL). The combined organics were dried (Na$_2$SO$_4$), filtered and concentrated. The residue was purified by flash chromatography (SiO$_2$, AcOEt/heptane 4:1) to give 57 mg (59%) of 3-(2-Methyl-1H-indol-4-yl)-5-(pyridin-3-ylamino)-phenol as beige solid. $^1$H NMR (400 MHz, DMSO-d$_6$): δ 10.99 (s, 1H), 9.32 (s, 1H), 8.35 (d, J=2.5 Hz, 1H), 8.31 (s, 1H), 8.00 (dd, J=4.5, 1.5 Hz, 1H), 7.48 (ddd, J=8.4, 2.7, 1.4 Hz, 1H), 7.24-7.19 (m, 2H), 7.01 (t, J=7.6 Hz, 1H), 6.94 (d, J=6.4 Hz, 1H), 6.76 (s, 1H), 6.56 (d, J=1.4 Hz, 1H), 6.50 (t, J=2.0 Hz, 1H), 6.25 (s, 1H), 2.36 (s, 3H).

Example 22

5-(Pyridin-3-ylamino)-[1,1';3',1"]terphenyl-3-ol

Wang resin (2 g, 0.7 mmol/g, 1.4 mmol) in a 50 mL glass reactor was treated with nicotinoyl azide (MW=148.12, 889 mg, 6.0 mmol) in toluene (20 mL), and the reaction mixture was heated to 90° C. for 16 h. The resin was washed then with toluene (4×20 mL), and refluxed in THF (30 mL) for 4 hours. The resin was then washed with THF (4×20 mL), MeOH (4×20 mL), methylene chloride (4×20 mL) and dried under vacuum.

An aliquot of this resin (100 mg, ca 0.06 mmol) was placed in a 50 mL glass reactor. Copper (I) iodide (MW 190.4, 0.06 mmol, 11.4 mg, 1 eq), cesium carbonate (MW 325.82, 98 mg, 0.03 mmol, 5 eq), dioxane (5 mL), 1,3-dibromo-5-(4-methoxybenzyloxy)benzene (MW 372.05, 0.6 mmol, 223 mg, 10 eq) and N,N'-dimethylethylenediamine (MW 88.15, 10.5 mg, 0.12 mmol, 2 eq) were added to the reactor, and the reactor was heated to 110° C. for 16h under N$_2$ atmosphere. After cooling the reaction mixture to room temperature, the resin was filtered, washed with THF (4×3 mL), MeOH (4×3 mL, H$_2$O(4×3 mL), THF (4×3 mL), methylene chloride (4×3 mL) and dried under vacuum.

The intermediate loaded on resin (300 mg, ca 0.6 mmol/g, 0.18 mmol) was placed into a 10 mL microwave reaction tube. Under the N$_2$ atmosphere, 3-biphenylboronic acid (356 mg, 1.8 mmol, 10 eq), 2-(di-t-butylphosphino)biphenyl (53 mg, 0.18 mmol), tris(dibenzylideneacetone)dipalladium 82 mg, 0.09 mmol), cesium carbonate (17 mg, 0.36 mmol, 2 eq) and dry dioxane (3 mL) were added to the resin. The reaction mixture was heated at 120° C. for 2 h using microwave. After cooling the reaction mixture at room temperature, the resin was filtered and washed with MeOH (4×3 mL), H$_2$O (4×3 mL), THF (4×3 mL), MeOH (4×3 mL), methylene chloride (4×3 mL), and dried under high vacuum. The resin was treated with 2% dimethylsulfide, 50% TFA/methylene chloride (2 mL) for 50 min in a 20 mL glass vial. The slurry of resin in cleavage cocktail was filtered through a fritted syringe to a 20 mL glass vial, washed with methylene chloride (2×2 mL), and the combined solution was evaporated by nitrogen blowing under mild heating to give the crude product which was purified by prep TLC (eluted with 20% MeOH in methylene chloride, Rf=0.6), and the product was further purified by preparative SFC to give 5-(pyridin-3-ylamino)-[1,1';3',1"]terphenyl-3-ol (15 mg). $^1$H NMR (400 MHz, CD$_3$OD) δ 8.3 (d, J=2.8, 1H) 7.96 (dd, J=4.8, 1.2, 1H), 7.73 (t, J=1.6, 1H), 7.28-7.64 (m, 9H), 7.25 (dd, J=8.0, 4.4, 1H), 6.85 (t, J=1.6, 1H), 6.69 (t, J=1.8, 1H), 6.61 (t, J=2.0, 1H).

Example 23

3-(6-Nitro-indol-1-yl)-5-(pyridin-3-ylamino)-phenol

The resin-bound (3-bromo-5-p-methoxybenzylphenyl)-3-pyridylamine described in Example 22 (200 mg, ca 0.12 mmol) was placed in a 50 mL glass reactor. Copper (I) iodide (0.6 mmol, 114 mg), potassium phosphate (127 mg, 0.6 mmol), toluene (5 mL), 6-nitroindole (0.6 mmol, 98 mg) and N,N'-dimethylethylenediamine (53 mg, 0.6 mmol) were added to the reactor, and the reactor was heated to 110° C. for 16 h under N$_2$ atmosphere. After cooling the reaction mixture to room temperature, the resin was filtered, washed with THF (4×3 mL), MeOH (4×3 mL), H$_2$O (4×3 mL), DMF (3×4 mL), THF (4×3 mL), methylene chloride (4×3 mL) and dried in vacuo. The resin was treated with 2% dimethylsulfide, 50% TFA/methylene chloride (2 mL) for 20 min in a 20 mL glass vial. The slurry of resin in cleavage cocktail was filtered through a fritted syringe to a 20 mL glass vial, washed with methylene chloride (2×1 mL), and the combined solution was evaporated by nitrogen blowing under mild heating to give the crude product which was confirmed by proton NMR and LC/MS analysis. The crude product was passed through a short pad of silica gel using 5% MeOH in methylene chloride. The combined fractions of product were concentrated, and the residue was further purified by prep SFC to obtain 3-(6-nitro-indol-1-yl)-5-(pyridin-3-ylamino)-phenol (4.3 mg, 0.012 mmol). $^1$H NMR (400 MHz, CD$_3$OD) δ 8.49 (d, J=2.0, 1H), 8.01 (dd, J=8.8, 2.4, 1H), 7.7 (m, 1H), 7.33 (m, 1H), 6.80 (d, J=3.2, 1H), 6.70 (t, J=1.8, 1H), 6.66 (t, J=2.0, 1H), 6.53 (t, J=2.0, 1H).

Example 24

3-(1H-Indol-4-yl)-5-(pyridin-2-ylamino)-phenol 3-p-Methoxybenzyloxy-5-bromo-phenyl)-pyridin-2-yl-amine was prepared from 2-aminopyridine in the same manner as described for the synthesis of 3-p-methoxybenzyloxy-5-bromo-phenyl)-pyridin-3-yl-amine. This material was converted to 3-(1H-indol-4-yl)-5-(pyridin-2-ylamino)-phenol in the same manner as described in Example 21, except that a shorter time was used for the deprotection. $^1$H NMR (400 MHz, acetone d$_6$): δ 10.34 (s, 1H), 8.24 (s, 1H), 8.19 (d, J=3.7 Hz, 1H), 7.54 (t, J=7.8 Hz, 1H), 7.49-7.37 (m, 3H), 7.20-7.12 (m, 2H), 6.90 (d, J=8.4 Hz, 1H), 6.80 (d, J=10.2 Hz, 2H), 6.73 (dd, J=6.9, 5.4 Hz, 1H).

Examples 25-26

[3-Hydroxy-5-(1H-indol-4-yl)-phenyl]-pyridin-3-yl-methanone 2,2,2-Trifluoro-1-{4-[3-hydroxy-5-(pyridine-3-carbonyl)-phenyl]-1H-indol-3-yl}-ethanone (a) 4-(4,4,5,5-tetramethyl-[1,3,2]dioxaborolan-2-yl)-1H-indole. A 50 mL flask was charged with 4-bromoindole (1.00 g, 5.10 mmol), bis(pinacolato)diboron (1.68 g, 6.63 mmol), KOAc (1.44 g, 15.3 mmol) and PdCl$_2$(dppf) CH$_2$Cl$_2$ complex (206 mg, 0.26 mmol) under argon. Dry DMSO (16 mL) was added and the mixture was heated at 90° C. for 4 h. The reaction mixture was cooled, filtered over silica gel and the filter cake was washed with TBME (2×50 mL). The filtrate was washed with brine (3×50 mL), dried (Na$_2$SO$_4$) and concentrated. The residue was purified by flash chromatography (AcOEt/heptane 1:4) to give 4-(4,4,5,5-tetramethyl-[1,3,2]dioxaborolan-2-yl)-1H-indole as an off-white solid (1.24 g, quant.).

(b) 4-(4,4,5,5-tetramethyl-[1,3,2]dioxaborolan-2-yl)-1-triisopropylsilanyl-1H-indole. To a stirred mixture of sodium hydride (60% disp. in oil, 365 mg, 9.1 mmol, 1.06 eq.) in THF (7 mL) at ca. 0° C. was added a THF (8 mL) solution of 4-(4,4,5,5-Tetramethyl-[1,3,2]dioxaborolan-2-yl)-1H-indole (2.1 g, 8.64 mmol, 1 eq., ~75% purity) dropwise under N$_2$. The mixture was stirred at 0°-5° C. for 30 min., whereupon triisopropylsilyl chloride (2.03 mL, 9.5 mmol, 1.1 eq.) was added dropwise. The reaction mixture was stirred under N$_2$ returning to ambient overnight. The reaction was quenched with the addition of water and the organics were extracted into EtOAc. The organic phase was washed with H$_2$O, brine, dried over MgSO$_4$, filtered and concentrated to an oil, which was chromatographed (2% EtOAc/hexanes) yielding 1.59 g of 4-(4,4,5,5-tetramethyl-[1,3,2]dioxaborolan-2-yl)-1-triisopropylsilanyl-1H-indole, as a white solid.

(c) [3-(4-methoxy-benzyloxy)-5-(1-triisopropylsilanyl-1H-indol-4-yl)-phenyl]-pyridin-3-yl-methanone. A 1.6 M solution of n-BuLi in hexane (1.1 eq) was added dropwise to a stirred mixture of 3,5-dibromo-1-p-methoxy-benzyloxy-benzene in dry ether (3 mL) at –78° C. The resulting solution was stirred at –78° C. for 30 min, and then 3-cyanopyridine in dry ether (2 mL) was added drop-wise. The mixture was stirred at –78° C. for 1 h, and then the temperature was allowed to rise to 0° C. 2N HCl was added with stirring, and the ether layer was extracted twice with 2N HCl. The aqueous was basified with 1N NaOH solution and extracted with methylene chloride three times. The combined organic phase was washed with brine, dried, and concentrated to afford the crude product which was further purified by flash chromatography (3:1 hexane/EtOAc).

[3-Bromo-5-(4-methoxy-benzyloxy)-phenyl]-pyridin-3-yl-methanone and chloro(di-2-norbornylphosphino)(2'dimethylamino-1,1'-biphenyl-2-yl)palladium (II) (15 mg) were dissolved in dioxane (6 mL) under nitrogen. A solution of 4-(4,4,5,5-tetramethyl-[1,3,2]dioxaborolan-2-yl)-1-triisopropylsilanyl-1H-indole in dioxane (6 mL) followed by aqueous 2M K$_3$PO$_4$ (0.6 mL, 1.2 mmol) was added and the mixture was heated at reflux for 24 hr. The reaction mixture was then diluted with methylene chloride and the organic phase was washed with brine. After removal of the solvents, the crude product was purified by flash chromatography (3:1 hexane/EtOAc) to afford the [3-(4-methoxy-benzyloxy)-5-(1-triisopropylsilanyl-1H-indol-4-yl)-phenyl]-pyridin-3-yl-methanane.

(d) [3-Hydroxy-5-(1H-indol-4-yl)-phenyl]-pyridin-3-yl-methanone and 2,2,2-Trifluoro-1-{4-[3-hydroxy-5-(pyridine-3-carbonyl)-phenyl]-1H-indol-3-yl}-ethanone. To the [3-(4-methoxy-benzyloxy)-5-(1-triisopropylsilanyl-1H-indol-4-yl)-phenyl]-pyridin-3yl-methanone in 1 mL of methylene chloride and 1 mL of Me$_2$S was added 2 mL of TFA. The resulting solution was stirred at room temperature for 2 h. TLC then indicated that all starting material was gone. Methylene chloride was added to the reaction mixture, followed by sat. NaHCO$_3$(aq). The aqueous phase was then adjusted to a pH of 6, and was extracted with methylene chloride twice. The organic phases were then dried over Na$_2$SO$_4$, filtered and concentrated to provide the crude product. The crude product was further purified by prep. TLC to give [3-hydroxy-5-(1H-indol-4-yl)-phenyl]-pyridin-3-yl-methanone. $^1$H NMR (400 MHz, CD$_3$OD) δ 8.97 (d, J=2.0 Hz, 1H), 8.70 (dd, J=4.8, 1.6 Hz, 1H), 8.21 (dt, J=8.0, 2.0 Hz, 1H), 7.54-7.50 (m, 2H), 7.46-7.45 (m, 1H), 7.41 (d, J=8.0 Hz, 1H), 7.27 (d, J=3.2 Hz, 1H), 7.22 (t, J=2.0 Hz, 1H), 7.17 (t, J=8.0 Hz, 1H), 7.09 (d, J=7.6 Hz, 1H), 6.61 (d, J=3.2 Hz, 1H).

2,2,2-Trifluoro-1-{4-[3-hydroxy-5-(pyridine-3-carbonyl)-phenyl]-1H-indol-3-yl}-ethanone was also formed in this reaction and was isolated by chromatography. $^1$H NMR (400 MHz, CD$_3$OD) δ 8.92 (d, J=1.2 Hz, 1H), 8.70 (dd, J=3.6, 1.6 Hz, 1H), 8.20-8.19 (m, 1H), 8.14 (td, J=4.0, 1.5 Hz, 1H), 7.53 (d, J=7.2 Hz, 1H), 7.45 (dd, J=7.6, 4.8 Hz, 1H), 7.37 (t, J=7.2 Hz, 1H), 7.23 (dd, J=3.2. 1.6 Hz, 1H), 7.21 (d, J=7.6 Hz, 1H), 7.07 (t, J=1.6 Hz, 1H), 7.06-7.05 (m, 1H).

Example 27

[3-Hydroxy-5-(1H-indol-4-yl)-phenyl]-pyridin-3-yl-methanone oxime

[3-(4-methoxy-benzyloxy)-5-(1-triisopropylsilanyl-1H-indol-4-yl)-phenyl]-pyridin-3-yl-methanone (50 mg, 0.085 mmol) and hydroxyamine hydrochloride (29 mg, 0.42 mmol) in 2 mL of ethanol was heated to reflux. After 2 hrs, the reaction was completed. The solvent was removed under reduced pressure. The crude product was redissolved in EtOAc and washed with 5% NaHCO$_3$ (aq) and brine. The organic phase was dried and concentrated to provide [3-(4-Methoxy-benzyloxy)-5-(1-triisopropylsilanyl-1H-indol-4-yl)phenyl]-pyridin-3-yl-methanone oxime which was further purified by prep TLC (10:1 EtOAc/MeOH). [3-(4-Methoxy-benzyloxy)-5-(1-triisopropylsilanyl-1H-indol-4-yl)-phenyl]pyridin-3-yl-methanone oxime was hydrolyzed as described above to give [3-hydroxy-5-(1H-indol-4-yl)-phenyl]-pyridin-3-yl-methanone oxime. NMR for the mixture of isomers: $^1$H NMR (400 MHz, CD$_3$OD): δ 8.69 (d, J=1.8 Hz, 0.3H), 8.59 (d, J=1.4 Hz, 0.7H), 8.55 (dd, J=5.1, 1.6 Hz, 0.7H), 8.50 (dd, J=4.9, 1.4 Hz, 0.3H), 7.95 (dt, J=5.0, 2.6 Hz, 0.3H), 7.89 (dt, J=4.9, 2.5 Hz, 0.7H), 7.53 (dd, J=7.8, 4.9 Hz, 0.7H), 7.42 (dd, J=8.1, 4.8 Hz, 0.3H), 7.37-7.32 (m, 1H), 7.23 (d, J=3.2 Hz, 0.3H), 7.22 (d, J=3.2 Hz, 0.7H), 7.20-7.00 (m, 5H), 6.91 (dd, J=2.3, 1.6 Hz, 0.7H), 6.79 (dd, J=2.4, 1.4 Hz, 0.3H), 6.59 (d, J=3.1 Hz, 0.3H), 6.49 (d, J=3.2 Hz, 0.7H).

Examples 28-29

(6-Chloro-pyridin-3-yl)-[3-hydroxy-5-(1H-indol-4-yl)-phenyl]-methanone

[3-Hydroxy-5-(1H-indol-4-yl)-phenyl]-(6-hydroxypyridin-3-yl)-methanone

In a similar manner to Example 25, compounds (6-chloro-pyridin-3-yl)-[3-hydroxy-5-(1H-indol-4-yl)-phenyl]-methanone and [3-hydroxy-5-(1H-indol-4-yl)-phenyl]-(6-hydroxypyridin-3-yl)-methanone were prepared from 6-chloro-nicotinonitrile and 6-(4-methoxy-benzyloxy)-nicotinonitrile. (6-Chloro-pyridin-3-yl)-[3-hydroxy-5-(1H-indol-4-yl)-phenyl]-methanone $^1$H NMR (400 MHz, CD$_3$OD): δ 8.78 (d, 1H, J=1.6 Hz), 8.18 (dd, 1H, J=8.0, 2.0 Hz), 7.56 (d, 1H, J=8.0 Hz), 7.50 (d, 1H, J=1.6 Hz), 7.45 (dd, 1H, J=2.4, 1.2 Hz), 7.41 (d, 1H, J=8.0 Hz), 7.28 (d, 1H, J=2.8 Hz), 7.20-7.19 (m, 1H), 7.16 (d, 1H, J=8.0 Hz), 7.09 (d, 1H, J=7.2 Hz), 6.58 (d, 1H, J=3.2 Hz).

[3-Hydroxy-5-(1H-indol-4-yl)-phenyl]-(6-hydroxypyridin-3-yl)-methanone $^1$H NMR (400 MHz, CD$_3$OD): δ 8.08-8.05 (m, 2H), 7.41-7.40 (m, 1H), 7.39 (d, 1H, J=7.2 Hz), 7.37-7.36 (m, 1H), 7.28 (d, 1H, J=3.6 Hz), 7.16 (t, 1H, J=8.0 Hz), 7.10-7.07 (m, 2H), 6.59 (d, 1H, J=3.2 Hz), 6.57 (m, 1H).

Example 30

6-(1H-indol-4-yl)-2-(pyridin-3-ylamino)-pyrimidin-4-ol (a) 4-Benzyloxy-6-chloro-pyrimidin-2-ylamine. In a 30 mL glass vial 725 mg of benzyl alcohol (6.7 mmol) and 293 mg of NaH (60%, 7.32 mmol) were stirred in THF (10 mL) at 0°-25° C. for 30 minutes. A solution of 4,6-dichloropyrimidin-2-ylamine (1.00 g, 6.1 mmol) in DMF was added and the vial was capped/sealed and the mixture was heated at 100° C. for 1 hour. The reaction was cooled and water was added, followed by extraction with CH$_2$Cl$_2$. The combined organics were washed (water, brine), dried (MgSO$_4$) and concentrated to afford 1.5 g of crude 4-benzyloxy-6-chloro-pyrimidin-2-ylamine (~80% pure) as a yellow solid. This material was used for the next reaction without further purification.

(b) (4-Benzyloxy-6-chloro-pyrimidin-2-yl)-pyridin-3-yl-amine. The 4-benzyloxy-6-chloro-pyrimidin-2-ylamine (0.5 g, 80% pure, 2.1 mmol) was combined with 349 mg of 3-bromopyridine (2.21 mmol), 245 mg of sodium t-butoxide (2.55 mmol), 159 mg of rac-BINAP (0.255 mmol), and 233 mg of Pd(dba)$_3$ in 30 mL toluene in a tube. The vessel was evacuated, then filled with nitrogen and sealed. The reaction was stirred at 110° C. overnight. The reaction was then cooled and water was added. The mixture was extracted with 3×20 mL ethyl acetate. The crude mixture was purified by preparative TLC plates (silica) with 95:5 methylene chloride/MeOH solvent mixture to afford 80 mg of (4-benzyloxy-6-chloro-pyrimidin-2-yl)-pyridin-3-yl-amine as a brown foam.

(c) [4-Benzyloxy-6-(1-triisopropylsilanyl-1H-indol-4-yl)-pyrimidin-2-yl]-pyridin-3-yl-amine. DMF (1 mL) and dioxane (2 mL) were added through a septum to a nitrogen-purged microwave tube containing (4-benzyloxy-6-chloro-pyrimidin-2-yl)-pyridin-3-yl-amine (80 mg, 0.256 mmol), potassium carbonate (71 mg, 0.50 mmol), Pd(PPh$_3$)$_4$ (59 mg, 0.51 mmol), and 4-(4,4,5,5-tetramethyl-[1,3,2]dioxaborolan-2-yl)-1-triisopropylsilanyl-1H-indole (153 mg, 0.384 mmol). The mixture was subjected to microwave conditions 100 W/130° C. for 1 hour. SFC/MS analysis showed mostly the desired product. A small amount of product with loss of the TIPS group was seen as well. The reaction mixture was cooled to room temperature and filtered through Celite®. The solvent was concentrated and the crude mixture was purified by a short silica column with 99:1 methylene chloride/MeOH solvent mixture to afford 100 mg of [4-benzyloxy-6-(1-triisopropylsilanyl-1H-indol-4-yl)-pyrimidin-2-yl]-pyridin-3-yl-amine (~75% pure by SFC/MS). This material was used without further purification.

(d) 6-(1H-Indol-4-yl)-2-(pyridin-3-ylamino)-pyrimidin-4-ol. [4-Benzyloxy-6-(1-triisopropylsilanyl-1H-indol-4-yl)- pyrimidin-2-yl]-pyridin-3-yl-amine (50 mg, 0.91 mmol) was dissolved in 1 mL of 1:1 TFA/methylene chloride. Several drops of $Me_2S$ were added and the resulting mixture was stirred overnight at room temperature. SFC/MS indicated the TIPS group was removed. The solvent was removed by nitrogen and the residue was re-dissolved in 1 mL MeOH and treated with hydrogen over palladium on carbon for 18 hours. SFC/MS indicated that the benzyl group was successfully removed. The reaction was filtered through Celite® and the filtrate was concentrated. Crude product was purified by prep. TLC plate to afford 1.8 mg of 6-(1H-indol-4-yl)-2-(pyridin-3-ylamino)-pyrimidin-4-ol as a yellow oil. $^1$H NMR (400 MHz, acetone-$d_6$): δ 12.25 (bs, 1H), 10.38 (s, 1H), 9.35 (d, J=2.3 Hz, 1H), 8.71 (d, J=8.4 Hz, 1H), 8.09 (d, J=4.7 Hz, 1H), 7.70 (q, J=2.8 Hz, 1H), 7.52 (d, J=8.2 Hz, 1H), 7.42 (d, J=2.5 Hz, 1H), 7.21 (m, 2H), 7.06 (d, J=2.1 Hz, 1H), 6.44 (s, 1H).

Example 31

[4-(1H-indol-4-yl)-6-methoxy-pyrimidin-2-yl]-pyridin-3-ylamine

In a similar manner to Example 30, [4-(1H-indol-4-yl)-6-methoxy-pyrimidin-2-yl]-pyridin-3-ylamine was prepared from 4-chloro-6-methoxy-pyrimidin-2-ylamine. $^1$H NMR (400 MHz, acetone-$d_6$): δ 10.50 (bs, 1H), 9.07 (d, J=2.0 Hz, 1H), 8.87 (bs, 1H), 8.51 (dt, 1H), 8.21 (m, J=2.0 Hz, 1H), 7.69 (d, J=2.8 Hz, 1H), 7.60 (d, J=3.0 Hz, 1H), 7.47 (t, J=2.8 Hz, 1H), 7.30 (q, J=4.4 Hz, 1H), 7.25 (t, J=7.8 Hz, 1H), 7.09 (m, 1H), 6.80 (s, 1H), 4.03 (s, 3H).

Example 32

1-[3-Hydroxy-5-(pyridin-3-ylamino)-phenyl]-1H-indole-5-carbonitrile

[3-Bromo-5-(4-methoxy-benzyloxy)-phenyl]-pyridin-3-yl-amine (193 mg, ca 0.5 mmol) was placed in a 5 mL glass reactor. Copper (I) iodide (0.5 mmol, 96 mg), potassium phosphate (213 mg, 1 mmol), toluene (3 mL), 5-cyanoindole (1.0 mmol, 142 mg) and N,N'-dimethylethylenediamine (53 mg, 0.6 mmol) were added to the reactor, and the sealed reactor was heated to 110° C. for 24 h. After cooling the reaction mixture to room temperature, the solution was filtered through a short pad of Celite®, and the filtrate was concentrated. The residue was extracted with methylene chloride and aqueous sodium bicarbonate solution. The organic layer was dried, concentrated, and the residue was purified by silica gel column (Biotage) using 2% MeOH in methylene chloride. Pure fractions were treated with 10% dimethylsulfide, 50% TFA in methylene chloride for 2 min. The volatiles were evaporated immediately with a stream of nitrogen with mild heating. The residue was purified by passing through a short pad of silica gel using 15% MeOH in methylene chloride as eluent to give 1-[3-hydroxy-5-(pyridin-3-ylamino)-phenyl]-1H-indole-5-carbonitrile (17.5 mg, 0.054 mmol) which solidified on standing. $^1$H NMR (400 MHz, $CD_3OD$) δ 8.33 (d, J=2.4, 1H), 8.00-8.30 (m, 2H), 7.65 (d, J=8.8, 1H), 7.61 (m, 1H), 7.54 (d, J=3.2, 1H), 7.43 (dd, J=8.4, 1.2, 1H), 7.28 (dd, J=8.4, 4.8, 1H), 6.74 (d, J=3.2, 1H), 6.48 (m, 1H), 6.20-6.42 (m, 2H).

Example 33

N-[3-(1H-Indol-4-yl)-phenyl]-N-pyridin-3-yl-acetamide (a) N-(3-Pyridyl)acetamide. To a solution of 3-aminopyridine (9.4 g, 0.1 mmol) in methylene chloride (40 mL) were added acetic anhydride (0.11 mmol), TEA (0.11 mmol), and the reaction mixture was stirred for 4 h at room temperature. The solution was extracted with saturated sodium bicarbonate (10 mL; use of minimal amount of water is essential because the product is well soluble in water). The organic layer was dried, concentrated to a volume of methylene chloride amounting 20 mL from which crystal of product formed on standing at room temperature. The crystal was collected, washed with methylene chloride to obtain N-(3-pyridyl)acetamide (9.8 g, 72%).

(b) N-(3-Bromo-phenyl)-N-pyridin-3-yl-acetamide. To a mixture of N-(3-pyridyl)acetamide (272 mg, 2 mmol), CuI (powdered, 190 mg, 1 mmol), cesium carbonate (651 mg, 2 mmol), 1,3-dibromobenzene (2.3 g, 10 mmol) in dioxane (10 mL) was added N,N'-dimethylethylenediamine (176 mg, 2 mmol), then the mixture was heated to 110° C. for 16 h. After cooling to room temperature, the reaction mixture was filtered through a pad of Celite®, and the filtrate was concentrated. The residue was extracted with methylene chloride (5 mL) and water (15 mL), and the organic layer was dried, concentrated by nitrogen blowing with heating to remove most of the excess 1,3-dibromobenzene. The residue was passed through a short pad of silica gel column using methylene chloride/MeOH (10:1) as eluent. The combined solution was concentrated under high vacuum to give N-(3-bromo-phenyl)-N-pyridin-3-yl-acetamide.

(c) N-Pyridin-3-yl-N-[3-(1-triisopropylsilanyl-1H-indol-4-yl)-phenyl]-acetamide. To the N-(3-bromo-phenyl)-N-pyridin-3-yl-acetamide (97 mg, 0.33 mmol) in a 10 mL microwave reaction tube was added 4-(4,4,5,5-tetramethyl-[1,3,2]dioxaborolan-2-yl)-1-triisopropylsilanyl-1H-indole (Example 25) (158 mg, 0.4 mmol), potassium phosphate (140 mg, 0.66 mmol), chloro(di-2-norbornylphosphino)(2'-dimethyl amino-1,1'-biphenyl-2-yl)palladium (II) (39 mg, 0.07 mmol) and dioxane (3 mL), and the reaction mixture was flushed with nitrogen before sealing the tube. After heating the reaction tube to 100° C. for 3 h using microwave, the reaction was cooled to room temperature, filtered through a pad of Celite®, and the filtrate was concentrated. The residue was purified by Silica gel column chromatography using 5% MeOH in methylene chloride to give N-pyridin-3-yl-N-[3-(1-triisopropylsilanyl-1H-indol-4-yl)-phenyl]-acetamide.

(d) The pure fractions of N-pyridin-3-yl-N-[3-(1-triisopropylsilanyl-1H-indol-4-yl)-phenyl]-acetamide obtained from the previous reaction were treated with 10% dimethylsulfide, 50% TFA in methylene chloride (1 mL) for 10 min. The volatiles were evaporated with a stream of nitrogen with mild heating. The residue was purified by prep SFC to obtain N-[3-(1H-indol-4-yl)-phenyl]-N-pyridin-3-yl-acetamide (33 mg, 0.1 mmol) as an oil. $^1$H NMR: (400 MHz, $CD_3OD$) δ 8.61 (d, J=2.0, 1H), 8.43 (bs, 1H), 7.70, (d, J=7.2, 2H), 7.61 (s, 1H), 7.52 (m, 1H), 7.39 (d, J=8.0, 1H), 7.23-7.33 (m, 4H), 7.15 (dd, J=7.2, 0.4, 1H), 6.58 (d, J=2.4, 1H), 2.16 (s, 3H).

Example 34

[3-(1H-indol-4-yl)-phenyl]-pyridin-3-yl-amine, hydrochloride salt

A solution of N-(3-bromo-phenyl)-N-pyridin-3-yl-acetamide (15 mg, 0.045 mmol) in 6 N HCl (1 mL) was heated to 110° C. for 1 h in a sealed reaction tube. Volatiles were evaporated by a gentle stream of nitrogen, and the residue was dissolved in $H_2O$, passed through a short pad of cotton filter. The clear solution was concentrated to give a 12.5 mg of [3-(1H-indol-4-yl)-phenyl]-pyridin-3-yl-amine, hydrochloride salt. $^1$H NMR (400 MHz, $D_2O$) δ 8.15 (t, J=4.6 Hz, 1H), 7.66 (s, 1H), 7.60 (s, 1H), 7.56-7.52 (2H), 7.46 (d, 4.8 Hz, 1H), 7.43-7.38 (4H), 7.31 (d, J=8.8 Hz, 1H), 7.07 (t, J=7.0 Hz, 1H), 7.00 (d, J=8.4 Hz, 1H).

Example 35

3-(1H-Indol-4-yl)-5-(1-oxy-pyridin-3-ylamino)-phenol (a) 3-Bromo-5-(4-methoxy-benzyloxy)-phenyl]-(1-oxy-pyridin-3-yl)-amine. To a solution of [3-bromo-5-(4-methoxy-benzyloxy)-phenyl]-pyridin-3-yl-amine (200 mg, 0.52 mmol) in dichloromethane (10 mL) at 0° C. was added MCPBA (taken as 77% purity) (170 mg, 0.78 mmol). The yellow solution turned into orange red immediately after the addition. The mixture was kept at 0° C. over the weekend. The solvent was removed, the residue was taken up in EtOAc, washed with 5% aqueous $Na_2S_2O_3$ solution and saturated $NaHCO_3$ several times. The organic extracts were separated, dried and concentrated. The crude was loaded directly to Celite®, and purification by ISCO afforded 3-bromo-5-(4-methoxy-benzyloxy)-phenyl]-(1-oxy-pyridin-3-yl)-amine as a light yellow solid (70.4 mg, 34%).

(b) 3-(1H-Indol-4-yl)-5-(1-oxy-pyridin-3-ylamino)-phenol. To a tube purged with nitrogen containing [3-bromo-5-(4-methoxy-benzyloxy)-phenyl]-(1-oxy-pyridin-3-yl)-amine (24 mg, 0.06 mmol), 4-(4,4,5,5-tetramethyl-[1,3,2]dioxaborolan-2-yl)-1-triisopropylsilanyl-1H-indole (24 mg, 0.06 mmol) and chloro(di-2-norbornylphosphino)(2'-dimethylamino-1,1'-biphenyl-2-yl)palladium (II) (3.4 mg, 0.006 mmol) in dioxane (2 mL) was added 2M aqueous $K_3PO_4$ (0.03 mL, 0.12 mmol). The tube was sealed and heated in a microwave reactor at 120° C. for an hour. SFC-MS indicated the formation of the desired product. The mixture was concentrated, and the residue was taken up in $CH_2Cl_2$, filtered through Celite®. The filtrate was washed with brine, dried and concentrated to give the crude product 3-(4-methoxy-benzyloxy)-5-(1-triisopropylsilanyl-1H-indol-4-yl)-phenyl]-(1-oxy-pyridin-3-yl)-amine as a brown oil, which was used directly in the next step without further purification.

To the crude 3-(4-methoxy-benzyloxy)-5-(1-triisopropyl-silanyl-1H-indol-4-yl)-phenyl]-(1-oxy-pyridin-3-yl)-amine (taken as 0.17 mmol) in DMS (5 mL) in an ice-NaCl bath was added $BF_3.OEt_2$ (0.43 mL, 3.4 mmol) dropwise. The resulting mixture was stirred in the cooling bath for 30 mins. Saturated aqueous $NaHCO_3$ was added to quench the reaction, and the pH was adjusted to around 7, extracted with ethyl acetate several times. The combined organic extracts were washed with brine, dried and concentrated. SFC-MS analysis indicated that PMB protective group had been completely removed, but TIPS group was largely unremoved. The reaction mixture was concentrated and subjected to the TBAF treatment.

To the crude 3-(1-oxy-pyridin-3-ylamino)-5-(1-triisopropylsilanyl-1H-indol-4-yl)-phenol (taken as 0.17 mmol) in THF (5 mL) at 0° C. was added 1M TBAF in THF (0.17 mL, 0.17 mmol). After stirring at 0° C. for half an hour, the mixture was concentrated, partitioned between EtOAc and a mixture of water and brine. The organic layer was separated, dried and concentrated. Purification by ISCO gave the desired product mixed with TBAF. Further purification by preparative SFC afforded the 3-(1H-indol-4-yl)-5-(1-oxy-pyridin-3-ylamino)-phenol as a light yellow solid (5.8 mg, 10.8% for 3 steps). $^1$H NMR (400 MHz, $CD_3OD$): δ 8.09-8.05 (m, 1H), 7.75-7.70 (m, 1H), 7.36 (d, J=8.0 Hz, 1H), 7.32-7.29 (m, 2H), 7.26 (d, J=3.3 Hz, 1H), 7.14 (t, J=7.7 Hz, 1H), 7.06 (d, J=7.2 Hz, 1H), 6.93 (t, J=1.6 Hz, 1H), 6.87 (t, J=1.8 Hz, 1H), 6.63-6.59 (m, 2H).

Example 36

5-[3-Hydroxy-5-(1H-indol-4-yl)-phenylamino]-pyridin-2-ol (a) 6-Benzyloxy-pyridin-3-ylamine. 6-Chloro-pyridin-3-ylamine (0.1 g, 0.78 mmol) in 1M NaOBn/BnOH (2 mL, 2 mmol) was heated at 120° C. for 16 h. TLC indicated the disapperance of starting material. The mixture was concentrated and loaded directly to Celite®. Chromatographic purification the 6-benzyloxy-pyridin-3-ylamine as an orange oil (68.3 mg, 44%).

(b) (6-benzyloxy-pyridin-3-yl)-[3-bromo-5-(4-methoxy-benzyloxy)-phenyl]-amine. A dry tube was charged with 6-benzyloxy-pyridin-3-ylamine (68 mg, 0.34 mmol), 1,3-dibromo-5-(4-methoxy-benzyloxy)-benzene (126 mg, 0.34 mmol), NaOtBu (46 mg, 0.48 mmol), $Pd_2(dba)_3$ (3.1 mg, 0.0034 mmol), BINAP (6.3 mg, 0.01 mmol) and degassed toluene (2 mL). The tube was heated in a microwave reactor at 120° C. for 1 h. After cooling down to room temperature, the reaction mixture was loaded directly on Celite®. Chromatographic purification afforded 6-benzyloxy-pyridin-3-yl)-[3-bromo-5-(4-methoxy-benzyloxy)-phenyl]-amine as a yellow oil (78.8 mg, 47%).

(c) (6-benzyloxy-pyridin-3-yl)-[3-(4-methoxy-benzyloxy)-5-(1-triisopropylsilanyl-1H-indol-4-yl)-phenyl]-amine. To a tube purged with nitrogen containing (6-benzyloxy-pyridin-3-yl)-[3-bromo-5-(4-methoxy-benzyloxy)-phenyl]-amine (78 mg, 0.158 mmol), 4-(4,4,5,5-tetramethyl-[1,3,2]dioxaborolan-2-yl)-1-triisopropylsilanyl-1H-indole (63 mg, 0.158 mmol) and chloro(di-2-norbornylphosphino)(2'dimethylamino-1,1'-biphenyl-2-yl)palladium (II) (9.0 mg, 0.0158 mmol) in dioxane (2 mL) was added 2M aqueous $K_3PO_4$ (0.16 mL, 0.32 mmol). The tube was sealed and heated in a microwave reactor at 120° C. for an hour. The crude mixture was loaded directly to Celite®, and purified by chromatography to afford the -[3-hydroxy-5-(1H-indol-4-yl)-phenylamino]-pyridin-2-ol as a white solid (62 mg, 57.1%).

(d) 5-[3-hydroxy-5-(1H-indol-4-yl)-phenylamino]-pyridin-2-ol. (6-Benzyloxy-pyridin-3-yl)-[3-(4-methoxy-benzyloxy)-5-(1-triisopropyl-silanyl-1H-indol-4-yl)-phenyl]-amine (62 mg, 0.09 mmol)) and 10% Pd/C (20 mg) in anhydrous DMF (2 mL) was hydrogenated at 50 psi over the weekend. SFC-MS analysis indicated that the benzyl group was cleaved, but the 4-methoxybenzyl group was intact, along with about 30% starting material. More Pd/C was added to the reaction mixture and the hydrogenation was kept on. After shaking at 50 psi for another 24 h, the reaction mixture was diluted with a large amount of EtOAc, and filtered through Celite® to remove palladium catalyst. The filtrate was concentrated, and the residue was taken up in dichloromethane, washed with brine, and dried over MgSO$_4$. After filtration and concentration, the crude product was used directly in the next reaction.

To the crude product from the previous experiment (taken as 0.09 mmol) in dimethyl sulfide (5 mL) in an ice-NaCl bath was added BF$_3$.OEt$_2$ (0.23 mL, 1.8 mmol) dropwise. The resulting mixture was stirred in the cooling bath for 10 minutes. A few drops of MeOH was added, and the mixture was kept for another 10 minutes. Saturated aqueous NaHCO$_3$ was added to quench the reaction, and the pH was adjusted to around 7, extracted with ethyl acetate several times. The combined organic extracts were washed with brine, dried and concentrated to give 5-[3-hydroxy-5-(1-triisopropylsilanyl-1H-indol-4-yl)-phenylamino]-pyridin-2-ol.

A solution of 5-[3-hydroxy-5-(1-triisopropylsilanyl-1H-indol-4-yl)-phenylamino]-pyridin-2-ol (taken as 0.126 mmol) in TFA/CH$_2$Cl$_2$ (5 mL/5 mL)) was stirred at 0° C. for 1 h. The resulting mixture was concentrated, and saturated aqueous NaHCO$_3$ was added. The pH was adjusted to around 7 and the mixture was extracted with EtOAc (with a small amount of MeOH) several times. After filtering through Celite®, the organic layer was separated, dried and concentrated. Purification by chromatography and further purification by prep-SFC afforded 5-[3-hydroxy-5-(1H-indol-4-yl)-phenylamino]-pyridin-2-ol as a brown solid (0.6 mg, 1.5%). $^1$H NMR (400 MHz, CDCl$_3$): δ 7.62 (dd, J=9.7, 2.8 Hz, 1H), 7.33 (d, J=8.0 Hz, 1H), 7.28 (d, J=2.9 Hz, 1H), 7.23 (d, J=3.3 Hz, 1H), 7.11 (t, J=7.7 Hz, 1H), 7.01 (d, J=7.2 Hz, 1H), 6.63-6.55 (m, 4H), 6.26 (t, J=2.0 Hz, 1H).

Example 37

3-(1H-Indol-4-yl)-5-(pyridin-3-yloxy)-phenol

A mixture of the 3,5-dibromo-1-p-methoxy-benzyloxy-benzene (250 mg, 0.672 mmol) and 3-hydroxypyridine (128 mg, 1.34 mmol) and 96 mg (0.67 mmol) copper oxide in 3 mL of collidine was treated with sodium hydride (27 mg, 0.67 mmol) in a stirred tube. After 10 minutes to allow off-gassing, the tube was sealed and the reaction mixture was heated to 210° C. bath temperature overnight. It was then cooled and treated with ethyl acetate and aqueous ammonium hydroxide, and filtered through Celite®. The phases were separated, and the aqueous phase was extracted with additional ethyl acetate. The combined organics were washed with brine, dried over sodium sulfate and concentrated. The product was chromatographed (33% ethyl acetate/hexane) to give 66 mg of product 3-[3-bromo-5-(4-methoxy-benzyloxy)-phenoxy]-pyridine (25% yield). This material was converted to 3-(1H-indol-4-yl)-5-(pyridin-3-yloxy)-phenol as described in Example 35. $^1$H NMR (400 MHz, CD$_3$OD): δ 11.22 (s, 1H), 9.77 (s, 1H), 8.43 (d, J=2.5 Hz, 1H), 8.36 (d, J=3.5 Hz, 1H), 7.53 (ddd, J=8.4, 2.7,1.3 Hz, 1H), 7.42 (dd, J=8.4, 4.7Hz, 1H), 7.36 (dd, J=5.4, 2.4Hz, 2H), 7.11 (t, J=7.7 Hz, 1H), 7.00 (d, J=7.0 Hz, 1H), 6.86 (s, 1H), 6.65 (s, 1H), 6.45 (s, 1H), 6.40 (t, J=2.0 Hz, 1H).

Example 38

3-(Pyridin-3-ylamino)-5-quinolin-8-yl-phenol 3-p-Methyoxybenzyloxy-5-(4,4,5,5-tetramethyl-[1,3,2]dioxaborolan-2-yl)-phenyl]-pyridin-3-yl-amine was coupled with 8-bromoquinoline as described for Example 8. Deprotection was carried out as described for Example 35. $^1$H NMR (400 MHz, CD$_3$OD): δ 8.83 (dd, J=4.2, 1.7 Hz, 1H), 8.35 (dd, J=8.5, 2.0 Hz, 2H), 7.94-7.88 (m, 2H), 7.72 (dd, J=7.0, 1.2 Hz, 1H), 7.66-7.58 (m, 2H), 7.51 (dd, J=8.3, 4.2 Hz, 1H), 7.24 (dd, J=8.4, 4.7 Hz, 1H), 6.85 (t, J=1.5 Hz, 1H), 6.65 (s, 2H).

Example 39

4-[3-Hydroxy-5-(pyridin-3-ylamino)-phenyl]-1,3-dihydro-indol-2-one 3-p-Methoxybenzyloxy-5-(4,4,5,5-tetramethyl-[1,3,2]dioxaborolan-2-yl)-phenyl]-pyridin-3-yl-amine was coupled with 4-bromooxindole (T. Kosuge, et al.; *Chem. Pharm. Bull.* 33:1414 (1985) as described for Example 8. Deprotection was carried out as described for Example 35. $^1$H NMR (400 MHz, acetone-d$_6$): δ 9.47 (s, 1H), 8.60 (bs, 1H), 8.45 (d, J=2.7 Hz, 1H), 8.09 (dd, J=4.7, 1.4 Hz, 1H), 7.67 (s, 1H), 7.58 (ddd, J=8.2, 2.8,1.4 Hz, 1H), 7.29-7.21 (m, 2H), 7.03 (dd, J=7.8, 0.6 Hz, 1H), 6.89 (d, J=7.6 Hz, 1H), 6.78 (t, J=1.7 Hz, 1H), 6.69 (t, J=2.0 Hz, 1H), 6.61 (t, J=1.8 Hz, 1H), 3.56 (s, 2H).

Example 40

N-[5'-Hydroxy-3'-(pyridin-3-ylamino)-biphenyl-3-yl]-methanesulfonamide (a) 3,5-Dibromoanisole. 3,5-Dibromonitrobenzene (21.07 g, 75 mmol), freshly powdered potassium hydroxide (7.57 g, 135 mmol) and tetrabutylammonium bromide (2.42 g, 7.5 mmol) were suspended in tetramethyl urea (80 mL). To the resulting brown slurry was slowly added a solution of methanol (4.81 g, 6.09 mL, 150 mmol) in 20 mL of tetramethyl urea at room temperature over a period of 15 minutes. The mixture was stirred for 24 hours at room temperature then poured on ice (150 g) and was extracted with t-butyl methyl ether (3×250 mL). The combined organics were dried over magnesium sulfate and concentrated to give the crude product which was distilled (124° C., 10 Torr) to provide 16.74 g (84%) of 3,5-dibromoanisole as a pale yellow solid.

(b) 3,5-Dibromophenol. 3,5-Dibromoanisole (15.57 g, 58.5 mmol) and tetrabutylammonium bromide (1.0 g, 3.1 mmol) were suspended in 48% hydrobromic acid (100 mL) and refluxed for 3 days. After cooling to room temperature the reaction mixture was extracted with methylene chloride (3×60 mL). The combined organic layers were washed with water, dried over magnesium sulfate, and evaporated. The crude product was filtered over a pad of silica gel (ethyl acetate/heptane 10:1). After removal of the solvent, 14.23 g (97% of 3,5-dibromophenol was obtained as pale brown needles.

(c) 3,5-Dibromotriisopropylsiloxybenzene. 3,5-Dibromoanisole 23.07 g, 56.5 mmol was dissolved in DMF (100 mL) under dry argon and cooled to 0° C. The 60% sodium hydride (2.49 g, 62.3 mmol) was added in small portions over a period of 15 min. Stirring was continued for 15 min., followed by dropwise addition of triisopropylsilyl chloride (12.1 mL, 56.5 mmol). The mixture was warmed to room temperature and stirred for 20 hours. The reaction mixture was diluted with t-butyl methyl ether and washed with water and brine. The organic layer was dried over magnesium sulfate and concentrated to give the crude product which was purified by silica gel chromatography. The product was obtained as a colorless oil (23.1 g, 100% yield).

(d) N-[5'-Hydroxy-3'-(pyridin-3-ylamino)-biphenyl-3-yl]-methanesulfonamide. 3,5-Dibromotriisopropylsiloxybenzene was converted to (3-bromo-5-triisopropylsilanyloxy-phenyl)-pyridin-3-yl-amine by the method of Example 5.

(3-Bromo-5-triisopropylsilanyloxy-phenyl)-pyridin-3-yl-amine was coupled with 3-methanesulfonamide-phenylboronic acid in a similar manner as described for Example 10 to give N-[3'-(Pyridin-3-ylamino)-5'-triisopropylsilanyloxy-biphenyl-3-yl]-methanesulfonamide.

The crude N-[3'-(Pyridin-3-ylamino)-5'-triisopropylsilanyloxy-biphenyl-3-yl]-methanesulfonamide was dissolved in 0.5 mL of THF and treated with 0.3 mL of 1M tetra t-butyl ammonium fluoride solution in THF. After ½ hour at room temperature, saturated sodium bicarbonate solution and ethyl acetate were added. The pH was 7-8. The phases were separated. The ethyl acetate phase was washed with brine, dried over sodium sulfate and evaporated. The product was chromatographed with 5%, then 10% methanol/methylene chloride to give 61 mg of an oily solid. This material was treated with a little methanol, filtered and dried to give 23 mg of N-[5'-hydroxy-3'-(pyridin-3-ylamino)-biphenyl-3-yl]-methanesulfonamide an off-white solid. $^1$H NMR (400 MHz, acetone-$d_6$): δ 8.54 (s, 2H), 8.45 (d, J=2.3 Hz, 1H), 8.10 (d, J=4.7 Hz, 1H), 7.65 (s, 1H), 7.61-7.56 (m, 2H), 7.45-7.36 (m, 2H), 7.32 (d, J=7.4 Hz, 1H), 7.24 (dd, J=8.2, 4.7 Hz, 1H), 6.89 (s, 1H), 6.69 (s, 2H), 3.03 (s, 3H).

Example 41

3-(1-Methyl-1H-indol-7-yl)-5-(pyridin-3-ylamino)-phenol (a) N-Methyl-7-bromoindole. A heterogenous solution of 7-bromoindole (196 mg, 1.0 mmol), potassium carbonate (414 mg, 0.3 mmol) and methyl iodide (1.42 g, 10 mmol) in acetone (20 mL) was vigorously stirred for 5 days at room temperature. The reaction mixture was filtered through a pad of Celite®, and the filtrate was concentrated to give the desired N-methyl-7-bromoindole (MW=210.07, 150 mg, 0.72 mmol, 72%) as a white solid.

(b) 3-(1-Methyl-1H-indol-7-yl)-5-(pyridin-3-ylamino)-phenol. 3-p-Methoxybenzyloxy-5-(4,4,5,5-tetramethyl-[1,3,2]dioxaborolan-2-yl)-phenyl]-pyridin-3-yl-amine was coupled with N-methyl-7-bromoindole as described for Example 8. Deprotection was carried out as described for Example 35. $^1$H NMR (400 MHz, CD$_3$OD) δ 8.29 (d, J=2.8 Hz, 1H), 7.92 (dd, J=4.8, 1.2 Hz, 1H), 7.55 (ddd, J=7.2, 2.8, 1.6 Hz, 1H), 7.48 (dd, J=8.0, 1.2 Hz, 1H), 7.22 (dd, J=4.8, 1.2 Hz, 1H), 7.01 (d, J=3.6 Hz, 1H), 7.00-6.90 (2H), 6.62 (t, J=2.0 Hz, 1H), 6.55 (t, J=1.6 Hz, 1H), 6.42 (d, J=3.2 Hz, 1H), 6.41 (t, J=1.6 Hz, 1H), 3.43 (s, 3H).

Example 42

3-Benzo[1,3]dioxol-5-yl-5-(pyridin-3-ylamino)-phenol

[3-bromo-5-(4-methoxy-benzyloxy)-phenyl]-pyridin-3-yl-amine (MW=385.26, 193 mg, 0.5 mmol) was placed into a 10 mL microwave reaction tube and placed under a nitrogen atmosphere. 3,4-(Methylenedioxy)phenylboronic acid (MW=165.94, 124 mg, 0.75 mmol), 2-(di-t-butylphosphino) biphenyl (FW 298.41, 15 mg, 0.05 mmol), tris(dibenzylideneacetone)dipalladium (FW 915.75, 13 mg, 0.025 mmol), cesium carbonate (FW 325.82, 326 mg, 1 mmol) and dry dioxane (3 mL) were added to the tube. After flushing with nitrogen, the reaction tube was sealed and heated at 110° C. for 16 h. After cooling, the reaction mixture was filtered through a short pad of silica gel, and the filtrate was concentrated. The residue was purified by silica gel column chromatography using 2% methanol in methylene chloride to give [3-benzo[1,3]dioxol-5-yl-5-(4-methoxy-benzyloxy)-phenyl]-pyridin-3-yl-amine.

3-Benzo[1,3]dioxol-5-yl-5-(4-methoxy-benzyloxy)-phenyl]-pyridin-3-yl-amine was treated with 10% dimethylsulfide, 50% TFA in methylene chloride for 2 min. The volatiles were evaporated immediately by evaporation with a gentle stream of nitrogen with mild heating. The residue was extracted with aqueous sodium bicarbonate/methylene chloride, and the organic layer was dried and concentrated. The residue was subjected to preparative TLC with 10% MeOH in methylene chloride to provide pure fractions of 3-benzo[1,3]dioxol-5-yl-5-(pyridin-3-ylamino)-phenol (15.5 mg). $^1$H NMR (400 MHz, CD$_3$OD) δ 8.28 (d, J=2.8 Hz, 1H), 7.93 (d, J=4.8, 1.2 Hz, 1H), 7.54 (ddd, J=7.2, 2.8, 1.6 Hz, 1H), 7.21 (dd, J=8.4, 4.8 Hz, 1H), 6.99 (dd, J=7.2, 1.6 Hz, 1H), 6.80 (dd, J=7.2, 1.6 Hz, 1H), 6.70 (t, J=1.8 Hz, 1H), 6.55 (t, J=1.8 Hz, 1H), 6.53 (t, J=2.0 Hz, 1H).

Example 43

3-(1H-Indol-5-yl)-5-(pyridin-3-ylamino)-phenol 3-p-Methoxybenzyloxy-5-(4,4,5,5-tetramethyl-[1,3,2]dioxaborolan-2-yl)-phenyl]-pyridin-3-yl-amine was coupled with 5-bromoindole as described for Example 8. Deprotection was carried out as described for Example 35. $^1$H NMR (400 MHz, CD$_3$OD) δ 8.31 (d, J=2.8 Hz, 1H), 7.93 (d J=4.0 Hz, 1H), 7.72 (d, J=1.6 Hz, 1H), 7.57 (ddd, J=7.2, 3.6, 2.0 Hz, 1H), 7.39 (d, J=8.4 Hz, 1H), 7.31 (dd, J=8.8, 2.0 Hz, 1H), 7.25 (m, 1H), 7.22 (d, J=3.2 Hz, 1H), 6.86 (t, J=1.6 Hz, 1H), 6.69 (t, J=2.0 Hz, 1H), 6.53 (t, J=2.0 Hz, 1H), 6.46 (dd, J=3.2, 0.4 Hz, 1H).

Example 44

3-(1H-Indol-4-yl)-5-(pyridin-4-ylamino)-phenol (a) [3-Bromo-5-(4-methoxy-benzyloxy)-phenyl]-pyridin-4-yl-amine. A solution of 4-aminopyridine (71 mg, 0.75 mmol), 1,3-dibromo-5-(4-methoxybenzyloxy)benzene (372.0 mg, 1.0 mmol), XantPhos (56 mg, 0.1 mmol), (dibenzylideneacetone)dipalladium (46 mg, 0.05 mmol), and sodium tert-butoxide (192 mg, 2.0 mmol) in dioxane (3 mL) was flushed with nitrogen and the reaction tube was sealed. The reaction mixture was heated to 110° C. for 16 h. After cooling, the reaction mixture was filtered through a short pad of Celite®, and the filtrate was concentrated. The residue was purified by silica gel column chromatography using 5% MeOH in methylene chloride to give a major fraction as a desired product which crystallized from a mixed solution of MeOH/methylene chloride. The crystals were filtered and washed with methanol to give 115 mg of pure 3-bromo-5-(4-methoxy-benzyloxy)-phenyl]-pyridin-4-yl-amine.

(b) 3-(1H-indol-4-yl)-5-(pyridin-4-ylamino)-phenol. The 3-bromo-5-(4-methoxy-benzyloxy)-phenyl]-pyridin-4-yl-amine was converted to 3-(1H-indol-4-yl)-5-(pyridin-4-ylamino)-phenol as described in Example 35. $^1$H NMR (400 MHz, CD$_3$OD) δ 8.09 (2H), 7.36 (m, 1H), 7.27 (m, 1H), 7.14 (1H), 7.07 (1H), 6.98-6.70 (3H), 6.88 (t, J=2.0 Hz, 1H), 6.68 (t, J=2.0 Hz, 1H), 6.62 (dd, J=3.2, 0.4 Hz, 1H).

Example 45

3-(1H-Indol-7-yl)-5-(pyridin-3-ylamino)-phenol

This compound was prepared from 7-bromoindole by the same method as Example 43. $^1$H NMR (400 MHz, CD$_3$OD) δ 8.32 (d, J=2.8 Hz, 1H), 7.94 (dd, J=4.8, 1.2 Hz, 1H), 7.64-7.58 (2H), 7.50 (dd, J=3.6, 1.6 Hz, 1H), 7.80-7.30 (1H), 7.24 (m, 1H), 7.21 (d, J=3.2 Hz, 1H), 7.09-7.02 (1H), 6.82 (m, 1H), 6.66 (m, 1H), 6.62 (m, 1H), 6.47 (d, J=3.2 Hz, 1H).

Example 46

3-(1H-Indol-4-yl)-5-(pyrazin-2-ylamino)-phenol

This compound was prepared by the method described in Example 44. $^1$H NMR (400 MHz, CD$_3$OD) δ 8.14 (d, J=1.6 Hz, 1H), 8.10 (dd, J=4.4, 1.6 Hz, 1H), 7.80 (d, J=2.8 Hz, 1H), 7.38 (t, J=1.6 Hz, 1H), 7.35 (m, 1H), 7.29 (t, J=2.2 Hz, 1H), 7.25 (d, J=3.2 Hz, 1H), 7.14 (t, J=7.6 Hz, 1H), 7.08 (dd, J=7.2, 1.2 Hz, 1H), 6.80 (dd, J=2.0, 1.2 Hz, 1H), 6.70 (dd, J=3.2, 1.2 Hz, 1H).

Example 47

3-(1H-Indol-6-yl)-5-(pyridin-3-ylamino)-phenol 3-p-Methoxybenzyloxy-5-(4,4,5,5-tetramethyl-[1,3,2]dioxaborolan-2-yl)-phenyl]-pyridin-3-yl-amine was coupled with 6-bromoindole as described for Example 8. Deprotection was carried out as described for Example 35. $^1$H NMR (400 MHz, CD$_3$OD) δ 8.31 (d, J=2.8 Hz, 1H), 7.93 (dd, J=4.8, 1.2 Hz, 1H), 7.57 (ddd, J=8.0, 3.6, 1.2 Hz, 1H), 7.54 (m 1H), 7.26-7.22 (3H), 6.87 (t, J=1.8 Hz, 1H), 6.71 (t, J=1.8 Hz, 1H), 6.54 (t, J=2.0 Hz, 1H), 6.14 (dd, J=3.2, 0.8 Hz, 1H).

Example 48

3-(Pyridin-3-ylamino)-5-quinolin-3-yl-phenol 3-p-Methoxybenzyloxy-5-(4,4,5,5-tetramethyl-[1,3,2]dioxaborolan-2-yl)-phenyl]-pyridin-3-yl-amine was coupled with 3-bromoquinoline as described for Example 8. Deprotection was carried out as described for Example 42. $^1$H NMR (400 MHz, CD$_3$OD) δ 8.97 (b, 1H), 8.35 (bs, 1H), 8.30 (bs, 1H), 7.98-7.96 (2H), 7.88 (d, J=8.8 Hz, 1H), 7.68 (t, J=7.6 Hz, 1H), 7.55-7.52 (2H), 7.23 (m, 1H), 6.87 (bs, 1H), 6.73 (d, J=1.2 Hz, 1H), 6.65 (d, J=1.6 Hz, 1H).

Example 49

3-(1H-Indol-4-yl)-5-(methyl-pyridin-3-yl-amino)-phenol (a) [3-Bromo-5-(4-methoxy-benzyloxy)-phenyl]-methyl-pyridin-3-yl-amine. To a suspension of KH (30% in mineral oil, 2.0 mmol, mineral oil washed with ether) in dry ether (20 mL) at 0° C. was added 3-bromo-5-(4-methoxy-benzyloxy)-phenyl]-pyridin-3-yl-amine (385 mg, 1.0 mmol) in THF/ether (1:1, 10 mL), and the reaction mixture was stirred for 10 min at 0° C. Iodomethane (74 μL, 1.2 mmol) was added, and the reaction mixture was stirred for 1 h at 0° C. (TLC analysis showed complete disappearance of the starting material). The reaction mixture was extracted with water, and the organic layer which was diluted with ethyl acetate was concentrated. The residue was dissolved in ethyl acetate, dried, concentrated. The crude product was passed through a short pad of silica gel using ethyl acetate/methylene chloride (1:5) to give pure 3-bromo-5-(4-methoxy-benzyloxy)-phenyl]-methyl-pyridin-3-yl-amine (340 mg, 0.85 mmol, 85%).

(b) 3-(1H-Indol-4-yl)-5-(methyl-pyridin-3-yl-amino)-phenol. 3-Bromo-5-(4-methoxy-benzyloxy)-phenyl]-methyl-pyridin-3-yl-amine was converted to 3-(1H-indol-4-yl)-5-(methyl-pyridin-3-yl-amino)-phenol as described for Example 35. $^1$H NMR (400 MHz, CD$_3$OD) δ 8.20 (d, J=2.7 Hz, 1H), 7.95 (dd, J=4.8, 1.3 Hz, 1H), 7.40 (ddd, J=8.4, 2.9, 1.4 Hz, 1H), 7.34 (dt, J=4.5, 2.7 Hz, 1H), 7.28-7.22 (m, 2H), 7.12 (t, J=7.7 Hz, 1H), 7.03 (dd, J=7.4, 1.0 Hz, 1H), 6.92 (dd, J=2.3, 1.4 Hz, 1H), 6.90-6.89 (m, 1H), 6.57 (t, J=2.1 Hz, 1H), 6.54 (dd, J=3.3, 1.0 Hz, 1H), 3.33 (s, 3H).

Example 50

3-(1-Methyl-1H-indol-4-yl)-5-(pyridin-3-ylamino)-phenol

1-Methyl-4-(4,4,5,5-tetramethyl-[1,3,2]dioxaborolan-2-yl)-1H-indole was prepared from 4-(4,4,5,5-tetramethyl-[1,3,2]dioxaborolan-2-yl)-1H-indole and methyl iodide, and was coupled with [3-bromo-5-(4-methoxy-benzyloxy)-phenyl]-pyridin-3-yl-amine in the same manner as described for Example 25. Deprotection was carried out as described for Example 34 to give 3-(1-methyl-1H-indol-4-yl)-5-(pyridin-3-ylamino)-phenol. $^1$H NMR (400 MHz, CD$_3$OD): δ 8.32 (br s, 1H), 7.98 (br s, 1H), 7.70 (d, J=8.6 Hz, 1H), 7.42-7.36 (m, 1H), 7.34 (d, J=8.2 Hz, 1H), 7.21 (d, J=7.2 Hz, 1H), 7.19-7.17 (m, 1H), 7.08 (dd, J=7.2, 0.8 Hz, 1H), 6.91 (t, J=1.7 Hz, 1H), 6.79-6.77 (m, 1H), 6.62 (t, J=2.0 Hz, 1H), 6.59 (d, J=3.1 Hz, 1H), 3.81 (s, 3H).

Example 51

[3-(1H-indol-4-yl)-5-methoxy-phenyl]-pyridin-3-yl-amine (3-Bromo-5-methoxy-phenyl)-pyridin-3-yl-amine was prepared from 1,3-dibromo-5-methoxy-benzene and pyridin-3-ylamine as described for Example 36. This material was converted to [3-(1H-indol-4-yl)-5-methoxy-phenyl]-pyridin-3-yl-amine by the method of Example 35. $^1$H NMR (400 MHz, CDCl$_3$): δ 8.44 (d, J=2.7 Hz, 1H), 8.34 (br s, 1H), 8.17 (dd, J=4.7, 1.2 Hz, 1H), 7.50 (ddd, J=8.2, 2.7, 1.4 Hz, 1H), 7.39 (d, J=8.2 Hz, 1H), 7.27-7.23 (m, 2H), 7.19-7.15 (m, 2H), 6.98 (t, J=1.7 Hz, 1H), 6.89 (dd, J=2.2, 1.4 Hz, 1H), 6.73 (t, J=2.1 Hz, 1H), 6.64 (t, J=2.2 Hz, 1H), 5.81 (s, 1H), 3.84 (s, 3H).

Example 52

3-(3-Chloro-1H-indol-4-yl)-5-(pyridin-3-ylamino)-phenol (a) 3-Chloro-4-(4,4,5,5-tetramethyl-[1,3,2]dioxaborolan-2-yl)-1-triisopropylsilanyl-1H-indole. To a solution of 4-(4,4,5,5-tetramethyl-[1,3,2]dioxaborolan-2-yl)-1-triisopropylsilanyl-1H-indole (250 mg, 0.626 mmol) in anhydrous DMF under N$_2$ is added N-chlorosuccinimide (88 mg, 0.659 mmol) followed by a catalytic amount of trifluoroacetic acid. The resulting solution was stirred for 18 h at room temperature. The solvent was removed in vacuo and the residue was dissolved in ethyl acetate, washed with water and brine, dried over magnesium sulfate, filtered and concentrated to afford 3-chloro-4-(4,4,5,5-tetramethyl-[1,3,2]dioxaborolan-2-yl)-

1-triisopropylsilanyl-1H-indole as a pale yellow solid (98%) which was used without further purification.

(b) 3-(3-Chloro-1H-indol-4-yl)-5-(pyridin-3-ylamino)-phenol. 3-Chloro-4-(4,4,5,5-tetramethyl-[1,3,2]dioxaborolan-2-yl)-1-triisopropylsilanyl-1H-indole was converted to 3-(3-chloro-1H-indol-4-yl)-5-(pyridin-3-ylamino)-phenol as described in Example 35. $^1$H NMR (400 MHz, CD$_3$OD): δ 8.31 (br s, 1H), 7.90 (br s, 1H), 7.59 (d, J=8.2 Hz, 1H), 7.35 (d, J=8.2 Hz, 1H), 7.24-7.18 (m, 2H), 7.15 (t, J=7.7 Hz, 1H), 6.92 (d, J=7.2 Hz, 1H), 6.66 (s, 1H), 6.59 (s, 1H), 6.50 (s, 1H).

Example 53

[3-(1H-indol-4-yl)-5-methyl-phenyl]-pyridin-3-yl-amine

3-Bromo-5-methyl-phenyl)-pyridin-3-yl-amine was prepared from 1,3-dibromo-5-methyl-benzene and pyridin-3-ylamine as described in Example 36. It was converted to [3-(1H-indol-4-yl)-5-methyl-phenyl]-pyridin-3-yl-amine as described in Example 35. $^1$H NMR (400 MHz, CD$_3$OD): δ 8.31 (br s, 1H), 7.93 (d, J=4.1 Hz, 1H), 7.56 (ddd, J=8.4, 2.5,1.2 Hz, 1H), 7.35 (d, J=8.2 Hz, 1H), 7.26-7.21 (m, 3H), 7.14 (t, J=7.6 Hz, 1H), 7.09 (s, 1H), 7.05 (d, J=7.3 Hz, 1H), 6.93 (s, 1H), 6.59 (d, J=3.1 Hz, 1H), 2.38 (s, 3H).

Example 54

[3-Hydroxy-5-(1H-indol-4-yl)-phenyl]-pyrazin-2-yl-methanone

In a similar manner to Example 25, compound 3-hydroxy-5-(1H-indol-4-yl)-phenyl-pyrazin-2-yl-methanone was prepared from pyrazine-2-carbonitrile. $^1$H NMR (400 MHz, CD$_3$OD): δ 9.14 (d, J=1.2 Hz, 1H), 8.77 (d, J=2.4 Hz, 1H), 8.73-8.72 (m, 1H), 7.80 (t, J=1.6 Hz, 1H), 7.44-7.43 (m, 1H), 7.41-7.40 (m, 1H), 7.39 (d, J=8.0 Hz, 1H), 7.28 (d, J=3.2 Hz, 1H), 7.15 (t, J=8.0 Hz, 1H), 7.08 (d, J=7.2 Hz, 1H), 6.54 (d, J=3.2 Hz, 1H).

Example 55

[3-Hydroxy-5-(1H-indol-4-yl)-phenyl]-(6-hydroxymethyl-pyridin-3-yl)-methanone (a) [3-Bromo-5-(4-methoxy-benzyloxy)-phenyl]-(6-methyl-pyridin-3-yl)-methanone. A 1.6 M solution of n-BuLi in hexane (1.8 mmol) was added dropwise to a stirred mixture of 1,3-dibromo-5-(4-methoxy-benzyloxy)-benzene (600 mg, 1.6 mmol) in dry ether (6 mL) at −78° C. The resulting solution was stirred at −78° C. for 30 min, and then 6-methyl-nicotinonitrile (190 mg, 1.6 mmol) in dry ether (4 mL) was added dropwise. The mixture was stirred at −78° C. for 1 h, and then the temperature was allowed to rise to 0° C. 2N HCl was added with stirring. The aqueous was then basified with 1N NaOH solution and extracted with methylene chloride three times. The combined organic phase was washed with brine, dried, and concentrated to afford the crude product which was further purified by flash chromatography (3:1 hexane/EtOAc) to yield the desired product as a yellow oil (600 mg, 90%).

(b) Acetic acid 5-[3-bromo-5-(4-methoxy-benzyloxy)-benzoyl]-pyridin-2-ylmethyl ester. To a stirred solution of 3-bromo-5-(4-methoxy-benzyloxy)-phenyl]-(6-methyl-pyridin-3-yl)-methanone (388 mg, 0.94 mmol) in dry methylene chloride (20 mL) at 0° C. was added dropwise a solution of MCPBA (0.371 mg, 1.50 mmol) in methylene chloride (10 mL). The resulting solution was stirred overnight. TLC indicated that the completion of the reaction. The organic phase was washed with sat. NaHCO$_3$, dried, and concentrated. The crude product was then dissolved in Ac$_2$O (2 mL) and the resulting solution was stirred at 150° C. for 30 min. TLC indicated that the completion of the reaction. The reaction mixture was then poured into an ice cold sat. NaHCO$_3$ solution and stirred for 20 min. The aqueous phase was the extracted with EtOAc for three times. After removal of the solvents, the crude product was purified by flash chromatography (4:1 Hexane/EtOAc) to afford the titled product (0.140 mg, 31% over two steps).

(c) Acetic acid 5-[3-(4-methoxy-benzyloxy)-5-(1-triisopropylsilanyl-1H-indol-4-yl)-benzoyl]-pyridin-2-ylmethyl ester. To the mixture of acetic acid 5-[3-bromo-5-(4-methoxy-benzyloxy)-benzoyl]-pyridin-2-ylmethyl ester (145 mg, 0.308 mmol) and chloro(di-2-norbornylphosphino)(2'dimethylamino-1,1'-biphenyl-2-yl)palladium (II) (15 mg) in dioxane (6 mL) under nitrogen was added a solution of 4-(4,4,5,5-tetramethyl-[1,3,2]dioxaborolan-2-yl)-1-triisopropylsilanyl-1H-indole (129 mg, 0.324 mmol) in dioxane (6 mL), followed by 2M K$_3$PO$_4$ (0.3 mL, 0.6 mmol). The resulting solution was heated at reflux for 24 hr. The reaction mixture was then diluted with methylene chloride and the organic phase washed with brine, dried, and concentrated. After removal of the solvents, the crude product was purified by flash chromatography (3:1 hexane/EtOAc) to afford the titled product which was carried to the next step without further purification.

(d) [3-Hydroxy-5-(1H-indol-4-yl)-phenyl]-(6-hydroxymethyl-pyridin-3-yl)-methanone. To the compound from the previous step, 5 mL of MeOH and 2 mL of H$_2$O was added solid K$_2$CO$_3$ (0.21 g, 1.5 mmol). The resulting reaction mixture was stirred at room temperature for 2 hr. At the end of the reaction, EtOAc was added and the organic phase washed with brine. After removal of the solvents, the crude product was purified by flash chromatography (EtOAc/Hexane 1:1) to afford (6-hydroxymethyl-pyridin-3-yl)-[3-(4-methoxy-benzyloxy)-5-(1-triisopropylsilanyl-1H-indol-4-yl)-phenyl]-methanone (120 mg, 60% over two steps).

In a similar manner to Example 25, [3-hydroxy-5-(1H-indol-4-yl)-phenyl]-(6-hydroxymethyl-pyridin-3-yl)-methanone was obtained from the above synthetic intermediate. $^1$H NMR (400 MHz, CD$_3$OD): δ 8.88 (d, J=3.2 Hz, 1H), 8.24 (dd, J=8.0, 2.0 Hz, 1H), 7.70 (d, J=8.0 Hz, 1H), 7.49 (m, 1H), 7.42-7.41 (m, 1H), 7.38 (d, J=8.0 Hz, 1H), 7.27 (d, J=3.2 Hz, 1H), 7.19-7.18 (m, 1H), 7.15 (t, J=8.0 Hz, 1H), 7.07 (d, J=7.2 Hz, 1H), 6.58 (d, J=3.6 Hz, 1H), 4.68 (s, 2H).

Example 56

3-(1-Hydroxy-1-pyridin-3-yl-ethyl)-5-(1H-indol-4-yl)-phenol 3,5-Dibromotriisopropylsiloxybenzene was converted to pyridin-3-yl-[3-(1-triisopropylsilanyl-1H-indol-4-yl)-5-triisopropylsilanyloxy-phenyl]-methanone by the method described in Example 25.

To pyridin-3-yl-[3-(1-triisopropylsilanyl-1H-indol-4-yl)-5-triisopropylsilanyloxy-phenyl]-methanone (64 mg, 0.102 mmol) in 2 mL of THF was added 2 mL of MeMgCl (1 M in THF) at 0° C. After 30 min TLC indicated the completion of the reaction. Brine was then added to quench the reaction. The aqueous phase was then extracted with EtOAc. The combined organic phases were dried and concentrated to afford the crude product. The residue was again dissolved in 2 mL of THF and followed by addition of 1 mL of TBAF (3M in THF)

at 0° C. After 30 min the solvent of the reaction was removed under reduced pressure. The residue was dissolved in EtOAc and the organic phase washed with water and brine, dried and concentrated to afford the crude product. The crude product was then purified by prep. TLC to afford 3-(1-hydroxy-1-pyridin-3-yl-ethyl)-5-(1H-indol-4-yl)-phenol (13 mg, 39% over two steps). $^1$H NMR (400 MHz, CD$_3$OD): δ 8.66 (d, 1H, J=1.6 Hz), 8.36 (d, 1H, J=4.0 Hz), 7.93 (d, 1H, J=6.4 Hz), 7.36 (dd, 1H, J=8.0, 4.8 Hz), 7.33 (d, 1H, J=8.0 Hz), 7.21 (d, 1H, J=2.8 Hz), 7.20-7.19 (m, 1H), 7.11 (t, 1H, J=8.0 Hz), 7.01 (d, 1H, J=7.2 Hz), 6.99-6.98 (m, 1H), 6.99 (t, 1H, J=1.6 Hz), 6.46 (d, 1H, J=3.6 Hz), 1.98 (s, 3H).

Example 57

[3-Hydroxy-5-(1H-indol-4-yl)-phenyl]-(6-methyl-pyridin-3-yl)-methanone

In a similar manner to Example 25, compound [3-hydroxy-5-(1H-indol-4-yl)-phenyl]-(6-methyl-pyridin-3-yl)-methanone was prepared from 6-methyl-nicotinonitrile. $^1$H NMR (400 MHz, CD$_3$OD): δ 8.83 (d, 1H, J=2.0 Hz), 8.13 (dd, 1H, J=8.0, 2.0 Hz), 7.46 (t, 1H, J=1.6 Hz), 7.44 (d, 1H, J=8.0 Hz), 7.40 (dd, 1H, J=2.2, 1.2 Hz), 7.38 (d, 1H, J=8.0 Hz), 7.27 (d, 1H, J=3.2 Hz), 7.17-7.16 (m, 1H), 7.14 (d, 1H, J=8.0 Hz), 7.07 (d, 1H, J=7.2 Hz), 6.58 (d, 1H, J=3.6 Hz), 2.60 (s, 3H).

Example 58

(6-Amino-pyridin-3-yl)-[3-hydroxy-5-(1H-indol-4-yl)-phenyl]-methanone

3-Bromo-5-(4-methoxy-benzyloxy)-phenyl]-(6-chloro-pyridin-3-yl)-methanone was mixed with aqueous NH$_4$OH (25%, 2 mL). The resulting reaction mixture was stirred at 136° C. overnight. Methylene chloride was then added to dilute the reaction mixture. The organic phase was dried and concentrated to afford crude (6-amino-pyridin-3-yl)-[3-bromo-5-(4-methoxy-benzyloxy)-phenyl]-methanone which was further purified by flash chromatography.

In a similar manner to Example 25, (6-amino-pyridin-3-yl)-[3-bromo-5-(4-methoxy-benzyloxy)-phenyl]-methanone was converted to (6-amino-pyridin-3-yl)-[3-hydroxy-5-(1H-indol-4-yl)-phenyl]-methanone. $^1$H NMR (400 MHz, CD$_3$OD): δ 8.46 (d, 1H, J=2.4 Hz), 7.97 (dd, 1H, J=7.2, 2.4 Hz), 7.40-7.37 (m, 2H), 7.36-7.34 (m, 1H), 7.28 (d, 1H, J=3.2 Hz), 7.16 (t, 1H, J=8.0 Hz), 7.10 (d, 1H, J=1.2 Hz), 7.08-7.06 (m, 1H), 6.63 (s, 1H), 6.61-6.60 (m, 1H).

Example 59

[3-Hydroxy-5-(1H-indol-4-yl)-phenyl]-(5-methyl-pyridin-3-yl)-methanone

In a similar manner to Example 25, compound [3-hydroxy-5-(1H-indol-4-yl)-phenyl]-(5-methyl-pyridin-3-yl)-methanone was prepared from 5-methyl-nicotinonitrile. $^1$H NMR (400 MHz, CD$_3$OD): δ 8.74 (d, 1H, J=1.2 Hz), 8.57 (d, 1H, J=1.6 Hz), 8.06-8.05 (m, 1H), 7.57 (t, 1H, J=1.6 Hz), 7.43-7.42 (m, 1H), 7.40 (d, 1H, J=8.0 Hz), 7.28 (d, 1H, J=3.2 Hz), 7.21-7.20 (m, 1H), 7.17 (t, 1H, J=8.0 Hz), 7.08 (d, 1H, J=7.2 Hz), 6.60 (d, 1H, J=1.2 Hz), 2.22 (s, 3H).

Example 60

(2-Chloro-pyridin-3-yl)-[3-hydroxy-5-(1H-indol-4-yl)-phenyl]-methanone

In a similar manner to Example 25, compound (2-chloro-pyridin-3-yl)-[3-hydroxy-5-(1H-indol-4-yl)-phenyl]-methanone was prepared from 2-chloro-nicotinonitrile. $^1$H NMR (400 MHz, CD$_3$OD): δ 8.50 (dd, 1H, J=5.2, 2.0 Hz), 7.89 (dd, 1H, J=7.6, 2.0 Hz), 7.49 (dd, 1H, J=7.6, 4.8 Hz), 7.45 (t, 1H, J=1.6 Hz), 7.43-7.42 (m, 1H), 7.38 (d, 1H, J=8.0 Hz), 7.26-7.23 (m, 2H), 7.15 (t, 1H, J=8.0 Hz), 7.04 (dd, 1H, J=7.2, 1.2 Hz), 6.53 (d, 1H, J=3.6 Hz).

Example 61

[3-(1H-indol-4-yl)-5-nitro-phenyl]-pyridin-3-yl-amine

This compound was prepared from 3,5-dibromonitrobenzene in the same manner as Example 53. $^1$H NMR (400 MHz, CDCl$_3$): δ 8.63 (s, 1H), 8.50 (d, J=2.3 Hz, 1H), 8.30 (d, J=4.3 Hz, 1H), 8.10 (t, J=1.8 Hz, 1H), 7.84 (t, J=2.1 Hz, 1H), 7.61 (t, J=1.8 Hz, 1H), 7.55 (ddd, J=8.3, 2.6, 1.3 Hz, 1H), 7.45 (d, J=8.2 Hz, 1H), 7.25-7.30 (m, 2H), 7.17 (d, J=7.3 Hz, 1H), 6.83 (s, 1H), 6.65-6.67 (m, 1H), 6.30 (s, 1H)

Example 62

2-Adamantan-1-yl-4-(hydroxy-pyridin-3-yl-methyl)-phenol (a) 2-Adamantan-1-yl-4-bromo-phenoxy)-tert-butyl-dimethyl-silane. 2-Adamantan-1-yl-4-bromo-phenol was prepared by the method of Charpentier, B. et al., *J. Med. Chem.* 38:4993-5006 (1995). A solution of 2-adamantan-1-yl-4-bromo-phenol (0.800 g, 2.6 mmol) in methylene chloride was immersed in a −78° C. bath. The reaction was then diluted with collidine and DMF. The t-butyldimethylsilyl triflate was then added via syringe and the reaction was allowed to warm to room temp. The reaction mixture was poured into 50 mL of ice/H$_2$O and then transferred to a 250 mL separatory funnel. The layers were diluted with brine and extracted 2× with brine, then DI water. The organic layers were dried over Na$_2$SO$_4$ and the compound was purified by column chromatography to give 0.915 g (83% yield) of 2-adamantan-1-yl-4-bromo-phenoxy)-tert-butyl-dimethyl-silane.

(b) [3-Adamantan-1-yl-4-(tert-butyl-dimethyl-silanyloxy)-phenyl]-pyridin-3-yl-methanol. A solution of 2-adamantan-1-yl-4-bromo-phenoxy)-tert-butyl-dimethyl-silane (0.260 g, 0.617 mmol) in THF under an atmosphere of argon was cooled to −78° C. nBuLi (0.26 mL, 2.5 M, 0.65 mmol) was added through the syringe. The reaction was allowed to stir for 45 min and then transferred into an acetonitrile/dry ice bath. Pyridine-3-carbaldehyde (0.066 g, 0.62 mmol) was then added. Upon completion of the aldehyde addition the cooling bath was removed and the reaction was allowed to warm to room temp and stir for ½ hour. The reaction was worked up by adding the reaction to a water/ice mixture and made basic by addition of saturated NaHCO$_3$. The0 aqueous layer was then extracted with ethyl acetate and then concentrated to afford a yellow oil. The material was then chromatographed to give [3-adamantan-1-yl-4-(tert-butyl-dimethyl-silanyloxy)-phenyl]-pyridin-3-yl-methanol.

(c) 2-Adamantan-1-yl-4-(hydroxy-pyridin-3-yl-methyl)-phenol. [3-adamantan-1-yl-4-(tert-butyl-dimethyl-silanyloxy)-phenyl]-pyridin-3-yl-methanol (0.277 g, 0.617 mmol)

was dissolved in 3 mL of and treated with 3 mL of 1M tetrabutylammonium fluoride solution in THF. The reaction was allowed to stir overnight, then was quenched with 15-20 mL of water. Ethyl acetate was added, and the organic layer was separated. The aqueous layer was extracted again with of EtOAc. The organic layers were combined, dried with $Na_2SO_4$ and concentrated to a red oil. The oil was taken up in 5% MeOH in $CH_2Cl_2$ and purified by chromatography to afford 0.117 g of 2-adamantan-1-yl-4-(hydroxy-pyridin-3-yl-methyl)-phenol as a white solid. $^1$H NMR (400 MHz, $CDCl_3$): δ 8.49 (s, 1H), 8.40 (d, J=4.5 Hz, 1H), 7.75 (d, J=8.0 Hz, 1H), 7.26 (dd, J=7.9, 4.8 Hz, 1H), 7.17 (d, J=2.0 Hz, 1H), 6.85 (dd, J=8.2, 2.0 Hz, 1H), 6.60 (d, J=8.2 Hz, 1H), 5.75 (s, 1H), 2.08 (s, 6H), 2.03 (s, 3H), 1.74 (s, 6H).

Example 63

(3-Adamantan-1-yl-4-hydroxy-phenyl)-pyridin-3-yl-methanone

[3-Adamantan-1-yl-4-(tert-butyl-dimethyl-silanyloxy)-phenyl]-pyridin-3-yl-methanol (55 mg, 0.112 mmol) was dissolved in methylene chloride. The Dess Martin periodane (0.104 g, 0.224 mmol) was then added to the reaction mixture. The reaction was complete within 10 min and was then diluted with ether. The organic layer was washed with $Na_2S_2O_4$ (2×30 mL) followed by $NaHCO_3$ (2×30 mL) followed by brine (1×30 mL) The organic layers were combined, dried with $Na_2SO_4$ and then evaporated to give [3-adamantan-1-yl-4-(tert-butyl-dimethyl-silanyloxy)-phenyl]-pyridin-3-yl-methanone, which was deprotected without further purification. The deprotection was carried out as described for Example 62, except the reaction was complete after 10 min. The product was purified by chromatography to give 17 mg of 3-adamantan-1-yl-4-hydroxy-phenyl)-pyridin-3-yl-methanone as a white solid. $^1$H NMR (400 MHz, methanol-$d_4$/$CDCl_3$): δ 8.81 (d, J=2.1 Hz, 1H), 8.68 (dd, J=5.0, 1.7 Hz, 1H), 8.07 (td, J=8.0, 2.0 Hz, 1H), 7.70 (d, J=2.3 Hz, 1H), 7.52 (dd, J=5.0, 2.9 Hz, 1H), 7.48 (dd, J=8.6, 2.5 Hz, 1H), 6.80 (d, J=8.4 Hz, 1H), 2.10 (d, J=2.9 Hz, 6H), 2.02 (s, 3H), 1.74 (t, J=2.8 Hz, 6H)

Example 64

5-[3-Hydroxy-5-(1H-indol-4-yl)-phenylamino]-pyrazine-2-carbonitrile

To 5-bromo-pyrazin-2-ylamine (0.46 g, 2.6 mmol), NaCN (1.3 g, 26 mmol) and CuCN (2.74 g, 26 mmol) in a nitrogen-purged vial was added DMF (10 mL). The resulting mixture was heated at 120° C. over the weekend. After cooling down to room temperature, DMF was removed under high vacuum. The residue was partitioned between EtOAc and water. The organic extracts were combined, dried and concentrated to give the crude product as a yellow solid (0.296 g, 93%), which was used in the subsequent reaction without further purification.

The Buchwald reaction was carried out as described above and the product was converted to 5-[3-hydroxy-5-(1H-indol-4-yl)-phenylamino]-pyrazine-2-carbonitrile as described for Example 35. $^1$H NMR (400 MHz, $CDCl_3$): δ 8.46 (d, J=1.4 Hz, 1H), 8.18 (d, J=1.4 Hz, 1H), 7.85 (s, 0H), 7.47 (d, J=1.6 Hz, 1H), 7.37 (d, J=8.0 Hz, 1H), 7.31 (t, J=2.1 Hz, 1H), 7.27 (d, J=3.3 Hz, 1H), 7.15 (t, J=7.6 Hz, 1H), 7.08 (d, J=6.4 Hz, 1H), 6.89 (t, J=1.9 Hz, 1H), 6.69 (d, J=2.3 Hz, 1H).

Example 65

[3-Chloro-5-(1H-indol-4-yl)-phenyl]-pyridin-3-yl-amine (3-Bromo-5-chloro)-pyridin-3-yl-amine was prepared from 1,3-dibromo-5-chlorobenzene and pyridin-3-ylamine as described for Example 36. This material was converted to [3-chloro-5-(1H-indol-4-yl)-phenyl]-pyridin-3-yl-amine by the method of Example 35. $^1$H NMR (400 MHz, $CD_3OD$): δ 8.35 (br s, 1H), 8.03 (d, J=4.3 Hz, 1H), 7.63 (ddd, J=8.3, 2.7, 1.3 Hz, 1H), 7.39 (d, J=8.2 Hz, 1H), 7.33-7.28 (m, 3H), 7.20-7.14 (m, 2H), 7.08-7.04 (m, 2H), 6.57 (d, J=3.2 Hz, 1H).

Example 66

3-(1H-Indol-4-yl)-5-(pyridin-3-ylamino)-benzoic acid methyl ester

3-Bromo-5-(pyridin-3-ylamino)-benzoic acid methyl ester was prepared from 3,5-dibromo-benzoic acid methyl ester and pyridin-3-ylamine in low yield as described for Example 36, except that the reaction was run at 130° C. This material was converted to 3-(1H-indol-4-yl)-5-(pyridin-3-ylamino)-benzoic acid methyl ester by the method of Example 35. $^1$H NMR (400 MHz, $CDCl_3$): δ 8.43 (d, J=14.4 Hz, 2H), 8.20 (s, 1H), 7.99 (s, 1H), 7.73 (s, 1H), 7.56 (s, 1H), 7.49 (d, J=8.2 Hz, 1H), 7.41 (d, J=8.0 Hz, 1H), 7.29-7.24 (m, 2H), 7.22-7.16 (m, 2H), 6.69 (s, 1H), 5.93 (s, 1H), 3.92 (s, 3H).

Example 67

3-(1H-Indol-4-yl)-5-(pyridin-3-ylamino)-benzonitrile

3-Bromo-5-(pyridin-3-ylamino)-benzonitrile was prepared from 3,5-dibromobenzonitrile and pyridin-3-ylamine as described for Example 36, except that the reaction was run at 130° C. This material was converted to 3-(1H-indol-4-yl)-5-(pyridin-3-ylamino)-benzonitrile by the method of Example 35. $^1$H NMR (400 MHz, $CDCl_3$): δ 8.47 (s, 2H), 8.28 (d, J=4.3 Hz, 1H), 7.55-7.49 (m, 3H), 7.44 (d, J=8.2 Hz, 1H), 7.30-7.23 (m, 4H), 7.12 (dd, J=7.3, 0.9 Hz, 1H), 6.63 (t, J=2.5 Hz, 1H), 6.05 (s, 1H).

Example 68

3-Benzo[1,3]dioxol-4-yl-5-(pyridin-3-ylamino)-phenol

3-Bromo-5-(pyridin-3-ylamino)-phenol:
[3-Bromo-5-(4-methoxy-benzyloxy)-phenyl]-pyridin-3-yl-amine (26.7 g, 69.2 mmol) was dissolved in thioanisole (62 mL, 529 mmol). Trifluoroacetic acid (81 mL, 1.06 mol) was added slowly with the temperature held between 20 and 25° C. over a period of 100 min. The solution was left to stand at room temperature for 2 hours. The reaction solution was diluted with water (100 mL) and concentrated to a small volume (~30 mL). To the residue were added TBME (250 mL), water (300 mL) and methanol (30 mL). The organic layer was extracted with a mixture of 4N hydrochloric acid and methanol. The combined aqueous layers were diluted with methanol (100 mL), washed with methylene chloride (3×150 mL) and neutralized with 4N NaOH (440 mL) to pH 7. The precipitated white solid was collected, washed with cold water (2×10 mL) and dried in a vacuum oven overnight at 60° C. 3-Bromo-5-(pyridin-3-ylamino)-phenol (9.21 g, 50%) was obtained as an off white solid.

Bromo-5-(tert-butyl-diphenyl-silanyloxy)-phenyl]-pyridin-3-yl-amine:

3-Bromo-5-(pyridin-3-ylamino)-phenol (11.62 g, 43.83 mmol) was dissolved in DMF (115 mL) under dry argon and cooled to 0° C. Then 60% NaH (1.93 g, 48.21 mmol) was added in small portions over a period of 45 min. Stirring was continued for 15 min, followed by drop wise addition of TBDPS-chloride (11.2 mL, 43.83 mmol). The mixture was warmed to room temperature and stirred for 20 h. The reaction mixture was diluted with tert-butylmethyl ether (200 mL) and washed with water and brine (2×50 mL each). The organic layer was dried (MgSO$_4$) and concentrated to give the crude product which was purified by flash chromatography on silica gel (600 g, AcOEt/heptane 1:2→1:1). [3-Bromo-5-(tert-butyl-diphenyl-silanyloxy)-phenyl]-pyridin-3-yl-amine (21.2 g, 96%) was obtained as a yellow resin.

[3-(tert-Butyl-diphenyl-silanyloxy)-5-(4,4,5,5-tetramethyl-[1,3,2]dioxaborolan-2-yl)-phenyl]-pyridin-3-yl-amine:

A round bottom flask was charged with [3-bromo-5-(tert-butyl-diphenyl-silanyloxy)-phenyl]-pyridin-3-yl-amine (500 mg, 0.99 mmol), bis(pinacolato)diboron (277 mg, 1.09 mmol), potassium acetate (292 mg, 2.98 mmol) and Pd(dppf)Cl$_2$.CH$_2$Cl$_2$ complex (40 mg, 0.05 mmol). Dioxane (5 mL) was added under argon and the mixture was heated to 80° for 16 h. After completion of the reaction and cooling down to room temperature ethyl acetate (10 mL) and brine (5 mL) were added under stirring. The mixture was filtered through a pad of Hyflo. After separation of the layers the aqueous one was extracted with AcOEt (2×10 mL). The combined organic layers were washed with brine (10 mL), dried over Na$_2$SO$_4$, filtered and evaporated to dryness. Flash chromatography on silica gel (36 g, AcOEt/heptane 1:1→2:1) provided [3-(tert-Butyl-diphenyl-silanyloxy)-5-(4,4,5,5-tetramethyl-[1,3,2]dioxaborolan-2-yl)-phenyl]-pyridin-3-yl-amine (365 mg, ~76%, 4:1 mixture with the free boronic acid as a pale yellow resin. This material was used without further purification.

3-Benzo[1,3]dioxol-4-yl-5-(tert-butyl-diphenyl-silanyloxy)-phenyl]-pyridin-3-yl-amine:

To a stirred solution of 4-bromo-1,3-benzodioxole (65 mg, 0.323 mmol, 1 eq.) and chloro(di-2-norbornylphosphino)(2'dimethylamino-1,1'-biphenyl-2-yl)palladium (II) (18 mg) in anhydrous dioxane (3 mL) under nitrogen$_2$ is added a dioxane (3 mL) solution of [3-(tert-butyl-diphenyl-silanyloxy)-5-(4,4,5,5-tetramethyl-[1,3,2]dioxaborolan-2-yl)-phenyl]-pyridin-3-yl-amine (196 mg, 0.356 mmol, 1.1 eq) followed by 2M aqueous K$_3$PO$_4$ (0.35 mL, 0.7 mmol). The mixture is heated to 100° C. in a sealed tube overnight.

The reaction mixture was returned to ambient temperature, and diluted with methylene chloride. The organic phase washed with brine, dried over MgSO$_4$, filtered and concentrated to a dark brown oil. Flash chromatography (1% MeOH/methylene chloride) gave 117 mg of 3-benzo[1,3]dioxol-4-yl-5-(tert-butyl-diphenyl-silanyloxy)-phenyl]-pyridin-3-yl-amine as a beige solid.

3-Benzo[1,3]dioxol-4-yl-5-(pyridin-3-ylamino)-phenol:

To a solution of 3-benzo[1,3]dioxol-4-yl-5-(tert-butyl-diphenyl-silanyloxy)-phenyl]-pyridin-3-yl-amine (114 mg, 0.209 mmol, 1 eq.) in THF (4 mL) at 0° C. was added 1 M TBAF in THF (0.23 mL, 0.23 mmol). After stirring for 75 min, the mixture was concentrated, the residue extracted into ethyl acetate, and the organics washed with water and brine. The organic layer was separated, dried over MgSO$_4$, filtered and concentrated. Flash chromatography (5% MeOH/methylene chloride) yielded 48.9 mg of 3-benzo[1,3]dioxol-4-yl-5-(pyridin-3-ylamino)-phenol as an off-white solid. $^1$H NMR (400 MHz, DMSO): δ 9.41 (s, 1H), 8.33 (s, 2H), 8.00 (dd, J=4.5, 1.2 Hz, 1H), 7.46 (ddd, J=8.3, 2.7, 1.4 Hz, 1H), 7.21 (dd, J=8.2, 4.6 Hz, 1H), 6.99 (dd, J=6.9, 2.4 Hz, 1H), 6.91-6.85 (m, 3H), 6.63 (t, J=1.7 Hz, 1H), 6.51 (s, 1H), 6.03 (s, 2H).

Example 69

3-(1H-Indol-4-yl)-5-phenylamino-phenol

1-Bromo-3-iodo-5-methoxy-benzene:

A 1.6 M solution of n-butyllithium in hexane (5.65 mL, 9.04 mmol) was dissolved in dry toluene (50 mL) under dry argon and cooled to −5° C. Then a 2M solution of n-butylmagnesium chloride (2.26 mL, 4.52 mmol) was added slowly with the temperature held below 0° C. over a period of 15 min. Stirring was continued for 45 min at −5° C., followed by drop wise addition of a solution of 1,3-dibromo-5-methoxy-benzene (3.00 g, 11.3 mmol) in toluene (30 mL) with the temperature held below 0° C. The mixture was stirred for 45 min at −5° C. A solution of iodine chloride (1.83 g, 11.3 mmol) in methylene chloride (20 mL) was added in the described manner and stirring continued for additional 20 min at −5° C. The mixture was warmed to room temperature. Water (50 mL) and toluene (50 mL) were added and the layers were separated. The organic layer was washed with a saturated aqueous solution of Na$_2$S$_2$O$_3$ (2×30 mL), water and brine (30 mL). The organic layer was dried (MgSO$_4$) and concentrated to give the crude product which was purified by flash chromatography on silica gel (100 g, AcOEt/heptane 1:9). 1-Bromo-3-iodo-5-methoxy-benzene (2.12 g, 60%) was obtained as a yellow oil, which crystallized quickly upon standing.

3-Bromo-5-iodo-phenol:

1-Bromo-3-iodo-5-methoxy-benzene (6.29 g, 20.1 mmol) was suspended in a solution of hydrogen bromide in acetic acid (33%, 150 mL). Tetrabutylammonium bromide (0.5 g, 1.55 mmol) was added and the mixture was heated to reflux under vigorous stirring for 2 d. After cooling to room temperature the mixture was extracted with methylene chloride (3×100 mL). The combined organic layers were washed with water (50 mL), dried (MgSO$_4$) and concentrated to give the crude product which was purified by flash chromatography on silica gel (300 g, AcOEt/heptane 1:9). 3-Bromo-5-iodo-phenol (21.2 g, 96%) was obtained as pale brown solid.

1-Bromo-3-iodo-5-(4-methoxy-benzyloxy)-benzene:

3-Bromo-5-iodo-phenol (8.48 g, 28.37 mmol) was dissolved in DMF (50 mL) under dry argon and cooled to 0° C. Then potassium carbonate (3.92 g, 28.37 mmol) was added, followed by drop wise addition of 4-methoxybenzyl chloride (3.7 mL, 27.0 mmol). The mixture was slowly warmed to room temperature and stirred for 20 h. Additional 4-methoxybenzyl chloride (0.19 mL, 1.4 mmol) was added and the mixture was stirred for additional 24 h at room temperature. The reaction mixture was diluted with tert-butylmethyl ether (300 mL) and water (150 mL). The layers were separated and the aqueous one extracted with tert-butylmethyl ether (2×150 mL). The combined organics were washed with water and brine (150 mL), dried (Na$_2$SO$_4$) and concentrated to give the crude product which was purified by flash chromatography on silica gel (330 g, AcOEt/heptane 1:9). 1-Bromo-3-iodo-5-(4-methoxy-benzyloxy)-benzene (8.80 g, 59%, purity 80%, HPLC 220 nm) was obtained as a yellow oil.

4-[3-Bromo-5-(4-methoxy-benzyloxy)-phenyl]-1-triisopropylsilanyl-1H-indole:

A 1 L flask was charged with 4-(4,4,5,5-tetramethyl-[1,3,2]dioxaborolan-2-yl)-1-triisopropylsilanyl-1H-indole (17.44 g, 43.67 mmol) and 1-Bromo-3-iodo-5-(4-methoxy-benzyloxy)-benzene (18.30 g, 43.67 mmol) in ethanol (180 mL) and toluene (180 mL) under argon. Tetrakis-triphenylphosphin-palladium (1.51 g, 1.31 mmol) was added. Then a solution of sodium carbonate (9.26 g, 87.34 mmol) in water (92.6 mL) was added and the mixture heated to 90° C. and stirred for 14 h. After cooling down to room temperature AcOEt (300 mL) and brine (200 mL) were added under stirring. The mixture was filtered through a pad of Hyflo. After separation of the layers the aqueous one was extracted with AcOEt (2×300 mL). The combined organic layers were washed with water and brine (150 mL), dried over $Na_2SO_4$, filtered and evaporated to dryness. After flash chromatography on silica gel (1 kg, AcOEt/heptane 1:19) 4-[3-bromo-5-(4-methoxy-benzyloxy)-phenyl]-1-triisopropylsilanyl-1H-indole (22.5 g, 91%) was obtained as a colorless oil.

3-(1H-Indol-4-yl)-5-phenylamino-phenol:

To a dry microwave tube under $N_2$ atmosphere was added 4-[3-bromo-5-(4-methoxy-benzyloxy)-phenyl]-1-triisopropylsilanyl-1H-indole (395 mg, 0.70 mmol, 1 eq.), aniline (66 mg, 0.71 mmol, 1 eq.), NaOtBu (94 mg, 0.98 mmol, 1.4 eq.), rac-BINAP (13.1 mg, 0.021 mmol, 0.03 eq.), and $Pd_2(dba)_3.CHCl_3$ (7.2 mg, 0.007 mmol, 0.01 eq.) in degassed anhydr. toluene (5 mL). The tube was microwaved at 130° C./300 W for 1 hr. and returned to room temperature. The reaction mixture was filtered through celite, washed with EtOAc (50 mL) and stripped to give 505 mg of a dark brown oily solid. Flash chromatography (1% MeOH/methylene chloride) yielded 273 mg of [3-(4-methoxy-benzyloxy)-5-(1-triisopropylsilanyl-1H-indol-4-yl)-phenyl]-phenyl-amine as a pale yellow crystalline foam. This material was deprotected to give 3-(1H-indol-4-yl)-5-phenylamino-phenol as described for Example 35. $^1$H NMR (400 MHz, $CDCl_3$): δ 8.23 (s, 1H), 7.37 (d, J=8.0 Hz, 1H), 7.30-7.21 (m, 4H), 7.18-7.12 (m, 3H), 6.97-6.92 (m, 2H), 6.76-6.70 (m, 2H), 6.58 (t, J=2.1 Hz, 1H), 5.76 (s, 1H), 4.78 (s, 1H).

Example 70

[3-Hydroxy-5-(1H-indol-4-yl)-phenyl]-(6-methoxy-pyridin-3-yl)-methanone

[3-Bromo-5-(4-methoxy-benzyloxy)-phenyl]-(6-methoxy-pyridin-3-yl)-methanol:

To 1,3-Dibromo-5-(4-methoxy-benzyloxy)-benzene (600 mg, 1.6 mmol) in dry ether (4 mL) at −76° C. was added nBuLi (1.6 M in hexane, 1.0 mL).

The resulting reaction mixture was stirred at same temperature for 30 min. 6-Methoxy-pyridine-3-carbaldehyde (220 mg, 1.6 mmol) in dry ether (2 mL) was then added dropwise. The reaction mixture was allowed to warm up to room temperature over 1 h. Sat. $NaHCO_3$ was added to quench the reaction. The organic phase was separated, washed with brine, dried, and concentrated. The crude product was further purified by flash chromatography to afford [3-Bromo-5-(4-methoxy-benzyloxy)-phenyl]-(6-methoxy-pyridin-3-yl)-methanol.

[3-Bromo-5-(4-methoxy-benzyloxy)-phenyl]-(6-methoxy-pyridin-3-yl)-methanone:

To [3-bromo-5-(4-methoxy-benzyloxy)-phenyl]-(6-methoxy-pyridin-3-yl)-methanol in methylene chloride (5 mL) at room temperature was added Dess-Martin reagent. The resulting reaction mixture was stirred at room temperature for 1 h. Sat. $NaHCO_3$ and $Na_2S_2O_3$ were then added and the stirring was continued until both phases become clear. The organic phase was separated, dried and concentrated to provide [3-bromo-5-(4-methoxy-benzyloxy)-phenyl]-(6-methoxy-pyridin-3-yl)-methanone which was carried on to the next step without further purification.

[3-(4-Methoxy-benzyloxy)-5-(1-triisopropylsilanyl-1H-indol-4-yl)-phenyl]-(6-methoxy-pyridin-3-yl)-methanone:

To [3-Bromo-5-(4-methoxy-benzyloxy)-phenyl]-(6-methoxy-pyridin-3-yl)-methanone (69 mg, 0.16 mmol) and 4-(4,4,5,5-yetramethyl-[1,3,2]dioxaborolan-2-yl)-1-triisopropylsilanyl-1H-indole (64 mg, 0.16 mmol) in dioxane (3 mL) was added chloro(di-2-norbornylphosphino) (2'dimethylamino-1,1'-biphenyl-2-yl)palladium (II) (10 mg) and aqueous 2M $K_3PO_4$ (0.160 mL, 0.32 mmol) under nitrogen. The resulting reaction mixture was heated at reflux for 24 hr. At the end of the reaction, methylene chloride was added and the organic phase washed with brine, dried, and concentrated. The crude product was purified by flash chromatography (3:1 hexane/EtOAc) to afford [3-(4-methoxy-benzyloxy)-5-(1-triisopropylsilanyl-1H-indol-4-yl)-phenyl]-(6-methoxy-pyridin-3-yl)-methanone (70 mg, 70%).

[3-Hydroxy-5-(1H-indol-4-yl)-phenyl]-(6-methoxy-pyridin-3-yl)-methanone:

To compound [3-(4-methoxy-benzyloxy)-5-(1-triisopropylsilanyl-1H-indol-4-yl)-phenyl]-(6-methoxy-pyridin-3-yl)-methanone in dimethylsulfide (2 mL) at 0° C. was added excess $BF_3$ etherate. The resulting reaction mixture was stirred at 0° C. for 20 min. TLC indicated that the disappearance of the starting material. EtOAc was added to dilute the reaction mixture and sat. $NaHCO_3$ was added to adjust the pH of the aqueous phase to 6-7. The aqueous phase was then extracted with EtOAc three times. The combined organic phases were dried over $Na_2SO_4$ and concentrated. The crude product was again dissolved in THF (1 mL) and treated with TBAF (1M in THF, 1 mL) at 0° C. The reaction mixture was allowed to warm up to room temperature. At the end of the reaction, the solvent was removed under reduced pressure. The residue was dissolved in EtOAc and washed with water three times. The organic phase was then dried and concentrated to afford the crude product which was further purified by preparative SFC to afford [3-hydroxy-5-(1H-indol-4-yl)-phenyl]-(6-methoxy-pyridin-3-yl)-methanone (29 mg, 75%). $^1$H NMR (400 MHz, $CD_3OD$): δ 8.57 (d, J=2.3 Hz, 1H), 8.04 (dd, J=8.6, 2.3 Hz, 1H), 7.42 (d, J=1.2 Hz, 1H), 7.36-7.30 (m, 2H), 7.17 (d, J=3.1 Hz, 1H), 7.12-7.08 (m, 2H), 7.03 (d, J=7.2 Hz, 1H), 6.76 (d, J=8.6 Hz, 1H), 6.55 (d, J=2.5 Hz, 1H), 3.90 (s, 3H).

Example 71

[3-(1H-indol-4-yl)-5-(pyridine-3-carbonyl)-phenyl]-carbamic acid benzyl ester (3,5-Dibromo-phenyl)-pyridin-3-yl-methanone:

1,3,5-Tribromo-benzene (31.4 g, 100 mmol) was dissolved under argon in a flame dried three-neck flask in 1000 mL diethylether and the solution was cooled to −72° C. A solution of 62 mL nBuLi (1.6 M in hexane, 100 mmol) was added to the resulting suspension in such a fashion that temperature did not rise above −70° C. The mixture was stirred for 30 min at −75° C. and the reaction was monitored by HPLC. A solution of 10.4 g (100 mmol) 3-cyanopyridine in 100 mL diethylether was added in such a fashion that temperature did not rise above −71° C. The mixture was stirred at −75° C. for 60 min and the reaction was monitored by HPLC. The cooling bath was removed and warmed to −25° C. 2 N HCl (250 mL) was added and the mixture was stirred for 20 min at room temperature. The mixture was made alkaline by addition of 1 N NaOH. The product was extracted with ethyl acetate and the combined organic layers were dried over $Na_2SO_4$. The product was purified by chromatography (700 g silica agel, $CH_2Cl_2$, then $CH_2Cl_2$/ethyl acetate 1:1, UV) to yield 27.7 g (81%) of (3,5-dibromo-phenyl)-pyridin-3-yl-methanone.

3-Bromo-5-(pyridine-3-carbonyl)-phenyl]-carbamic acid benzyl ester:

In a 1 L four neck flask equiped with a reflux condenser, a mechanical stirrer, and a thermometer were placed together 15.35 g (45.0 mmol) of (3,5-dibromo-phenyl)-pyridin-3-yl-methanone and 16.33 g (108.0 mmol) of benzyl carbamate. The flask was flushed under argon for 15 min. Then 20.50 g (63.0 mmol) of $Cs_2CO_3$ and 270 mL of dioxane were added. The flask was then heated to 80° C. internal temperature. In the mean time, in a 100 mL Schlenk were placed together 0.465 g of $[Pd_2(dba)_3]$.$CHCl_3$ (0.9 mmol Pd), 0.780 g Xantphos ligand (1.35 mmol) and 60 mL of a 1:4 toluene/dioxane mixture. The orange suspension thus obtained was stirred at room temperature for 20 min. Once the temperature in the large reaction flask reached 80° C., 10 mL of the Pd catalyst suspension were added. The reaction temperature was then increased to 105° C. internal temperature. In the following 5 h, more of the catalyst was added every hour by portions of 10 mL each. After refluxing overnight the reaction afforded a yellow solution and a brown precipitate. The reaction mixture was cooled down to room temperature and the precipitate filtered and washed with 3×50 mL of ethyl acetate. The yellow solution was evaporated to afford a yellow brown oil. The compound was purified by chromatography (900 g silica gel, 15:20:10:2 toluene/$CH_2Cl_2$/ethyl acetate/HCOOH) to yield a pale yellow oil. A further purification involved the precipitation of the product by dissolving the oil in a minimum of ethyl acetate and addition of hexane to yield 8.51 g (46%) 3-bromo-5-(pyridine-3-carbonyl)-phenyl]-carbamic acid benzyl ester as a white solid.

[3-(1H-Indol-4-yl)-5-(pyridine-3-carbonyl)-phenyl]-carbamic acid benzyl ester:

3-Bromo-5-(pyridine-3-carbonyl)-phenyl]-carbamic acid benzyl ester was converted to [3-(pyridine-3-carbonyl)-5-(1-triisopropylsilanyl-1H-indol-4-yl)-phenyl]-carbamic acid benzyl ester, then deprotected to give [3-(1H-indol-4-yl)-5-(pyridine-3-carbonyl)-phenyl]-carbamic acid benzyl ester by the method of Example 35. $^1$H NMR (400 MHz, methanol-$d_4$): δ 9.07 (s, 1H), 8.77 (d, J=4.8 Hz, 1H), 8.57 (s, 1H), 8.14 (dt, J=4.9, 2.6 Hz, 1H), 8.08 (s, 1H), 7.84 (s, 1H), 7.77 (t, J=1.5 Hz, 1H), 7.42-7.29 (m, 8H), 7.26-7.13 (m, 3H), 6.69 (s, 1H), 5.20 (s, 2H).

Example 72

[3-Amino-5-(1H-indol-4-yl)-phenyl]-pyridin-3-yl-methanone

[3-(Pyridine-3-carbonyl)-5-(1-triisopropylsilanyl-1H-indol-4-yl)-phenyl]-carbamic acid benzyl ester (40 mg, 0.066 mmol) in 40% KOH in MeOH/$H_2O$ (5 mL/5 mL) was brought to reflux for 2 hours. After cooling down to room temperature, the mixture was diluted with water, and extracted with EtOAc. The organic layers were separated, dried and concentrated. Purification on silica gel afforded [3-amino-5-(1H-indol-4-yl)-phenyl]-pyridin-3-yl-methanone as a yellow solid (11.9 mg, 57%). $^1$H NMR (400 MHz, CDCl$_3$): δ 9.01 (d, J=1.6 Hz, 1H), 8.71 (dd, J=4.8, 1.7 Hz, 1H), 8.29 (s, 1H), 8.09 (dt, J=4.9, 2.6 Hz, 1H), 7.38-7.31 (m, 3H), 7.20-7.15 (m, 4H), 7.11-7.07 (m, 2H) 6.64-6.60 (m, 1H).

Example 73

N-[3-(1H-Indol-4-yl)-5-(pyridine-3-carbonyl)-phenyl]-acetamide (3-Amino-5-bromo-phenyl)-pyridin-3-yl-methanone:

A stirred slurry of 1 g of 3-bromo-5-(pyridine-3-carbonyl)-phenyl]-carbamic acid benzyl ester (2.43 mmol) in 50 mL of 12N HCl was heated at 80° C. for 20 min. Methanol (10 mL) was added until the material went into solution. Starting material was consumed within 10 min. of the addition of methanol. The material was neutralized with NaHCO$_3$ and extracted 3× with EtOAc. The organics were combined, dried over Na$_2$SO$_4$, filtered and the solution was concentrated under reduced pressure affording 0.63 g (93%) of (3-amino-5-bromo-phenyl)-pyridin-3-yl-methanone.

N-[3-Bromo-5-(pyridine-3-carbonyl)-phenyl]-acetamide:

To 0.2 g of (3-amino-5-bromo-phenyl)-pyridin-3-yl-methanone in 10 mL of dichloroethane was added 0.126 mL of diisopropyl ethyl amine and 0.051 mL of acetyl chloride. The reaction mixture was stirred for 10 minutes then poured into water and extracted twice with CH$_2$Cl$_2$. The organic phase was dried over sodium sulfate, filtered and and concentrated to give 154 mg of N-[3-bromo-5-(pyridine-3-carbonyl)-phenyl]-acetamide, which was used without further purification. $^1$H NMR (400 MHz, methanol-d$_4$/CDCl$_3$): δ 8.89 (d, J=2.0 Hz, 1H), 8.76 (dd, J=4.9, 1.6 Hz, 1H), 8.17 (dt, J=4.9, 2.7 Hz, 1H), 8.11 (t, J=1.8 Hz, 1H), 7.90 (t, J=1.6 Hz, 1H), 7.61-7.55 (m, 2H), 2.11 (s, 3H).

N-[3-(1H-Indol-4-yl)-5-(pyridine-3-carbonyl)-phenyl]-acetamide:

N-[3-bromo-5-(pyridine-3-carbonyl)-phenyl]-acetamide was converted to N-[3-(pyridine-3-carbonyl)-5-(1-triisopropylsilanyl-1H-indol-4-yl)-phenyl]-acetamide, and the triisopropylsilyl group was removed with tetra n-butylammonium fluoride to give N-[3-(1H-indol-4-yl)-5-(pyridine-3-carbonyl)-phenyl]-acetamide as described in Example 35. $^1$H NMR (400 MHz, methanol-d$_4$): δ 10.61 (s, 1H), 8.94 (s, 1H), 8.70 (s, 1H), 8.13-8.19 (m, 2H), 7.99 (s, 1H), 7.74 (s, 1H), 7.49 (s, 1H), 7.37 (d, J=8.0 Hz, 1H), 7.25 (s, 1H), 7.13 (t, J=7.7 Hz, 1H), 7.06 (d, J=7.0 Hz, 1H), 6.62 (s, 1H), 2.12 (s, 3H).

Example 74

N-[3-(1H-Indol-4-yl)-5-(pyridine-3-carbonyl)-phenyl]-methanesulfonamide

N-[3-Bromo-5-(pyridine-3-carbonyl)-phenyl]-methanesulfonamide:

To a stirred solution of 0.200 grams of (3-amino-5-bromo-phenyl)-pyridin-3-yl-methanone (0.72 mmol) in 10 mL of dichloroethane was added 0.87 mL (10.82 mmol) of pyridine followed by the addition of 0.56 mL (7.2 mmol) of methanesulfonyl chloride. The reaction was stirred at 80° C. for 2 hours. The volatiles were removed under reduced pressure affording material which was flash chromatographed (25% EtOAc/hexane to 1:1 EtOAc:hexane to 100% EtOAc) to give 0.150 grams of N-[3-bromo-5-(pyridine-3-carbonyl)-phenyl]-methanesulfonamide.

N-[3-(1H-Indol-4-yl)-5-(pyridine-3-carbonyl)-phenyl]-methanesulfonamide:

N-[3-bromo-5-(pyridine-3-carbonyl)-phenyl]-methanesulfonamide was converted to N-[3-(pyridine-3-carbonyl)-5-(1-triisopropylsilanyl-1H-indol-4-yl)-phenyl]-methanesulfonamide, and the triisopropylsilyl group was removed with tetra n-butylammonium fluoride to give N-[3-(1H-indol- 4-yl)-5-(pyridine-3-carbonyl)-phenyl]-methanesulfonamide as described in Example 75. $^1$H NMR (400 MHz, methanol-d$_4$/CDCl$_3$): δ 8.97 (s, 1H), 8.71 (s, 1H), 8.14 (d, J=7.8 Hz, 1H), 7.87 (t, J=1.8 Hz, 1H), 7.78 (t, J=1.5 Hz, 1H), 7.56 (t, J=1.9 Hz, 1H), 7.44 (dd, J=7.8, 4.9 Hz, 1H), 7.38 (d, J=8.0 Hz, 1H), 7.22 (d, J=3.1 Hz, 1H), 7.17 (t, J=7.7 Hz, 1H), 7.09 (d, J=7.3 Hz, 1H), 6.60 (d, J=3.3 Hz, 1H), 3.00 (s, 3H).

Example 75

[3-(1H-indol-4-yl)-5-(pyridine-3-carbonyl)-phenyl]-carbamic acid methyl ester

[3-Bromo-5-(pyridine-3-carbonyl)-phenyl]-carbamic acid methyl ester:

To a stirred solution of 0.20 g of (3-amino-5-bromo-phenyl)-pyridin-3-yl-methanone (0.72 mmol) in 5 mL of dichloroethane was added 0.58 mL of pyridine and 0.55 mL of methylchloroformate, and the mixture was heated to 60° C. for 20 minutes. The reaction was diluted with dichloromethane and washed with saturated aqueous sodium bicarbonate, dried over NaSO$_4$ and the volatiles were removed under reduced pressure to give 208 mg (86% yield) of [3-bromo-5-(pyridine-3-carbonyl)-phenyl]-carbamic acid methyl ester.

[3-(1H-Indol-4-yl)-5-(pyridine-3-carbonyl)-phenyl]-carbamic acid methyl ester:

[3-Bromo-5-(pyridine-3-carbonyl)-phenyl]-carbamic acid methyl ester (316 mg, 0.94 mmol), 4-(4,4,5,5-tetramethyl-[1,3,2]dioxaborolan-2-yl)-1-triisopropylsilanyl-1H-indole (0.377 mg, 0.94 mmol) and chloro(di-2-norbornylphosphino)(2'dimethylamino-1,1'-biphenyl-2-yl)palladium (II) (53 mg, 0.094 mmol) were dissolved in dioxane (6 mL) under nitrogen. Aqueous 2M K$_3$PO$_4$ (1 mL, 1.2 mmol) was added and the mixture was heated at reflux overnight. The reaction mixture was filtered through Celite® and the solvent was removed. The product was chromatographed to give 0.350 g (70% yield) of [3-(pyridine-3-carbonyl)-5-(1-triisopropylsilanyl-1H-indol-4-yl)-phenyl]-carbamic acid methyl ester.

To a stirred solution of 0.160 g (0.31 mmol) of [3-(pyridine-3-carbonyl)-5-(1-triisopropylsilanyl-1H-indol-4-yl)-phenyl]-carbamic acid methyl ester in 5 mL of THF was added 0.310 mL of 1M tetra-n-butylammonium fluoride in THF. The reaction was stirred 10 min, poured into water and ethyl acetate. The phases were separated, and the aqueous phase was extracted with ethyl acetate. The organic phases were combined, washed with saturated sodium bicarbonate and brine and dried over sodium sulfate, and the volatiles were removed under reduced pressure. The crude product was chromatographed using 1-5% methanol/chloroform to give [3-(1H-indol-4-yl)-5-(pyridine-3-carbonyl)-phenyl]-carbamic acid methyl ester. $^1$H NMR (400 MHz, methanol-d$_4$): δ 9.08 (s, 1H), 8.79 (d, J=3.9 Hz, 1H), 8.43 (s, 1H), 8.16 (d, J=7.8 Hz, 1H), 8.08 (s, 1H), 7.81 (s, 1H), 7.78 (s, 1H), 7.38-7.46 (m, 2H), 7.22-7.27 (m, 2H), 7.19 (d, J=7.0 Hz, 1H), 7.01 (s, 1H), 6.72 (s, 1H), 3.79 (s, 3H).

Example 76

N-[3-(1H-Indol-4-yl)-5-(pyridine-3-carbonyl)-phenyl]-propionamide

N-[3-Bromo-5-(pyridine-3-carbonyl)-phenyl]-propionamide:

To 0.20 g of (3-amino-5-bromo-phenyl)-pyridin-3-yl-methanone (0.72 mmol) in 10 mL of dichloroethane was added 0.25 mL of diisopropylethylamine and 0.065 mL of propionyl chloride. The reaction was stirred 1 h at ambient temperature, then poured into saturated aqueous sodium bicarbonate. The phases were separated and the aqueous phase was washed once with methylene chloride, dried over sodium sulfate, filtered and concentrated to give 0.24 g (quantitative yield) of N-[3-bromo-5-(pyridine-3-carbonyl)-phenyl]-propionamide.

N-[3-(1H-Indol-4-yl)-5-(pyridine-3-carbonyl)-phenyl]-propionamide: N-[3-bromo-5-(pyridine-3-carbonyl)-phenyl]-propionamide was converted to N-[3-(pyridine-3-carbonyl)-5-(1-triisopropylsilanyl-1H-indol-4-yl)-phenyl]-propionamide, and the triisopropylsilyl group was removed with tetra n-butylammonium fluoride to give N-[3-(1H-indol-4-yl)-5-(pyridine-3-carbonyl)-phenyl]-propionamide as described in Example 35. $^1$H NMR (400 MHz, DMSO-d$_6$): δ 11.30 (s, 1H), 10.20 (s, 1H), 8.95 (s, 1H), 8.82 (d, J=3.5 Hz, 1H), 8.32 (s, 1H), 8.17 (d, J=7.8 Hz, 1H), 8.02 (s, 1H), 7.66 (s, 1H), 7.60 (dd, J=7.7, 5.0 Hz, 1H), 7.45-7.41 (m, 2H), 7.17 (t, J=7.6 Hz, 1H), 7.10 (d, J=6.6 Hz, 1H), 6.62 (s, 1H), 2.35 (q, J=7.5 Hz, 2H), 1.08 (t, J=7.6 Hz, 3H).

Example 77

[2-Hydroxy-5-(1H-indol-4-yl)-phenyl]-pyridin-3-yl-methanone 2,4-Dibromo-1-(4-methoxy-benzyloxy)-benzene:

4-Methoxybenzylchloride (0.6 mL, 4.4 mmol) was added to a mixture of 2,4-dibromo-phenol (1 g, 4 mmol) and potassium carbonate (0.61 g, 4.4 mmol) in DMF (20 mL) at room temperature. The resulting mixture was stirred at room temperature for 1 hr. After adding cesium carbonate (1.3 g, 4 mmol), the resulting mixture was stirred at 90° C. for 2 hrs. The mixture was then cooled to room temperature, diluted with water, and extracted with EtOAc twice. The combined EtOAc extracts were washed with a mixture of water and brine several times, then concentrated to afford 1.45 g (98% yield) of 2,4-dibromo-1-(4-methoxy-benzyloxy)-benzene as a light yellow oil, which was used directly in the next reaction.

5-Bromo-2-(4-methoxy-benzyloxy)-phenyl]-pyridin-3-yl-methanone:

A solution of 1.6 M n-BuLi in hexanes (1.8 mL, 2.9 mmol) was added dropwise into a stirred solution of 2,4-dibromo-1-(4-methoxy-benzyloxy)-benzene (1 g, 2.69 mmol) in anhydrous ether (8 mL) at −78° C. The resultant mixture was stirred at −78° C. for half an hour. 3-Cyanopyridine (0.28 g, 2.69 mmol) in ether (3 mL) was added dropwise. The mixture was kept at −78° C. for 1 hr, then warmed to 0° C. Aqueous 1N HCl was added and stirred for 5 mins. The organic layer was washed with aqueous 1N HCl several times. The combined organic extracts were basified with aqueous 1N NaOH, then extracted with dichloromethane several times. The combined organic extracts were washed with brine, dried and concentrated. Purification by column chromatography gave 5-bromo-2-(4-methoxy-benzyloxy)-phenyl]-pyridin-3-yl-methanone as a yellow sticky oil (82.8 mg).

[2-(4-Methoxy-benzyloxy)-5-(1-triisopropylsilanyl-1H-indol-4-yl)-phenyl]-pyridin-3-yl-methanone:

5-Bromo-2-(4-methoxy-benzyloxy)-phenyl]-pyridin-3-yl-methanone was converted to [2-(4-Methoxy-benzyloxy)-5-(1-triisopropylsilanyl-1H-indol-4-yl)-phenyl]-pyridin-3-yl-methanone as described in Example 35.

[2-Hydroxy-5-(1H-indol-4-yl)-phenyl]-pyridin-3-yl-methanone:

To a solution of [2-(4-methoxy-benzyloxy)-5-(1-triisopropylsilanyl-1H-indol-4-yl)-phenyl]-pyridin-3-yl-methanone (42 mg, 0.07 mmol) in dichloromethane (0.5 mL) and dimethylsulfide (0.5 mL) at 0° C. was added TFA (1 mL) dropwise. After stirring at 0° C. for 30 mins, the starting material was gone. Saturated aqueous NaHCO$_3$ was added to adjust the pH of the mixture to around 6, and the reaction mixture was extracted with EtOAc several times. The combined EtOAc layers were washed with brine, dried and concentrated. Purification by silica gel column chromatography, followed by further preparative SFC chromatography afforded 3.1 mg (14%) of [2-hydroxy-5-(1H-indol-4-yl)-phenyl]-pyridin-3-yl-methanone as a yellow solid. $^1$H NMR (400 MHz, CDCl$_3$): δ 11.87 (s, 1H), 9.13-8.89 (m, 1H), 8.88-8.69 (m, 1H), 8.37-8.23 (m, 1H), 8.04 (d, J=7.6 Hz, 1H), 7.91 (dd, J=8.6, 2.1 Hz, 1H), 7.81 (d, J=2.1 Hz, 1H), 7.49-7.40 (m, 1H), 7.37 (d, J=8.2 Hz, 1H), 7.27-7.19 (m, 4H), 7.05 (d, J=7.4 Hz, 1H), 6.57 (s, 1H).

Example 78

[3-(5-Fluoro-indol-1-yl)-5-hydroxy-phenyl]-pyridin-3-yl-methanone (3-Bromo-5-hydroxy-phenyl)-pyridin-3-yl-methanone:

A 50 mL tube was charged with (3,5-dibromo-phenyl)-pyridin-3-yl-methanone (2.55 g, 7.5 mmol), bis(pinacolato) diboron (1.26 g, 5.0 mmol), potassium acetate (1.47 g, 15.0 mmol) and Pd(dppf)Cl$_2$.CH$_2$Cl$_2$ (200 mg). DMSO (15 mL) was added, and the solution was degassed with nitrogen, then the tube was sealed. After heating the tube for 16 h at 80° C., the mixture was diluted with ethyl acetate (10 mL) and extracted with brine (10 mL, three times), and saturated sodium bicarbonate (5 mL), and the organic layer was dried. To a solution of the crude product prepared above in acetone (20 mL) was added an aqueous solution of Oxone (6.15 g in 30 mL water), and the reaction mixture was stirred vigorously for 10 min at room temperature. The reaction was quenched with aqueous sodium hydrogen sulfite. The brown solution was extracted with ethyl acetate, and the organic layer was extracted with brine followed by water, then dried and concentrated. The residue was passed through a short pad of Silica gel column using a gradient of 2% MeOH in methylene chloride to 4% MeOH in methylene chloride as an eluent to give (3-bromo-5-hydroxy-phenyl)-pyridin-3-yl-methanone (800 mg, 2.87 mmol, 57%) as a foam.

[3-(5-Fluoro-indol-1-yl)-5-hydroxy-phenyl]-pyridin-3-yl-methanone:

To a 50 mL syringe charged with Wang resin (0.9 mmol/g, 2.2 g, 2 mmol) were added a mixed solution of 3-bromo-5-hydroxy-phenyl)-pyridin-3-yl-methanone (800 mg, 2.87 mmol) and triphenyl phosphine (1.0 g, 4 mmol) in THF (20 mL). After cooling the syringe in dry ice for a few minutes, a solution of diisopropyl azodicarboxylate (DIAD, 707 mg, 3.5 mmol) in THF (5 mL) was added to the syringe, and the syringe was shaken for 16 h at rt. The resin was washed with THF (4×20 mL), MeOH (4×20 mL), DCM (4×20 mL), and dried under high vacuum.

An aliquot of the resin intermediate (200 mg, ca 0.15 mmol) was placed in a 5 mL glass tube reactor. Copper (I) iodide (0.6 mmol, 114 mg), cesium carbonate (117 mg, 0.6 mmol), dioxane (4 mL), 5-fluoro indole (1.0 mmol, 135 mg), and N,N'-dimethylethylenediamine (53 mg, 0.6 mmol) were added to the reactor, and the reactor was heated to 110° C. for 16 h under a N$_2$ atmosphere. After cooling the reaction mixture to room temperature, the resin was filtered, washed with THF (4×3 mL), MeOH (4×3 mL), H$_2$O (4×3 mL), DMF (5×3 mL), THF (4×3 mL), methylene chloride (4×3 mL) and dried in vacuo. The resin was treated with 5% DMS, 50% TFA/methylene chloride (2 mL) for 20 min in a 20 mL glass vial. The slurry of resin in the cleavage cocktail was filtered through a fritted syringe to a 20 mL glass vial, washed with methylene chloride (2×1 mL), and the combined solution was evaporated with a stream of nitrogen under mild heating to give the crude product. The crude product was extracted with ethyl acetate and saturated sodium bicarbonate and the organic layer was dried and concentrated. The residue was purified by silica gel column chromatography using a gradient of 2% MeOH in methylene chloride to 3% MeOH in methylene chloride to provide [3-(5-fluoro-indol-1-yl)-5-hydroxy-phenyl]-pyridin-3-yl-methanone (9.5 mg, 0.029 mmol, 19%) as a solid. $^1$H NMR (400 MHz, CD$_3$OD) δ 8.94 (d, 1.6 Hz, 1H), 8.71 (dd, J=5.2, 1.6 Hz, 1H), 8.14 (dt, J=8.0, 1.8 Hz, 1H), 7.48-7.43 (2H), 7.32 (d, J=3.2 Hz, 1H), 7.29 (1H), 7.23 (dd, J=9.2, 2.4 Hz, 1H), 7.19 (t, J=2.0 Hz, 1H), 7.13 (t, 2.0 Hz, 1H), 6.90 (td, J=8.8, 2.4 Hz, 1H), 6.56 (d, J=3.2 Hz, 1H).

Example 79

5-[3-Hydroxy-5-(1H-indol-4-yl)-phenylamino]-pyridine-2-carboxylic acid amide

5-[3-Bromo-5-(4-methoxy-benzyloxy)-phenylamino]-pyridine-2-carbonitrile was prepared from 5-amino-pyridine-2-carbonitrile by the method described in Example 44. 5-[3-Bromo-5-(4-methoxy-benzyloxy)-phenylamino]-pyridine-2-carbonitrile was converted to 5-[3-hydroxy-5-(1H-indol-4-yl)-phenylamino]-pyridine-2-carbonitrile by the method describe in Example 35.

To a solution of 5-[3-hydroxy-5-(1H-indol-4-yl)-phenylamino]-pyridine-2-carbonitrile (83 mg, 0.25 mmol) in MeOH (1 mL) was added 50% NaOH solution in H$_2$O (200 µL) and 30% H$_2$O$_2$ (500 µL), and the mixture was stirred for 16 h at room temperature. The solution was concentrated to half the volume with a gentle stream of nitrogen, and the solution was diluted by addition of water (2 mL). The aqueous solution was extracted with ethyl acetate (2 mL, three times). The combined solution of organic layer was dried and concentrated to give 5-[3-hydroxy-5-(1H-indol-4-yl)-phenylamino]-pyridine-2-carboxylic acid amide (58 mg, 0.168 mmol, 66%) as a solid. $^1$H NMR (400 MHz, CD$_3$OD) δ 8.34 (dd, J=2.4, 0.4 Hz, 1H), 7.91 (dd, J=8.8, 0.4 Hz, 1H), 7.55 (m, 1H), 7.35 (dd, J=8.0, 0.4 Hz, 1H), 7.25 (d, J=3.2 Hz, 1H), 7.14 (t, J=7.8 Hz, 1H), 7.06 (dt, J=7.2, 0.8 Hz, 1H), 6.97 (m, 1H), 6.82 (m, 1H), 6.67 (m, 1H), 6.63 (dd, J=2.4, 0.4 Hz, 1H).

Example 80

5-[3-Hydroxy-5-(1H-indol-4-yl)-phenylamino]-pyridine-2-carbonitrile (a) 4-(3-Bromo-5-triisopropylsilanyloxy-phenylamino)-benzonitrile To 1.0 g (2.45 mmol) of 3,5-dibromotriisopropylsiloxybenzene in 20.0 mL of anhydrous 1,4-dioxane was added 1.12 g (3.43 mmol) of Cs$_2$CO$_3$, 0.32 g (2.7 mmol) of 5-amino-pyridine-2-carbonitrile and 43 mg (0.074 mmol) Xantphos. The reaction mixture was deoxygenated by bubbling argon for 30 mins and then treated with 57 mg (0.049 mmol) of Pd(PPh$_3$)$_4$. The reaction vial was capped and heated at 100° C. for 4 hours. The reaction mixture was cooled to room temperature, filtered through Celite®, and the filter cake was washed with ethyl acetate. The ethyl acetate layer was washed with water and brine, dried over anhydrous sodium sulfate, filtered and concentrated. The crude product was chromatographed on silica gel using 5:1 hexane:ethyl acetate to give 506 mg of 4-(3-bromo-5-triisopropylsilanyloxy-phenylamino)-benzonitrile.

(b) 5-[3-Hydroxy-5-(1H-indol-4-yl)-phenylamino]-pyridine-2-carbonitrile 4-(3-Bromo-5-triisopropylsilanyloxy-phenylamino)-benzonitrile was converted to 5-[3-(1-triisopropylsilanyl-1H-indol-4-yl)-5-triisopropylsilanyloxy-phenylamino]-pyridine-2-carbonitrile, and the triisopropylsilyl groups were removed with tetra n-butylammonium fluoride to give 5-[3-hydroxy-5-(1H-indol-4-yl)-phenylamino]-pyridine-2-carbonitrile as described in Example 35. $^1$H NMR (400 MHz, CD$_3$OD) δ 8.31 (dd, J=2.8, 0.4 Hz, 1H), 7.57 (dd, J=8.8, 0.8 Hz, 1H), 7.49 (dd, J=8.8, 2.8 Hz, 1H), 7.35 (m, 1H), 7.26 (d, J=3.2 Hz, 1H), 7.14 (t, J=7.6 Hz, 1H), 7.05 (dd, J=7.2, 1.2 Hz, 1H), 6.97 (m, 1H), 6.89 (dd, J=2.4, 1.6 Hz, 1H), 6.66 (m, 1H), 6.61 (m, 1H).

Example 81

3-[3-(1H-Indol-4-yl)-5-(pyridine-3-carbonyl)-phenyl]-1,1-dimethyl-urea

To 0.2 g (3-amino-5-bromo-phenyl)-pyridin-3-yl-methanone (0.72 mmol) in 5 mL of methylene chloride was added 0.16 g of 4-nitrophenyl chloroformate (0.79 mmol) and 0.12 mL of pyridine. An additional 10 mL of methylene chloride was added, and the reaction was stirred for 3 hours at room temperature at which time 0.15 mL (0.866 mmol) diisopropylethyl amine and 0.873 mL (1.75 mmol) 2 N dimethylamine in THF were added. The reaction was stirred at ambient temperature overnight, then transferred to a separatory funnel. The methylene chloride phase was washed with saturated sodium bicarbonate, dried over anhydrous sodium sulfate and concentrated. The crude product was chromatographed to give 3-[3-bromo-5-(pyridine-3-carbonyl)-phenyl]-1,1-dimethyl-urea. This material was converted to 3-[3-(1H-Indol-4-yl)-5-(pyridine-3-carbonyl)-phenyl]-1,1-dimethyl-urea as described for Example 75. $^1$H NMR (400 MHz, CD$_3$OD) δ 8.97 (s, 1H), 8.75 (d, J=3.7 Hz, 1H), 8.25 (td, J=7.9, 1.9 Hz, 1H), 8.09 (t, J=1.9 Hz, 1H), 7.84 (t, J=1.9 Hz, 1H), 7.73 (t, J=1.6 Hz, 1H), 7.58 (dd, J=7.8, 4.9 Hz, 1H), 7.39 (td, J=8.0, 1.0 Hz, 1H), 7.28 (d, J=3.1 Hz, 1H), 7.17 (t, J=7.6 Hz, 1H), 7.12 (dd, J=7.3, 1.1 Hz, 1H), 6.67 (dd, J=3.1, 1.0 Hz, 1H), 3.02 (s, 6H).

Example 82

N-[3-(1H-Indol-4-yl)-5-(pyridine-4-carbonyl)-phenyl]-acetamide a) 3,5-Dibromo-phenyl)-pyridin-4-yl-methanone 3,5-Dibromo-phenyl)-pyridin-4-yl-methanone was prepared from 1,3,5-tribromobenzene and 4-cyanopyridine as described in Example 25.

b) N-[3-Bromo-5-(pyridine-4-carbonyl)-phenyl]-acetamide

To a flask under argon was added Pd$_2$(dba)$_3$ (Strem, 0.016 g, 0.018 mmol) and Xantphos (Strem, 0.016 g, 0.027 mmol) followed by 1 mL 1,4-dioxane. The mixture was stirred at room temperature for 15 min. In a separate vial was added 0.307 g 3,5-dibromo-phenyl)-pyridin-4-yl-methanone (0.900 mmol), 0.074 g acetamide (1.26 mmol) and 0.411 g cesium carbonate (1.26 mmol). The atmosphere was flushed with argon and the vial was capped; then 5 mL of 1,4-dioxane was added. The catalyst mixture was added to the vial via syringe, using 0.6 mL additional dioxane to transfer the remaining catalyst. The vial was heated at 110° C. and monitored by SFC-MS. At 6 h, the reaction was cooled and filtered through Celite®, eluting with ethyl acetate, then the solvent was removed in vacuo. The material was absorbed onto silica and purified by flash column chromatography using to give 0.080 mg (27% yield) of N-[3-bromo-5-(pyridine-4-carbonyl)-phenyl]-acetamide.

c) N-[3-(1H-Indol-4-yl)-5-(pyridine-4-carbonyl)-phenyl]-acetamide

N-[3-Bromo-5-(pyridine-4-carbonyl)-phenyl]-acetamide was converted to N-[3-(1H-indol-4-yl)-5-(pyridine-4-carbonyl)-phenyl]-acetamide as described in Example 75. $^1$H NMR (400 MHz, CDCl$_3$): δ 10.50 (s, 1H), 8.78-8.68 (m, 2H), 8.19 (t, J=1.7 Hz, 1H), 8.04 (t, J=1.7 Hz, 1H), 7.80 (t, J=1.4 Hz, 1H), 7.73-7.69 (m, 2H), 7.61 (d, J=1.0 Hz, 1H), 7.41 (d, J=8.2 Hz, 1H), 7.28-7.25 (m, 1H), 7.18 (t, J=7.7 Hz, 1H), 7.11 (d, J=6.6 Hz, 1H), 6.63 (d, J=2.3 Hz, 1H), 2.14 (s, 3H).

Example 83

N-[3-(2-Chloro-pyridine-4-carbonyl)-5-(1H-indol-4-yl)-phenyl]-acetamide (2-Chloro-pyridin-4-yl)-(3,5-dibromo-phenyl)-methanone was prepared from 1,3,5-tribromobenzene and 2-chloro-isonicotinonitrile as described in Example 25. This was converted to N-[3-(2-chloro-pyridine-4-carbonyl)-5-(1-triisopropylsilanyl-1H-indol-4-yl)-phenyl]-acetamide in the same manner as described for Example 82. N-[3-(2-Chloro-pyridine-4-carbonyl)-5-(1-triisopropylsilanyl-1H-indol-4-yl)-phenyl]-acetamide was deprotected to give N-[3-(2-chloro-pyridine-4-carbonyl)-5-(1H-indol-4-yl)-phenyl]-acetamide as described in Example 75. $^1$H NMR (400 MHz, CD$_3$COCD$_3$): δ 10.48 (s, 1H), 9.53 (s, 1H), 8.63 (d, J=5.0 Hz, 1H), 8.41 (t, J=1.7 Hz, 1H), 8.14 (t, J=1.6 Hz, 1H), 7.82 (t, J=1.5 Hz, 1H), 7.79 (s, 1H), 7.71 (dd, J=5.0, 1.3 Hz, 1H), 7.49 (d, J=7.8 Hz, 1H), 7.43 (t, J=2.8 Hz, 1H), 7.23-7.15 (m, 2H), 6.74 (s, 1H), 2.15 (s, 3H).

Example 84

N-[3-(1H-Indol-4-yl)-5-(2-methoxy-pyridine-4-carbonyl)-phenyl]-acetamide

To N-[3-(2-Chloro-pyridine-4-carbonyl)-5-(1-triisopropylsilanyl-1H-indol-4-yl)-phenyl]-acetamide (Example 83, 0.120 g, 0.22 mmol) in 25 mL of anhydrous methanol was added 0.036 g (0.66 mmol) NaOMe. The reaction mixture was refluxed overnight. The methanol was removed under vacuum and water added to the reaction mixture. The aqueous phase was extracted with ethyl acetate, washed with water and brine and dried over anhydrous sodium sulfate. The crude product was purifed on the preparative SFC to give 10 mg N-[3-(1H-indol-4-yl)-5-(2-methoxy-pyridine-4-carbonyl)-phenyl]-acetamide. $^1$H NMR (400 MHz, CD$_3$COCD$_3$): δ 10.46 (s, 1H), 9.50 (s, 1H), 8.41 (q, J=1.7 Hz, 1H), 8.37 (dd, J=5.1, 0.7 Hz, 1H), 8.11 (q, J=1.5 Hz, 1H), 7.82 (t, J=1.6 Hz, 1H), 7.49 (d, J=8.0 Hz, 1H), 7.45-7.42 (m, 1H), 7.28 (dd, J=5.1, 1.4 Hz, 1H), 7.20 (m, 2H), 7.08 (t, J=1.1 Hz, 1H), 6.75-6.73 (m, 1H), 3.96 (s, 3H), 2.14 (s, 3H).

Example 85

[3-Amino-5-(1H-indol-4-yl)-phenyl]-(2-methoxy-pyridin-4-yl)-methanone

To N-[3-(2-Chloro-pyridine-4-carbonyl)-5-(1-triisopropylsilanyl-1H-indol-4-yl)-phenyl]-acetamide (Example 83, 0.150 g, 0.27 mmol) in 25 mL of anhydrous methanol was added 0.022 g (0.41 mmol) NaOMe. The reaction mixture was refluxed overnight. The methanol was removed under vacuum and water was added to the reaction mixture. The aqueous phase was extracted with ethyl acetate, washed with water and brine and dried over anhydrous sodium sulfate. The crude product was purifed by preparative TLC using 10:1 methylene chloride:methanol to give 12 mg [3-amino-5-(1H-indol-4-yl)-phenyl]-(2-methoxy-pyridin-4-yl)-methanone. $^1$H NMR (400 MHz, CDCl$_3$): δ 8.23 (s, 1H), 8.22 (s, 1H), 7.38 (t, J=1.5 Hz, 1H), 7.34 (t, J=1.0 Hz, 1H), 7.32 (t, J=0.9 Hz, 1H), 7.21-7.16 (m, 4H), 7.13 (dd, J=5.1, 1.3 Hz, 1H), 7.10-7.07 (m, 2H), 7.00 (s, 1H), 6.62-6.59 (m, 1H), 3.91 (s, 3H).

Example 86

N-[3-(1H-Indol-4-yl)-5-(pyridine-4-carbonyl)-phenyl]-methanesulfonamide

To a microwave tube was added 0.250 g 3,5-dibromo-phenyl)-pyridin-4-yl-methanone (0.733 mmol), methanesulfonamide (0.077 g, 0.81 mmol), cesium carbonate (0.334 g, 1.03 mmol), Xantphos (Strem, 0.013 g, 0.022 mmol) and 5.0 mL of anhydrous 1,4-dioxane. The atmosphere was flushed with argon, then 0.025 g (0.022 mmol) of Pd(PPh$_3$)$_4$ was added. The vial was capped and heated at 110° C. and monitored by SFC-MS. At 18 h, the reaction was cooled and filtered through Celite®, eluting with ethyl acetate; then solvent was removed in vacuo. The crude product was redissolved in ethyl acetate, and the organic phase was washed with water and brine, then dried over anhydrous sodium sulfate. The solution was filtered and concentrated. The crude product was chromatographed on silica gel using 10:1 methylene chloride:methanol to give to give 0.084 mg (32.3% yield) of N-[3-bromo-5-(pyridine-4-carbonyl)-phenyl]-methanesulfonamide. This compound was converted to N-[3-(1H-indol-4-yl)-5-(pyridine-4-carbonyl)-phenyl]-methanesulfonamide as described for Example 75. $^1$H NMR (400 MHz, CD$_3$COCD$_3$): δ 10.50 (s, 1H), 8.97 (s, 1H), 8.85 (d, J=1.6 Hz, 1H), 8.84 (d, J=1.7 Hz, 1H), 8.07 (t, J=1.9 Hz, 1H), 7.90 (t, J=1.5 Hz, 1H), 7.83 (t, J=1.9 Hz, 1H), 7.75-7.73 (m, 2H), 7.51 (td, J=7.5, 1.2 Hz, 1H), 7.46-7.44 (m, 1H), 7.25-7.19 (m, 2H), 6.75-6.72 (m, 1H), 3.15 (s, 3H).

Example 87

N-[3-(2-Chloro-pyridine-4-carbonyl)-5-(1H-indol-4-yl)-phenyl]-methanesulfonamide (2-Chloro-pyridin-4-yl)-(3,5-dibromo-phenyl)-methanone was converted to N-[3-bromo-5-(2-chloro-pyridine-4-carbonyl)-phenyl]-methanesulfonamide as described in Example 86. The Suzuki reaction and removal of the triisopropylsilyl protecting group were carried out as described in Example 35. $^1$H NMR (400 MHz, CDCl$_3$): δ 8.58 (d, J=5.0 Hz, 1H), 8.37 (s, 1H), 7.89 (t, J=1.9 Hz, 1H), 7.85 (t, J=1.5 Hz, 1H), 7.68 (s, 1H), 7.63 (t, J=1.8 Hz, 1H), 7.55 (dd, J=5.1, 1.4 Hz, 1H), 7.47 (s, 1H), 7.45 (s, 1H), 7.31 (t, J=3.0 Hz, 1H), 7.27 (d, J=8.0 Hz, 1H), 7.17 (dd, J=7.2, 0.7 Hz, 1H), 6.76 (s, 1H), 6.68-6.66 (m, 1H), 3.12 (s, 3H).

Example 88

N-[3-(1H-Indol-4-yl)-5-(2-methoxy-pyridine-4-carbonyl)-phenyl]-methanesulfonamide To a mixture of 0.080 g (0.21 mmol) of N-[3-bromo-5-(2-chloro-pyridine-4-carbonyl)-phenyl]-methanesulfonamide in 10.0 mL of anhydrous methanol in a pressure tube was added 0.007 g (0.21 mmol) of sodium methoxide. The tube was sealed and the reaction was heated at 80° C. for 18 hours. The methanol was removed under vacuum and water was added to the reaction mixture. The aqueous phase was extracted with ethyl acetate, washed with water and brine and dried over anhydrous sodium sulfate. The solution was filtered and concentrated to give 0.035 g of N-[3-bromo-5-(2-methoxy-pyridine-4-carbonyl)-phenyl]-methanesulfonamide. The Suzuki reaction and removal of the triisopropylsilyl protecting group were carried out as described in Example 35. $^1$H NMR (400 MHz, CD$_3$COCD$_3$): δ 10.49 (s, 1H), 8.96 (s, 1H), 8.38 (d, J=5.1 Hz, 1H), 8.07 (t, J=1.9 Hz, 1H), 7.90 (t, J=1.6 Hz, 1H), 7.83 (t, J=1.9 Hz, 1H), 7.51 (d, J=7.8 Hz, 1H), 7.45 (t, J=2.8 Hz, 1H), 7.30 (dd, J=5.1, 1.3 Hz, 1H), 7.26-7.18 (m, 2H), 7.10 (s, 1H), 6.75-6.72 (m, 1H), 3.96 (s, 3H), 3.15 (s, 3H).

Example 89

N-[3-(2-Chloro-6-methyl-pyridine-4-carbonyl)-5-(1H-indol-4-yl)-phenyl]-methanesulfonamide a) 2-Chloro-N-methoxy-6,N-dimethyl-isonicotinamide To 0.500 g (2.91 mmol) 2-chloro-6-methyl-isonicotinic acid in 5.0 mL of anhydrous methylene chloride and 0.5 mL of anhydrous DMF was added 0.47 g (3.5 mmol) 1-hydroxy-benzotriazole hydrate. The reaction mixture was stirred for 20 minutes at 0° C. 1-(3-Dimethylaminopropyl)-3-ethylcarbodiimide hydrochloride (0.67 g, 3.5 mmol) was added to the reaction mixture. Stirring was continued for 1 hour allowing the reaction mixture to slowly warm up to room temperature. The reaction mixture was re-cooled to 0° C. and 0.750 g (5.8 mmol) of diisopropylethylamine and 0.340 g (3.5 mmol) of O,N-dimethyl-hydroxylamine were added. The reaction mixture was allowed to warm to room temperature and was stirred overnight. The reaction mixture was diluted with water and extracted with 50 mL of methylene chloride. The organic phase was washed with water, and brine, dried over anhydrous sodium sulfate, filtered and concentrated. The crude product was chromatographed on silica gel using 5:1 hexane:ethyl acetate to give 360 mg of the 2-chloro-N-methoxy-6,N-dimethyl-isonicotinamide.

b) (2-Chloro-6-methyl-pyridin-4-yl)-(3,5-dibromo-phenyl)-methanone

To 0.45 grams (1.4 mmol) of 1,3,5-tribromobenzene in 25.0 mL of anhydrous ether at −78° C. was added 0.57 mL of 2.5 M n-BuLi (1.4 mmol) at a rate that maintained the internal temperature of the reaction at less than −70° C. After the addition was complete, the reaction was stirred 1 hour at −78° C., then 0.220 grams (1.1 mmol) of 2-chloro-N-methoxy-6,N-dimethyl-isonicotinamide in 2 mL of THF was added, again keeping the temperature below −70° C. After the addition was complete, the reaction was allowed to stir at −25° C. for 45 minutes; then 100 mL saturated aqueous sodium bicarbonate was added and the reaction was stirred at room temperature for 30 minutes. The phases were separated and the aqueous phase was extracted with ether. The organic fractions were combined and dried with sodium sulfate. The volatiles were removed under reduced pressure and the crude product was chromatographed on silica gel using 5:1 hexane:ethyl acetate to give 330 mg (77% yield) of (2-chloro-6-methyl-pyridin-4-yl)-(3,5-dibromo-phenyl)-methanone.

c) N-[3-Bromo-5-(2-chloro-6-methyl-pyridine-4-carbonyl)-phenyl]-methanesulfonamide The Buchwald reaction on (2-chloro-6-methyl-pyridin-4-yl)-(3,5-dibromo-phenyl)-methanone was carried out under the conditions described in Example 82, using methanesulfonamide in place of acetamide.

d) N-[3-(2-Chloro-6-methyl-pyridine-4-carbonyl)-5-(1H-indol-4-yl)-phenyl]-methanesulfonamide The Suzuki reaction and removal of the triisopropylsilyl protecting group were carried out as described in Example 35. $^1$H NMR (400 MHz, CD$_3$COCD$_3$): δ 10.51 (s, 1H), 8.96 (s, 1H), 8.06 (t, J=1.9 Hz, 1H), 7.89 (t, J=1.5 Hz, 1H), 7.83 (t, J=1.8 Hz, 1H), 7.60 (d, J=6.2 Hz, 2H), 7.52 (d, J=7.8 Hz, 1H), 7.46 (t, J=2.8 Hz, 1H), 7.26-7.18 (m, 2H), 6.74-6.72 (m, 1H), 3.15 (s, 3H), 2.60 (s, 3H).

Example 90

N [3-(2-Chloro-6-methyl-pyridine-4-carbonyl)-5-(1H-indol-4-yl)-phenyl]-carbamic acid methyl ester (2-Chloro-6-methyl-pyridin-4-yl)-(3,5-dibromo-phenyl)-methanone (Example 89) was converted to 3-bromo-5-(2-chloro-6-methyl-pyridine-4-carbonyl)-phenyl]-carbamic acid methyl ester under the palladium catalyzed conditions described for Example 86, using carbamic acid methyl ester in place of methanesulfonamide. The Suzuki reaction to give [3-(2-chloro-6-methyl-pyridine-4-carbonyl)-5-(1-triisopropylsilanyl-1H-indol-4-yl)-phenyl]-carbamic acid methyl ester and removal of the triisopropylsilyl protecting group were carried out as described in Example 35. $^1$H NMR (400 MHz, CD$_3$COCD$_3$): δ 10.12 (s, 1H), 8.75 (s, 1H), 8.26 (s, 1H), 7.99 (s, 1H), 7.78 (t, J=1.5 Hz, 1H), 7.64 (s, 1H), 7.50 (d, J=6.1 Hz, 2H), 7.45 (d, J=7.8 Hz, 1H), 7.34 (t, J=2.8 Hz, 1H), 7.24-7.16 (m, 2H), 6.74-6.71 (m, 1H), 3.77 (s, 3H), 2.63 (s, 3H).

Example 91

[3-(2-Cyano-6-methyl-pyridine-4-carbonyl)-5-(1H-indol-4-yl)-phenyl]-carbamic acid methyl ester To 0.057 g (0.099 mmol) of [3-(2-chloro-6-methyl-pyridine-4-carbonyl)-5-(1-triisopropylsilanyl-1H-indol-4-yl)-phenyl]-carbamic acid methyl ester in 4.0 mL of 1,4-dioxane in a pressure tube was added 0.023 g of zinc cyanide (0.20 mmol), and the solution was degassed with argon for 20 minutes. Pd(PPh$_3$)$_4$ (0.011 g, 0.01 mmol) was added to the reaction mixture, the tube was sealed, and heated at 110° C. overnight. The reaction mixture was filtered through Celite® and concentrated. The crude product was redissolved in ethyl acetate, and the organic phase was washed with water and brine, then dried over anhydrous sodium sulfate. The solution was filtered and concentrated. The crude product was chromatographed on silica gel to give 0.024 g of [3-(2-cyano-6-methyl-pyridine-4-carbonyl)-5-(1-triisopropylsilanyl-1H-indol-4-yl)-phenyl]-carbamic acid methyl ester. This compound was deprotected as described in Example 75 to give [3-(2-cyano-6-methyl-pyridine-4-carbonyl)-5-(1H-indol-4-yl)-phenyl]-carbamic acid methyl ester. $^1$H NMR (400 MHz, CD$_3$COCD$_3$): δ 10.48 (s, 1H), 9.02 (s, 1H), 8.31 (s, 1H), 8.08 (d, J=5.7 Hz, 2H), 7.92 (s, 1H), 7.78 (s, 1H), 7.50 (d, J=7.8 Hz, 1H), 7.45 (s, 1H), 7.25-7.16 (m, 2H), 6.74 (s, 1H), 3.75 (s, 3H), 2.69 (s, 3H).

Example 92

[3-(2,6-Dimethyl-pyridine-4-carbonyl)-5-(1H-indol-4-yl)-phenyl]-carbamic acid methyl ester To 0.100 g (0.174 mmol) [3-(2-chloro-6-methyl-pyridine-4-carbonyl)-5-(1-triisopropylsilanyl-1H-indol-4-yl)-phenyl]-carbamic acid methyl ester in 2.0 mL of anhydrous dioxane in a pressure tube was added 0.034 g (0.24 mmol) potassium carbonate and 0.015 g (0.24 mmol) methylboronic acid. The reaction mixture was degassed with argon and then 0.006 g (0.005 mmol) Pd(PPh$_3$)$_4$ was added. The reaction mixture was capped and heated at 110° C. for 24 hours. The reaction mixture was diluted with water and extracted with ethyl acetate. The ethyl acetate phase was washed with brine and dried over anhydrous sodium sulfate. The solution was filtered and concentrated. The crude product was chromatographed on silica gel using 10:1 methylene chloride:methanol to give 0.060 g of [3-(2,6-dimethyl-pyridine-4-carbonyl)-5-(1-triisopropylsilanyl-1H-indol-4-yl)-phenyl]-carbamic acid methyl ester. The protecting group was removed as described in Example 75 to give [3-(2,6-dimethyl-pyridine-4-carbonyl)-5-(1H-indol-4-yl)-phenyl]-carbamic acid methyl ester. $^1$H NMR (400 MHz, CDCl$_3$): δ 8.50 (s, 1H), 8.12 (s, 1H), 7.79-7.75 (m, 2H), 7.40 (d, J=8.2 Hz, 1H), 7.29 (s, 2H), 7.27-7.22 (m, 2H), 7.17 (dd, J=7.3, 0.9 Hz, 1H), 7.05 (s, 1H), 6.72 (s, 1H), 3.79 (s, 3H), 2.60 (s, 6H).

Example 93

[3-(1H-Indol-4-yl)-5-(2-methoxy-pyridine-4-carbonyl)-phenyl]-carbamic acid methyl ester (3,5-Dibromo-phenyl)-(2-methoxy-pyridin-4-yl)-methanone was prepared from 2-methoxy-isonicotinic acid (available from CombiBlocks) by the method described in Example 89. This was converted to 3-bromo-5-(2-methoxy-pyridine-4-carbonyl)-phenyl]-carbamic acid methyl ester under the palladium catalyzed conditions described for Example 86, using carbamic acid methyl ester in place of methanesulfonamide. The Suzuki reaction and removal of the triisopropylsilyl protecting group were carried out as described in Example 35. $^1$H NMR (400 MHz, CD$_3$COCD$_3$): δ 10.48 (s, 1H), 9.03 (s, 1H), 8.37 (d, J=5.3 Hz, 1H), 8.31 (t, J=1.7 Hz, 1H), 8.07 (t, J=1.8 Hz, 1H), 7.80 (t, J=1.5 Hz, 1H), 7.50 (d, J=7.8 Hz, 1H), 7.44 (t, J=2.7 Hz, 1H), 7.29 (dd, J=5.2, 1.2 Hz, 1H), 7.25-7.17 (m, 2H), 7.09 (s, 1H), 6.76-6.73 (m, 1H), 3.96 (s, 3H), 3.74 (s, 3H).

Example 94

[3-(2-Chloro-pyridine-4-carbonyl)-5-(1H-indol-4-yl)-phenyl]-carbamic acid methyl ester (2-Chloro-pyridin-4-yl)-(3,5-dibromo-phenyl)-methanone was converted to [3-bromo-5-(2-chloro-pyridine-4-carbonyl)-phenyl]-carbamic acid methyl ester under the palladium catalyzed conditions described for Example 86, using carbamic acid methyl ester in place of methanesulfonamide. The Suzuki reaction and removal of the triisopropylsilyl protecting group were carried out as described in Example 35. $^1$H NMR (400 MHz, CDCl$_3$): δ 8.56 (d, J=4.9 Hz, 1H), 8.35 (s, 1H), 8.07 (s, 1H), 7.82 (s, 1H), 7.77 (t, J=1.5 Hz, 1H), 7.69 (s, 1H), 7.55 (dd, J=5.0, 1.3 Hz, 1H), 7.43 (d, J=8.2 Hz, 1H), 7.30-7.25 (m, 2H), 7.18 (dd, J=7.2, 0.8 Hz, 1H), 6.85 (s, 1H), 6.71 (s, 1H), 3.81 (s, 3H).

Example 95

[3-(1H-Indol-4-yl)-5-(2-morpholin-4-yl-pyridine-4-carbonyl)-phenyl]-carbamic acid methyl ester To (2-chloro-pyridin-4-yl)-(3,5-dibromo-phenyl)-methanone (0.200 g, 0.53 mmol) in 1.0 mL of 1,4-dioxane in a microwave tube was added 0.070 g (0.80 mmol) morpholine. The reaction was subjected to microwave irradiation at 120° C. for 60 minutes. The reaction mixture was cooled and concentrated. The crude product was chromatographed on silica gel using 1:1 hexane:ethyl acetate to give 0.118 g of the (3,5-dibromo-phenyl)-(2-morpholin-4-yl-pyridin-4-yl)-methanone. This compound was converted to [3-(1H-indol-4-yl)-5-(2-morpholin-4-yl-pyridine-4-carbonyl)-phenyl]-carbamic acid methyl ester as described for Example 90. $^1$H NMR (400 MHz, CDCl$_3$): δ 8.28 (d, J=5.3 Hz, 1H), 8.07 (t, J=1.8 Hz, 1H), 7.95 (s, 1H), 7.76 (t, J=1.6 Hz, 1H), 7.41 (d, J=8.2 Hz, 1H), 7.29 (d, J=3.3 Hz, 1H), 7.18 (t, J=7.7 Hz, 1H), 7.10 (d, J=7.4 Hz, 1H), 7.08 (s, 1H), 6.95 (dd, J=5.1, 1.0 Hz, 1H), 6.62 (d, J=3.1 Hz, 1H), 3.78 (t, J=4.9 Hz, 4H), 3.75 (s, 3H), 3.54 (t, J=4.9 Hz, 4H).

Example 96

1-[3-(1H-Indol-4-yl)-5-(pyridine-3-carbonyl)-phenyl]-pyrrolidin-2-one

To a nitrogen-flushed tube were added 0.20 grams (0.72 mmol) (3,5-dibromo-phenyl)-pyridin-3-yl-methanone, 0.137 g (0.72 mmol) copper (I) iodide, 0.235 (0.72 mmol) cesium carbonate, 0.063 g (0.72 mmol) N,N'-dimethyl-ethane-1,2-diamine, 0.061 g (0.72 mmol) pyrrolidin-2-one and 5 mL dioxane. The tube was sealed and heated at 80° C. overnight. The reaction mixture was allowed to cool, and was filtered. The volatiles were removed under reduced pressure and the resulting material was chromatographed on silica gel with 2% methanol/chloroform to give 0.018 g of 1-[3-bromo-5-(pyridine-3-carbonyl)-phenyl]-pyrrolidin-2-one. This material was converted to 1-[3-(1H-indol-4-yl)-5-(pyridine-3-carbonyl)-phenyl]-pyrrolidin-2-one as described in Example 75. $^1$H NMR (400 MHz, CD$_3$OD): δ 9.01 (s, 1H), 8.79 (s, 1H), 8.26-8.31 (m, 2H), 8.06 (s, 1H), 7.86 (s, 1H), 7.62 (s, 1H), 7.42 (d, J=8.0 Hz, 1H), 7.30 (d, J=3.1 Hz, 1H), 7.19 (t, J=7.5 Hz, 1H), 7.14 (d, J=7.2 Hz, 1H), 6.67 (d, J=3.1 Hz, 1H), 4.03 (t, J=7.0 Hz, 2H), 2.63 (t, J=8.1 Hz, 2H), 2.16-2.26 (m, 2H).

Example 97

4-[3-Hydroxy-5-(pyridin-3-ylamino)-phenyl]-1H-indole-2-carbonitrile a) Trifluoro-methanesulfonic acid 2-cyano-1H-indol-4-yl ester 4-Hydroxy-1H-indole-2-carbonitrile was made as described by Estep, K. G., *Synth. Comm.* 25: 507-14 (1995). It was converted to the triflate by the procedure in Example 21.

b) 4-(4,4,5,5-Tetramethyl-[1,3,2]dioxaborolan-2-yl)-1-triisopropylsilanyl-1H-indole A tube was charged with trifluoro-methanesulfonic acid 2-cyano-1H-indol-4-yl ester (0.136 g, 0.469 mmol), 0.150 g (0.61 mmol) bis(pinacolato)diboron, 0.138 g (1.41 mmol) potassium acetate, Pd(dppf)Cl$_2$.CH$_2$Cl$_2$ complex (0.039 g, 0.047 mmol) and 3 mL anhydrous DMSO. The tube was flushed with nitrogen and sealed, and the reaction mixture was heated at 90° C. overnight. The reaction mixture was cooled, filtered through silica gel and the filter cake was washed with ethyl acetate. The filtrate was washed with brine, dried over sodium sulfate and concentrated. The residue was purified by silica gel chromatography to give 0.049 g (39% yield) of 4-(4,4,5,5-tetramethyl-[1,3,2]dioxaborolan-2-yl)-1H-indole. This material was protected with triisopropylsilyl chloride to give 4-(4,4,5,5-tetramethyl-[1,3,2]dioxaborolan-2-yl)-1-triisopropylsilanyl-1H-indole using conditions similar to those described in Example 21.

c) 4-[3-Hydroxy-5-(pyridin-3-ylamino)-phenyl]-1H-indole-2-carbonitrile

The Suzuki coupling of 4-(4,4,5,5-tetramethyl-[1,3,2]dioxaborolan-2-yl)-1-triisopropylsilanyl-1H-indole to 3-bromo-5-(4-methoxy-benzyloxy)-phenyl]-pyridin-3-yl-amine and removal of the triisopropylsilyl group was carried out as described in Example 75. Phenol deprotection was carried out as described in Example 35 to give 4-[3-hydroxy-5-(pyridin-3-ylamino)-phenyl]-1H-indole-2-carbonitrile. $^1$H NMR (400 MHz, CD$_3$COCD$_3$): δ 8.47 (d, J=2.7 Hz, 1H), 8.10 (dd, J=4.7, 1.2 Hz, 1H), 7.68 (s, 1H), 7.61 (d, J=8.2 Hz, 1H), 7.52 (d, J=8.2 Hz, 1H), 7.44 (dd, J=8.2, 7.2 Hz, 1H), 7.30-7.22 (m, 2H), 6.93 (s, 1H), 6.77-6.73 (m, 2H).

Example 98

N-[3-(2-Cyano-1H-indol-4-yl)-5-(pyridine-3-carbonyl)-phenyl]-methanesulfonamide

The Suzuki coupling of 4-(4,4,5,5-tetramethyl-[1,3,2]dioxaborolan-2-yl)-1-triisopropylsilanyl-1H-indole to N-[3-bromo-5-(pyridine-3-carbonyl)-phenyl]-methanesulfonamide and removal of the triisopropylsilyl group was carried out as described in Example 75 to give N-[3-(2-cyano-1H-indol-4-yl)-5-(pyridine-3-carbonyl)-phenyl]-methanesulfonamide. $^1$H NMR (400 MHz, CD$_3$COCD$_3$): δ 11.5 (bs, 1H), 9.05 (d, J=1.6 Hz, 1H), 8.84 (dd, J=4.9, 1.6 Hz, 1H), 8.26 (dt, J=5.0, 2.6 Hz, 1H), 8.03 (t, J=1.9 Hz, 1H), 7.88-7.85 (m, 2H), 7.64-7.58 (m, 2H), 7.53-7.48 (m, 2H), 7.38 (dd, J=7.2, 1.0 Hz, 1H), 3.17 (s, 3H).

Example 99

[3-Benzofuran-4-yl-5-(2-methoxy-pyridine-4-carbonyl)-phenyl]-carbamic acid methyl ester 6,7-Dihydro-5H-benzofuran-4-one was converted to benzofuran-4-ol using conditions similar to those described in Estep, K. G., *Synth. Comm.* 25: 507-14 (1995). for the conversion of 4-oxo-4,5,6,7-tetrahydro-1H-indole-2-carbonitrile to 4-hydroxy-1H-indole-2-carbonitrile. This was converted to the triflate as described in Example 21.

Trifluoro-methanesulfonic acid benzofuran-4-yl ester was converted to 4-(4,4,5,5-tetramethyl-[1,3,2]dioxaborolan-2-yl)-benzofuran using conditions described in Wang, Y.-C. and Georghiou, P. E., *Org. Lett.* 4: 2675-78 (2002). The Suzuki coupling of 4-(4,4,5,5-tetramethyl-[1,3,2]dioxaborolan-2-yl)-benzofuran to [3-bromo-5-(2-methoxy-pyridine-4-carbonyl)-phenyl]-carbamic acid methyl ester was carried out as described in Example 75 to give [3-benzofuran-4-yl-5-(2-methoxy-pyridine-4-carbonyl)-phenyl]-carbamic acid methyl ester. $^1$H NMR (400 MHz, CDCl$_3$): δ 9.08 (s, 1H), 8.38 (dd, J=5.2, 0.5 Hz, 1H), 8.29 (t, J=1.6 Hz, 1H), 8.06 (t, J=1.7 Hz, 1H), 7.96 (d, J=2.1 Hz, 1H), 7.75 (t, J=1.6 Hz, 1H), 7.62-7.56 (m, 1H), 7.48-7.42 (m, 2H), 7.29 (dd, J=5.2, 1.3 Hz, 1H), 7.15 (dd, J=2.1, 1.0 Hz, 1H), 7.08 (s, 1H), 3.96 (s, 3H), 3.75 (s, 3H).

Example 100

[3-(7-Fluoro-1H-indol-4-yl)-5-(pyridine-3-carbonyl)-phenyl]-carbamic acid methyl ester a) 4-Bromo-7-fluoro-1-triisopropylsilanyl-1H-indole 4-Bromo-7-fluoro-1H-indole was converted to [3-(pyridine-3-carbonyl)-5-(4,4,5,5-tetramethyl-[1,3,2]dioxaborolan-2-yl)-phenyl]-carbamic acid methyl ester using conditions similar to Example 21.

b) [3-(Pyridine-3-carbonyl)-5-(4,4,5,5-tetramethyl-[1,3,2]dioxaborolan-2-yl)-phenyl]-carbamic acid methyl ester To a 3-neck round bottom flask were added 1.0 grams (2.98 mmol) [3-bromo-5-(pyridine-3-carbonyl)-phenyl]-carbamic acid methyl ester, 0.30 g (2.98 mmol) potassium acetate, 0.757 g (2.98 mmol) bis(pinacolato)diboron, 0.100 mg (0.14 mmol) Pd(dppf)Cl$_2$.CH$_2$Cl$_2$ complex and 10 mL dioxane. Argon was bubbled through the reaction mixture for 30 min; then it was heated to 100° C. and held overnight. The reaction mixture was cooled and filtered. The volatiles were removed under reduced pressure and the resulting material was chromatographed on silica gel eluting with 2% methanol/chloroform to afford [3-(pyridine-3-carbonyl)-5-(4,4,5,5-tetramethyl-[1,3,2]dioxaborolan-2-yl)-phenyl]-carbamic acid methyl ester.

c) [3-(7-Fluoro-1H-indol-4-yl)-5-(pyridine-3-carbonyl)-phenyl]-carbamic acid methyl ester The Suzuki coupling of [3-(pyridine-3-carbonyl)-5-(4,4,5,5-tetramethyl-[1,3,2]dioxaborolan-2-yl)-phenyl]-carbamic acid methyl ester to 4-bromo-7-fluoro-1-triisopropylsilanyl-1H-indole and removal of the triisopropylsilyl group was carried out as described in Example 75 to give [3-(7-fluoro-1H-indol-4-yl)-5-(pyridine-3-carbonyl)-phenyl]-carbamic acid methyl ester. $^1$H NMR (400 MHz, CD$_3$COCD$_3$): δ 10.87 (s, 1H), 9.04 (d, J=1.4 Hz, 2H), 8.83 (dd, J=4.9, 1.6 Hz, 1H), 8.28 (t, J=1.8 Hz, 1H), 8.24 (dt, J=4.9, 2.5 Hz, 1H), 8.04 (t, J=1.8 Hz, 1H), 7.76 (t, J=1.5 Hz, 1H), 7.60 (dd, J=8.0, 4.9 Hz, 1H), 7.53 (t, J=2.8 Hz, 1H), 7.17 (dd, J=8.0, 4.5 Hz, 1H), 7.02 (dd, J=11.1, 8.0 Hz, 1H), 6.85-6.81 (m, 1H), 3.75 (s, 3H).

Example 101

3-(1H-Indol-4-yl)-5-pyridin-3-yl-phenol

To a 30 mL vial equipped with stir-bar was added 0.400 g (0.71 mmol) 4-[3-bromo-5-(4-methoxy-benzyloxy)-phenyl]-1-triisopropylsilanyl-1H-indole followed by 0.096 g (0.78 mmol) 3-pyridinyl boronic acid, 3 mL toluene, 3 mL ethanol, 0.71 mL 2 M aqueous sodium carbonate and 0.011 g (0.035 mmol) tetra n-butylammonium bromide. The starting indole did not dissolve, so 3 mL DME (ethylene glycol dimethyl ether) were added. The reaction mixture was degassed for 30 min by bubbling nitrogen into the mixture. Pd(PPh$_3$)$_4$ (0.018 g, 0.022 mmol) was added and the reaction mixture was heated to 100° C. overnight. The reaction mixture was cooled and filtered through Celite®, washing with ethyl acetate. The solvent was removed and the crude product was purified by preparative TLC (eluent: 30:70 ethyl acetate:hexane) to give 0.184 g of 4-[3-(4-methoxy-benzyloxy)-5-pyridin-3-yl-phenyl]-1-triisopropylsilanyl-1H-indole. This compound was deprotected as described in Example 34. $^1$H NMR (400 MHz, CDCl$_3$): δ 10.07 (d, J=2.1 Hz, 1H), 9.74 (dd, J=4.9, 1.3 Hz, 1H), 9.30 (dt, J=4.9, 2.6 Hz, 1H), 8.70 (q, J=4.3 Hz, 1H), 8.65-8.61 (m, 2H), 8.53 (d, J=3.3 Hz, 1H), 8.45-8.36 (m, 3H), 8.29 (t, J=1.9 Hz, 1H), 7.89 (d, J=3.1 Hz, 1H).

Example 102

N-[3-(1H-Indol-4-yl)-5-(pyridin-3-ylamino)-phenyl]-acetamide a) N-[3-Bromo-5-(pyridin-3-ylamino)-phenyl]-acetamide 3-Aminopyridine was coupled with 1,3,5-tribromobenzene to give (3,5-dibromo-phenyl)-pyridin-3-yl-amine by the method described in Example 44. The reaction was complete in 1 hour. The dibromide was converted to N-[3-bromo-5-(pyridin-3-ylamino)-phenyl]-acetamide by the method of Example 82.

b) N-[3-(1H-Indol-4-yl)-5-(pyridin-3-ylamino)-phenyl]-acetamide

To a vial containing N-[3-bromo-5-(pyridin-3-ylamino)-phenyl]-acetamide (0.109 g, 0.36 mmol) in 0.7 mL toluene, 0.7 mL EtOH and 0.27 mL H$_2$O was added 0.076 g (0.719 mmol) sodium carbonate followed by 0.005 g (0.02 mmol) tetra n-butylammonium bromide and 4-(4,4,5,5-tetramethyl-[1,3,2]dioxaborolan-2-yl)-1-triisopropylsilanyl-1H-indole (0.158 g, 0.39 mmol). The vial atmosphere was purged with nitrogen before and after addition of Pd(Ph$_3$P)$_4$ (0.020 g, 0.017 mol). The vial was capped and the reaction mixture was stirred at 110° C. for 18 h. The reaction was cooled, and filtered through Celite®, eluting with MeOH. The solvent was removed in vacuo giving a mixture of N-[3-(pyridin-3-ylamino)-5-(1-triisopropylsilanyl-1H-indol-4-yl)-phenyl]-acetamide and N-[3-(1H-indol-4-yl)-5-(pyridin-3-ylamino)-phenyl]-acetamide. The deprotection was completed using the conditions given in Example 75. Purification by preparative SFC gave 0.071 g of N-[3-(1H-indol-4-yl)-5-(pyridin-3-ylamino)-phenyl]-acetamide. $^1$H NMR (400 MHz, acetone-d$_6$): δ 10.41 (s, 1H), 9.28 (s, 1H), 8.51 (d, J=2.5 Hz, 1H), 8.09 (dd, J=4.6, 1.1 Hz, 1H), 7.77 (d, J=17.0 Hz, 1H), 7.69 (s, 1H), 7.62 (ddd, J=8.2, 2.7, 1.3 Hz, 1H), 7.53 (s, 1H), 7.43 (d, J=7.8 Hz, 1H), 7.38 (t, J=2.8 Hz, 1H), 7.23 (q, J=4.3 Hz, 1H), 7.20-7.17 (m, 2H), 7.16-7.11 (m, 1H), 6.76-6.72 (m, 1H), 2.11 (s, 3H).

Example 103

N-[3-(1H-Indol-4-yl)-5-(pyridin-3-ylamino)-phenyl]-methanesulfonamide (3,5-Dibromo-phenyl)-pyridin-3-yl-amine was converted to N-[3-bromo-5-(pyridin-3-ylamino)-phenyl]-methanesulfonamide using the conditions in Example 86. N-[3-bromo-5-(pyridin-3-ylamino)-phenyl]-methanesulfonamide was converted to N-[3-(1H-indol-4-yl)-5-(pyridin-3-ylamino)-phenyl]-methanesulfonamide as described in Example 102. $^1$H NMR (400 MHz, acetone-d$_6$): δ 10.44 (s, 1H), 8.78 (s, 1H), 8.54 (d, J=2.7 Hz, 1H), 8.13 (dd, J=4.7, 1.2 Hz, 1H), 7.89 (s, 1H), 7.66 (ddd, J=8.2, 2.7, 1.4 Hz, 1H), 7.46 (dt, J=4.3, 2.5 Hz, 1H), 7.40 (t, J=2.8 Hz, 1H), 7.32 (t, J=1.6 Hz, 1H), 7.29-7.14 (m, 5H), 6.76-6.73 (m, 1H), 3.08 (d, J=6.8 Hz, 3H).

Example 104

[3-(6-Cyano-pyridin-3-ylamino)-5-(1H-indol-4-yl)-phenyl]-carbamic acid methyl ester 5-Amino-pyridine-2-carbonitrile was coupled with 1,3,5-tribromobenzene to give 5-(3,5-dibromo-phenylamino)-pyridine-2-carbonitrile by the method described in Example 44. 5-(3,5-Dibromo-phenylamino)-pyridine-2-carbonitrile was converted to [3-bromo-5-(6-cyano-pyridin-3-ylamino)-phenyl]-carbamic acid methyl ester using the conditions in Example 86, replacing methylsulfonamide with carbamic acid methyl ester. [3-Bromo-5-(6-cyano-pyridin-3-ylamino)-phenyl]-carbamic acid methyl ester was converted to [3-(6-cyano-pyridin-3-ylamino)-5-(1H-indol-4-yl)-phenyl]-carbamic acid methyl ester as described in Example 102. $^1$H NMR (400 MHz, acetone-$d_6$): δ 10.41 (s, 1H), 8.84 (s, 1H), 8.50 (d, J=2.5 Hz, 1H), 8.44 (s, 1H), 7.72-7.63 (m, 4H), 7.46 (d, J=7.6 Hz, 1H), 7.42 (t, J=2.7 Hz, 1H), 7.26 (s, 1H), 7.23-7.14 (m, 2H), 6.75 (s, 1H), 3.73 (s, 3H).

Example 105

4-[3-Hydroxy-5-(1H-indol-4-yl)-phenylamino]-benzonitrile

4-[3-Bromo-5-(4-methoxy-benzyloxy)-phenyl]-1-triisopropylsilanyl-1H-indole was coupled with 4-amino-benzonitrile to give 4-[3-(4-methoxy-benzyloxy)-5-(1-triisopropylsilanyl-1H-indol-4-yl)-phenylamino]-benzonitrile using the conditions of Example 80. This compound was deprotected to give 4-[3-hydroxy-5-(1H-indol-4-yl)-phenylamino]-benzonitrile as described in Example 35. $^1$H NMR (400 MHz, CD$_3$OD): δ 7.46 (d, J=2.0 Hz, 1H), 7.45 (d, J=2.0 Hz, 1H), 7.35 (d, J=8.0 Hz, 1H), 7.25 (d, J=3.1 Hz, 1H), 7.15-7.11 (m, 3H), 7.06 (dd, J=7.2, 1.0 Hz, 1H), 6.96 (t, J=1.7 Hz, 1H), 6.84 (dd, J=2.1, 1.4 Hz, 1H), 6.66 (t, J=2.1 Hz, 1H), 6.62 (q, J=1.4 Hz, 1H).

Example 106

N-[3-(1H-Indol-4-yl)-5-oxazolo[4,5-b]pyridin-2-yl-phenyl]-acetamide 3,5-Dibromo-benzoic acid and 2-amino-pyridin-3-ol were condensed to give 2-(3,5-dibromo-phenyl)-oxazolo[4,5-b]pyridine using the conditions of Clark, R. L., et al., *J. Med. Chem.* 21: 1158-62 (1978). This compound was converted to N-(3-bromo-5-oxazolo[4,5-b]pyridin-2-yl-phenyl)-acetamide as described in Example 82. Conversion to N-[3-(1H-Indol-4-yl)-5-oxazolo[4,5-b]pyridin-2-yl-phenyl]-acetamide was carried out as described in Example 75. $^1$H NMR (400 MHz, CD$_3$OD): δ 8.39-8.43 (m, 2H), 8.28 (d, J=1.4 Hz, 1H), 8.15 (t, J=1.7 Hz, 1H), 7.95 (dt, J=4.7, 2.7 Hz, 1H), 7.38-7.41 (m, 1H), 7.30-7.34 (m, 1H), 7.25 (d, J=3.1 Hz, 1H), 7.14-7.17 (m, 2H), 6.67 (d, J=3.1 Hz, 1H), 2.13 (s, 3H).

Example 107

[3-(1H-Indol-4-yl)-5-oxazolo[4,5-b]pyridin-2-yl-phenyl]-carbamic acid methyl ester 2-(3,5-Dibromo-phenyl)-oxazolo[4,5-b]pyridine was converted to (3-bromo-5-oxazolo[4,5-b]pyridin-2-yl-phenyl)-carbamic acid methyl ester as described in Example 82, replacing acetamide with carbamic acid methyl ester. Conversion to [3-(1H-indol-4-yl)-5-oxazolo[4,5-b]pyridin-2-yl-phenyl]-carbamic acid methyl ester was carried out as described in Example 75. $^1$H NMR (400 MHz, DMSO-$d_6$): δ 11.34 (s, 1H), 10.09 (s, 1H), 8.54 (dd, J=4.8, 1.2 Hz, 1H), 8.43 (s, 1H), 8.27 (dd, J=8.2, 1.3 Hz, 1H), 8.13 (t, J=1.5 Hz, 1H), 8.11 (s, 1H), 7.44-7.48 (m, 3H), 7.16-7.24 (m, 2H), 6.65 (d, J=1.8 Hz, 1H), 3.72 (s, 3H).

Example 108

N-[3-Benzoxazol-2-yl-5-(1H-indol-4-yl)-phenyl]-acetamide 3,5-Dibromo-benzoic acid and 2-aminophenol were condensed to give 2-(3,5-dibromo-phenyl)-benzoxazole, which was converted to N-[3-benzoxazol-2-yl-5-(1H-indol-4-yl)-phenyl]-acetamide as described in Example 106. $^1$H NMR (400 MHz, DMSO-$d_6$): δ 11.35 (s, 1H), 10.36 (s, 1H), 8.57 (t, J=1.6 Hz, 1H), 8.13 (d, J=1.6 Hz, 2H), 7.77-7.84 (m, 2H), 7.44-7.48 (m, 2H), 7.39-7.43 (m, 2H), 7.21 (t, J=7.5 Hz, 1H), 7.17 (dd, J=7.2, 1.0 Hz, 1H), 6.64-6.67 (m, 1H), 2.11 (s, 3H).

Example 109

[3-Benzoxazol-2-yl-5-(1H-indol-4-yl)-phenyl]-carbamic acid methyl ester 2-(3,5-Dibromo-phenyl)-benzoxazole was converted to [3-benzoxazol-2-yl-5-(1H-indol-4-yl)-phenyl]-carbamic acid methyl ester by the method of Example 107. $^1$H NMR (400 MHz, CD$_3$OD): δ 8.28 (s, 1H), 8.17 (s, 1H), 8.00 (s, 1H), 7.69 (d, J=5.7 Hz, 1H), 7.60 (d, J=4.1 Hz, 1H), 7.41 (d, J=7.2 Hz, 1H), 7.32-7.37 (m, 2H), 7.29 (d, J=2.9 Hz, 1H), 7.14-7.21 (m, 2H), 6.71 (d, J=2.9 Hz, 1H), 3.76 (s, 3H).

Example 110

N-[3-Benzoxazol-2-yl-5-(1H-indol-4-yl)-phenyl]-methanesulfonamide a) (3-Benzoxazol-2-yl-5-bromo-phenyl)-carbamic acid benzyl ester 2-(3,5-Dibromo-phenyl)-benzoxazole (0.4 g, 1.10 mmol), carbamic acid benzyl ester (0.17 g, 1.10 mmol), cesium carbonate (0.74 g, 2.30 mmol), Xantphos (46.0 mg, 0.08 mmol) and Pd(dba)$_2$ (62.0 mg, 0.74 mmol) were placed into a dry two-neck flask, which was then flushed with nitrogen. 1,4-Dioxane (5.0 mL) was added into the flask, and the reaction mixture was degassed with argon at room temperature for 40 min. The mixture was heated to 60° C. and stirred for 18 h. The solvent was removed under reduced pressure and the residue was purified by silica gel chromatography eluting with 5:1/hexanes:ethyl acetate to give (3-benzoxazol-2-yl-5-bromo-phenyl)-carbamic acid benzyl ester (0.22 g, 46%) as a yellow solid.

b) 3-Benzoxazol-2-yl-5-bromo-phenylamine

To a solution of (3-benzoxazol-2-yl-5-bromo-phenyl)-carbamic acid benzyl ester (0.160 g, 0.38 mmol) in chloroform (5.0 mL) at room temperature was added BF$_3$-Et$_2$O (0.21 g, 1.5 mmol) and dimethylsulfide (0.24 g, 3.78 mmol). The reaction mixture was stirred at room temperature for 20 hours. The solvent was removed and residue was purified by preparative TLC eluting with 3:1/hexanes:ethyl acetate to give 3-benzoxazol-2-yl-5-bromo-phenylamine (0.10 g, 92%) as a yellow solid.

c) N-(3-Benzoxazol-2-yl-5-bromo-phenyl)-methanesulfonamide

To a solution of 3-benzoxazol-2-yl-5-bromo-phenylamine (0.12 g, 0.42 mmol) in pyridine (2.0 mL) at room temperature was added methanesulfonyl chloride (0.14 g, 1.30 mmol) and catalytic DMAP. The resulting mixture was stirred at room temperature for 17 hours. The solvent was removed under vacuum and the residue was purified by preparative TLC eluting with 4:1/hexanes:ethyl acetate to give N-(3-benzoxazol-2-yl-5-bromo-phenyl)-methanesulfonamide (85.0 mg, 55%) as a yellow solid.

d) N-[3-Benzoxazol-2-yl-5-(1H-indol-4-yl)-phenyl]-methanesulfonamide

N-(3-benzoxazol-2-yl-5-bromo-phenyl)-methanesulfonamide was converted to N-[3-benzoxazol-2-yl-5-(1H-indol-4-yl)-phenyl]-methanesulfonamide by the method described in Example 75. $^1$H NMR (400 MHz, CDCl$_3$): δ 8.85 (s, 1H), 8.37 (t, J=1.4 Hz, 1H), 8.09 (t, J=1.6 Hz, 1H), 7.79 (t, J=1.8 Hz, 1H), 7.72-7.76 (m, 1H), 7.51-7.56 (m, 1H), 7.37-7.41 (m, 1H), 7.29-7.34 (m, 2H), 7.19-7.22 (m, 3H), 6.71 (t, J=2.4 Hz, 1H), 3.07 (s,3H).

Example 111

N-[3-(1H-Indol-4-yl)-5-(pyridine-3-sulfonyl)-phenyl]-acetamide a) 3-(3,5-Dichloro-phenylsulfanyl)-pyridine A solution of 0.018 g (0.020 mmol) Pd$_2$dba$_3$ and 0.021 g (0.039 mmol) DPEphos in toluene (3 mL) was stirred under an argon atmosphere for 5 minutes. 3-Iodo-pyridine (0.100 g, 0.49 mmol), 3,5-dichlorobenzenethiol (0.087 g, 0.49 mmol) and 0.060 g (0.54 mmol) potassium t-butoxide were added and the reaction mixture was heated to 100° C. and held for 2 hours, then cooled. Ethyl acetate was added to the reaction mixture and the organic phase was washed with water, dried and concentrated. The crude product was purified using flash chromatography to give 0.90 g (72% yield) 3-(3,5-dichlorophenylsulfanyl)-pyridine.

b) 3-(3,5-Dichloro-benzenesulfonyl)-pyridine 3-(3,5-dichloro-phenylsulfanyl)-pyridine (0.085 g, 0.33 mmol), 0.022 g (0.066 mmol) Na$_2$WO$_4$, 0.020 g (0.33 mmol) acetic acid and 2 equivalents of hydrogen peroxide were mixed and heated to 76° C. for one half hour. Solid precipitated from the reaction. Saturated aqueous sodium bicarbonate solution was added followed by methylene chloride. The organic phase was dried and evaporated to give crude 3-(3,5-dichloro-benzenesulfonyl)-pyridine which was carried on to the next step without further purification.

c) N-[3-Chloro-5-(pyridine-3-sulfonyl)-phenyl]-acetamide

To a microwave vial was added Pd$_2$(dba)$_3$ (Strem, 0.027 g, 0.030 mmol) and XANTPHOS (Strem, 0.019 g, 0.032 mmol) followed by 1 mL 1,4-dioxane. The mixture was stirred at room temperature. After 15 minutes 0.85 g 3-(3,5-cichlorobenzenesulfonyl)-pyridine (0.300 mmol), 0.026 g acetamide (0.44 mmol) and 0.24 g cesium carbonate (0.74 mmol) in 1 mL of dioxane were added. The vial was capped and heated at 126° C. in the microwave for 1 hour. The mixture was diluted with ethyl acetate. The organic phase was washed with water and brine, dried and concentrated. Flash chromatography provided 0.040 g of N-[3-chloro-5-(pyridine-3-sulfonyl)-phenyl]-acetamide.

d) N-[3-(1H-Indol-4-yl)-5-(pyridine-3-sulfonyl)-phenyl]-acetamide

N-[3-chloro-5-(pyridine-3-sulfonyl)-phenyl]-acetamide was converted to N-[3-(pyridine-3-sulfonyl)-5-(1-triisopropylsilanyl-1H-indol-4-yl)-phenyl]-acetamide and the triisopropylsilyl protecting group was removed as described in Example 35. $^1$H NMR (400 MHz, CD$_3$OD): δ 9.17 (br s, 1H), 8.82 (br s, 1H), 8.38 (d, J=8.4 Hz, 1H), 8.30 (s, 1H), 8.12 (s, 1H), 7.96 (d, J=1.4 Hz, 1H), 7.63 (s, 1H), 7.44 (d, J=8.2 Hz, 1H), 7.31 (d, J=3.3 Hz, 1H), 7.19 (t, J=7.7 Hz, 1H), 7.10 (d, J=7.4 Hz, 1H), 6.53 (d, J=3.2 Hz, 1H), 2.15 (s, 3H).

Example 112

N-[3-(1H-Indol-4-yl)-5-(pyridin-3-ylmethylsulfanyl)-phenyl]-acetamide

Sodium hydroxide (0.154 g. 3.85 mmol) in 2 mL water was added to 3,5-dichloro-benzenethiol (0.328 g, 1.83 mmol) in 5 mL of ethanol. After 10 min stirring, 3-chloromethyl-pyridine hydrochloride (0.301 g, 1.83 mmol) in 2 mL water was added slowly. The resulting reaction mixture was stirred at room temperature overnight. Methylene chloride was added to the reaction mixture. The organic phase was washed with saturated aqueous sodium bicarbonate solution and brine. After removal of the solvent, the crude product was purified with flash chromatography to give 0.470 g (95% yield) of 3-(3,5-dichloro-phenylsulfanylmethyl)-pyridine. This compound was converted to N-[3-(1H-indol-4-yl)-5-(pyridin-3-ylmethylsulfanyl)-phenyl]-acetamide as described in Example 35. $^1$H NMR (400 MHz, CD$_3$OD): δ 8.42 (s, 1H), 8.35 (d, J=4.7 Hz, 1H), 7.79 (d, J=7.8 Hz, 1H), 7.66 (s, 2H), 7.38-7.31 (m, 2H), 7.27-7.23 (m, 2H), 7.13 (t, J=7.7 Hz, 1H), 6.97 (d, J=7.2 Hz, 1H), 6.44 (d, J=3.1 Hz, 1H), 4.20 (s, 2H), 2.12 (s, 3H).

Example 113

3-(2-Ethyl-pyridin-3-ylamino)-5-(1H-indol-4-yl)-phenol a) 3-Nitro-2-vinyl-pyridine A mixture of 0.92 g (5.80 mmol) of 2-chloro-3-nitro-pyridine, 1.60 g (5.80 mmol) tripropyl-vinyl-stannane, 0.335 g (0.290 mmol) Pd(PPh$_3$)$_4$ and 10 mL of toluene were combined and refluxed under an inert atmosphere overnight. After routine aqueous workup the crude product was purified by chromatography on silica gel to give 0.470 g (54% yield) of 3-nitro-2-vinyl-pyridine.

b) 2-Ethyl-pyridin-3-ylamine

To a solution of 0.220 g (1.47 mmol) of 3-nitro-2-vinyl-pyridine dissolved in 1:1 methanol/ethyl acetate was added 0.010 g of Pd/C. The resulting mixture was hydrogenated overnight at 50 psi. Filtration and removal of solvent provided 0.160 g (89% yield) of 2-ethyl-pyridin-3-ylamine.

c) 3-(2-Ethyl-pyridin-3-ylamino)-5-(1H-indol-4-yl)-phenol (3,5-Dibromo-phenoxy)-triisopropyl-silane and 2-ethylpyridin-3-ylamine were coupled to give (3-bromo-5-triisopropylsilanyloxy-phenyl)-(2-ethyl-pyridin-3-yl)-amine as described for Example 80. (3-Bromo-5-triisopropylsilanyloxy-phenyl)-(2-ethyl-pyridin-3-yl)-amine was converted to 3-(2-ethyl-pyridin-3-ylamino)-5-(1H-indol-4-yl)-phenol as described in Example 35. $^1$H NMR (400 MHz, CD$_3$OD): δ 8.02 (d, J=4.8 Hz 1H), 7.66 (dd, J=8.0, 1.5 Hz, 1H), 7.32 (d, J=8.1 Hz, 1H), 7.22 (d, J=3.1 Hz, 1H), 7.14-7.10 (m, 2H), 7.03 (d, J=7.0 Hz, 1H), 6.76 (t, J=1.6 Hz, 1H), 6.69 (s, 1H), 6.61 (d, J=3.3 Hz, 1H), 6.40 (t, J=2.1 Hz, 1H), 2.86 (q, J=7.5 Hz, 2H), 1.25 (t, J=7.5 Hz, 3H).

Example 114

3-(2-Dimethylamino-pyridin-3-ylamino)-5-(1H-indol-4-yl)-phenol

Dimethyl-(3-nitro-pyridin-2-yl)-amine was obtained as a byproduct from the reaction of 2-chloro-3-nitro-pyridine with pent-4-en-1-ol (2 eq.) and sodium hydride (3 eq.) in DMF at 100° C. overnight. To this compound (0.122 g) in a mixture of ethyl acetate/methanol (5 mL, 1:1) was added 10% Pd on carbon (24 mg). The reaction mixture was hydrogenated at 50 psi hydrogen overnight. After filtration and removal of the solvents, dimethyl-(3-amino-pyridin-2-yl)-amine (0.100 g, 100%) was obtained. 4-[3-bromo-5-(4-methoxy-benzyloxy)-phenyl]-1-triisopropylsilanyl-1H-indole and dimethyl-(3-amino-pyridin-2-yl)-amine were coupled as described for Example 82. Deprotection as described in Example 35 gave 3-(2-dimethylamino-pyridin-3-ylamino)-5-(1H-indol-4-yl)-phenol. $^1$H NMR (400 MHz, CD$_3$OD): δ 7.74 (dd, J=4.8, 1.5 Hz, 1H), 7.57 (dd, J=7.9, 1.4 Hz, 1H), 7.32 (d, J=8.0 Hz, 1H), 7.22 (d, J=3.3 Hz, 1H), 7.11 (t, J=7.7 Hz, 1H), 7.05 (dd, J=7.3, 0.8 Hz, 1H), 6.86-6.81 (m, 2H), 6.72 (t, J=1.7 Hz, 1H), 6.62 (d, J=3.1 Hz, 1H), 6.52-6.48 (m, 1H), 2.80 (s, 6H).

Example 115

[2-Amino-5-(1H-indol-4-yl)-phenyl]-pyridin-3-yl-methanone (2-Amino-5-bromo-phenyl)-pyridin-3-yl-methanone was prepared as described in Earley, J. V. and Gilman, N. W., *Synth. Comm.* 15:1271-76 (1985).

To (2-amino-5-bromo-phenyl)-pyridin-3-yl-methanone (0.120 g, 0.43 mmol) and 4-(4,4,5,5-tetramethyl-[1,3,2]dioxaborolan-2-yl)-1-triisopropylsilanyl-1H-indole (0.210 g, 0.52 mmol) in 1 mL of dioxane and 0.5 mL of DMF was added chloro(di-2-norbornylphosphino)(2'-dimethylamino-1,1'-biphenyl-2-yl)palladium (II) and 2M aqueous K$_3$PO$_4$ (0.5 mL, 1 mmol). The resulting reaction mixture was heated at 120° C. for 1 h. Ethyl acetate was then added to the reaction mixture and the organic phase was washed with water and brine, dried, filtered and concentrated. The crude product was purified by preparative TLC to afford [2-amino-5-(1H-indol-4-yl)-phenyl]-pyridin-3-yl-methanone. $^1$H NMR (400 MHz, CD$_3$OD): δ 8.82 (s, 1H), 8.63 (d, J=4.9 Hz, 1H), 8.03 (d, J=7.8 Hz, 1H), 7.70 (d, J=8.4 Hz, 1H), 7.63 (d, J=2.1 Hz, 1H), 7.47 (dd, J=7.8, 5.0 Hz, 1H), 7.30 (d, J=8.0 Hz, 1H), 7.21 (d, J=3.2 Hz, 1H), 7.10 (t, J=7.7 Hz, 1H), 6.97-6.93 (m, 2H), 6.48 (d, J=3.3 Hz, 1H).

Example 116

3-(1H-Indol-4-yl)-5-(pyrazin-2-ylamino)-benzamide 3,5-Dibromo-benzamide and pyrazin-2-ylamine were coupled to give 3-bromo-5-(pyrazin-2-ylamino)-benzamide as described for Example 44. 3-Bromo-5-(pyrazin-2-ylamino)-benzamide was converted to 3-(1H-indol-4-yl)-5-(pyrazin-2-ylamino)-benzamide as described in Example 75. $^1$H NMR (400 MHz, CDCl$_3$): δ 10.61 (s, 1H), 8.24 (t, J=1.8 Hz, 1H), 8.17-8.12 (m, 3H), 8.06 (s, 1H), 7.88 (s, 1H), 7.78 (t, J=1.5 Hz, 1H), 7.40 (dd, J=6.6, 2.1 Hz, 1H), 7.30 (d, J=3.1 Hz, 1H), 7.21-7.16 (m, 2H), 6.74 (d, J=2.7 Hz, 1H).

Example 117

3-(1H-Indol-4-yl)-5-(pyridin-3-ylamino)-benzamide 3,5-Dibromo-benzamide and pyridin-3-ylamine were coupled to give 3-bromo-5-(pyridin-3-ylamino)-benzamide as described for Example 44. 3-Bromo-5-(pyridin-3-ylamino)-benzamide was converted to 3-(1H-indol-4-yl)-5-(pyridin-3-ylamino)-benzamide as described in Example 75. $^1$H NMR (400 MHz, CDCl$_3$): δ 10.58 (s, 1H), 8.36 (s, 1H), 8.00 (s, 1H), 7.72 (s, 1H), 7.65 (d, J=7.4 Hz, 1H), 7.58 (d, J=1.2 Hz, 2H), 7.39 (d, J=7.8 Hz, 1H), 7.32-7.25 (m, 2H), 7.20-7.10 (m, 2H), 6.62 (d, J=2.9 Hz, 1H).

Example 118

Formic acid 2-{3-[3-hydroxy-5-(1H-indol-4-yl)-phenylamino]-pyridin-2-ylmethoxy}-ethyl ester 3-(1H-Indol-4-yl)-5-(pyridin-3-ylamino)-phenol was dissolved in dioxane. A slight excess of 4N HCl in dioxane was added. The HCl salt of 3-(1H-indol-4-yl)-5-(pyridin-3-ylamino)-phenol immediately oiled out of solution. The solvent was removed under vacuum, and enough ethanol was added to dissolve the salt. The ethanol was removed under vacuum. A sample of the HCl salt of 3-(1H-indol-4-yl)-5-(pyridin-3-ylamino)-phenol was partitioned between ethyl acetate and 1N aqueous sodium hydroxide. The ethyl acetate phase was separated, washed with brine, and dried over sodium sulfate, then filtered and evaporated. A small byproduct was observed in the sample. Chromatography on silica gel with 3 to 5% methanol/methylene chloride provided formic acid 2-{3-[3-hydroxy-5-(1H-indol-4-yl)-phenylamino]-pyridin-2-ylmethoxy}-ethyl ester. $^1$H NMR (400 MHz, CDCl$_3$): δ 10.37 (s, 1H), 8.37 (s, 1H), 8.14 (s, 1H), 8.04 (dd, J=4.5, 1.4 Hz, 1H), 7.80 (dd, J=8.2, 1.2 Hz, 1H), 7.43 (d, J=7.8 Hz, 1H), 7.40-7.38 (m, 1H), 7.30 (s, 1H), 7.25 (dd, J=8.2, 4.7 Hz, 1H), 7.17 (t, J=7.6 Hz, 1H), 7.11 (dd, J=7.2, 1.0 Hz, 1H), 6.94 (t, J=1.7 Hz, 1H), 6.83 (t, J=1.8 Hz, 1H), 6.70-6.67 (m, 1H), 6.64 (t, J=2.1 Hz, 1H), 4.80 (s, 2H), 4.41-4.37 (m, 2H), 3.85-3.81 (m, 2H).

Example 119

[3-(1H-Indol-4-yl)-5-pyridin-3-yl-phenyl]-carbamic acid methyl ester a) 3-Bromo-5-iodo-benzoyl azide To a stirred solution of 3-bromo-5-iodo benzoic acid (5.0 g, 15 mmol) in methanol (30 mL) was added diisopropylethylamine (2.9 mL, 16.8 mmol) and diphenylphosphoryl azide (3.6 mL, 16.8 mmol). The reaction mixture was stirred for 12 hours at room temperature and then quenched with the addition of 100 mL water. A solid precipitated out. The solid was filtered, washed with water and dried to give 5.0 g (96%) of 3-bromo-5-iodo-benzoyl azide.

b) (3-Bromo-5-iodo-phenyl)-carbamic acid tert-butyl ester

To a stirred solution of 3-bromo-5-iodo-benzoyl azide (5.0 g, 14 mmol) in toluene (50 mL) was added t-butanol (1.5 mL, 15.6 mmol). The reaction mixture was heated to reflux for 2 hours and then cooled to room temperature. The reaction mixture was evaporated to dryness to afford 5.6 g (99% yield) of (3-bromo-5-iodo-phenyl)-carbamic acid tert-butyl ester.

c) 3-Bromo-5-iodoaniline (3-Bromo-5-iodo-phenyl)-carbamic acid tert-butyl ester (5.6 g, 14 mmol) was dissolved in 1 M HCl in dioxane (35 mL, 141 mmol). The reaction mixture was stirred at room temperature for 12 hours and then cooled to 0° C. Concentrated NaOH (aq) was added to the reaction mixture until the pH was 14. Water (100 mL) was then added. The aqueous layer was extracted with 3 times with 20 mL ethyl acetate. The organic layers were combined, dried over MgSO$_4$, and was evaporated to dryness. The crude product was purified by silica gel chromatography to give 2.8 (67% yield) of 3-bromo-5-iodoaniline.

d) (3-Bromo-5-iodo-phenyl)-carbamic acid methyl ester

To a stirred solution of 3-bromo-5-iodo-aniline (0.60 g, 2.01 mmol) and pyridine (0.65 mL, 8.06 mmol) in CH$_2$Cl$_2$ (15 mL) at 0° C. was added methyl chloroformate (0.17 mL, 2.22 mmol). The reaction mixture was allowed to warm to room temperature and was stirred for 12 hours. The reaction mixture was washed with twice with 5 mL 1 M HCl and 5 mL brine. The organic layer was dried over Na$_2$SO$_4$ and concentrated to give 0.71 g (99%) of (3-bromo-5-iodo-phenyl)-carbamic acid methyl ester.

e) (3-Bromo-5-pyridin-3-yl-phenyl)-carbamic acid methyl ester (3-Bromo-5-iodo-phenyl)-carbamic acid methyl ester (0.22 g, 0.62 mmol), 3-pyridylboronic acid (0.11 g, 0.93 mmol), and Pd(dppf)Cl$_2$.CH$_2$Cl$_2$ complex (0.051 g, 0.062 mmol) were dissolved in dioxane (6 mL). Aqueous 2 M potassium carbonate (0.26 g, 1.9 mmol) was added and the reaction mixture was stirred at room temperature for 1 hr. The reaction mixture was then heated to 60° C. for 24 hrs. The reaction mixture was filtered through Celite® and the solvent was removed. The product was chromatographed to give 0.073 g (38% yield) of (3-bromo-5-pyridin-3-yl-phenyl)-carbamic acid methyl ester.

f) [3-(1H-Indol-4-yl)-5-pyridin-3-yl-phenyl]-carbamic acid methyl ester (3-Bromo-5-pyridin-3-yl-phenyl)-carbamic acid methyl ester was converted to [3-(1H-indol-4-yl)-5-pyridin-3-yl-phenyl]-carbamic acid methyl ester by the method described in Example 75. $^1$H NMR (400 MHz, CD$_3$OD): δ 8.86 (d, J=2.3 Hz, 1H), 8.52 (dd, J=4.7, 1.3 Hz, 1H), 8.10 (dt, J=4.9, 2.5 Hz, 1H), 7.89 (s, 1H), 7.79 (s, 1H), 7.59 (s, 1H), 7.49 (dd, J=8.1, 5.0 Hz, 1H), 7.41 (dd, J=6.5, 2.6 Hz, 1H), 7.30 (d, J=3.1 Hz, 1H), 7.21-7.15 (m, 2H), 6.70 (d, J=3.1 Hz, 1H), 4.64 (s, 2H), 3.76 (s, 3H).

Example 120

N-[3-(1H-Indol-4-yl)-5-pyridin-3-yl-phenyl]-acetamide

3-Bromo-5-iodo-aniline was converted to N-(3-bromo-5-iodo-phenyl)-acetamide by the method described in Example 119, using acetic anhydride in place of methyl chloroformate. N-(3-Bromo-5-iodo-phenyl)-acetamide was converted to N-[3-(1H-indol-4-yl)-5-pyridin-3-yl-phenyl]-acetamide using the method described in Example 119. $^1$H NMR (400 MHz, CD$_3$OD): δ 8.96 (d, J=2.0 Hz, 1H), 8.60 (dd, J=4.7, 1.4 Hz, 1H), 8.15 (dt, J=5.0, 2.7 Hz, 1H), 8.09 (t, J=1.5 Hz, 1H), 8.02 (t, J=1.8 Hz, 1H), 7.71 (t, J=1.4 Hz, 1H), 7.56-7.46 (m, 2H), 7.41 (d, J=3.1 Hz, 1H), 7.26-7.22 (m, 2H), 6.79 (d, J=3.1 Hz, 1H), 2.20 (s, 3H).

Example 121

[3-(1H-Indol-4-yl)-5-pyridin-4-yl-phenyl]-carbamic acid methyl ester (3-Bromo-5-iodo-phenyl)-carbamic acid methyl ester was converted to (3-bromo-5-pyridin-4-yl-phenyl)-carbamic acid methyl ester, which in turn was converted to [3-(1H-indol-4-yl)-5-pyridin-4-yl-phenyl]-carbamic acid methyl ester by the method of Example 119. $^1$H NMR (400 MHz, CD$_3$OD): δ 8.67 (dd, J=4.7, 1.7 Hz, 2H), 7.99 (dt, J=9.8, 5.9 Hz, 2H), 7.79 (dd, J=4.7, 1.7 Hz, 2H), 7.74 (t, J=1.5 Hz, 1H), 7.50-7.45 (m, 1H), 7.39 (d, J=3.1 Hz, 1H), 7.24 (d, J=2.1 Hz, 1H), 7.23 (s, 1H), 6.76 (d, J=3.3 Hz, 1H), 3.79 (s, 3H).

Example 122

N-[3-(1H-Indol-4-yl)-5-pyridin-4-yl-phenyl]-methanesulfonamide

3-Bromo-5-iodo-aniline was converted to N-(3-bromo-5-iodo-phenyl)-methanesulfonamide by the method described in Example 119, using methanesulfonyl chloride in place of methyl chloroformate. 3-Bromo-5-iodo-aniline was converted to N-(3-bromo-5-iodo-phenyl)-methanesulfonamide was converted to N-[3-(1H-indol-4-yl)-5-pyridin-4-yl-phenyl]-methanesulfonamide using the method described in Example 119. $^1$H NMR (400 MHz, CD$_3$OD): δ 8.60 (dd, J=4.8, 1.6 Hz, 2H), 7.75 (dd, J=4.5, 1.7 Hz, 2H), 7.72 (dt, J=5.2, 2.6 Hz, 2H), 7.57 (t, J=1.9 Hz, 1H), 7.42 (d, J=7.2 Hz, 1H), 7.32 (d, J=3.1 Hz, 1H), 7.23-7.16 (m, 2H), 6.67 (d, J=3.1 Hz, 1H), 3.04 (s, 3H).

Example 123

N-[3-(1H-Indol-4-yl)-5-pyridin-4-yl-phenyl]-acetamide

N-(3-bromo-5-iodo-phenyl)-acetamide was converted to N-(3-bromo-5-pyridin-4-yl-phenyl)-acetamide, which in turn was converted N-[3-(1H-indol-4-yl)-5-pyridin-4-yl-phenyl]-acetamide by the method of Example 119. $^1$H NMR (400 MHz, CD$_3$OD): δ 8.60 (dd, J=4.5, 1.6 Hz, 2H), 8.01 (dt, J=8.7, 5.3 Hz, 2H), 7.76-7.73 (m, 3H), 7.42 (dt, J=4.3, 2.5 Hz, 1H), 7.31 (d, J=3.1 Hz, 1H), 7.22-7.15 (m, 2H), 6.68 (dd, J=3.2, 0.9 Hz, 1H), 2.18 (s, 3H).

Example 124

N-[3-(1H-Indol-4-yl)-5-(6-methoxy-pyridin-3-yl)-phenyl]-acetamide

N-(3-bromo-5-iodo-phenyl)-acetamide was converted to N-[3-bromo-5-(6-methoxy-pyridin-3-yl)-phenyl]-acetamide, which in turn was converted N-[3-(1H-indol-4-yl)-5-(6-methoxy-pyridin-3-yl)-phenyl]-acetamide by the method of Example 119. $^1$H NMR (400 MHz, CD$_3$OD): δ 8.31 (d, J=2.5 Hz, 1H), 7.83 (t, J=1.7 Hz, 1H), 7.75 (dd, J=8.7, 2.6 Hz, 1H), 7.69 (t, J=1.9 Hz, 1H), 7.47 (t, J=1.5 Hz, 1H), 7.35 (d, J=7.8 Hz, 1H), 7.22 (d, J=3.1 Hz, 1), 7.14-7.06 (m, 2H), 6.67 (d, J=8.6 Hz, 1H), 6.65 (d, J=3.1 Hz, 1H), 3.82 (s, 3H), 2.09 (s, 3H).

Example 125

Cell Viability Assays

Jurkat and Hela cells were cultured in RPMI and EMEM media, respectively, containing 0.5% fetal calf serum. Cells were plated in a volume of 100 μL in a 96 well format. Test compounds were included in the culture media at concentrations ranging from 1 nM to 10 μM for a period of 48-72 hrs. Cell viability was determined using the WST-1 colorimetric mitochondrial reduction assay. Briefly, 10 μL of WST-1 reagent was included in the culture well for a period of 1 to 4 hrs. The WST-1 reaction was read on a multiwell spectrophotometer as the difference in the absorbance between 450 nm and 600 nm (baseline). Absorbance was proportional to the number of living cells in the culture well. Concentration response curves and $IC_{50}$ values were calculated using GraphPAD Prism graphing and curve fitting program. The results of these assays are tabulated below. In the table A refers to an $IC_{50}$ of 0.001 to 0.999 μM, B refers to an $IC_{50}$ of 1 to 30 μM, and IA refers to compounds with an $IC_{50}$ that was not determined, but that is greater than 3 μM.

TABLE 1

| Compound | Jurkat $IC_{50}$ (μM) | Hela $IC_{50}$ (μM) |
| --- | --- | --- |
| 3-(1H-indazol-7-yl)-5-(pyridin-3-ylamino)-phenol | A | B |
| 3-(1H-indol-4-yl)-5-(pyridin-3-ylamino)-phenol | A | A |
| 3'-dimethylamino-5-(pyridin-3-ylamino)-biphenyl-3-ol | B | B |
| 5-(pyridin-3-ylamino)-2'-trifluoromethyl-biphenyl-3-ol | IA | B |
| 2'-chloro-5-(pyridin-3-ylamino)-biphenyl-3-ol | IA | B |
| 5-(pyridin-3-ylamino)-biphenyl-3-ol | IA | B |
| 3-benzo[b]thiophen-4-yl-2-(4-methoxybenzyl)-5-(pyridin-3-ylamino)-phenol | B | B |
| 3-benzo[b]thiophen-4-yl-5-(pyridin-3-ylamino)-phenol | B | B |
| 2-benzyl-3-(1H-indol-4-yl)-5-(pyridin-3-ylamino)-phenol | B | B |
| 3-(1H-indazol-4-yl)-5-(pyridin-3-ylamino)-phenol | A | B |
| 3-(2-methyl-1H-indol-4-yl)-5-(pyridin-3-ylamino)-phenol | A | A |
| [3-benzo[b]thiophen-4-yl-(4-methoxybenzyloxy)-phenyl]-pyridin-3-yl-amine | B | B |
| 5-(pyridin-3-ylamino)-[1,1';3',1'']terphenyl-3-ol |  | B |
| 3-(1H-indol-4-yl)-5-(pyridin-2-ylamino)-phenol |  | A |
| 3-(indan-5-yl)-5-(pyridin-3-ylamino)-phenol |  | B |
| 3-(indan-4-yl)-5-(pyridin-3-ylamino)-phenol |  | B |
| 3-(pyridin-3-ylamino)-5-quinolin-8-yl-phenol |  | B |
| [4-(1H-indol-4-yl)-6-methoxypyrimidin-2-yl]-pyridin-3-yl-amine |  | B |
| [3-hydroxy-5-(1H-indol-4-yl)-phenyl]-pyridin-3-yl-methanone |  | A |
| N-[3-(1H-indol-4-yl)-phenyl]-N-pyridin-3-yl-acetamide |  | B |
| [3-(1H-indol-4-yl)-phenyl]-pyridin-3-yl-amine, hydrochloride salt |  | B |
| 2,2,2-trifluoro-1-{4-[3-hydroxy-5-(pyridine-3-carbonyl)-phenyl]-1H-indol-3-yl-ethanone |  | B |
| 3-(1H-indol-4-yl)-5-(1-oxypyridin-3-ylamino)-phenol |  | A |
| [3-hydroxy-5-(1H-indol-4-yl)-phenyl]-pyridin-3-yl-methanone oxime |  | B |
| 3-(6-nitro-indol-1-yl)-5-(pyridin-3-ylamino)-phenol |  | A |
| 1-[3-hydroxy-5-(pyridin-3-ylamino)-phenyl]-1H-indole-5-carbonitrile |  | B |
| (6-chloropyridin-3-yl)-[3-hydroxy-5-(1H-indol-4-yl)-phenyl]-methanone |  | A |
| [3-hydroxy-5-(1H-indol-4-yl)-phenyl]-(6-hydroxypyridin-3-yl)-methanone | B | A |
| 6-(1H-indol-4-yl)-2-(pyridin-3-ylamino)-pyrimidin-4-ol |  | B |
| 5-[3-hydroxy-5-(1H-indol-4-yl)-phenylamino]-pyridin-2-ol | B | A |
| 3-(1H-indol-4-yl)-5-(pyridin-3-yloxy)-phenol |  | A |
| [3-hydroxy-5-(1H-indol-4-yl)-phenyl]-pyrazin-2-yl-methanone | A | A |
| 2-adamantan-2-yl-4-(hydroxy-pyridin-3-yl-methyl)-phenol | B | IA |
| 3-(1-methyl-1H-indol-7-yl)-5-(pyridin-3-ylamino)-phenol | B | IA |
| 3-benzo[1,3]dioxol-5-yl-5-(pyridin-3-ylamino)-phenol | B | IA |
| 3-(1-methyl-1H-indol-4-yl)-5-(pyridin-3-ylamino)-phenol | B | IA |
| [3-(1H-indol-4-yl)-5-methoxyphenyl]-pyridin-3-yl-amine | B | IA |
| [3-hydroxy-5-(1H-indol-4-yl)-phenyl]-(6-hydroxymethyl-pyridin-3-yl)-methanone | B | IA |
| 4-[3-hydroxy-5-(pyridin-3-ylamino)-phenyl]-1,3-dihydro-indol-2-one | A | A |
| 3-(1-hydroxy-1-pyridin-3-yl-ethyl)-5-(1H-indol-4-yl)-phenol | B | A |
| [3-hydroxy-5-(1H-indol-4-yl)-phenyl]-(6-methyl-pyridin-3-yl)-methanone | A | B |
| N-[5'-hydroxy-3'-(pyridin-3-ylamino)-biphenyl-3-yl]-methanesulfonamide | B | B |
| (3-adamantan-2-yl-4-hydroxyphenyl)-pyridin-3-yl-methanone | B | IA |
| [3-(1H-indol-4-yl)-5-nitrophenyl]-pyridin-3-yl-amine | A | B |
| 3-(1H-indol-5-yl)-5-(pyridin-3-ylamino)-phenol | A | B |
| 3-(1H-indol-4-yl)-5-(pyridin-4-ylamino)-phenol | A | A |
| 3-(1H-indol-7-yl)-5-(pyridin-3-ylamino)-phenol | B | IA |
| 3-(1H-indol-4-yl)-5-(pyrazin-2-ylamino)-phenol | A | A |
| 3-(1H-indol-6-yl)-5-(pyridin-3-ylamino)-phenol | B | B |
| 3-(pyridin-3-ylamino)-5-quinolin-3-yl-phenol | A | B |
| 3-(1H-indol-4-yl)-5-(methyl-pyridin-3-yl-amino)-phenol | A | A |
| 3-(3-chloro-1H-indol-4-yl)-5-(pyridin-3-ylamino)-phenol | A | B |
| (6-amino-pyridin-3-yl)-[3-hydroxy-5-(1H-indol-4-yl)-phenyl]-methanone | A | B |
| [3-(1H-Indol-4-yl)-5-methyl-phenyl]-pyridin-3-yl-amine | IA | B |
| [3-Hydroxy-5-(1H-indol-4-yl)-phenyl]-(5-methyl-pyridin-3-yl)-methanone | A | A |
| (2-Chloro-pyridin-3-yl)-[3-hydroxy-5-(1H-indol-4-yl)-phenyl]-methanone | B | B |
| 5-[3-Hydroxy-5-(1H-indol-4-yl)-phenylamino]-pyrazine-2-carbonitrile | IA | B |

Example 126

Cell Cycle Assay

Methods

MCF-7 breast cancer cells and Jurkat T-cell leukemic cells were grown (and maintained) in EMEM and RPMI media, respectively, containing 10% fetal calf serum.

MCF-7 cells were plated in 24 well cell culture plates at a density of $5 \times 10^5$ cells/mL at a volume of 1 mL/well. Cells were allowed to adhere for 24 hrs. After adherence, cell culture media was changed to that containing 0.5% FCS. Thirty minutes post-media change, test compounds were added at a concentration of 1 μM. Twenty-fours after test agent addition, cells were analyzed for cell cycle status as described below.

Jurkat cells were resuspended in culture media containing 0.5% serum and added to wells of 24 well cell culture plate at a concentration of $5 \times 10^5$ cells/mL at a volume of 1 mL/well. Test agents were added a concentration of 0.1 μM. Twenty-fours after test agent addition, cells were analyzed for cell cycle status as described below.

Cell Cycle Analysis

Cell cycle status was analyzed by flow cytometry. Briefly, cells were collected and washed with FACs buffer (Pharmingen) and resuspended and fixed in 1 mL of 80% ethanol for 1 hr. Cells were washed with FACs buffer and resuspended in propidium iodide(PI)/RNase staining buffer (Pharmingen). PI is a fluorescent dye that labels nucleic acids such as DNA. The fluorescence within a cell (in the presence of PI) is proportional to the amount of DNA within a cell. The cell content of DNA is an indices of status in the cell cycle. For example, cells in the G2/M (mitotic stage) of the cell cycle have twice as much DNA as cells in the G1/0 phase. Cells in the S phase have DNA content that lies between these extremes.

For testing of cell cycle effects of test agents the percentage of cells within the G1 and G2/M phase were measured. If a test compound evoked a 50% increase in the number of cells in the G2/M phase, as compared to control, it was considered to be an active compound. In Table 2, Y indicates a 50% or greater increase in the number of cells in the G2/M phase, as compared to control, and N indicates a less than 50% increase at this dose.

TABLE 2

| Compound | Jurkat G2/M Block 0.1 μM | MCF-7 G2/M Block 1 μM |
|---|---|---|
| 3-(1H-indazol-7-yl)-5-(pyridin-3-ylamino)-phenol | N | N |
| 3-(1H-indol-4-yl)-5-(pyridin-3-ylamino)-phenol | Y | Y |
| 3'-dimethylamino-5-(pyridin-3-ylamino)-biphenyl-3-ol | N | N |
| 5-(pyridin-3-ylamino)-2'-trifluoromethyl-biphenyl-3-ol | Y | N |
| 2'-chloro-5-(pyridin-3-ylamino)-biphenyl-3-ol | N | N |
| 5-(pyridin-3-ylamino)-biphenyl-3-ol | N | N |
| 3-benzo[b]thiophen-4-yl-2-(4-methoxybenzyl)-5-(pyridin-3-ylamino)-phenol | Y | N |
| 3-benzo[b]thiophen-4-yl-5-(pyridin-3-ylamino)-phenol | N | N |
| 2-benzyl-3-(1H-indol-4-yl)-5-(pyridin-3-ylamino)-phenol | N | N |
| 3-(1H-indazol-4-yl)-5-(pyridin-3-ylamino)-phenol | N | N |
| 3-(2-methyl-1H-indol-4-yl)-5-(pyridin-3-ylamino)-phenol | Y | Y |
| [3-benzo[b]thiophen-4-yl-(4-methoxybenzyloxy)-phenyl]-pyridin-3-yl-amine | | |
| 5-(pyridin-3-ylamino)-[1,1';3',1'']terphenyl-3-ol | | |
| 3-(1H-indol-4-yl)-5-(pyridin-2-ylamino)-phenol | Y | N |
| 3-(indan-5-yl)-5-(pyridin-3-ylamino)-phenol | | |
| 3-(indan-4-yl)-5-(pyridin-3-ylamino)-phenol | N | N |
| 3-(pyridin-3-ylamino)-5-quinolin-8-yl-phenol | N | N |
| [4-(1H-indol-4-yl)-6-methoxypyrimidin-2-yl]-pyridin-3-yl-amine | N | N |
| [3-hydroxy-5-(1H-indol-4-yl)-phenyl]-pyridin-3-yl-methanone | Y | Y |
| N-[3-(1H-indol-4-yl)-phenyl]-N-pyridin-3-yl-acetamide | | |
| [3-(1H-indol-4-yl)-phenyl]-pyridin-3-yl-amine, hydrochloride salt | Y | Y |
| 2,2,2-trifluoro-1-{4-[3-hydroxy-5-(pyridine-3-carbonyl)-phenyl]-1H-indol-3-yl-ethanone | N | N |
| 3-(1H-indol-4-yl)-5-(1-oxypyridin-3-ylamino)-phenol | Y | Y |
| [3-hydroxy-5-(1H-indol-4-yl)-phenyl]-pyridin-3-yl-methanone oxime | N | N |

TABLE 2-continued

| Compound | Jurkat G2/M Block 0.1 μM | MCF-7 G2/M Block 1 μM |
|---|---|---|
| 3-(6-nitro-indol-1-yl)-5-(pyridin-3-ylamino)-phenol | Y | |
| 1-[3-hydroxy-5-(pyridin-3-ylamino)-phenyl]-1H-indole-5-carbonitrile | Y | N |
| (6-chloropyridin-3-yl)-[3-hydroxy-5-(1H-indol-4-yl)-phenyl]-methanone | Y | N |
| [3-hydroxy-5-(1H-indol-4-yl)-phenyl]-(6-hydroxypyridin-3-yl)-methanone | N | |
| 6-(1H-indol-4-yl)-2-(pyridin-3-ylamino)-pyrimidin-4-ol | Y | |
| 5-[3-hydroxy-5-(1H-indol-4-yl)-phenylamino]-pyridin-2-ol | N | |
| 3-(1H-indol-4-yl)-5-(pyridin-3-yloxy)-phenol | | |
| [3-hydroxy-5-(1H-indol-4-yl)-phenyl]-pyrazin-2-yl-methanone | N | N |
| 2-adamantan-2-yl-4-(hydroxy-pyridin-3-yl-methyl)-phenol | N | |
| 3-(1-methyl-1H-indol-7-yl)-5-(pyridin-3-ylamino)-phenol | N | |
| 3-benzo[1,3]dioxol-5-yl-5-(pyridin-3-ylamino)-phenol | N | |
| 3-(1-methyl-1H-indol-4-yl)-5-(pyridin-3-ylamino)-phenol | N | |
| [3-(1H-indol-4-yl)-5-methoxyphenyl]-pyridin-3-yl-amine | N | |
| [3-hydroxy-5-(1H-indol-4-yl)-phenyl]-(6-hydroxymethyl-pyridin-3-yl)-methanone | N | N |
| 4-[3-hydroxy-5-(pyridin-3-ylamino)-phenyl]-1,3-dihydro-indol-2-one | Y | Y |
| 3-(1-hydroxy-1-pyridin-3-yl-ethyl)-5-(1H-indol-4-yl)-phenol | N | |
| [3-hydroxy-5-(1H-indol-4-yl)-phenyl]-(6-methyl-pyridin-3-yl)-methanone | N | |
| N-[5'-hydroxy-3'-(pyridin-3-ylamino)-biphenyl-3-yl]-methanesulfonamide | N | Y |
| (3-adamantan-2-yl-4-hydroxyphenyl)-pyridin-3-yl-methanone | N | N |
| [3-(1H-indol-4-yl)-5-nitrophenyl]-pyridin-3-yl-amine | N | N |
| 3-(1H-indol-5-yl)-5-(pyridin-3-ylamino)-phenol | Y | N |
| 3-(1H-indol-4-yl)-5-(pyridin-4-ylamino)-phenol | Y | Y |
| 3-(1H-indol-7-yl)-5-(pyridin-3-ylamino)-phenol | N | N |
| 3-(1H-indol-4-yl)-5-(pyrazin-2-ylamino)-phenol | Y | Y |
| 3-(1H-indol-6-yl)-5-(pyridin-3-ylamino)-phenol | N | N |
| 3-(pyridin-3-ylamino)-5-quinolin-3-yl-phenol | N | N |
| 3-(1H-indol-4-yl)-5-(methyl-pyridin-3-yl-amino)-phenol | Y | Y |
| 3-(3-chloro-1H-indol-4-yl)-5-(pyridin-3-ylamino)-phenol | N | N |
| (6-amino-pyridin-3-yl)-[3-hydroxy-5-(1H-indol-4-yl)-phenyl]-methanone | N | Y |
| [3-(1H-Indol-4-yl)-5-methyl-phenyl]-pyridin-3-yl-amine | N | Y |
| [3-Hydroxy-5-(1H-indol-4-yl)-phenyl]-(5-methyl-pyridin-3-yl)-methanone | Y | Y |
| (2-Chloro-pyridin-3-yl)-[3-hydroxy-5-(1H-indol-4-yl)-phenyl]-methanone | N | N |
| 5-[3-Hydroxy-5-(1H-indol-4-yl)-phenylamino]-pyrazine-2-carbonitrile | N | Y |
| [2-Hydroxy-5-(1H-indol-4-yl)-phenyl]-pyridin-3-yl-methanone | Y | Y |
| [3-Chloro-5-(1H-indol-4-yl)-phenyl]-pyridin-3-yl-amine | Y | N |
| [3-(5-Fluoro-indol-1-yl)-5-hydroxy-phenyl]-pyridin-3-yl-methanone | Y | Y |
| [3-Hydroxy-5-(1H-indol-4-yl)-phenyl]-(6-methoxy-pyridin-3-yl)-methanone | Y | Y |
| [3-(1H-Indol-4-yl)-5-(pyridine-3-carbonyl)-phenyl]-carbamic acid benzyl ester | N | Y |
| 3-Amino-5-(1H-indol-4-yl)-phenyl]-pyridin-3-yl-methanone | Y | Y |
| 3-Benzo[1,3]dioxol-4-yl-5-(pyridin-3-ylamino)-phenol | Y | Y |

TABLE 2-continued

| Compound | Jurkat G2/M Block 0.1 μM | MCF-7 G2/M Block 1 μM |
|---|---|---|
| 3-(1H-Indol-4-yl)-5-(pyridin-3-ylamino)-benzoic acid methyl ester | Y | Y |
| 3-(1H-Indol-4-yl)-5-(pyridin-3-ylamino)-benzonitrile | Y | Y |
| 5-[3-Hydroxy-5-(1H-indol-4-yl)-phenylamino]-pyridine-2-carboxylic acid amide | Y | Y |
| N-[3-(1H-Indol-4-yl)-5-(pyridine-3-carbonyl)-phenyl]-acetamide | Y | Y |
| 3-(1H-Indol-4-yl)-5-phenylamino-phenol | Y | Y |
| N-[3-(1H-Indol-4-yl)-5-(pyridine-3-carbonyl)-phenyl]-methanesulfonamide | Y | Y |
| [3-(1H-Indol-4-yl)-5-(pyridine-3-carbonyl)-phenyl]-carbamic acid methyl ester | Y | Y |
| N-[3-(1H-Indol-4-yl)-5-(pyridine-3-carbonyl)-phenyl]-propionamide | N | Y |
| 5-[3-Hydroxy-5-(1H-indol-4-yl)-phenylamino]-pyridine-2-carbonitrile | Y | Y |
| 3-[3-(1H-Indol-4-yl)-5-(pyridin-3-ylamino)-phenyl]-1,1-dimethyl-urea | N | Y |
| 3-(1H-Indol-4-yl)-5-(pyrazin-2-ylamino)-benzamide | N | Y |
| N-[3-(1H-Indol-4-yl)-5-(pyridine-3-sulfonyl)-phenyl]-acetamide | N | Y |
| N-[3-(1H-Indol-4-yl)-5-(pyridine-4-carbonyl)-phenyl]-acetamide | Y | Y |
| 3-(1H-Indol-4-yl)-5-(pyridin-3-ylamino)-benzamide | Y | Y |
| N-[3-(1H-Indol-4-yl)-5-(pyridin-3-ylmethylsulfanyl)-phenyl]-acetamide | N | Y |
| Formic acid 2-{3-[3-hydroxy-5-(1H-indol-4-yl)-phenylamino]-pyridin-2-ylmethoxy}-ethyl ester | N | Y |
| [3-(1H-Indol-4-yl)-5-(pyridin-3-ylamino)-phenyl]-carbamic acid methyl ester | N | Y |
| N-[3-(1H-Indol-4-yl)-5-(pyridin-3-ylamino)-phenyl]-methanesulfonamide | N | Y |
| N-[3-(1H-Indol-4-yl)-5-(2-methoxy-pyridine-4-carbonyl)-phenyl]-acetamide | Y | Y |
| [3-Amino-5-(1H-indol-4-yl)-phenyl]-(2-methoxy-pyridin-4-yl)-methanone | Y | Y |
| N-[3-(2-Chloro-pyridine-4-carbonyl)-5-(1H-indol-4-yl)-phenyl]-acetamide | Y | Y |
| 1-[3-(1H-Indol-4-yl)-5-(pyridine-3-carbonyl)-phenyl]-pyrrolidin-2-one | N | Y |
| N-[3-(1H-Indol-4-yl)-5-oxazolo[4,5-b]pyridin-2-yl-phenyl]-acetamide | N | Y |
| 3-(1H-Indol-4-yl)-5-pyridin-3-yl-phenol | Y | Y |
| 4-[3-Hydroxy-5-(pyridin-3-ylamino)-phenyl]-1H-indole-2-carbonitrile | Y | N |
| N-[3-(2-Cyano-1H-indol-4-yl)-5-(pyridine-3-carbonyl) | Y | Y |
| N-[3-(1H-Indol-4-yl)-5-(pyridine-4-carbonyl)-phenyl]-methanesulfonamide | Y | Y |
| N-[3-(2-Chloro-pyridine-4-carbonyl)-5-(1H-indol-4-yl) | Y | Y |
| N-[3-(2-Chloro-6-methyl-pyridine-4-carbonyl)-5-(1H-indol-4-yl)-phenyl]-methanesulfonamide | Y | Y |
| N-[3-Bromo-5-(pyridine-3-carbonyl)-phenyl-acetamide | Y | Y |

Example 127

Cell Cycle Assay

Methods

The adherent MCF-7 breast cancer cells and NCI-H522 non small cell lung cancer cells were grown and maintained in EMEM cell culture media containing 10% fetal calf serum.

MCF-7 and NCI-H522 cells were plated in 24 well cell culture plates at a density of $5 \times 10^5$ cells/mL at a volume of 1 mL/well. Cells were allowed to adhere for 24 hrs. After adherence, cell culture media was changed to that containing 0.5% FCS. Thirty minutes post-media change, test compounds were added at a concentration of either 1.0 or 0.1 μM (as specified in the Tables). Twenty-four hours after test agent addition, cells were analyzed for cell cycle status as described below.

Cell Cycle Analysis

Cell cycle status was analyzed by flow cytometry. Briefly, cells were collected and washed with FACs buffer (Pharmingen) and resuspended and fixed in 1 mL of 80% ethanol for 1 hr. Cells were washed with FACs buffer and resuspended in propidium iodide(PI)/RNase staining buffer (Pharmingen). PI is a fluorescent dye that labels nucleic acids such as DNA. The fluorescence within a cell (in the presence of PI) is proportional to the amount of DNA within a cell. The cell content of DNA is an indicator of status in the cell cycle. For example, cells in the G2/M (mitotic stage) of the cell cycle have twice as much DNA as cells in the G1/0 phase. Cells in the S phase have DNA content that lies between these extremes.

For testing of cell cycle effects of test agents the percentage of cells within the G1 and G2/M phase were measured. If a test compound evoked a 50% increase in the number of cells in the G2/M phase, as compared to control, it was considered to be an active compound. In Tables 3 and 4, Y indicates a 50% or greater increase in the number of cells in the G2/M phase, as compared to control, and N indicates a less than 50% increase at this dose.

TABLE 3

| Compound | MCF-7 G2/M Block 1 μM | H522 G2/M Block 0.1 μM |
|---|---|---|
| Methyl 3-(6-cyanopyridin-3-ylamino)-5-(1H-indol-4-yl)phenylcarbamate | Y | N |
| (2-Amino-5-(1H-indol-4-yl)phenyl) (pyridin-3-yl)methanone | Y | Y |
| 3-(2-Ethylpyridin-3-ylamino)-5-(1H-indol-4-yl)phenol | Y | Y |
| 4-(3-Hydroxy-5-(1H-indol-4-yl)phenylamino)benzonitrile | N | Y |
| 3-(2-(dimethylamino)pyridin-3-ylamino)-5-(1H-indol-4-yl)phenol | Y | Y |
| N-[3-(2-Methoxy-pyridine-4-carbonyl)-5-(1H-indol-4-yl)-phenyl]-methanesulfonamide | Y | Y |
| [3-(1H-indol-4-yl)-5-oxazolo[4,5-b]pyridin-2-yl-phenyl]carbamic acid methyl ester | N | Y |

TABLE 4

| Compound | MCF-7 G2/M Block 0.1 μM | H522 G2/M Block 0.1 μM |
|---|---|---|
| [3-(1H-Indol-4-yl)-5-(2-methoxy-pyridin-4-ylamino)-phenyl]-carbamic acid methyl ester | Y | N |
| [3-(2-Chloro-6-methyl-pyridin-4-ylamino)-5-(1H-indol-4-yl)-phenyl]-carbamic acid methyl ester | Y | Y |
| 3-(2-Cyano-6-methyl-pyridin-4-ylamino)-5-(1H-indol-4-yl)-phenyl]-carbamic acid methyl ester | Y | Y |
| N-[3-Benzooxazol-2-yl-5-(1H-indol-4-yl)-phenyl]-acetamide | Y | Y |
| [3-Benzooxazol-2-yl-5-(1H-indol-4-yl)-phenyl]-carbamic acid methyl ester | Y | Y |
| N-[3-Benzooxazol-2-yl-5-(1H-indol-4-yl)-phenyl]-methanesulfonamide | Y | Y |

TABLE 4-continued

| Compound | MCF-7 G2/M Block 0.1 μM | H522 G2/M Block 0.1 μM |
|---|---|---|
| [3-Benzofuran-4-yl-5-(2-methoxy-pyridin-4-ylamino)-phenyl]-carbamic acid methyl ester | N* | N* |
| [3-(2,6-Dimethyl-pyridin-4-ylamino)-5-(1H-indol-4-yl)-phenyl]-carbamic acid methyl ester | Y | Y |
| 3-(2-Chloro-pyridin-4-ylamino)-5-(1H-indol-4-yl)-phenyl]-carbamic acid methyl ester | N* | N |
| [3-(1H-Indol-4-yl)-5-(2-morpholin-4-yl-pyridin-4-ylamino)-phenyl]-carbamic acid methyl ester | Y | Y |
| [3-(1H-Indol-4-yl)-5-pyridin-3-yl-phenyl]-carbamic acid methyl ester | N | Y |
| N-[3-(1H-Indol-4-yl)-5-pyridin-3-yl-phenyl]-acetamide | Y | Y |
| [3-(1H-Indol-4-yl)-5-pyridin-4-yl-phenyl]-carbamic acid methyl ester | Y | Y |
| N-[3-(1H-Indol-4-yl)-5-pyridin-4-yl-phenyl]-methanesulfonamide | Y | Y |
| N-[3-(1H-Indol-4-yl)-5-pyridin-4-yl-phenyl]-acetamide | Y | Y |
| N-[3-(1H-Indol-4-yl)-5-(6-methoxy-pyridin-3-yl)-phenyl]-acetamide | Y | Y |
| [3-(7-Fluoro-1H-indol-4-yl)-5-(pyridin-3-ylamino)-phenyl]-carbamic acid methyl ester | Y | Y |

*IC50 between 0.5 and 5 μM

Example 128

Tablet Preparation

Tablets containing 25.0, 50.0, and 100.0 mg, respectively, of the compound of Example 1 ("active compound") are prepared as illustrated below:

TABLET FOR DOSES CONTAINING FROM 25-100 MG OF THE ACTIVE COMPOUND

| | Amount-mg | | |
|---|---|---|---|
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 83

Intravenous Solution Preparation

An intravenous dosage form of the compound of Example 1 ("active compound") is prepared as follows:

| Active compound | 0.5-10.0 mg |
|---|---|
| Sodium citrate | 5-50 mg |
| Citric acid | 1-15 mg |
| Sodium chloride | 1-8 mg |
| Water for injection (USP) | q.s. to 1 mL |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound of Formula I:

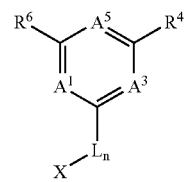

or a pharmaceutically-acceptable salt thereof, wherein:

$A^1$ is $CR^1$, wherein $R^1$ is hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, aminocarbonylamino, monoalkylaminocarbonylamino, dialkylaminocarbonylamino, N-alkyl-N-alkoxycarbonyl-amino, N-alkyl-N-aminocarbonyl-amino, N-alkyl-N-monoalkylaminocarbonyl-amino or N-alkyl-N-dialkylaminocarbonyl-amino;

$A^3$ is $CR^3$, wherein $R^3$ is hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, aminocarbonylamino, monoalkylaminocarbonylamino, dialkylaminocarbonylamino, N-alkyl-N-alkoxycarbonyl-amino, N-alkyl-N-aminocarbonyl-amino, N-alkyl-N-monoalkylaminocarbonyl-amino or N-alkyl-N-dialkylaminocarbonyl-amino;

A⁵ is CR⁵;

R⁴ is 1-H-indol-4-yl which is optionally substituted by one or two substituents independently selected from the group consisting of halo, hydroxy, nitro, cyano, alkyl, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl and dialkylaminocarbonylalkyl;

R⁵ and R⁶ are independently selected from the group consisting of hydrogen, halo, hydroxy, alkyl, alkenyl, alkynyl, cycloalkyl, haloalkyl, hydroxyalkyl, alkoxy, nitro, cyano, aminoalkyl, monoalkylaminoalkyl, dialkylaminoalkyl, amino, monoalkylamino, dialkylamino, formylamino, alkylcarbonylamino, alkoxycarbonylamino, benzyloxycarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonylamino, alkylsulfonylamino, aminosulfonyl, monoalkylaminosulfonyl, dialkylaminosulfonyl, alkoxycarbonylamino, ureido, N-alkylureido, N'-alkylureido, N,N'-dialkylureido, N,N',N'-trialkylureido, N',N'-dialkylureido, N'-alkoxy-N'-alkylureido, tetrazolyl, 2-oxo-pyrrolidin-1-yl, 2-oxo-piperidin-1-yl, benzyl and benzyloxy, wherein said benzyl and benzyloxy are optionally substituted with one or two substituents independently selected from the group consisting of halo, hydroxy, alkyl, alkoxy, amino, monoalkylamino, dialkylamino, nitro and cyano;

n is 1, and L is —C(O)—

X is Ar, HetAr or BiHetAr, wherein Ar is an aryl group having 6-10 carbons in the ring portion, HetAr is a 6-membered heteroaryl group having 1-3 nitrogen atoms in the ring portion, or HetAr is a 5-membered heteroaryl group having 0-4 nitrogen atoms in the ring portion and optionally having 1 sulfur atom or 1 oxygen atom in the ring portion, and BiHetAr is a heteroaryl group in which a 6-membered ring is fused either to a 5-membered ring or to a 6-membered ring, wherein in each case 1, 2, 3 or 4 ring atoms are heteroatoms independently selected from nitrogen, oxygen and sulfur;

wherein Ar, HetAr and BiHetAr are each optionally substituted with one or two substituents independently selected from the group consisting of halo, hydroxy, alkyl, alkenyl, alkynyl, cycloalkyl, haloalkyl, hydroxyalkyl, alkoxy, alkoxyalkyl, nitro, cyano, aminoalkyl, monoalkylaminoalkyl, dialkylaminoalkyl, amino, monoalkylamino, dialkylamino, formylamino, alkylcarbonylamino, carboxy, alkoxycarbonyl, aminocarbonyl, monoalkylaminocarbonyl, dialkylaminocarbonyl, carboxyalkyl, alkoxycarbonylalkyl, aminocarbonylalkyl, monoalkylaminocarbonylalkyl, dialkylaminocarbonylalkyl, sulfonyl-amino, alkylsulfonylamino, aminosulfonyl, monoalkylaminosulfonyl, dialkylaminosulfonyl, morpholinyl and formyloxyalkoxyalkyl;

provided that:

(1) when A¹ is CR¹, A³ is CR³, A⁵ is CR⁵ and X is optionally-substituted phenyl:

at least one of R¹, R⁵ or R⁶ is other than hydrogen, halo, alkyl, alkenyl, alkynyl, cycloalkyl, haloalkyl, hydroxyalkyl, alkoxy, nitro, aminoalkyl, monoalkylaminoalkyl, dialkylaminoalkyl; and (2) when each of R¹, R⁵ and R⁶ is independently hydrogen, halo, alkyl, alkenyl, alkynyl, cycloalkyl, haloalkyl, hydroxyalkyl, alkoxy, nitro, aminoalkyl, monoalkylaminoalkyl, dialkylaminoalkyl or amino:

X is HetAr or BiHetAr.

2. The compound according to claim 1, or a pharmaceutically-acceptable salt thereof, wherein:
A¹ is CR¹;
A³ is CR³, and R³ is hydrogen;
A⁵ is CR⁵; and
at least one of R¹, R⁵ or R⁶ is other than hydrogen.

3. The compound according to claim 1, or a pharmaceutically-acceptable salt thereof, wherein:
A¹ is CR¹, and R¹ is hydrogen;
A³ is CR³, and R³ is hydrogen;
A⁵ is CR⁵, and R⁵ is hydrogen; and
R⁶ is other than hydrogen.

4. The compound according to claim 1, or a pharmaceutically-acceptable salt thereof, wherein X is HetAr.

5. The compound according to claim 1, or a pharmaceutically-acceptable salt thereof, wherein:
R¹ is hydrogen or hydroxy;
R³ is hydrogen;
R⁵ is selected from the group consisting of hydrogen, benzyl and ($C_{1-4}$ alkoxy)benzyl;
R⁶ is selected from the group consisting of hydrogen, halo, hydroxyl, $C_{1-4}$ alkyl, halo($C_{1-4}$alkyl), hydroxy($C_{1-4}$)alkyl, $C_{1-4}$ alkoxy, benzyloxy, ($C_{1-4}$ alkoxy)benzyloxy, amino, mono($C_{1-4}$alkyl)amino, di($C_{1-4}$alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl) aminocarbonyl, di($C_{1-4}$ alkyl)aminocarbonyl, ($C_{1-4}$ alkoxy)carbonyl, cyano, nitro and 2-oxo-pyrrolidin-1-yl; and
X is selected from the group consisting of pyridinyl, 1-oxy-pyridinyl and pyrazinyl, each of which is optionally substituted with one or two substituents selected from the group consisting of halo, $C_{1-4}$ alkyl, halo($C_{1-4}$alkyl), hydroxy, hydroxy($C_{1-4}$alkyl, $C_{1-4}$ alkoxy, $C_{1-4}$ alkoxy ($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

6. The compound according to claim 1, or a pharmaceutically-acceptable salt thereof, wherein R¹ is selected from the group consisting of hydrogen and hydroxy.

7. The compound according to claim 1, or a pharmaceutically-acceptable salt thereof, wherein R¹ is hydrogen.

8. The compound according to claim 1, or a pharmaceutically-acceptable salt thereof, wherein R³ is hydrogen.

9. The compound according to claim 1, or a pharmaceutically-acceptable salt thereof, wherein R⁵ is selected from the group consisting of hydrogen, benzyl and ($C_{1-4}$ alkoxy)benzyl.

10. The compound according to claim 1, or a pharmaceutically-acceptable salt thereof, wherein R⁵ is hydrogen.

11. The compound according to claim 1, or a pharmaceutically-acceptable salt thereof, wherein R⁶ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxo-pyrrolidin-1-yl.

12. The compound according to claim 1, or a pharmaceutically-acceptable salt thereof, wherein $R^6$ is selected from the group consisting of hydrogen, halo, hydroxyl, $C_{1-4}$ alkyl, $C_{1-4}$ alkoxy, benzyloxy, ($C_{1-4}$ alkoxy)benzyloxy, amino, ($C_{1-4}$ alkyl)carbonylamino, ($C_{1-4}$ alkoxy)carbonylamino, benzyloxycarbonylamino, ($C_{1-4}$ alkyl)sulfonylamino, N',N'-di($C_{1-4}$ alkyl)ureido, carbamoyl, ($C_{1-4}$ alkoxy)carbonyl, cyano, nitro and 2-oxo-pyrrolidin-1-yl.

13. The compound according to claim 1, or a pharmaceutically-acceptable salt thereof, wherein $R^6$ is selected from the group consisting of hydrogen, chloro, hydroxyl, methyl, methoxy, 4-methoxybenzyloxy, amino, acetylamino, propanoylamino, methoxycarbonylamino, benzyloxycarbonylamino, methyl sulfonylamino, N',N'-dimethylureido, carbamoyl, methoxycarbonyl, cyano, nitro and 2-oxo-pyrrolidin-1-yl.

14. The compound according to claim 1, or a pharmaceutically-acceptable salt thereof, wherein $R^6$ is hydroxyl, ($C_{1-4}$ alkyl)carbonylamino, ($C_{1-4}$ alkoxy)carbonylamino or ($C_{1-4}$ alkyl)sulfonylamino.

15. The compound according to claim 1, or a pharmaceutically-acceptable salt thereof, wherein X is selected from the group consisting of pyridinyl, 1-oxy-pyridinyl and pyrazinyl, each of which is optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

16. The compound according to claim 1, or a pharmaceutically-acceptable salt thereof, wherein X is selected from the group consisting of pyridine-2-yl, pyridine-3-yl, 1-oxy-pyridin-3-yl, pyridin-4-yl and pyrazinyl, each of which is optionally substituted with one or two substituents selected from the group consisting of chloro, methyl, ethyl, hydroxy, hydroxymethyl, methoxy, amino, dimethylamino, cyano, carbamoyl, morpholin-1-yl and (2-formyloxyethoxy)methyl.

17. The compound according to claim 1, or a pharmaceutically-acceptable salt thereof, wherein X is selected from the group consisting of pyridin-2-yl, pyridin-3-yl, 6-cyano-pyridin-3-yl, 6-chloro-pyridin-3-yl, 2-chloro-pyridin-3-yl, 6-hydroxy-pyridin-3-yl, 6-methyl-pyridin-3-yl, 5-methyl-pyridin-3-yl, 2-ethyl-pyridin-3-yl, 6-hydroxymethyl-pyridin-3-yl, 6-amino-pyridin-3-yl, 2-dimethylamino-pyridin-3-yl, 6-carbamoyl-pyridin-3-yl, 6-methoxy-pyridin-3-yl, 2-((2-formyloxyethoxy)methyl)-pyridin-3-yl, 1-oxy-pyridin-3-yl, pyridine-4-yl, 2-chloro-pyridin-4-yl, 2-chloro-6-methyl-pyridin-4-yl, 2,6-dimethyl-pyridin-4-yl, 2-cyano-6-methyl-pyridin-4-yl, 2-methoxy-pyridin-4-yl, 3-methoxy-pyridin-4-yl, 2-(morpholin-1-yl)-pyridin-4-yl, pyrazinyl and 5-cyano-pyrazin-2-yl.

18. The compound according to claim 1, or a pharmaceutically-acceptable salt thereof, wherein X is pyridyl optionally substituted by one substituent selected from the group consisting of methyl, cyano, chloro, hydroxy, hydroxymethyl, amino, methoxy and carbamoyl.

19. The compound according to claim 1, or a pharmaceutically-acceptable salt thereof, wherein X is pyridyl.

20. The compound according to claim 1, or a pharmaceutically-acceptable salt thereof, wherein:
$R^1$, $R^3$ and $R^5$ are each hydrogen;
R4 is optionally substituted with substituent selected from the group consisting of halo, $C_{1-4}$ alkyl, cyano, $C_{2-5}$ alkanoyl and halo($C_{2-5}$)alkanoyl;
$R^6$ is selected from the group consisting of hydrogen, halo, hydroxyl, $C_{1-4}$ alkyl, halo($C_{1-4}$)alkyl, hydroxy($C_{1-4}$) alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl) ureido, N,N'-di($C_{1-4}$ alkyl)ureido, N,N',N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxo-pyrrolidin-1-yl; and
X is selected from the group consisting of pyridinyl, 1-oxy-pyridinyl and pyrazinyl, each of which is optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy ($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

21. The compound according to claim 20, or a pharmaceutically-acceptable salt thereof, wherein $R^6$ is hydroxyl, ($C_{1-4}$ alkyl)carbonylamino, ($C_{1-4}$ alkoxy)carbonylamino or ($C_{1-4}$ alkyl)sulfonylamino.

22. The compound according to claim 20, or a pharmaceutically-acceptable salt thereof, wherein $R^6$ is hydroxyl, acetylamino, methoxycarbonylamino or methylsulfonylamino.

23. The compound according to claim 20, or a pharmaceutically-acceptable salt thereof, wherein X is pyridyl optionally substituted once with a substituent selected from the group consisting of cyano, halo; $C_{1-4}$ alkoxy, $C_{1-4}$ alkyl, carbamoyl and morpholin-1-yl.

24. The compound according to claim 20, or a pharmaceutically-acceptable salt thereof, wherein X is pyridyl optionally substituted once with a substituent selected from the group consisting of cyano, chloro, methoxy, methyl, ethyl, carbamoyl and morpholin-1-yl.

25. The compound according to claim 20, or a pharmaceutically-acceptable salt thereof, wherein X is pyridyl.

26. A compound selected from the group consisting of:
(6-chloropyridin-3-yl)-[3-hydroxy-5-(1H-indol-4-yl)-phenyl]-methanone;
[3-hydroxy-5-(1H-indol-4-yl)-phenyl]-(6-hydroxypyridin-3-yl)-methanone;
[3-hydroxy-5-(1H-indol-4-yl)-phenyl]-(6-methyl-pyridin-3-yl)-methanone;
(6-amino-pyridin-3-yl)-[3-hydroxy-5-(1H-indol-4-yl)-phenyl]-methanone;
[3-hydroxy-5-(1H-indol-4-yl)-phenyl]-(5-methyl-pyridin-3-yl)-methanone;
(2-chloro-pyridin-3-yl)-[3-hydroxy-5-(1H-indol-4-yl)-phenyl]-methanone;
[3-hydroxy-5-(1H-indol-4-yl)-phenyl]-(6-methoxy-pyridin-3-yl)-methanone;
[3-(1H-indol-4-yl)-5-(pyridin-3-carbonyl)-phenyl]-carbamic acid benzyl ester;
[3-amino-5-(1H-indol-4-yl)-phenyl]-pyridin-3-yl-methanone;
N-[3-(1H-indol-4-yl)-5-(pyridin-3-carbonyl)-phenyl]-acetamide;

N-[3-(1H-indol-4-yl)-5-(pyridin-3-carbonyl)-phenyl]-methanesulfonamide;
[3-(1H-indol-4-yl)-5-(pyridin-3-carbonyl)-phenyl]-carbamic acid methyl ester;
N-[3-(1H-indol-4-yl)-5-(pyridin-3-carbonyl)-phenyl]-propionamide;
N-[3-(1H-indol-4-yl)-5-(pyridine-4-carbonyl)-phenyl]-acetamide;
N-[3-(1H-indol-4-yl)-5-(2-methoxy-pyridine-4-carbonyl)-phenyl]-acetamide;
[3-amino-5-(1H-indol-4-yl)-phenyl]-(2-methoxy-pyridin-4-yl)-methanone;
N-[3-(2-chloro-pyridine-4-carbonyl)-5-(1H-indol-4-yl)-phenyl]-acetamide;
1-[3-(1H-indol-4-yl)-5-(pyridin-3-carbonyl)-phenyl]-pyrrolidin-2-one;
N-[3-(2-cyano-1H-indol-4-yl)-5-(pyridin-3-carbonyl)-phenyl]-methanesulfonamide;
N-[3-(1H-indol-4-yl)-5-(pyridine-4-carbonyl)-phenyl]-methanesulfonamide;
N-[3-(2-chloro-pyridine-4-carbonyl)-5-(1H-indol-4-yl)-phenyl]-methanesulfonamide;
N-[3-(2-chloro-6-methyl-pyridine-4-carbonyl)-5-(1H-indol-4-yl)-phenyl]-methanesulfonamide; and
N-[3-(2-Methoxy-pyridine-4-carbonyl)-5-(1H-indol-4-yl)-phenyl]-methanesulfonamide;
3-(1H-indazol-4-yl)-5-(pyriding-3-ylamino)-phenol;
or a pharmaceutically-acceptable salt or thereof.

27. The compound according to claim 1, or a pharmaceutically-acceptable salt thereof, wherein:
$R^4$ 1H-indol-4-yl;
$R^5$ and $R^6$ are independently selected from the group consisting of ($C_{1-4}$ alkyl)sulfonylamino, ($C_{1-4}$ alkoxy)carbonylamino, ($C_{1-4}$ alkyl)carbonylamino, hydroxyl, benzyl and ($C_{1-4}$ alkoxy)benzyl; and
X is pyridyl optionally substituted once with a substituent selected from the group consisting of cyano, halo, $C_{1-4}$ alkoxy, $C_{1-4}$ alkyl and carbamoyl.

28. The compound according to claim 27, or a pharmaceutically-acceptable salt thereof, wherein $R^5$ and $R^6$ are independently selected from the group consisting of hydroxyl, benzyl and ($C_{1-4}$ alkoxy)benzyl.

29. The compound according to claim 27, or a pharmaceutically-acceptable salt thereof, wherein $R^5$ is benzyl or methoxybenzyl.

30. The compound according to claim 27, or a pharmaceutically-acceptable salt thereof, wherein $R^6$ is hydroxyl.

31. The compound according to claim 27, or a pharmaceutically-acceptable salt thereof, wherein X is pyridyl.

32. A compound selected from the group consisting of:
2-benzyl-3-(1H-indol-4-yl)-5-(pyridin-3-ylamino)-phenol; and
or a pharmaceutically-acceptable salt thereof.

33. The compound according to claim 1, or a pharmaceutically-acceptable salt thereof, wherein:
$R^4$ 1H-indol-4-yl;
$R^1$ is selected from the group consisting of ($C_{1-4}$ alkyl)sulfonylamino, ($C_{1-4}$ alkoxy)carbonylamino, ($C_{1-4}$ alkyl)carbonylamino, hydroxyl and amino; and
X is pyridyl optionally substituted once with a substituent selected from the group consisting of cyano, halo, $C_{1-4}$ alkoxy, $C_{1-4}$ alkyl and carbamoyl.

34. The compound according to claim 33, or a pharmaceutically-acceptable salt thereof, wherein $R^1$ is hydroxyl or amino.

35. The compound according to claim 33, or a pharmaceutically-acceptable salt thereof, wherein X is pyridyl.

36. A compound selected from the group consisting of:
(2-amino-5-(1H-indol-4-yl)phenyl)-(pyridin-3-yl)methanone
or a pharmaceutically-acceptable salt or thereof.

37. The compound according to claim 1, or a pharmaceutically-acceptable salt thereof, wherein X is Ar.

38. The compound according to claim 37, or a pharmaceutically-acceptable salt thereof, wherein:
$R^1$, $R^3$ and $R^5$ are each hydrogen; and
$R^6$ is other than hydrogen.

39. The compound according to claim 37, or a pharmaceutically-acceptable salt thereof, wherein:
$R^1$ is hydrogen or hydroxy;
$R^3$ is hydrogen;
$R^5$ is selected from the group consisting of hydrogen, benzyl and ($C_{1-4}$ alkoxy)benzyl;
$R^4$ optionally substituted with one substituent selected from the group consisting of halo, $C_{1-4}$ alkyl, cyano, $C_{2-5}$ alkanoyl and halo($C_{2-5}$)alkanoyl;
$R^6$ is selected from the group consisting of hydrogen, halo, hydroxyl, $C_{1-4}$ alkyl, halo($C_{1-4}$)alkyl, hydroxy($C_{1-4}$)alkyl, $C_{1-4}$ alkoxy, benzyloxy, ($C_{1-4}$ alkoxy)benzyloxy, amino, mono($C_{1-4}$)alkylamino, di($C_{1-4}$)alkylamino, ($C_{1-4}$ alkyl)carbonylamino, ($C_{1-4}$ alkoxy)carbonylamino, benzyloxycarbonylamino, ($C_{1-4}$ alkyl)sulfonylamino, ureido, N—($C_{1-4}$ alkyl)ureido, N'—($C_{1-4}$ alkyl)ureido, N,N'-di($C_{1-4}$ alkyl)ureido;. N,N,N'-tri($C_{1-4}$ alkyl)ureido, N',N'-di($C_{1-4}$ alkyl)ureido, carbamoyl, mono($C_{1-4}$ alkyl)aminocarbonyl, di($C_{1-4}$ alkyl)aminocarbonyl, ($C_{1-4}$ alkoxy)carbonyl, cyano, nitro and 2-oxo-pyrrolidin-1-yl; and
X is phenyl optionally substituted with one or two substituents selected from the group consisting of halo, $C_{1-4}$ alkyl, halo($C_{1-4}$)alkyl, hydroxy, hydroxy($C_{1-4}$)alkyl, $C_{1-4}$ alkoxy, $C_{1-4}$ alkoxy($C_{1-4}$)alkyl, amino, mono($C_{1-4}$ alkyl)amino, di($C_{1-4}$ alkyl)amino, cyano, carbamoyl, mono($C_{1-4}$ alkyl)aminocarbonyl, di($C_{1-4}$ alkyl)aminocarbonyl, morpholin-1-yl and formyloxy($C_{1-4}$)alkoxy($C_{1-4}$)alkyl.

40. The compound according to claim 37, or a pharmaceutically-acceptable salt thereof, wherein $R^6$ is ($C_{1-4}$ alkyl)sulfonylamino, ($C_{1-4}$ alkoxy)carbonylamino, ($C_{1-4}$ alkyl)carbonylamino or hydroxyl.

41. The compound according to claim 37, or a pharmaceutically-acceptable salt thereof, wherein X is phenyl optionally substituted once with a substituent selected from the group consisting of cyano, halo, $C_{1-4}$ alkoxy, $C_{1-4}$ alkyl and carbamoyl.

42. The compound according to claim 37, or a pharmaceutically-acceptable salt thereof, wherein:
$R^1$, $R^3$ and $R^5$ are each hydrogen;
$R^4$ 1H-indol-4-yl;
$R^6$ is ($C_{1-4}$ alkyl)sulfonylamino, ($C_{1-4}$ alkoxy)carbonylamino, ($C_{1-4}$ alkyl)carbonylamino or hydroxyl; and
X is phenyl optionally substituted once with a substituent selected from the group consisting of cyano, halo, $C_{1-4}$ alkoxy, $C_{1-4}$ alkyl and carbamoyl.

43. The compound according to claim 42, or a pharmaceutically-acceptable salt thereof, wherein $R^6$ is hydroxyl.

44. The compound according to claim 42, or a pharmaceutically-acceptable salt thereof, wherein X is phenyl or cyanophenyl.

45. A compound selected from the group consisting of:
3-(1H-indol-4-yl)-5-phenylamino-phenol; and
4-(3-hydroxy-5-(1H-indol-4-yl)phenylamino)benzonitrile;
or a pharmaceutically-acceptable salt or solvate thereof.

46. The compound according to claim 1, or a pharmaceutically-acceptable salt thereof, wherein $R^6$ is acetylamino, methoxycarbonylamino, methylsulfonylamino or hydroxyl.

47. The compound according to claim 1, or a pharmaceutically-acceptable salt thereof, wherein X is selected from the group consisting of pyridinyl, pyrazinyl, benzoxazol-2-yl and oxazolo[4,5-b]pyridin-2-yl, each of which is optionally substituted once with a substituent selected from the group consisting of cyano, halo, $C_{1-4}$ alkoxy, $C_{1-4}$ alkyl and carbamoyl.

48. The compound according to claim 1, or a pharmaceutically-acceptable salt thereof, wherein X is selected from the group consisting of pyridin-3-yl, pyridin-4-yl, benzoxazol-2-yl and oxazolo[4,5-b]pyridin-2-yl, each of which is optionally substituted once with $C_{1-4}$ alkoxy.

49. The compound according to claim 1 or a pharmaceutically-acceptable salt thereof, wherein X is selected from the group consisting of pyridin-3-yl, 6-methoxy-pyridin-3-yl, pyridin-4-yl, benzoxazol-2-yl and oxazolo[4,5-b]pyridin-2-yl.

50. The compound according to claim 1, or a pharmaceutically-acceptable salt thereof, wherein:
   $R^1$, $R^3$ and $R^1$ are each hydrogen;
   $R^4$ 1H-indol-4-yl;
   $R^6$ is $(C_{1-4}$ alkyl)carbonylamino, $(C_{1-4}$ alkoxy)carbonylamino, $(C_{1-4}$ alkyl)sulfonylamino or hydroxyl; and
   X is selected from the group consisting of pyridinyl, pyrazinyl, benzoxazol-2-yl and oxazolo[4,5-b]pyridin-2-yl, each of which is optionally substituted once with a substituent selected from the group consisting of cyano, halo, $C_{1-4}$ alkoxy, $C_{1-4}$ alkyl and carbamoyl.

51. The compound according to claim 50, or a pharmaceutically-acceptable salt thereof, wherein $R^6$ is acetylamino, methoxycarbonylamino, methylsulfonylamino or hydroxyl.

52. The compound according to claim 50, or a pharmaceutically-acceptable salt thereof, wherein X is selected from the group consisting of pyridin-3-yl, pyridin-4-yl, benzoxazol-2-yl and oxazolo[4,5-b]pyridin-2-yl, each of which is optionally substituted once with $C_{1-4}$ alkoxy.

53. The compound according to claim 50, or a pharmaceutically-acceptable salt thereof, wherein X is selected from the group consisting of pyridin-3-yl, pyridin-4-yl and benzoxazol-2-yl.

54. A compound selected from the group consisting of:
   N-[3-(1H-indol-4-yl)-5-(6-methoxy-pyridin-3-yl)-phenyl]-acetamide;
   or a pharmaceutically-acceptable salt thereof.

55. A pharmaceutical composition comprising the compound according to claim 1, or a pharmaceutically-acceptable salt thereof, and a pharmaceutically-acceptable carrier or diluent.

56. The composition of claim 55, wherein said compound is present in a concentration of about 0.01 µM to about 100 µM.

57. The composition of claim 55, wherein said compound is present in a concentration of about 0.03 µg/mL to about 30 µg/mL.

58. The composition of claim 55, suitable for administration by a subcutaneous, intravenous, intramuscular, intraperitoneal, buccal or ocular route, rectally, parenterally, instrasystemically, intravaginally, topically, orally, or as an oral or nasal spray.

59. The composition of claim 55, suitable for oral administration, wherein said compound is present in a concentration of about 0.01 µM to about 100 µM.

60. The composition of claim 55, suitable for oral administration, wherein said compound is present in a concentration of about 0.03 µg/mL to about 30 µg/mL.

* * * * *